US012728105B2

(12) United States Patent
Wang et al.

(10) Patent No.: US 12,728,105 B2
(45) Date of Patent: Sep. 8, 2026

(54) COMPOUNDS FOR THE TREATMENT OF BACTERIAL INFECTIONS AND POTENTIATION OF ANTIBIOTICS

(71) Applicant: GEORGIA STATE UNIVERSITY RESEARCH FOUNDATION, INC., Atlanta, GA (US)

(72) Inventors: Binghe Wang, Marietta, GA (US); David W. Boykin, Atlanta, GA (US); Arvind Kumar, Lilburn, GA (US); Mengyuan Zhu, Cary, NC (US); Manjusha Roy Choudhury, Atlanta, GA (US); Bingchen Yu, Atlanta, GA (US)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 741 days.

(21) Appl. No.: 17/757,644

(22) PCT Filed: Dec. 18, 2020

(86) PCT No.: PCT/US2020/066036

§ 371 (c)(1),
(2) Date: Jun. 17, 2022

(87) PCT Pub. No.: WO2021/127452

PCT Pub. Date: Jun. 24, 2021

(65) Prior Publication Data

US 2023/0105108 A1 Apr. 6, 2023

Related U.S. Application Data

(60) Provisional application No. 62/950,852, filed on Dec. 19, 2019.

(51) Int. Cl.

| | |
|---|---|
| ***C07D 307/36*** | (2006.01) |
| ***A61K 31/137*** | (2006.01) |
| ***A61K 31/155*** | (2006.01) |
| ***A61K 31/165*** | (2006.01) |
| ***A61K 31/277*** | (2006.01) |

(Continued)

(52) U.S. Cl.

CPC .......... *A61K 31/155* (2013.01); *A61K 31/137* (2013.01); *A61K 31/165* (2013.01); *A61K 31/277* (2013.01); *A61K 31/33* (2013.01); *A61K 31/341* (2013.01); *A61K 31/381* (2013.01); *A61K 31/407* (2013.01); *A61K 31/4178* (2013.01); *A61K 31/4184* (2013.01); *A61K 31/43* (2013.01); *A61K 31/431* (2013.01); *A61K 31/437* (2013.01); *A61K 31/4375* (2013.01); *A61K 31/44* (2013.01); *A61K 31/4709* (2013.01); *A61K 31/496* (2013.01); *A61K 31/505* (2013.01); *A61K 31/506* (2013.01); *A61K 31/5383* (2013.01); *A61K 31/55* (2013.01); *A61K 31/575* (2013.01); *A61K 31/65* (2013.01); *A61K 31/702* (2013.01); *A61K 31/704* (2013.01); *A61K 31/7048* (2013.01); *A61K 31/7052* (2013.01); *A61K 31/7056* (2013.01); *A61K 38/12* (2013.01); *A61P 31/04* (2018.01); *C07C 219/28* (2013.01); *C07C 257/18* (2013.01); *C07C 279/18* (2013.01); *C07C 323/45* (2013.01); *C07D 213/30* (2013.01); *C07D 233/20* (2013.01); *C07D 233/22* (2013.01); *C07D 235/18* (2013.01); *C07D 239/06* (2013.01); *C07D 307/52* (2013.01); *C07D 307/54* (2013.01); *C07D 307/68* (2013.01); *C07D 333/20* (2013.01); *C07D 333/22* (2013.01); *C07D 345/00* (2013.01); *C07D 403/04* (2013.01);

(Continued)

(58) Field of Classification Search

CPC .. C07D 307/36; A61K 31/341; A61K 31/155; C07C 279/18

See application file for complete search history.

(56) References Cited

U.S. PATENT DOCUMENTS

| | | |
|---|---|---|
| 4,034,010 A | 7/1977 | Hamano et al. |
| 4,064,169 A | 12/1977 | Hamano et al. |

(Continued)

FOREIGN PATENT DOCUMENTS

| | | |
|---|---|---|
| DE | 2833135 A1 | 2/1980 |
| EP | 1726589 A2 | 11/2006 |

(Continued)

OTHER PUBLICATIONS

Stephens, C., R. Brun, M. Salem, K. Werbovetz, F. Tanious, W. D. Wilson and D. Boykin. "The Activity of Diguanidino and 'Reversed' Diamidino 2,5-Diarylfurans versus Trypanosoma cruzi and Leishmania donovani" Bioorg. Med. Chem. Lett. 13 (2003), pp. 2065-2069. (Year: 2003).*

(Continued)

*Primary Examiner* — Kamal A Saeed
*Assistant Examiner* — Sagar Patel
(74) *Attorney, Agent, or Firm* — Kilpatrick Townsend & Stockton LLP

(57) ABSTRACT

Compounds and methods for use to treat a bacterial infection caused by, for example, gram positive bacteria, gram negative bacteria, and/or mycobacteria are provided herein. Also provided herein are compounds and methods for use in potentiating the effect of an antibiotic in the treatment of a bacterial infection. Pharmaceutical compositions including the compounds as described herein are also provided.

20 Claims, 22 Drawing Sheets

(51) Int. Cl.

| | |
|---|---|
| *A61K 31/33* | (2006.01) |
| *A61K 31/341* | (2006.01) |
| *A61K 31/381* | (2006.01) |
| *A61K 31/407* | (2006.01) |
| *A61K 31/4178* | (2006.01) |
| *A61K 31/4184* | (2006.01) |
| *A61K 31/43* | (2006.01) |
| *A61K 31/431* | (2006.01) |
| *A61K 31/437* | (2006.01) |
| *A61K 31/4375* | (2006.01) |
| *A61K 31/44* | (2006.01) |
| *A61K 31/4709* | (2006.01) |
| *A61K 31/496* | (2006.01) |
| *A61K 31/505* | (2006.01) |
| *A61K 31/506* | (2006.01) |
| *A61K 31/5383* | (2006.01) |
| *A61K 31/55* | (2006.01) |
| *A61K 31/575* | (2006.01) |
| *A61K 31/65* | (2006.01) |
| *A61K 31/702* | (2006.01) |
| *A61K 31/704* | (2006.01) |
| *A61K 31/7048* | (2006.01) |
| *A61K 31/7052* | (2006.01) |
| *A61K 31/7056* | (2006.01) |
| *A61K 38/12* | (2006.01) |
| *A61P 31/04* | (2006.01) |
| *C07C 219/28* | (2006.01) |
| *C07C 257/18* | (2006.01) |
| *C07C 279/18* | (2006.01) |
| *C07C 323/45* | (2006.01) |
| *C07D 213/30* | (2006.01) |
| *C07D 233/20* | (2006.01) |
| *C07D 233/22* | (2006.01) |
| *C07D 235/18* | (2006.01) |
| *C07D 239/06* | (2006.01) |
| *C07D 307/52* | (2006.01) |
| *C07D 307/54* | (2006.01) |
| *C07D 307/68* | (2006.01) |
| *C07D 333/20* | (2006.01) |
| *C07D 333/22* | (2006.01) |
| *C07D 345/00* | (2006.01) |
| *C07D 403/04* | (2006.01) |
| *C07D 405/04* | (2006.01) |
| *C07D 409/04* | (2006.01) |
| *C07D 409/14* | (2006.01) |

(52) U.S. Cl.
CPC ......... *C07D 405/04* (2013.01); *C07D 409/04* (2013.01); *C07D 409/14* (2013.01)

(56) References Cited

U.S. PATENT DOCUMENTS

| | | | |
|---|---|---|---|
| 4,619,942 | A | 10/1986 | Tidwell et al. |
| 4,983,593 | A | 1/1991 | Miyajima et al. |
| 5,013,557 | A | 5/1991 | Tai |
| 5,456,923 | A | 10/1995 | Nakamichi et al. |
| 5,576,025 | A | 11/1996 | Akiyama et al. |
| 5,723,269 | A | 3/1998 | Akagi et al. |
| 5,858,411 | A | 1/1999 | Nakagami et al. |
| 6,221,338 | B1 | 4/2001 | Staniforth |
| 6,254,889 | B1 | 7/2001 | Kigoshi et al. |
| 6,303,148 | B1 | 10/2001 | Hennink et al. |
| 6,395,302 | B1 | 5/2002 | Hennink et al. |
| 6,497,903 | B1 | 12/2002 | Hennink et al. |
| 6,582,678 | B2 | 6/2003 | Staniforth |
| 6,948,496 | B2 | 9/2005 | Eason et al. |
| 6,989,155 | B1 | 1/2006 | Ganderton et al. |
| 7,060,296 | B2 | 6/2006 | Hennink et al. |
| 7,078,057 | B2 | 7/2006 | Kerkhof |
| 7,383,837 | B2 | 6/2008 | Robertson et al. |
| 7,404,828 | B1 | 7/2008 | Nicola |
| 7,541,022 | B2 | 6/2009 | Staniforth et al. |
| 7,744,855 | B2 | 6/2010 | Staniforth et al. |
| 7,845,349 | B2 | 12/2010 | Eason et al. |
| 7,994,225 | B2 | 8/2011 | Bostian et al. |
| 8,101,160 | B2 | 1/2012 | Staniforth et al. |
| 8,137,657 | B2 | 3/2012 | Staniforth |
| 8,202,912 | B2 | 6/2012 | Curatolo et al. |
| 8,205,611 | B2 | 6/2012 | Olsson et al. |
| 8,257,741 | B2 | 9/2012 | Curatolo et al. |
| 8,263,128 | B2 | 9/2012 | Curatolo et al. |
| 8,337,899 | B2 | 12/2012 | Curatolo et al. |
| 8,431,159 | B2 | 4/2013 | Curatolo et al. |
| 8,580,306 | B2 | 11/2013 | Staniforth et al. |
| 8,910,625 | B2 | 12/2014 | Mullinger et al. |
| 9,028,870 | B2 | 5/2015 | Appel et al. |
| 9,060,938 | B2 | 6/2015 | Miller et al. |
| 9,095,670 | B2 | 8/2015 | Briant et al. |
| 9,211,261 | B2 | 12/2015 | Appel et al. |
| 9,265,731 | B2 | 2/2016 | Ray et al. |
| 9,358,478 | B2 | 6/2016 | Dobry et al. |
| 9,387,252 | B2 | 7/2016 | Babcock et al. |
| 9,960,588 | B2 | 5/2018 | Kreuter et al. |
| 2003/0199521 | A1 | 10/2003 | Dykstra et al. |
| 2003/0202944 | A1 | 10/2003 | Staniforth |
| 2005/0152849 | A1 | 7/2005 | Staniforth |
| 2006/0293540 | A1 | 12/2006 | Tidwell et al. |
| 2007/0010533 | A1 | 1/2007 | Dykstra et al. |
| 2007/0021483 | A1 | 1/2007 | Chalifour et al. |
| 2007/0043030 | A1 | 2/2007 | Morton et al. |
| 2007/0088067 | A1 | 4/2007 | Tidwell et al. |
| 2008/0132457 | A1 | 6/2008 | Bostian et al. |
| 2009/0269412 | A1 | 10/2009 | Staniforth et al. |
| 2010/0249175 | A1 | 9/2010 | Wilson et al. |
| 2010/0285142 | A1 | 11/2010 | Staniforth et al. |
| 2010/0330188 | A1 | 12/2010 | Staniforth |
| 2012/0114709 | A1 | 5/2012 | Staniforth et al. |
| 2013/0287854 | A1 | 10/2013 | Morgan et al. |
| 2014/0037737 | A1 | 2/2014 | Staniforth et al. |
| 2014/0352690 | A1 | 12/2014 | Kolb et al. |
| 2015/0050350 | A1 | 2/2015 | Staniforth et al. |
| 2015/0165137 | A1 | 6/2015 | Mullinger et al. |
| 2015/0174343 | A1 | 6/2015 | Muellinger et al. |
| 2018/0221456 | A1 | 8/2018 | Schuch et al. |

FOREIGN PATENT DOCUMENTS

| | | | | |
|---|---|---|---|---|
| WO | 9628427 | A1 | 9/1996 | |
| WO | 9729067 | A1 | 8/1997 | |
| WO | 0031068 | A1 | 6/2000 | |
| WO | 02055025 | A2 | 7/2002 | |
| WO | WO-02057224 | A2 * | 7/2002 | ........... C07D 307/10 |
| WO | 03017994 | A1 | 3/2003 | |
| WO | 2003103598 | A2 | 12/2003 | |
| WO | 2005033065 | A1 | 4/2005 | |
| WO | 2005040132 | A1 | 5/2005 | |
| WO | 2005044186 | A2 | 5/2005 | |
| WO | 2005086754 | A2 | 9/2005 | |
| WO | 2005086808 | A2 | 9/2005 | |
| WO | 2005089738 | A2 | 9/2005 | |
| WO | 2006021833 | A2 | 3/2006 | |
| WO | 2006033584 | A1 | 3/2006 | |
| WO | 2008090831 | A1 | 7/2008 | |
| WO | 2009051796 | A2 | 4/2009 | |
| WO | 2009105691 | A2 | 8/2009 | |
| WO | 2010133748 | A1 | 11/2010 | |
| WO | 2013038170 | A2 | 3/2013 | |
| WO | 2017223260 | A1 | 12/2017 | |
| WO | 2018045104 | A1 | 3/2018 | |
| WO | 2018045106 | A1 | 3/2018 | |

(56) References Cited

FOREIGN PATENT DOCUMENTS

WO 2019241566 A1 12/2019
WO 2021127452 A1 6/2021

OTHER PUBLICATIONS

"WHO Publishes List of Bacteria for Which New Antibiotics are Urgently Needed", Available Online at: https://www.who.int/news/item/27-02-2017-who-publishes-list-of-bacteria-for-which-new-antibiotics-are-urgently-needed, Feb. 27, 2017, pp. 1-4.
Allen Richard et al., "Modified Antibiotic Adjuvant Ratios Can Slow and Steer the Evolution of Resistance: Co-Amoxiclav as a Case Study", American Society for Microbiology, vol. 10, No. 5, Sep. 17, 2019, pp. 1-13.
Arafa et al., "Novel linear Triaryl guanidines, N-substituted Guanidines and Potential Prodrugs as Antiprotozoal Agents", European Journal of Medicinal Chemistry, vol. 43(12): 2901-2908, Dec. 2008.
Asokan et al., "WHO Global Priority Pathogens List: A Bibliometric Analysis of Medline-PubMed for Knowledge Mobilization to Infection Prevention and Control Practices in Bahrain", Oman Medical Journal, vol. 34, No. 3, May 2019, pp. 184-193.
Ayres , "Cooperative Microbial Tolerance Behaviors in Host-Microbiota Mutualism", Cell, vol. 165, No. 6, Jun. 2, 2016, pp. 1323-1331.
Bai et al., "A Polymeric Approach Toward Resistance-Resistant Antimicrobial Agent With Dual-Selective Mechanisms of Action", Science Advances, vol. 7, No. 5, Jan. 27, 2021, pp. 1-16.
Balusek et al., "Accelerating Membrane Simulations with Hydrogen Mass Repartitioning", Journal of Chemical Theory and Computation, vol. 15, No. 8, Aug. 13, 2019, pp. 4673-4686.
Balusek et al., "Role of the Native Outer-Membrane Environment on the Transporter BtuB", Biophysical Journal, vol. 111, No. 7, Oct. 4, 2016, pp. 1409-1417.
Barker et al., "Degradation of MAC13243 and Studies of the Interaction of Resulting Thiourea Compounds with the Lipoprotein Targeting Chaperone LolA", Bioorganic & Medicinal Chemistry Letters, vol. 23, No. 8, Apr. 15, 2013, pp. 2426-2431.
Bazydlo et al., "Calcium, Magnesium, and Phosphate", Laboratory Medicine, vol. 45, No. 1, Feb. 1, 2014, pp. e44-e50.
Bean et al., "Pentamidine: A Drug to Consider Re-Purposing in the Targeted Treatment of Multi-Drug Resistant Bacterial Infections?", Journal of Laboratory and Precision Medicine, vol. 2, No. 49, Jul. 27, 2017, pp. 1-4.
Benoit et al., "Molecular Hydrogen Metabolism: A Widespread Trait of Pathogenic Bacteria and Protists", Microbiology and Molecular Biology Reviews, vol. 84, No. 1, Jan. 29, 2020, 52 pages.
Blair et al., "Molecular Mechanisms of Antibiotic Resistance", Nature Reviews Microbiology, vol. 13, No. 1, Jan. 2015, pp. 42-51.
Blankson et al., "Structure-Activity Relationships of Potentiators of the Antibiotic Activity of Clarithromycin Against *Escherichia coli*", European Journal of Medicinal Chemistry, vol. 178, Sep. 15, 2019, pp. 30-38.
Blondiaux et al., "Reversion of Antibiotic Resistance in *Mycobacterium tuberculosis* by Spiroisoxazoline SMARt-420", Science, vol. 355, No. 6330, Mar. 17, 2017, pp. 1206-1211.
Boekema et al., "The Effect of a Honey Based Gel and Silver Sulphadiazine on Bacterial Infections of in Vitro Burn Wounds", Burns, vol. 39, No. 4, Jun. 2013, pp. 754-759.
Brochado et al., "Species-Specific Activity of Antibacterial Drug Combinations", Nature, vol. 559, No. 7713, Jul. 12, 2018, 24 pages.
Brown et al., "Antibacterial Drug Discovery in the Resistance Era", Nature, vol. 529, Jan. 21, 2016, pp. 336-343.
Brown et al., "Wall Teichoic Acids of Gram-Positive Bacteria", Annual Review of Microbiology, vol. 67, 2013, pp. 313-336.
Cadelis et al., "Spermine Derivatives of Indole-3-Carboxylic Acid, Indole-3-Acetic Acid and Indole-3-Acrylic Acid as Gram-Negative Antibiotic Adjuvants", ChemMedChem, vol. 16, No. 3, Feb. 4, 2021, pp. 513-523.
Case et al., "The Amber Biomolecular Simulation Programs", Journal Computer Chemistry, vol. 26, No. 16, Dec. 2005, pp. 1668-1688.
Cebrian et al., "The Cathelicidin-Derived Close-to-Nature Peptide D-11 Sensitises Klebsiella Pneumoniae to a Range of Antibiotics in Vitro, Ex Vivo and in Vivo", International Journal of Antimicrobial Agents, vol. 58, No. 5, Nov. 2021, pp. 1-8.
Chen et al., "In Vitro Activity of Ceftazidime-Avibactam Alone and in Combination with Amikacin Against Colistin-Resistant Gram-Negative Pathogens", Microbial Drug Resistance, vol. 27, No. 3, Mar. 2020, pp. 401-409.
Chen et al., "Synergistic Activity and Biofilm Formation Effect of Colistin Combined with PFK-158 Against Colistin-Resistant Gram-Negative Bacteria", Infection and Drug Resistance, vol. 14, Jun. 9, 2021, pp. 2143-2154.
Chew et al., "Colistin and Polymyxin B Susceptibility Testing for Carbapenem-Resistant and Mcr-Positive Enterobacteriacea: Comparison of Sensititre, MicroScan, Vitek 2, and Etest with Broth Microdilution", Journal of Clinical Microbiology, vol. 55, No. 9, Sep. 2017, pp. 2609-2616.
Clifton et al., "Effect of Divalent Cation Removal on the Structure of Gram-Negative Bacterial Outer Membrane Models", Langmuir, vol. 31, No. 1, 2015, pp. 404-412.
Codjoe et al., "Carbapenem Resistance: A Review", Medical Sciences (Basel), vol. 6, No. 1, Dec. 21, 2017, pp. 1-28.
Corbett et al., "Potentiation of Antibiotic Activity by a Novel Cationic Peptide: Potency and Spectrum of Activity of SPR741", Antimicrobial Agents and Chemotherapy, vol. 61, No. 8, Aug. 2017, pp. 1-10.
Cox et al., "A Common Platform for Antibiotic Dereplication and Adjuvant Discovery", Cell Chemical Biology, vol. 24, No. 1, Jan. 19, 2017, pp. 98-109.
Cui et al., "Synthesis and Bioactivity Investigation of the Individual Components of Cyclic Lipopeptide Antibiotics", Journal of Medicinal Chemistry, vol. 61, No. 5, Mar. 8, 2018, pp. 1845-1857.
Davies et al., "Annual Report of the Chief Medical Officer: Infection and the Rise of Antimicrobial Resistance", Lancet, vol. 381, No. 9878, May 11, 2013, pp. 1606-1609.
De Breij et al., "The Antimicrobial Peptide SAAP-148 Combats Drug-Resistant Bacteria and Biofilms", Science Translational Medicine, vol. 10, Jan. 10, 2018, pp. 1-14.
De La Cruz et al., "Click, Release, and Fluoresce: A Chemical Strategy for a Cascade Prodrug System for Codelivery of Carbon Monoxide, a Drug Payload, and a Fluorescent Reporter", Organic Letters, vol. 20, No. 4, Feb. 16, 2018, pp. 897-900.
Dominguez-Medina et al., "Outer Membrane Protein Size and LPS O-antigen Define Protective Antibody Targeting to the *Salmonella* Surface", Nature Communications, vol. 11, No. 851, 2020, pp. 1-11.
Douafer et al., "Antibiotic Adjuvants: Make Antibiotics Great Again!", Journal of Medicinal Chemistry, vol. 62, No. 19, Oct. 10, 2019, pp. 8665-8681.
Fidai et al., "Interaction of Cationic Peptides with Bacterial Membranes", Methods in Molecular Biology, vol. 78, 1997, pp. 187-204.
Fischer et al., "In Vitro Cytotoxicity Testing of Polycations: Influence of Polymer Structure on Cell Viability and Hemolysis", Biomaterials, vol. 24, No. 7, Mar. 2003, pp. 1121-1131.
Garcia-Fernandez et al., "Membrane Microdomain Disassembly Inhibits MRSA Antibiotic Resistance", Cell, vol. 171, No. 6, Nov. 30, 2017, pp. 1354-1367.
Garcia-Quintanilla et al., "Inhibition of LpxC Increases Antibiotic Susceptibility in Acinetobacter Baumannii", Antimicrobial Agents and Chemotherapy, vol. 60, No. 8, Jul. 22, 2016, pp. 5076-5079.
Geratz et al., "Novel Bis(Benzamidino) Compounds With an Aromatic Central Link. Inhibitors of Thrombin, Pancreatic Kallikrein, Trypsin, and Complement", Journal of Medicinal Chemistry, vol. 19, No. 5, May 1, 1976, pp. 634-639.
Giordani et al., "Green Fluorescent Diamidine as Diagnostic Probes for Trypanosomes", Antimicrobial Agents and Chemotherapy, vol. 58, No. 3, Mar. 2014, pp. 1793-1796.
Gonzalez et al., "Synthesis and Antiparasitic Evaluation of bis-2,5-[4-guanidinophenyl]thiophenes", European Journal of Medicinal Chemistry, vol. 42, Apr. 2007, pp. 552-557.

(56) References Cited

OTHER PUBLICATIONS

Gorityala et al., "Adjuvants Based on Hybrid Antibiotics Overcome Resistance in Pseudomonas Aeruginosa and Enhance Fluoroquinolone Efficacy", Angewandte Chemie, vol. 55, No. 2, Jan. 11, 2016, pp. 555-559.
Guo et al., "Compound Shape Effects in Minor Groove Binding Affinity and Specificity for Mixed Sequence DNA", Journal of the American Chemical Society, vol. 140, No. 44, Nov. 7, 2018, pp. 14761-14769.
Haisma et al., "Antimicrobial Peptide P60.4Ac-Containing Creams and Gel for Eradication of Methicillin-Resistant *Staphylococcus aureus* from Cultured Skin and Airway Epithelial Surfaces", Antimicrobial Agents and Chemotherapy, vol. 60, No. 7, Jun. 20, 2016, pp. 4063-4072.
Hall et al., "The Fractional Inhibitory Concentration (FIC) Index as a Measure of Synergy", Journal of Antimicrobial Chemotherapy, vol. 11, No. 5, May 1983, pp. 427-433.
Han et al., "Factors that Impact the Developability of Drug Candidates", Drug Delivery: Principles and Applications, 2nd edition, Mar. 25, 2016, pp. 1-19.
Hancock et al., "Compounds Which Increase the Permeability of the Pseudomonas Aeruginosa Outer Membrane", Antimicrobial Agents and Chemotherapy, vol. 26, No. 1, Jul. 1984, pp. 48-52.
Haque et al., "Developments in Strategies for Quorum Sensing Virulence Factor Inhibition to Combat Bacterial Drug Resistance", Microbial Pathogenesis, vol. 121, Aug. 2018, pp. 293-302.
Hart et al., "A Small-Molecule Inhibitor of BamA Impervious to Efflux and the Outer Membrane Permeability Barrier", Proceedings of the National Academy of Sciences, vol. 116, No. 43, Oct. 7, 2019, pp. 1-10.
Heesterbeek et al., "Outer Membrane Permeabilization by the Membrane Attack Complex Sensitizes Gram-Negative Bacteria to Antimicrobial Proteins in Serum and Phagocytes", PLoS Pathogens, vol. 17, No. 1, Jan. 22, 2021, pp. 1-22.
Holmes et al., "Understanding the Mechanisms and Drivers of Antimicrobial Resistance", Lancet, vol. 387, No. 10014, Jan. 9, 2016, pp. 176-187.
Hopkins et al., "Long-Time-Step Molecular Dynamics through Hydrogen Mass Repartitioning", Journal of Chemical Theory and Computation, vol. 11, No. 4, Apr. 14, 2015, pp. 1864-1874.
Hopper et al., "Role of Carbon Monoxide in Host-Gut Microbiome Communication", Chemical Reviews, vol. 120, No. 24, Dec. 23, 2020, pp. 13273-13311.
Idowu et al., "Homodimeric Tobramycin Adjuvant Repurposes Novobiocin as an Effective Antibacterial Agent Against Gram-Negative Bacteria", Journal of Medicinal Chemistry, vol. 62, No. 20, Oct. 24, 2019, pp. 9103-9115.
Imai et al., "A New Antibiotic Selectively Kills Gram-Negative Pathogens", Nature, vol. 576, No. 7787, Dec. 2019, pp. 459-464.
Ismail et al., "An efficient synthesis of 2,5'-diarylbichalcophenes", Tetrahedron Letters, vol. 47, 2006, pp. 795-797.
Jahnen-Dechent et al., "Magnesium Basics", Clinical Kidney Journal, vol. 5, No. 1, Feb. 1, 2012, pp. i3-i14.
Jo et al., "CHARMM-GUI: A Web-Based Graphical User Interface for CHARMM", Journal of Computational Chemistry, vol. 29, No. 11, Aug. 2008, pp. 1859-1865.
Karo-Atar et al., "Helminth-Mediated Disease Tolerance in TB: A Role for Microbiota?", PLoS Pathogens, vol. 17, No. 7, Jul. 15, 2021, 6 pages.
Kim et al., "Pyrazole-Thiazole Core-Containing Analogs Exhibit Adjunctive Activity with Meropenem against Carbapenem-Resistant Enterobacteriaceae (CRE)", ChemMedChem, vol. 16, No. 18, Sep. 16, 2021, pp. 2775-2780.
King et al., "Aspergillomarasmine A Overcomes Metallo-β-Lactamase Antibiotic Resistance", Nature, vol. 510, No. 7506, Jun. 26, 2014, pp. 503-506.
Klauda et al., "Update of the Charmm All-Atom Additive Force Field for Lipids: Validation on Six Lipid Types", The Journal of Physical Chemistry B, vol. 114, No. 23, Jun. 17, 2010, pp. 7830-7843.
Koebnik et al., "Structure and Function of Bacterial Outer Membrane Proteins: Barrels in a Nutshell", Molecular Microbiology, vol. 37, No. 2, Jul. 2000, pp. 239-253.
Konai et al., "Lysine-Based Small Molecule Sensitizes Rifampicin and Tetracycline Against Multidrug-Resistant Acinetobacter Baumannii and Pseudomonas Aeruginosa", ACS Infectious Diseases, vol. 6, No. 1, 2020, pp. 91-99.
Laxminarayan et al., "Achieving Global Targets for Antimicrobial Resistance", Science, vol. 353, No. 6302, Aug. 26, 2016, pp. 874-875.
Li et al., "The Challenge of Efflux-Mediated Antibiotic Resistance in Gram-Negative Bacteria", Clinical Microbiology Reviews, vol. 28, No. 2, Apr. 2015, pp. 337-418.
Liu et al., "Emergence of Plasmid-Mediated Colistin Resistance Mechanism MCR-1 in Animals and Human Beings in China: A Microbiological and Molecular Biological Study", The Lancet Infectious Diseases, vol. 16, No. 2, Feb. 2016, pp. 1-8.
Liu et al., "Metformin Restores Tetracyclines Susceptibility Against Multidrug Resistant Bacteria", Advanced Science, vol. 7, No. 12, May 12, 2020, pp. 1-13.
Lyu et al., "One-Pot, Two-Step Synthesis and Photophysical Properties of 2-(5-Phenylindol-3-Yl)Benzimidazole Derivatives", RSC Advances, vol. 7, Oct. 23, 2017, pp. 49374-49385.
Macnair et al., "Creative Targeting of the Gram-Negative Outer Membrane in Antibiotic Discovery", Annals of the New York Academy of Sciences, vol. 1459, No. 1, Jan. 2020, pp. 69-85.
Macnair et al., "Overcoming mcr-1 Mediated Colistin Resistance with Colistin in Combination with Other Antibiotics", Nature Communications, vol. 9, No. 1, Jan. 2018, pp. 1-8.
Martin et al., "Small Molecule Potentiation of Gram-Positive Selective Antibiotics Against Acinetobacter Baumannii", ACS Infectious Diseases, vol. 5, No. 7, Jul. 12, 2019, pp. 1223-1230.
Martin II et al., "A Dual-Mechanism Antibiotic Kills Gram-Negative Bacteria and Avoids Drug Resistance", Cell, vol. 181, No. 7, Jun. 25, 2020, pp. 1518-1532.e14.
Martynowycz et al., "*Salmonella* Membrane Structural Remodeling Increases Resistance to Antimicrobial Peptide LL-37", ACS Infectious Diseases, vol. 5, No. 7, Jul. 12, 2019, pp. 1214-1222.
Mattingly et al., "Screening an Established Natural Product Library Identifies Secondary Metabolites That Potentiate Conventional Antibiotics", ACS Infectious Diseases, vol. 6, No. 10, Oct. 9, 2020, pp. 2629-2640.
May et al., "The Bacterial Outer Membrane is an Evolving Antibiotic Barrier", Proceedings of the National Academy of Sciences, vol. 115, No. 36, Sep. 4, 2018, pp. 8852-8854.
Mayne et al., "Rapid Parameterization of Small Molecules Using the Force Field Toolkit", Journal of Computational Chemistry, vol. 34, No. 32, Dec. 15, 2013, pp. 2757-2770.
Moellering , "NDM-1—A Cause for Worldwide Concern", The New England Journal of Medicine, vol. 363, No. 25, Dec. 16, 2010, pp. 2377-2379.
Moison et al., "A Fluorescent Probe Distinguishes Between Inhibition of Early and Late Steps of Lipopolysaccharide Biogenesis in Whole Cells", ACS Chemical Biology, vol. 12, No. 4, Apr. 21, 2017, pp. 1-9.
Muheim et al., "Increasing the Permeability of *Escherichia coli* Using MAC13243", Scientific Reports, vol. 7, No. 1, Dec. 2017, pp. 1-11.
Munde et al., "Structure-dependent Inhibition of the ETS-family Transcription Factor PU.1 by Novel Heterocyclic Diamidines", Nucleic Acids Research, vol. 42, 2014, pp. 1379-1390.
Munde et al., "The Unusual Monomer Recognition of Guanine-Containing Mixed Sequence DNA by a Dithiophene Heterocyclic Diamidine", Biochemistry, vol. 53, 2014, pp. 1218-1227.
Namivandi-Zangeneh et al., "Synergy between Synthetic Antimicrobial Polymer and Antibiotics: A Promising Platform To Combat Multidrug-Resistant Bacteria", ACS Infectious Diseases, vol. 5, No. 8, Aug. 9, 2019, pp. 1357-1365.
Nguyen et al., "In Vitro Synergistic Activity of NCL195 in Combination with Colistin Against Gram-Negative Bacterial Pathogens", International Journal of Antimicrobial Agents, vol. 57, No. 5, May 2021, 13 pages.

(56) References Cited

OTHER PUBLICATIONS

Ni et al., "Inhibitors and Antagonists of Bacterial Quorum Sensing", Medicinal Research Reviews, vol. 29, No. 1, Jan. 2009, pp. 65-124.
Schieber et al., "Disease Tolerance Mediated by Microbiome *E. coli* Involves Inflammasome and IGF-1 Signaling", Science, vol. 350, No. 6260, Oct. 30, 2015, pp. 558-563.
Papisov , "Acyclic Polyacetals from Polysaccharides: Biomimetic Biomedical "Stealth" Polymers", American Chemical Society Symposium Series, vol. 786, Feb. 2001, pp. 301-314.
Parrish et al., "Structure-Activity Relationships for the Inhibition of Acrosin by Benzamidine Derivatives", Journal of Medicinal Chemistry, vol. 21, No. 11, Nov. 1978, pp. 1132-1136.
Patrick et al., "Synthesis and Antiprotozoal Activities of Dicationic Bis(Phenoxymethyl)Benzenes, Bis(Phenoxymethyl)Naphthalenes, and Bis(Benzyoxy)Naphthalenes", European Journal of Medicinal Chemistry, vol. 44, No. 9, Sep. 2009, pp. 3543-3551.
Paul et al., "A New Generation of Minor-Groove-Binding-Heterocyclic Diamidines That Recognize G•C Base Pairs in an AT Sequence Context", Molecules, vol. 24, No. 5, Mar. 7, 2019, 22 pages.
Pavlova et al., "Living on the Edge: Simulations of Bacterial Outer-Membrane Proteins", Biochimica et Biophysica Acta, vol. 1858, No. 7, Jul. 2016, pp. 1753-1759.
PCT/US2020/066036 , "International Preliminary Report on Patentability", Jun. 30, 2022, 10 pages.
PCT/US2020/066036 , "International Search Report and Written Opinion", Apr. 6, 2021, 15 pages.
PCT/US2020/066036 , "Invitation to Pay Additional Fees and, Where Applicable, Protest Fee", Feb. 8, 2021, 3 pages.
Phillips et al., "Scalable Molecular Dynamics with NAMD", Journal of Computational Chemistry, vol. 26, No. 16, Dec. 2005, pp. 1781-1802.
Piewngam et al., "Alternative Approaches to Treat Bacterial Infections: Targeting Quorum-Sensing", Expert Review of Anti-Infective Therapy, vol. 18, No. 6, Jun. 2020, pp. 499-510.
Rabanal et al., "Recent Advances and Perspectives in the Design and Development of Polymyxins", Natural Product Reports, vol. 34, No. 7, Jul. 6, 2017, pp. 886-908.
Relman et al., "Microbiome as a Tool and a Target in the Effort to Address Antimicrobial Resistance", Proceedings of the National Academy of Sciences of the United States of America, vol. 115, No. 51, Dec. 18, 2018, pp. 12902-12910.
Rice , "Progress and Challenges in Implementing the Research on ESKAPE Pathogens", Infection Control & Hospital Epidemiology, vol. 31, No. 1, Nov. 2010, pp. S7-S10.
Ruiz et al., "Chemical Conditionality: A Genetic Strategy to Probe Organelle Assembly", Cell, vol. 121, No. 2, Apr. 22, 2005, pp. 307-317.
Rutherford et al., "Bacterial Quorum Sensing: Its Role in Virulence and Possibilities for Its Control", Cold Spring Harbor Perspectives in Medicine, vol. 2, No. 11, Nov. 1, 2012, pp. 1-25.
Sands et al., "Pentamidine: A Review", Reviews of Infectious Diseases, vol. 7, No. 5, Sep.-Oct. 1985, pp. 625-634.
Savage et al., "Antibacterial Properties of Cationic Steroid Antibiotics", FEMS Microbiology Letters, vol. 217, No. 1, Nov. 19, 2002, pp. 1-7.
Savage , "Multidrug-Resistant Bacteria: Overcoming Antibiotic Permeability Barriers of Gram-Negative Bacteria", Annals of Medicine, vol. 33, No. 3, Apr. 2001, pp. 167-171.
Schmalstig et al., "Noncatalytic Antioxidant Role for Helicobacter Pylori Urease", Journal of Bacteriology, vol. 200, No. 17, Sep. 2018, pp. 1-11.
Si et al., "Antimicrobial Effect of a Novel Chitosan Derivative and its Synergistic Effect with Antibiotics", ACS Applied Materials & Interfaces, vol. 13, No. 2, Jan. 6, 2021, pp. 3237-3245.
Sieber et al., "On the Evolutionary Origins of Host-Microbe Associations", Proceedings of the National Academy of Sciences of the United States of America, vol. 118, No. 9, Mar. 2, 2021, 8 pages.
Silhavy et al., "The Bacterial Cell Envelope", Cold Spring Harbor Perspectives in Biology, vol. 2, No. 5, May 2010, pp. 1-16.
Skaar et al., "Editorial Overview: Microbe-Microbe Interactions: The Enemy of My Enemy is My Friend", Current Opinion in Microbiology, vol. 53, Feb. 2020, pp. iii-v.
Smith et al., "Optimized Arylomycins are a New Class of Gram-Negative Antibiotics", Nature, vol. 561, Sep. 13, 2018, pp. 189-194.
Soeiro et al., "Novel Amidines and Analogues as Promising Agents Against Intracellular Parasites: A Systematic Review", Parasitology, vol. 140, No. 8, Jul. 2013, pp. 929-951.
Song et al., "A Broad-Spectrum Antibiotic Adjuvant Reverses Multidrug-Resistant Gram-Negative Pathogens", Nature Microbiology, vol. 5, No. 8, Aug. 2020, pp. 1040-1050.
Steimle et al., "Structure and function: Lipid A Modifications in Commensals and Pathogens", International Journal of Medical Microbiology, vol. 306, No. 5, Aug. 2016, pp. 290-301.
Stephens et al., "Diguanidino and "Reversed" Diamidino 2,5-Diarylfurans as Antimicrobial Agents", Journal of Medicinal Chemistry, vol. 44, Apr. 28, 2001, pp. 1741-1748.
Stoesser et al., "Colistin Resistance Gene mcr-1 and pHNSHP45 Plasmid in Human Isolates of *Escherichia coli* and Klebsiella Pneumoniae", The Lancet Infectious Diseases, vol. 16, No. 3, Mar. 2016, pp. 285-286.
Stokes et al., "Pentamidine Sensitizes Gram-Negative Pathogens to Antibiotics and Overcomes Acquired Colistin Resistance", Nature Microbiology, vol. 2, No. 5, Mar. 6, 2017, 21 pages.
Sun et al., "Resensitizing Carbapenem- and Colistin-Resistant Bacteria to Antibiotics Using Auranofin", Nature Communications, vol. 11, No. 1, Oct. 16, 2020, pp. 1-13.
Tantisuwanno et al., "Synergism between Rifampicin and Cationic Polyurethanes Overcomes Intrinsic Resistance of *Escherichia coli*", Biomacromolecules, vol. 22, No. 7, Jun. 4, 2021, pp. 2910-2920.
Tsubery et al., "Structure-Function Studies of Polymyxin B Nonapeptide: Implications to Sensitization of Gram-Negative Bacteria", Journal of Medicinal Chemistry, vol. 43, No. 16, Aug. 10, 2000, pp. 3085-3092.
Tyle , "Iontophoretic devices for drug delivery", Pharmaceutical Research, vol. 3, No. 6, Dec. 1986, pp. 318-326.
Vaara , "Agents that Increase the Permeability of the Outer Membrane", Microbiological Reviews, vol. 56, No. 3, Sep. 1992, pp. 395-411.
Vaara , "New Polymyxin Derivatives That Display Improved Efficacy in Animal Infection Models as Compared to Polymyxin B and Colistin", Medicinal Research Reviews, vol. 38, No. 5, Sep. 2018, pp. 1661-1673.
Vaara , "Polymyxin Derivatives that Sensitize Gram-Negative Bacteria to Other Antibiotics", Molecules, vol. 24, No. 2, Jan. 11, 2019, pp. 1-15.
Van Meer et al., "Membrane Lipids: Where They are and How They Behave", Nature Reviews Molecular Cell Biology, vol. 9, No. 2, Feb. 2008, pp. 112-124.
Vanommeslaeghe et al., "Automation of the CHARMM General Force Field (CGenFF) I: Bond Perception and Atom Typing", Journal of Chemical Information and Modeling, vol. 52, No. 12, Dec. 21, 2012, pp. 3144-3154.
Vanommeslaeghe et al., "Automation of the CHARMM General Force Field (CGenFF) II: Assignment of Bonded Parameters and Partial Atomic Charges", Journal of Chemical Information and Modeling, vol. 52, No. 12, Nov. 2012, pp. 3155-3168.
Ventola , "The Antibiotic Resistance Crisis: Part 1: Causes and Threats", Pharmacology & Therapeutics, vol. 40, No. 4, Apr. 2015, pp. 277-283.
Wang et al., "Evaluation of the Influence of Compound Structure on Stacked-Dimer Formation in the DNA Minor Groove", Biochemistry, vol. 40, No. 8, Mar. 2001, pp. 2511-2521.
Wang et al., "Prevalence, Risk Factors, Outcomes, and Molecular Epidemiology of MCR-1-positive Enterobacteriaceae in Patients and Healthy Adults From China: an Epidemiological and Clinical Study", The Lancet Infectious Diseases, vol. 17, No. 4, Apr. 2017, pp. 390-399.
Wesseling et al., "Structure-Activity Studies with Bis-Amidines That Potentiate Gram-Positive Specific Antibiotics Against Gram-Negative Pathogens", ACS Infectious Diseases, vol. 7, No. 12, Dec. 10, 2021, pp. 3314-3335.

(56) References Cited

OTHER PUBLICATIONS

Wouters et al., "Estimated Research and Development Investment Needed to Bring a New Medicine to Market, 2009-2018", JAMA, vol. 323, No. 9, Mar. 3, 2020, pp. 844-853.
Wu et al., "CHARMM-GUI Membrane Builder Toward Realistic Biological Membrane Simulations", Journal of Computational Chemistry, vol. 35, No. 27, Oct. 15, 2014, pp. 1997-2004.
Yorke , "Recent Work on the Chemotherapy of Protozoal Infections", Transactions of The Royal Society of Tropical Medicine and Hygiene, vol. 33, No. 5, Mar. 20, 1940, pp. 463-476.
Yu et al., "Restoring and Enhancing the Potency of Existing Antibiotics Against Drug-resistant Gram-negative Bacteria Through the Development of Potent Small-molecule Adjuvants", Department of Chemistry and Center for Diagnostics and Therapeutics, 32 pages.
Zhang et al., "Equisetin Restores Colistin Sensitivity against Multi-Drug Resistant Gram-Negative Bacteria", Antibiotics, vol. 10, No. 10, Oct. 18, 2021, pp. 1-12.
Zhivkova et al., "Studies on Drug-human Serum Albumin Binding: The Current State of the Matter", Current Pharmaceutical Design, vol. 21, No. 14, 2015, pp. 1817-1830.
Zhu et al., "Precision Editing of the Gut Microbiota Ameliorates Colitis", Nature, Letter, vol. 553, Jan. 11, 2018, pp. 208-211.
Zimmerman et al., "A Whole-Cell Screen Identifies Small Bioactives That Synergize with Polymyxin and Exhibit Antimicrobial Activities Against Multidrug-Resistant Bacteria", Antimicrobial Agents and Chemotherapy, vol. 64, No. 3, Feb. 21, 2020, pp. 1-18.
EP20903547.6, "Extended European Search Report", Feb. 14, 2024, 13 pages.
EP20903547.6, "Partial Supplementary European Search Report", Nov. 24, 2023, 12 pages.
CN202080088030.6, "Office Action", Aug. 12, 2024, 10 pages.
CN202080088030.6, "Office Action", Mar. 18, 2024, 17 pages.
Wang et al., "Design and Synthesis of 2-(5-Phenylindol-3-yl)benzimidazole Derivatives with Antiproliferative Effects towards Triple-Negative Breast Cancer Cells by Activation of ROS-Mediated Mitochondria Dysfunction", Chemistry: An Asian Journal, vol. 14, No. 15, Aug. 31, 2019, pp. 2648-2655.
Application No. EP20903547.6 , Office Action, Mailed On Aug. 19, 2025, 4 pages.
EP25187316.2 , "Partial European Search Report", Oct. 1, 2025, 15 pages.
"RN67833-99-2 Registry Database Compound", Nov. 16, 1984, 3 pages.
U.S. Appl. No. 17/251,658 , Final Office Action, Mailed On Dec. 20, 2024, 5 pages.
U.S. Appl. No. 17/251,658 , Non-Final Office Action, Mailed On Jul. 25, 2025, 5 pages.
U.S. Appl. No. 17/251,658 , Non-Final Office Action, Mailed On Jun. 12, 2024, 6 pages.
U.S. Appl. No. 17/251,658 , Notice of Allowance, Mailed On Dec. 8, 2025, 8 pages.
Chauhan et al., "Antiparasitic Agents Part VI. Synthesis Of 1 2-1 3 And 1 4 Bis(4-Substituted-Aryloxy) Benzenes and their Biological Activities", Indian Journal of Chemistry, Council of Scientific and Industrial Research (CSIR), vol. 27, No. 1, Jan. 1, 1988, pp. 38-42.
Application No. CN201980053282.2 , Office Action, Mailed On Feb. 29, 2024, 14 pages.
Application No. CN201980053282.2 , Office Action, Mailed On Mar. 22, 2023, 25 pages.
Application No. CN201980053282.2 , Office Action, Mailed On Oct. 18, 2023, 8 pages.
Application No. EP19819942.4 , Extended European Search Report, Mailed On Jun. 20, 2022, 12 pages.
EP19819942.4 , "Partial Supplementary European Search Report", Mar. 16, 2022, 12 pages.
Application No. EP25187316.2 , Extended European Search Report, Mailed On Dec. 22, 2025, 12 pages.
Liang et al., "Human Kallikrein 6 Inhibitors With a Para-amidobenzylamine P1 Group Identified Through Virtual Screening", 2012:323481 Caplus, 2012, 2 pages.
Munde et al., "DNA Minor Groove Induced Dimerization of Heterocyclic Cations: Compound Structure, Binding Affinity, and Specificity for a TTAA Site", Journal of Molecular Biology, vol. 402, No. 5, Oct. 8, 2010, pp. 847-864.
Application No. PCT/US2019/037065 , International Preliminary Report on Patentability, Mailed On Dec. 24, 2020, 8 pages.
Application No. PCT/US2019/037065 , International Search Report and Written Opinion, Mailed On Oct. 18, 2019, 11 pages.

* cited by examiner

MD-124

COMPOUNDS FOR THE TREATMENT OF BACTERIAL INFECTIONS AND POTENTIATION OF ANTIBIOTICS

CROSS REFERENCE TO PRIORITY APPLICATION

This application claims priority to U.S. Provisional Application No. 62/950,852, filed Dec. 19, 2019, which is incorporated by reference herein in its entirety.

FIELD OF THE INVENTION

The invention provides compounds for use in the treatment of medical disorders caused by bacteria or for use as a potentiator of an antibiotic in the treatment of medical disorders caused by bacteria.

BACKGROUND OF THE INVENTION

Despite the overall success of antibiotics in diminishing the effects of infectious disease in the modern world, their ease of access has led to overuse, resulting in the development of bacterial resistance. Antibiotic resistance is on the rise globally, leading the World Health Organization to classify antibiotic resistance as a "serious threat [that] is no longer a prediction for the future" ("Antimicrobial resistance: global report on surveillance 2014" The World Health Organization, April 2014). Antibiotic resistance is linked to inappropriate prescribing of antibiotics, incorrect dosing, and missing doses. In the United States, approximately 2.8 million people become infected with antibiotic resistant bacteria each year and roughly 35,000 die as a result ("Antibiotic/Antimicrobial Resistance (AR/AMR)" Centers for Disease Control and Prevention, https://www.cdc.gov/drugresistance/). Some bacteria harbor a natural resistance to certain types of antibiotics, while others may gain resistance by genetic mutation or horizontal gene transfer from already-resistant species. Bacteria diminish the effectiveness of antibiotics by modifying or inactivating the drug, altering the target or binding site, altering the metabolic pathways that propagate the drug's effects, or reducing accumulation of the drug within the cell by decreasing drug permeability or increasing efflux. Certain bacteria, colloquially known as "superbugs", may eventually develop resistance to multiple types of antibiotics, requiring alternative medications at higher doses, often with higher cost and greater toxicity.

Several preventative measures have been proposed to slow bacterial resistance to currently available antibiotics. Proper antibiotic stewardship along with increased hygiene provides significant strides in preventing future resistance. Despite this, new therapeutics are necessary to treat infections caused by currently resistant bacterial strains. The period from the 1950s until the 1970s represented the peak of antibiotic discovery, but since that time no new classes of antibiotics have been discovered, and development of new antibiotics within existing classes has been low. Alternative strategies, such as the development of bacterial vaccines and phage therapy, have not seen the success necessary to become widely used.

Investigators in the 1920s discovered that an anti-diabetic drug, Synthalin, had therapeutic activity against *Trypanosoma brucei* infections in mice. Out of a series of subsequently developed analogs, pentamidine was found to be curative of murine *T. rhodesiense* infections (Yorke W. "Recent work on the chemotherapy of protozoal infections", Trans. R., Soc. Trop. Med. Hyg. 1940, 33:463). It was not until the 1960s that pentamidine became available on a restricted basis for use in the treatment of protozoal infections, and only in the 1980s did it see more extensive use as a treatment of pnuemocystis pneumonia in immunocompromised individuals such as HIV patients (Sands et al. "Pentamidine: A Review", Reviews of Infectious Diseases 1985, 7(5):625-634). In recent years, pentamidine has received renewed interest as a possible therapeutic in the treatment of infections by antibiotic resistant bacteria. For example, pentamidine has been demonstrated to sensitize resistant bacteria to colistin, one of the antibiotics of last resort (Stokes et al. "Pentamidine sensitizes Gram-negative pathogens to antibiotics and overcomes acquired colistin resistance", Nat. Microbiol. 2017, 2:17028; Bean et al. "Pentamidine: a drug to consider re-purposing in the targeted treatment of multi-drug resistant bacterial infections?" J. Lab. Precis. Med. 2017, 2:49).

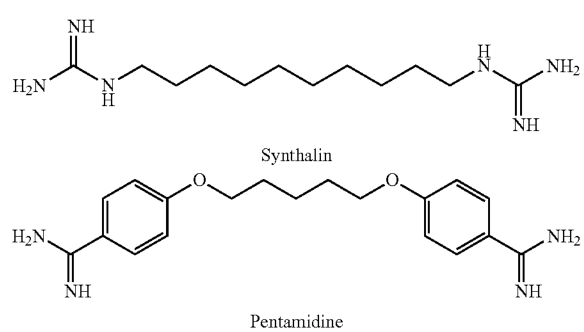

Synthalin

Pentamidine

The use of amidine compounds for biological applications is described in Geratz et al. "Novel Bis(benzamidino) Compounds with an Aromatic Central Link. Inhibitors of Thrombin, Pancreatic Kallikrein, Trypsin, and Complement" *J. Med. Chem.* 1976, 19(5):634; Parrish et al. "Structure-Activity Relationships for the Inhibition of Acrosin by Benzamidine Derivatives" *J. Med. Chem.* 1978, 21(11)1132; Patrick et al. "Synthesis and antiprotozoal activities of dicationic bis(phenoxymethyl)benzenes, bis(phenoxymethyl)naphthalenes, and bis(benzyoxy)naphthalenes" *Eur. J. Med. Chem.* 2009, 44:3543; Giordani et al. "Green Fluorescent Diamidine as Diagnostic Probes for Trypanosomes" Antimicrobial Agents and Chemotherapy 2014, 58:1793; Munde et al. "The Unusual Monomer Recognition of Guanine-Containing Mixed Sequence DNA by a Dithiophene Heterocyclic Diamidine" *Biochemistry* 2014, 53:1218; Arafa et al. "Novel linear triaryl guanidines, N-substituted guanidines and potential prodrugs as antiprotozoal agents" *European Journal of Medicinal Chemistry,* 2008, 43:2901; Stephens et al. "Diguanidino and "Reversed" Diamidino 2,5-Diarylfurans as Antimicrobial Agents" *J. Med. Chem,* 2001, 44:1741; Munde et al. "Structure-dependent inhibition of the ETS-family transcription factor PU.1 by novel heterocyclic diamidines" Nucleic Acids Research, 2014, 42: 1379; Gonzalez, et al. "Synthesis and antiparasitic evaluation of bis-2,5-[4-guanidinophenyl]thiophenes" *Eur J Med Chem,* 2007, 42: 552; and Wang et al. "Evaluation of the Influence of Compound Structure on Stacked-Dimer Formation in the DNA Minor Groove" *Biochemistry,* 2001, 40, 2511.

University of North Carolina describes the use of amidine compounds to inhibit RSV-induced cell fusion in U.S. Pat. No. 4,619,942 titled "Inhibition of Respiratory Syncytial Virus-Induced Cell Fusion by Amidino Compounds".

Eisai Co., Ltd. describes the use of amidine compounds as antifungal, antibacterial, and anti-trichomonal therapeutics in "U.S. Pat. No. 4,034,010 titled "Bis-(Meta-Amidinophenoxy)-Compounds and Pharmacologically Acceptable Acid Addition Salts Thereof".

Berlex Laboratories describes the use of amidine compounds as anticoagulants in International Patent Application Publication Nos. WO96/28427 titled "Benzamidine Derivatives Their Preparation and Their Use as Anti-Coagulants"; WO97/29067 titled "Benzamidine Derivatives Substituted by Amino Acid and Hydroxy Acid Derivatives and Their Use as Anti-Coagulants"; and WO00/31068 titled "Polyhydroxylated Heterocyclic Derivatives as Anticoagulants".

Georgia State University Research Foundation, Inc. and the University of North Carolina jointly disclosed the use of amidine compounds in amyloidosis and the treatment of microbial infections in International Patent Application Publication Nos. WO2003/103598 titled "Amidine Derivatives for Treating Amyloidosis" and WO2005/033065 titled "Novel Amidine Compounds for Treating Microbial Infections". The use of compounds for the treatment of microbial infections, including protozoa are disclosed in WO 2005/086808 and WO 2005/040132. Bichalcophenes as antiprotozoal agents are also described in US 2006/0293540 assigned to the University of North Carolina and the Georgia State University Research Foundation, Inc.

Georgia State University Research Foundation and the Albert Einstein College of Medicine, Inc. disclosed the use of amidine and diamidine compounds for the inhibition of PU.1 and for the treatment of disorders associated with abnormal PU.1 levels in WO 2017/223260.

Georgia State University Research Foundation and the Ohio State Innovation Foundation disclosed the use of amidine compounds for the treatment of fungal infections in WO 2018/045106 and compounds for the treatment of parasites in WO 2018/045104.

Georgia State University Research Foundation, Inc. has also disclosed the use of amidine compounds as DNA-targeting agents in US 2010/0249175 and compounds for the use of protozoa in WO 2009/051796 and WO 2005/086754.

Neurochem, Inc. describes the use of amidine compounds in the treatment of amyloidosis in International Patent Application Publication No. WO03/017994 titled "Amidine Derivatives for Treating Amyloidosis".

Altana Pharma AG describes compounds including amidine derivatives for use as tryptase inhibitors in U.S. Pat. No. 9,960,588 titled "Tryptase Inhibitors".

Mpex Pharmaceuticals describes the use of amidine compounds as bacterial efflux inhibitors in International Patent Application Publication No. WO2005/089738 title "Use and Administration of Bacterial Efflux Inhibitors". Bostian et al. also describe a similar use of amidine compounds as bacterial efflux inhibitors in the treatment of ophthalmic and otic infections in U.S. Patent Application Publication No. US2008/0132457 titled "Bacterial Efflux Inhibitors for the Treatment of Ophthalmic and Otic Infections".

The University of Cincinnati describes the use of amidine compounds for the treatment of pneumonia in International Patent Application Publication No. WO2006/021833 titled "Bisbenzamidines for the Treatment of Pneumonia". Xavier University of Louisiana describes the use of amidine compounds for the treatment of trypanosomiasis in International Patent Application Publication No. WO2008/090831 titled "Bisbenzamidines and Bisbenzamidoximes for the Treatment of Human African Trypanosomiasis".

The University of Oregon describes the use of pentamidine and related compounds in the treatment of myotonic dystrophy in International Patent Application Publication No. WO2009/105691 titled "Use of Pentamidine and Related Compounds".

Orion Corporation describes the use of amidine compounds as protease inhibitors in Intemationla Patent Application Publication No. WO2010/133748 titled "Protease Inhibitors".

There remains a need for the development of novel therapeutics and pharmaceutical compositions and their use for the treatment of bacterial infections, including therapeutics that potentiate the effect of antibiotics on bacterial strains, including bacterial strains resistant to certain antibiotics.

SUMMARY OF THE INVENTION

The present invention provides compounds and methods for the treatment of bacterial infections as well as for the potentiation of the therapeutic effect of antibiotics in the treatment of bacterial infections that comprise administering an effective amount of a compound described herein or its pharmaceutically acceptable salt, optionally in a pharmaceutically acceptable carrier. The bacterial infection may be caused by gram-positive bacteria, gram-negative bacteria, and/or antibiotic resistant bacteria. In one embodiment, the bacterial infection is caused by mycobacteria.

In one aspect, the invention is a compound of Formula I or a pharmaceutically acceptable salt thereof:

(I)

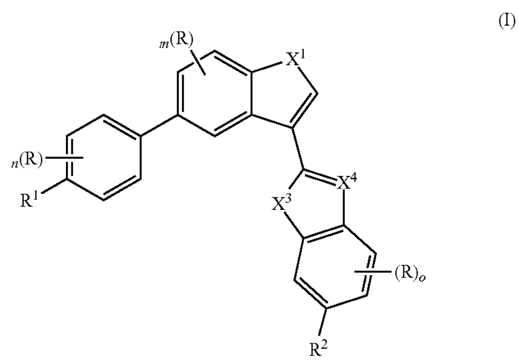

wherein:

m and o are independently selected from 0, 1, 2, or 3;

n is 0, 1, 2, 3, or 4;

$X^1$ is O, S, or $NR^4$;

$X^3$ is independently at each occurrence selected from the group consisting of $C(R^3)_2$, O, S, and $NR^4$;

$X^4$ is independently at each occurrence selected from the group consisting of $CR^3$ and N;

$X^5$ is $C(R^3)_2$, O, or S;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, — N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$R^1$ and $R^2$ are independently at each occurrence selected from the group consisting of:

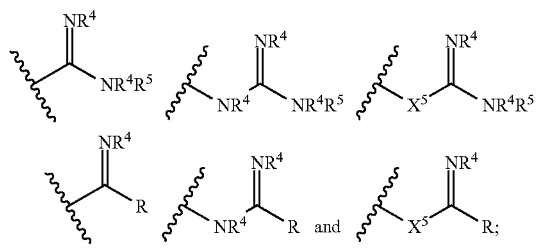

and $R^3$ is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, heteroaryl, aryl, heterocyclyl, —COOR, —C(O)R, fluorine, chlorine, bromine, and iodine; and $R^4$ and $R^5$ are independently at each occurrence selected from the group consisting of hydrogen and $C_1$-$C_6$alkyl.

In one aspect a method is provided for treating a bacterial infection in a host, typically a human, comprising administering an effective amount of a compound of Formula I or a pharmaceutically acceptable salt thereof, optionally in a pharmaceutically acceptable carrier.

In one aspect a method is provided for potentiating the effect of a bacterial infection in a host, typically a human, comprising administering an effective amount of a compound of Formula I or a pharmaceutically acceptable salt thereof, optionally in a pharmaceutically acceptable carrier, in combination with an antibiotic.

A pharmaceutical composition is also provided comprising an effective amount of a compound of Formula I or a pharmaceutically acceptable salt thereof in a pharmaceutically acceptable carrier either alone or in combination with an effective amount of an additional antibiotic.

In another aspect, a method is provided for treating a bacterial infection comprising administering an effective amount of a compound of Formula II, Formula III, Formula IV, or Formula V or a pharmaceutically acceptable salt thereof to a host in need thereof:

(II)

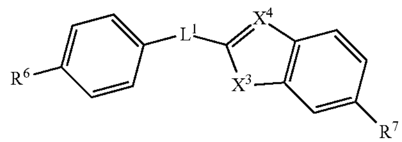

(III)

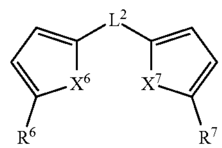

(IV)

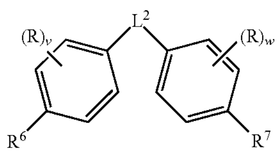

-continued (V)

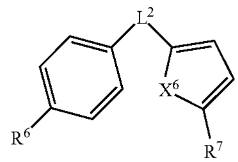

wherein $L^1$ is selected from

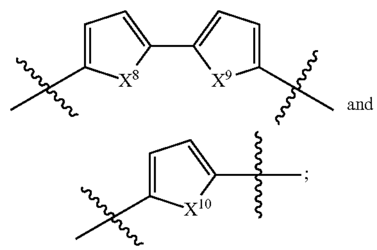

and $L^2$ is selected from

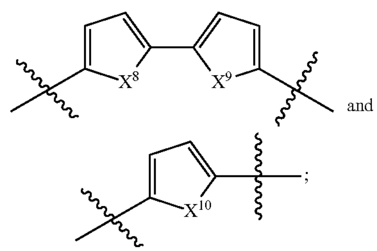

and v and w are independently selected from 0, 1, 2, 3, and 4;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$X^6$, $X^7$, $X^8$, and $X^9$ are independently selected from O, S, NH, and Se;

$X^{10}$ is selected from Se, S, or NH;

$R^6$ and $R^7$ are independently at each occurrence selected from the group consisting of:

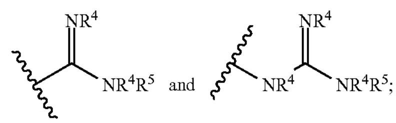

and $X^3$, $X^4$, $R^4$, and $R^5$ are as defined herein.

In some embodiments of Formula II, Formula III, Formula IV, and/or Formula V, $X^{10}$ is not S.

In some embodiments of Formula II, Formula III, Formula IV, and/or Formula V, $X^{10}$ is not NH.

In some embodiments of Formula II, Formula III, Formula IV and/or Formula V, $L^2$ is not

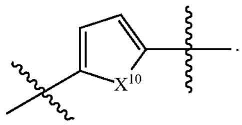

In some embodiments of Formula II, Formula III, Formula IV and/or Formula V, one or more of $X^6$, $X^7$, $X^8$, and $X^9$ is not NH.

In another aspect, a method is provided for treating a bacterial infection comprising administering an effective amount of Compound A, Compound B, or Comp und C Compound A

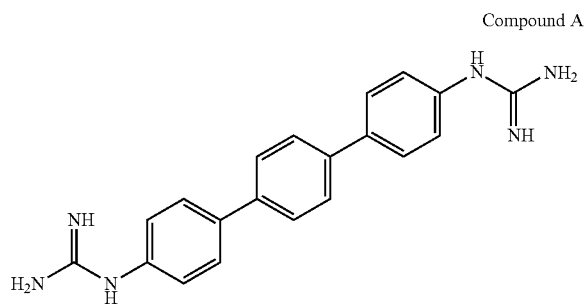

Compound B

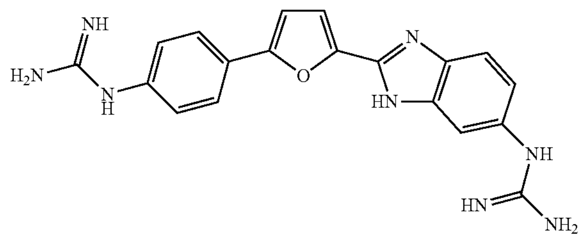

Compound C

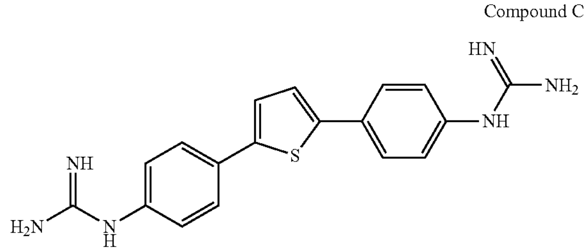

or a pharmaceutically acceptable salt thereof to a host in need thereof.

In certain embodiments a compound of Formula I, Formula II, Formula III, Formula IV, or Formula V or a pharmaceutically acceptable salt thereof can be used to potentiate the effect of an antibiotic in the treatment of a bacterial infection.

In certain embodiments Compound A, Compound B, or Compound C or a pharmaceutically acceptable salt thereof can be used to potentiate the effect of an antibiotic in the treatment of a bacterial infection.

In certain embodiment, the bacterial infection is caused by a gram-positive bacterium.

In certain embodiment, the bacterial infection is caused by a gram-negative bacterium.

In certain embodiment, the bacterial infection is caused by a mycobacterium.

In another aspect, a method is provided for treating a gram-positive or a gram-negative bacterial infection comprising administering an effective amount of a compound of Formula VI:

(VI)

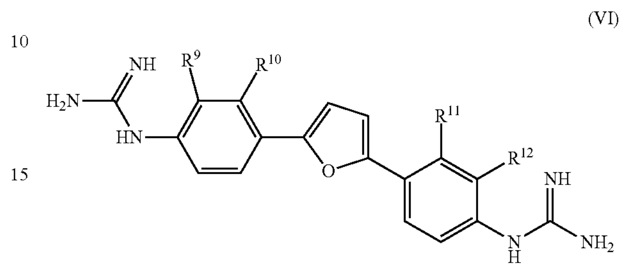

or a pharmaceutically acceptable salt thereof wherein $R^9$ and $R^{12}$ are independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano; and $R^{10}$ and $R^{11}$ are independently at each occurrence selected from the group consisting of hydroxyl, $C_1$-$C_6$alkanoyl, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —C(O)R, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, bromine, iodine, thiol, and cyano.

In another aspect, a method is provided for treating a gram-positive or a gram-negative bacterial infection comprising administering an effective amount of Compound D or Compound E:

Compound D

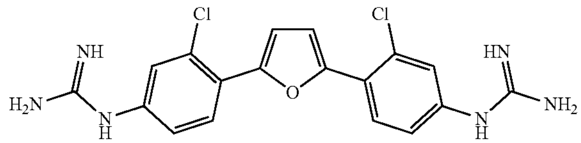

Compound E

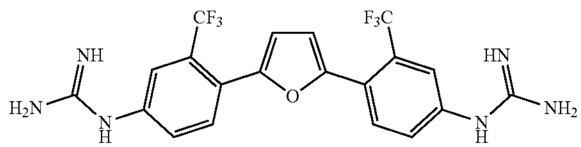

or a pharmaceutically acceptable salt thereof to a host in need thereof.

In some cases, the compound for use in treating a bacterial infection is not Compound D or Compound E.

In one aspect, the invention is a compound selected from Compound F-Compound L or a pharmaceutically acceptable salt thereof:

Compound F

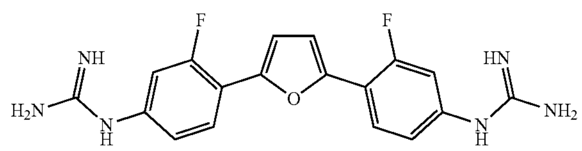

Compound G

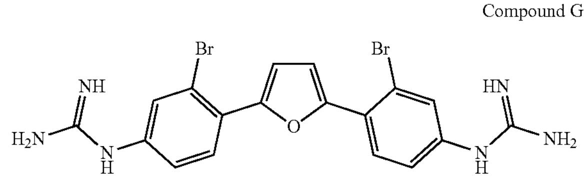

Compound H

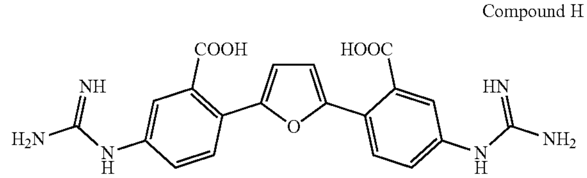

Compound I

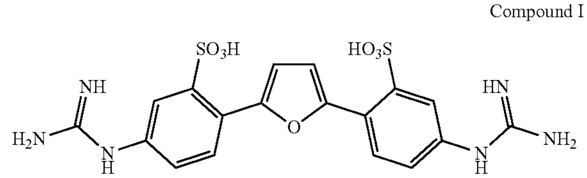

Compound J

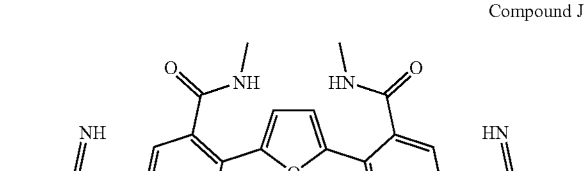

Compound K

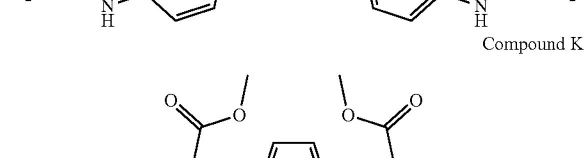

Compound L

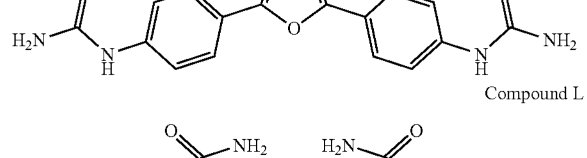

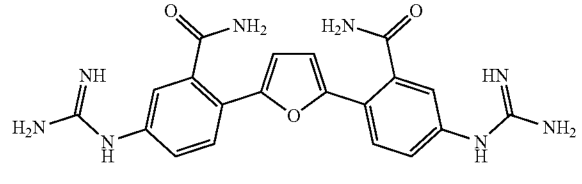

A pharmaceutical composition is also provided comprising an effective amount of a compound of Formula I, Formula II, Formula III, Formula IV, Formula V, or Formula VI or a compound selected from Compound A-Compound L or a pharmaceutically acceptable salt thereof in a pharmaceutically acceptable carrier in combination with an effective amount of an additional antibiotic. In one embodiment, the pharmaceutical composition is suitable for topical administration, for example a cream or an ointment. The topical composition can include any carrier or carriers that do not adversely interact with the active agent and achieve the desired effect.

In another aspect, provided herein is a compound of Formula VII or a pharmaceutically acceptable salt thereof:

(VII)

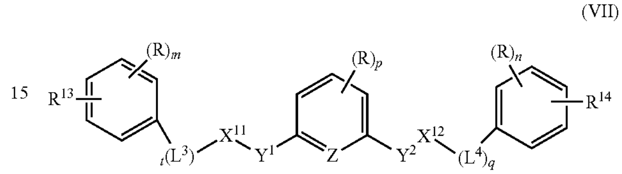

wherein:

m and n are independently selected from 1, 2, 3, or 4;

p is 0, 1, 2, or 3;

q and t are independently at each occurrence 0, 1, 2, 3, 4, 5, 6, 7, 8, 9, or 10;

$L^3$ and La are each independently $C(R^3)_2$, O, or S;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$R^3$ is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, heteroaryl, aryl, heterocyclyl, —COOR, —C(O)R, fluorine, chlorine, bromine, and iodine;

$R^{13}$ and $R^{14}$ are independently at each occurrence selected from the group consisting of

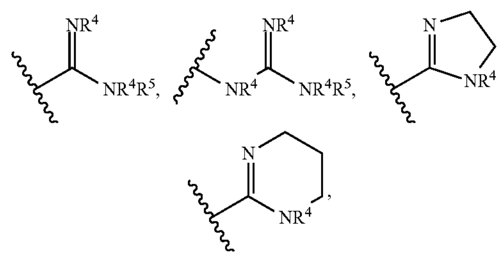

and —$C(R^3)_oNR^4R^5$ wherein $R^4$ and $R^5$ are independently at each occurrence selected from the group consisting of hydrogen and $C_1$-$C_6$alkyl and o is 0, 1, 2, 3, 4, 5, 6, 7, 8, 9, or 10;

$X^{11}$ and $X^{12}$ are each independently selected from the group consisting of $C(R^3)_2$, O, NH, or S;

$Y^1$ and $Y^2$ are each independently selected from the group consisting of $C(R^3)_2$, O, NH, or S; and Z is $CR^3$ or N.

Optionally, $R^4$ and $R^5$ are hydrogen.

Optionally, $X^{11}$ and $X^{12}$ are the same. In some cases, $X^{11}$ and $X^{12}$ are selected from the group consisting of O, $CH_2$, and S.

Optionally, $Y^1$ and $Y^2$ are the same. In some cases, $Y^1$ and $Y^2$ are selected from the group consisting of O and $CH_2$.

Optionally, each R is independently selected from the group consisting of hydrogen, $C_1$-$C_6$alkyl, $C_1$-$C_6$alkoxy, $C_1$-$C_6$haloalkyl, and fluorine.

Optionally, the compound has the following structure:

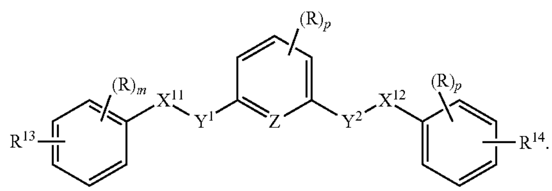

In another aspect, a method is provided for treatment of a bacterial infection comprising administering a compound of Formula VII or a pharmaceutically acceptable salt thereof. Also provided is a method of potentiating the therapeutic effect of an antibiotic during the treatment of a bacterial infection comprising administering a compound of Formula VII or a pharmaceutically acceptable salt thereof. In some cases, the bacterial infection is caused by gram-positive bacteria. In other cases, the bacterial infection is caused by gram-negative bacteria. Optionally, the bacterial infection is caused by a mycobacterium.

In another aspect, provided herein is a compound of Formula VIII or a pharmaceutically acceptable salt thereof:

(VIII)

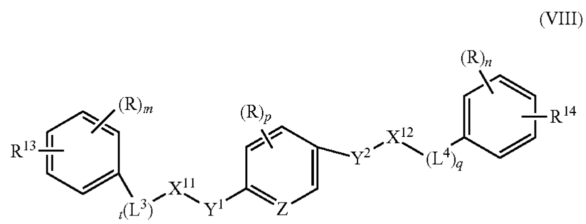

wherein:

m and n are independently selected from 1, 2, 3, or 4;

p is 0, 1, 2, or 3;

q and t are independently at each occurrence 0, 1, 2, 3, 4, 5, 6, 7, 8, 9, or 10;

$L^3$ and $L^4$ are each independently $C(R^3)_2$, O, or S;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$R^3$ is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, heteroaryl, aryl, heterocyclyl, —COOR, —C(O)R, fluorine, chlorine, bromine, and iodine;

$R^{13}$ and $R^{14}$ are independently at each occurrence selected from the group consisting of

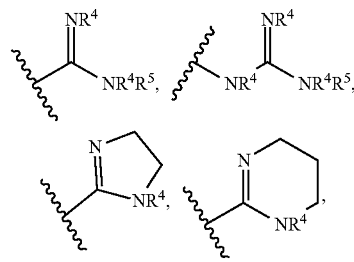

and —$C(R^3)_oNR^4R^5$ wherein $R^4$ and $R^5$ are independently at each occurrence selected from the group consisting of hydrogen and $C_1$-$C_6$alkyl and o is 0, 1, 2, 3, 4, 5, 6, 7, 8, 9, or 10;

$X^{11}$ and $X^{12}$ are each independently selected from the group consisting of $C(R^3)_2$, O, NH, or S;

$Y^1$ and $Y^2$ are each independently selected from the group consisting of $C(R^3)_2$, O, NH, or S; and Z is $CR^3$ or N.

Optionally, $R^4$ and $R^5$ are hydrogen.

Optionally, $X^{11}$ and $X^{12}$ are the same. In some cases, $X^{11}$ and $X^{12}$ are selected from the group consisting of O, $CH_2$, and S.

Optionally, $Y^1$ and $Y^2$ are the same. In some cases, $Y^1$ and $Y^2$ are selected from the group consisting of O and $CH_2$.

Optionally, each R is independently selected from the group consisting of hydrogen, $C_1$-$C_6$alkyl, $C_1$-$C_6$alkoxy, $C_1$-$C_6$haloalkyl, and fluorine.

Optionally, the compound has the following structure:

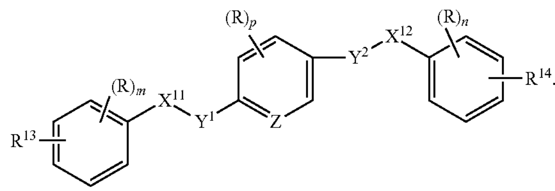

In another aspect, a method is provided for treatment of a bacterial infection comprising administering a compound of Formula VIII or a pharmaceutically acceptable salt thereof. Also provided is a method of potentiating the therapeutic effect of an antibiotic during the treatment of a bacterial infection comprising administering a compound of Formula VIII or a pharmaceutically acceptable salt thereof. In some cases, the bacterial infection is caused by gram-positive bacteria. In other cases, the bacterial infection is caused by gram-negative bacteria. Optionally, the bacterial infection is caused by a mycobacterium.

In another aspect, provided herein is a pharmaceutical composition comprising a compound of Formula VII or Formula VIII or a pharmaceutically acceptable salt thereof, optionally in a pharmaceutically acceptable carrier.

The present invention also provides a topical composition containing, either alone or in combination with an effective amount of an antibiotic, an effective amount of a compound selected from Formula I, Formula II, Formula III, Formula IV, Formula V, Formula VI, Formula VII, or Formula VIII or a compound selected from Compound A-Compound L or a pharmaceutically acceptable salt thereof for the treatment of acne vulgaris. The compounds used in the topical compositions and methods provided herein have an anti-microbial effect that helps alleviate the symptoms of acne vulgaris and treat the underlying overgrowth of bacterial that cause acne, for example, the bacterium *Propionibacterium acnes* or *Staphylococcus epidermidis*.

The present invention also provides treatment options that may complement or replace those currently available in the treatment of this highly common dermatological condition.

For example, the topical carrier can be water-based or anhydrous. Water-based topical compositions are well known and described further below. Anhydrous pharmaceutically acceptable topical materials are also well known, and include silicon-based oils, aliphatic-based compositions, oleaginous materials, jellies, mineral oil, dimethicone, and other substantially anhydrous lipophilic carriers.

The active compound of Formula I, Formula II, Formula III, Formula IV, Formula V, Formula VI, Formula VII, or Formula VIII or a compound selected from Compound A-Compound L can be provided in the topical formulation in any amount that achieves the desired effect. In certain non-limiting examples, the weight percentage of the active compound in the topical formulation is from about 0.1% to about 50%, or from about 0.1% to about 40%, or about 1% to about 30%, or from about 2, 3, 4 or 5% to about 20%, or between about 5% to about 10%.

Examples include at least about 0.5, 1, 2, 3, 4, 5, 10 or 15% by weight. In one embodiment, the topical formulation contains a compound of Formula I, Formula II, Formula III, Formula IV, Formula V, Formula VI, Formula VII, or Formula VIII or a compound selected from Compound A-Compound L or a pharmaceutically acceptable salt thereof in combination with an additional active agent, for example benzoyl peroxide, a retinoid, azelaic acid, an antibiotic, or salicylic acid, as long as it does not adversely affect the active agent.

In one embodiment, at least one hydrogen within a compound of Formula I, Formula II, Formula III, Formula IV, Formula V, Formula VI, Formula VII, or Formula VIII is replaced with a deuterium. In one aspect, the deuterium is at a location of metabolism. In one embodiment, at least one hydrogen within Compound A-Compound L is replaced with a deuterium. In one aspect, the deuterium is at a location of metabolism.

Thus, the present invention includes at least the following features:

(a) a compound of Formula I or a pharmaceutically salt thereof;

(b) a pharmaceutical composition comprising a compound of Formula I or a pharmaceutically acceptable salt thereof optionally in a pharmaceutically acceptable carrier;

(c) a method for the treatment of a bacterial infection comprising administering a compound of Formula I, Formula II, Formula III, Formula IV, or Formula V or a pharmaceutically acceptable salt to a host in need thereof;

(d) a method for the treatment of a bacterial infection comprising administering a compound of Formula I, Formula II, Formula III, Formula IV, or Formula V or a pharmaceutically acceptable salt in combination with an effective amount of an antibiotic to a host in need thereof;

(e) a method for potentiating the effect of an antibiotic in the treatment of a bacterial infection comprising administering the antibiotic in combination with a compound of Formula I, Formula II, Formula III, Formula IV, or Formula V or a pharmaceutically acceptable salt thereof to a host in need thereof;

(f) the method of (c), (d), or (e) wherein the bacterial infection is caused by a gram-positive bacterial infection;

(g) the method of (c), (d), or (e) wherein the bacterial infection is caused by a gram-negative bacterial infection;

(h) the method of (c), (d), or (e) wherein the bacterial infection is caused by a mycobacterium;

(i) a method for the treatment of acne vulgaris comprising administering a compound of Formula I, Formula II, Formula III, Formula IV, Formula V, or Formula VI or a pharmaceutically acceptable salt thereof, either alone or in combination with an antibiotic, to a host in need thereof;

(j) the method of (i) wherein the acne vulgaris is caused by the bacterium *Propionibacterium acnes* or *Staphylococcus epidermidis;*

(k) a compound of Formula I, Formula II, Formula III, Formula IV, or Formula V or a pharmaceutically acceptable salt thereof for use to treat a bacterial infection in a host in need thereof;

(l) a compound of Formula I, Formula II, Formula III, Formula IV, or Formula V or a pharmaceutically acceptable salt thereof in combination with an effective amount of an antibiotic for use to treat a bacterial infection in a host in need thereof;

(m) a compound of Formula I, Formula II, Formula III, Formula IV, or Formula V or a pharmaceutically acceptable salt thereof for use in the potentiation of the effect of an antibiotic in the treatment of a bacterial infection;

(n) the compound of (k), (l) or (m) wherein the bacterial infection is caused by a gram-positive bacterial infection;

(o) the compound of (k), (l) or (m) wherein the bacterial infection is caused by a gram-negative bacterial infection;

(p) the compound of (k), (l) or (m) wherein the bacterial infection is caused by a mycobacterium;

(q) a compound of Formula I, Formula II, Formula III, Formula IV, Formula V, or Formula VI or a pharmaceutically acceptable salt thereof for use to treat acne vulgaris in a host in need thereof;

(r) the compound of (q) wherein the acne vulgaris is caused by the bacterium *Propionibacterium acnes* or *Staphylococcus epidermidis;*

(s) the use of a compound of Formula I, Formula II, Formula III, Formula IV, or Formula V or a pharmaceutically acceptable salt thereof in the manufacture of a medicament for the treatment of a bacterial infection in a host in need thereof;

(t) the use of a compound of Formula I, Formula II, Formula III, Formula IV, or Formula V or a pharmaceutically acceptable salt thereof in combination with an effective amount of an antibiotic in the manufacture of a medicament for the treatment of a bacterial infection in a host in need thereof;

(u) the use of a compound of Formula I, Formula II, Formula III, Formula IV, or Formula V or a pharmaceutically acceptable salt thereof in the manufacture of a medicament for the potentiation of the effect of an antibiotic in the treatment of a bacterial infection in a host in need thereof;

(v) the use of (s), (t), or (u) wherein the bacterial infection is caused by a gram-positive bacterial infection;

(w) the use of (s), (t), or (u) wherein the bacterial infection is caused by a gram-negative bacterial infection;

(x) the use of (s), (t), or (u) wherein the bacterial infection is caused by a mycobacterium;

(y) the use of a compound of Formula I, Formula II, Formula III, Formula IV, Formula V, or Formula VI or a pharmaceutically acceptable salt thereof in the manufacture of a medicament for the treatment of acne vulgaris in a host in need thereof;

(z) the use of (y) wherein the acne vulgaris is caused by the bacterium *Propionibacterium acnes* or *Staphylococcus epidermidis;*

(aa) a method for the treatment of a bacterial infection comprising administering a compound selected from Compound A, Compound B, Compound C, or Compound F-Compound L or a pharmaceutically acceptable salt to a host in need thereof;

(bb) a method for the treatment of a bacterial infection comprising administering a compound selected from Compound A, Compound B, Compound C, or Compound F-Compound L or a pharmaceutically acceptable salt in combination with an effective amount of an antibiotic to a host in need thereof;

(cc) a method for potentiating the effect of an antibiotic in the treatment of a bacterial infection comprising administering the antibiotic in combination with a compound selected from Compound A, Compound B, Compound C, or Compound F-Compound L or a pharmaceutically acceptable salt thereof to a host in need thereof;

(dd) the method of (aa), (bb), or (cc) wherein the bacterial infection is caused by a gram-positive bacterial infection;

(ee) the method of (aa), (bb), or (cc) wherein the bacterial infection is caused by a gram-negative bacterial infection; the method of (aa), (bb), or (cc) wherein the bacterial infection is caused by a mycobacterium;

(ff) a method for the treatment of acne vulgaris comprising administering a compound selected from Compound A, Compound B, Compound C, or Compound F-Compound L or a pharmaceutically acceptable salt thereof, either alone or in combination with an antibiotic, to a host in need thereof;

(gg) the method of (ff) wherein the acne vulgaris is caused by the bacterium *Propionibacterium acnes* or *Staphylococcus epidermidis;*

(hh) a method for the treatment of a gram-positive or a gram-negative bacterial infection comprising administering a compound of Formula VI or a pharmaceutically acceptable salt to a host in need thereof;

(ii) a method for the treatment of a gram-positive or a gram-negative bacterial infection comprising administering a compound of Formula VI or a pharmaceutically acceptable salt in combination with an effective amount of an antibiotic to a host in need thereof;

(jj) a method for potentiating the effect of an antibiotic in the treatment of a gram-positive or a gram-negative bacterial infection comprising administering the antibiotic in combination with a compound of Formula VI or a pharmaceutically acceptable salt thereof to a host in need thereof;

(kk) a method for the treatment of a gram-positive or a gram-negative bacterial infection comprising administering Compound D or Compound E or a pharmaceutically acceptable salt to a host in need thereof;

(ll) a method for the treatment of a gram-positive or a gram-negative bacterial infection comprising administering a compound selected from Compound D or Compound E or a pharmaceutically acceptable salt in combination with an effective amount of an antibiotic to a host in need thereof;

(mm) a method for potentiating the effect of an antibiotic in the treatment of a gram-positive or a gram-negative bacterial infection comprising administering the antibiotic in combination with a compound selected from Compound D or Compound E or a pharmaceutically acceptable salt thereof to a host in need thereof;

(nn) a pharmaceutical composition comprising an effective amount of a compound of Formula I, Formula II, Formula III, Formula IV, Formula V, or Formula VI or a pharmaceutically acceptable salt thereof, optionally in a pharmaceutically acceptable carrier in combination with an effective amount of an antibiotic;

(oo) a topical formulation comprising an effective amount of a compound Formula I, Formula II, Formula III, Formula IV, Formula V, or Formula VI or a pharmaceutically acceptable salt thereof in a topically acceptable carrier for the treatment of acne;

(pp) a pharmaceutical composition comprising an effective amount of a compound selected from Compound A, Compound B, Compound C, or Compound F-Compound L or a pharmaceutically acceptable salt thereof, optionally in a pharmaceutically acceptable carrier in combination with an effective amount of an antibiotic;

(qq) a topical formulation comprising an effective amount of a compound selected from Compound A, Compound B, Compound C, or Compound F-Compound L or a pharmaceutically acceptable salt thereof in a topically acceptable carrier for the treatment of acne;

(rr) a compound of Formula VII or Formula VIII or a pharmaceutically salt thereof;

(ss) a pharmaceutical composition comprising a compound of Formula VII or Formula VIII or a pharmaceutically acceptable salt thereof optionally in a pharmaceutically acceptable carrier;

(tt) a method for the treatment of a bacterial infection comprising administering a compound of Formula VII or Formula VIII or a pharmaceutically acceptable salt to a host in need thereof;

(uu) a method for the treatment of a bacterial infection comprising administering a compound of Formula VII or Formula VIII or a pharmaceutically acceptable salt in combination with an effective amount of an antibiotic to a host in need thereof;

(vv) a method for potentiating the effect of an antibiotic in the treatment of a bacterial infection comprising administering the antibiotic in combination with a compound of Formula VII or Formula VIII or a pharmaceutically acceptable salt thereof to a host in need thereof;

(ww) the method of (tt), (uu), or (vv) wherein the bacterial infection is caused by a gram-positive bacterial infection;

(xx) the method of (tt), (uu), or (vv) wherein the bacterial infection is caused by a gram-negative bacterial infection;

(yy) the method of (tt), (uu), or (vv) wherein the bacterial infection is caused by a mycobacterium;

(zz) a process for the preparation of a therapeutic product that contains an effective amount of a compound of Formula I, Formula II, Formula III, Formula IV, Formula V, Formula VI, Formula VII, or Formula VIII or a pharmaceutically acceptable salt thereof, either alone or in combination with an effective amount of an antibiotic.

The details of one or more embodiments are set forth in the drawings and the description below. Other features, objects, and advantages will be apparent from the description and drawings, and from the claims.

NR698 was cultured with the antibiotic at various concentrations in the presence or absence of bacterial sensitizer for 24 h at 37° C. Then bacterial growth density was determined by measuring $OD_{600}$. Panel (B) shows the LPS and high concentration of $Mg^{2+}$ decreased the sensitization ability of MD-100. *E. coli* was treated with 10 μg/ml MD-100 and erythromycin combination in the presence and absence of 40 μM LPS for 20 h at 37° C. Then the growth density/% was calculated based on $OD_{600}$. *E. coli* was treated with 10 μg/ml MD-100 and erythromycin combination in the presence and absence of 20 mM $Mg^{2+}$ for 20 h at 37° C., then the growth density/% was calculated based on $OD_{600}$.

Figure 8:
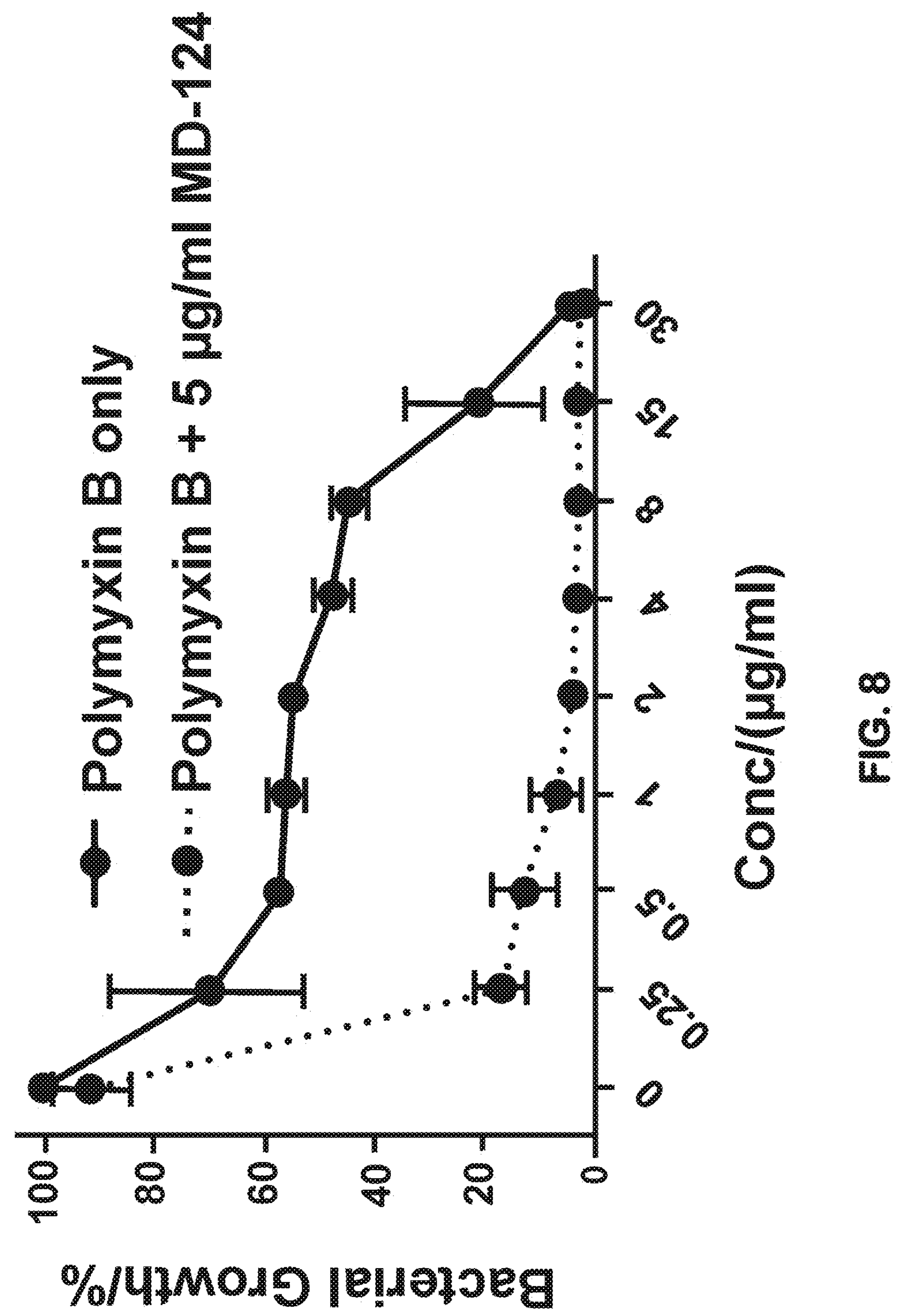

FIG. 8 demonstrates that 5 μg/ml MD-124 sensitizes *E. coli* towards polymyxin B. *E. coli* was cultured with the polymyxin B at various concentrations in the presence or absence of 5 μg/ml MD-124 for 20 h at 37° C. Then bacterial growth density was determined by measuring $OD_{600}$.

Figure 9:
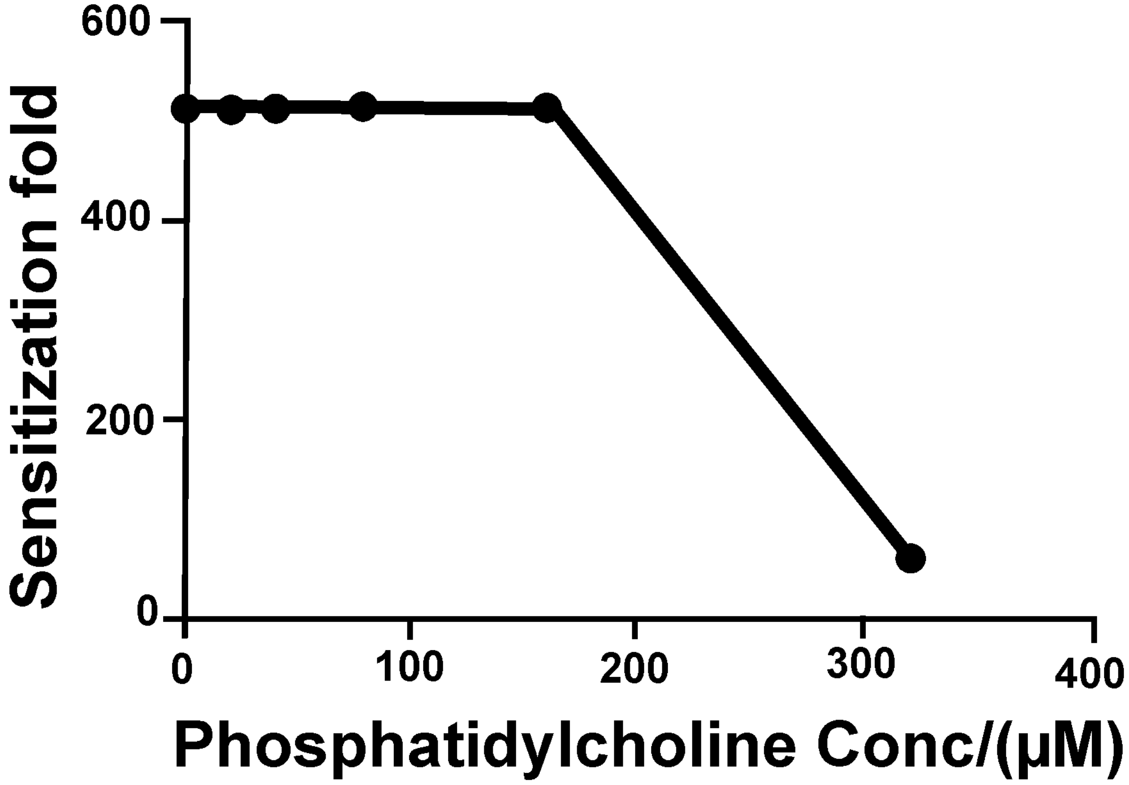

FIG. 9 shows the effect of phosphatidylcholine on MD-124 sensitization activity.

FIG. 10 contains graphs showing that Membrane disruptor sensitize *B. subtilis* (Panel A) and MRSA (Panel B) towards Rifampicin. Bacteria was cultured with antibiotics at various concentrations in the presence or absence of bacteria sensitizer for 24 hours at 37° C. Then bacterial growth density was determined by measuring $OD_{600}$. ***: $p<0.01$.

Figure 11A:
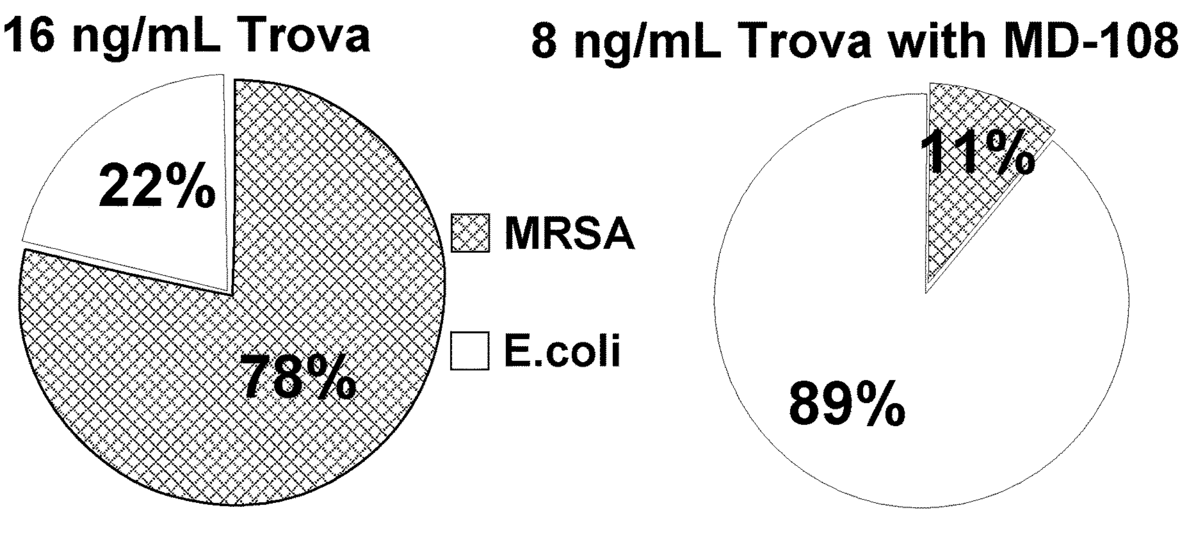
Figure 11B:
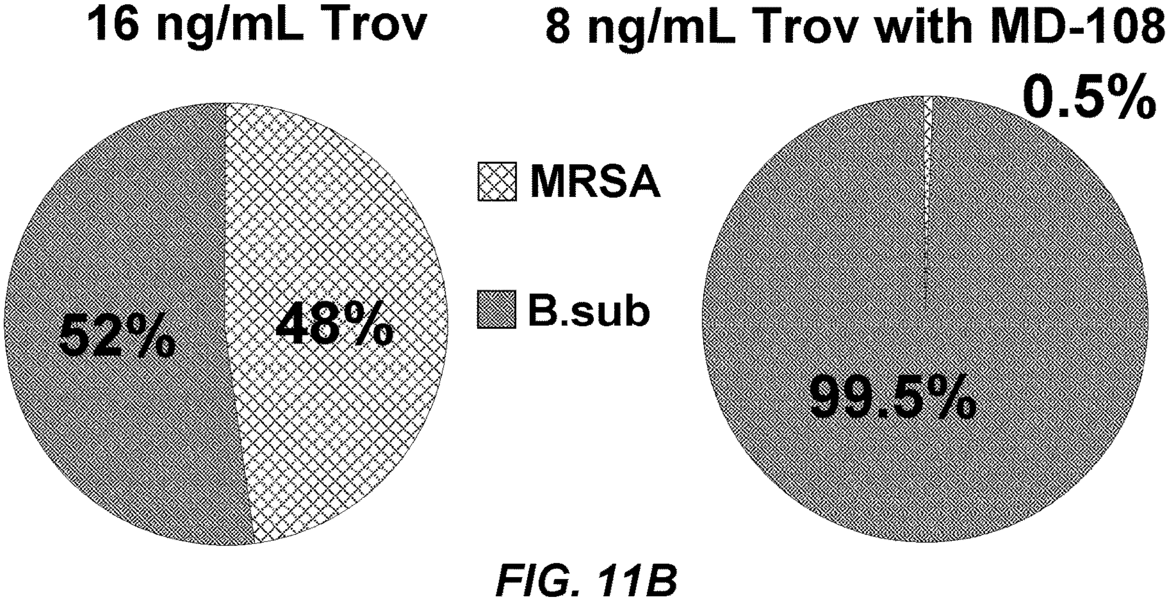

FIG. 11 contains graphs showing that MD-108 can change the composition between MRSA and *E. coli* (Panel A) or MRSA and *B. subtilis* (Panel B) when the bacteria strains are under the same antibiotic pressure.

DETAILED DESCRIPTION OF THE INVENTION

Described herein are compounds and methods for the treatment of bacterial infections as well as for the potentiation of the therapeutic effect of antibiotics in the treatment of bacterial infections. The methods include administering an effective amount of a compound described herein or its pharmaceutically acceptable salt, optionally in a pharmaceutically acceptable carrier. The bacterial infection may be caused by gram-positive bacteria, gram-negative bacteria, and/or antibiotic resistant bacteria. In one embodiment, the bacterial infection is caused by mycobacteria.

I. DEFINITIONS

Compounds are described using standard nomenclature. Unless defined otherwise, all technical and scientific terms used herein have the same meaning as is commonly understood by one of skill in the art to which the invention belongs.

The terms "a" and "an" do not denote a limitation of quantity, but rather denote the presence of at least one of the referenced item. The term "or" means "and/or". Recitation of ranges of values merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of example, or exemplary language (e.g. "such as"), is intended merely to better illustrate the invention and does not pose a limitation on the scope of the invention unless otherwise claimed.

A dash ("-") that is not between two letters or symbols is used to indicate a point of attachment for a substituent. For example, $-(C{=}O)NH_2$ is attached through the carbon of the keto (C=O) group.

"Alkyl" is a branched or straight chain saturated aliphatic hydrocarbon group. In one non-limiting, preferred embodiment, the alkyl group generally contains from 1 to about 12 carbon atoms, from 1 to about 8 carbon atoms, from 1 to about 6 carbon atoms, or from 1 to about 4 carbon atoms. In certain embodiments, the alkyl is $C_1$-$C_2$, $C_1$-$C_3$, $C_1$-$C_4$, $C_1$-$C_5$, $C_1$-$C_6$, $C_1$-$C_7$, $C_1$-$C_8$, $C_1$-$C_9$, or $C_1$-$C_{10}$. In one embodiment, the alkyl group contains from about 1 to about 50 carbon atoms or from about 1 to about 36 carbon atoms. For example, the term $C_1$-$C_6$alkyl as used herein indicates a straight chain or branched alkyl group having from 1, 2, 3, 4, 5, or 6 carbon atoms and is intended to mean that each of these are described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, sec-pentyl, 3-pentyl, active pentyl, neopentyl, n-hexyl, sec-hexyl, tert-hexyl, isohexyl, 2-methylpentance, 3-methylpentane, 2,2-dimethylbutane, and 2,3-dimethylbutane. In some embodiments, the alkyl group is optionally substituted as defined herein.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

When a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, etc. can all be considered to include the cyclic forms of alkyl, unless unambiguously excluded by context.

For example, "cycloalkyl" is an alkyl group that forms or includes a ring. When composed of two or more rings, the rings may be joined together in a fused fashion. Non-limiting examples of typical cycloalkyl groups include cyclopropyl, cyclobutyl, cyclopentyl, cyclohexyl, cycloheptyl, and cyclooctyl.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic system ("$C_6$-$C_{14}$aryl"). In some embodiments, an aryl group has 6 ring carbon atoms ("$C_6$aryl"; e.g., phenyl). In some embodiments, an aryl group has 10 ring carbon atoms ("$C_{10}$aryl"; e.g., naphthyl such as 1-naphthyl and 2-naphthyl). In some embodiments, an aryl group has 14 ring carbon atoms ("$C_{14}$aryl"; e.g., anthracyl). "Aryl" also includes ring systems wherein the aryl ring, as defined above, is fused with one or more cycloalkyl or heterocycloalkyl groups wherein the point of attachment is on the aryl ring, and in such instances, the number of carbon atoms continue to designate the number of carbon atoms in the aryl ring system. The one or more fused cycloalkyl or heterocycloalkyl groups can be 4 to 7 or 5 to 7-membered cycloalkyl or heterocycloalkyl groups that optionally contain 1, 2, or 3 heteroatoms independently selected from nitrogen, oxygen, phosphorous, sulfur, silicon, and boron. In one non-limiting embodiment, aryl groups are pendant. An example of a pendant ring is a phenyl group substituted with a phenyl group. In some embodiments, the aryl group is optionally substituted as defined herein.

In one embodiment "aryl" is a 6-carbon aromatic group (phenyl).

In one embodiment "aryl" is a 10-carbon aromatic group (naphthyl).

In one embodiment "aryl" is a 6-carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

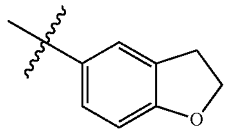 [SMILES: *c1ccc2c(c1)CCO2]

is an "aryl" group.

However,

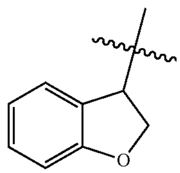 [SMILES: *C1COc2ccccc21]

is a "heterocycle" group.

In one embodiment "aryl" is a 6-carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example

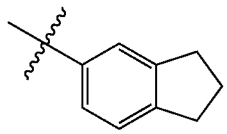 [SMILES: *c1ccc2c(c1)CCC2]

is an "aryl" group.

However,

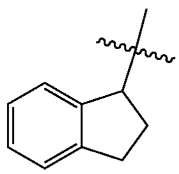 [SMILES: *C1CCc2ccccc21]

is a "cycloalkyl" group.

In one embodiment "aryl" is "substituted aryl".

In one embodiment "heteroaryl" is a 5-membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

In one embodiment "heteroaryl" is a 6-membered aromatic group containing 1, 2, or 3 nitrogen atoms (i.e. pyridinyl, pyridazinyl, triazinyl, pyrimidinyl, and pyrazinyl).

In one embodiment "heteroaryl" is a 9-membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

In one embodiment "heteroaryl" is a 10-membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

In one embodiment "heteroaryl" is "substituted heteroaryl".

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl. "Alkoxy" is alkyl group as defined above covalently bounds through an oxygen bridge (—O—). Examples of alkoxy include, but are not limited to, methoxy, ethoxy, n-propoxy, isopropoxy, n-butoxy, 2-butoxy, t-butoxy, n-pentoxy, 2-pentoxy, 3-pentoxy, isopentoxy, neopentoxy, n-hexyoxy, 2-hexoxy, 3-hexoxy, and 3-methylpentoxy. "Haloalkoxy" indicates a haloalkyl group as defined herein attached through an oxygen bridge (—O—).

As used herein, the term "active agent" refers to any type of drug, medicine, pharmaceutical, hormone, antibiotic, protein, gene, growth factor, bioactive material, etc., used for treating, controlling, or preventing diseases or medical conditions as described herein. The term "active agent" also includes the active compounds as described in the present application.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein means an amount which provides a therapeutic or prophylactic benefit.

"Parenteral" administration of a pharmaceutical composition includes, e.g., subcutaneous (s.c.), intravenous (i.v.), intramuscular (i.m.), intrasternal injection, or infusion techniques.

To "treat" a disease as the term is used herein means to reduce the frequency or severity of at least one sign or symptom of a disease or disorder experienced by a subject (i.e., palliative treatment) or to decrease a cause or effect of the disease or disorder (i.e. disease-modifying treatment).

As used herein, "pharmaceutical compositions" are compositions comprising at least one active agent and at least one other substance, such as a carrier. "Pharmaceutical combinations" are combinations of at least two active agents which may be combined in a single dosage form or provided together in separate dosage forms with instructions that the active agents are to be used together to treat any disorder described herein.

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders specifically described herein. Typically, the host is a human. A "host" may alternatively refer to for example, a mammal, primate (e.g. human), cow, sheep, goat, horse, dog, cat, rabbit, rat, mice, fish, bird, and the like.

A "therapeutically effective amount" of a pharmaceutical composition/combination of this invention means an amount effective, when administered to a host, to provide a therapeutic benefit such as an amelioration of symptoms or reduction or diminution of the disease itself.

The compounds in any of the Formulas described herein or Compound A-Compound L may be in the form of a racemate, enantiomer, mixture of enantiomers, diastereomer, mixture of diastereomers, tautomer, N-oxide, or other isomers, such as a rotamer, as if each is specifically described unless specifically excluded by context.

The present invention includes compounds of Formula I, Formula II, Formula III, Formula IV, or Formula V with at least one desired isotopic substitution of an atom, at an amount above the natural abundance of the isotope, i.e., enriched. The present invention also includes compounds selected from Compound A-Compound L with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^{2}H$, $^{3}H$, $^{11}C$, $^{13}C$, $^{14}C$, $^{15}N$, $^{17}O$, $^{18}O$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of one or more hydrogen atoms for a deuterium atoms can be provided in any of Formula I, Formula II, Formula III, Formula IV, Formula V, or Formula VI. In one non-limiting embodiment, the substitution of one or more hydrogen atoms for a deuterium atoms can be provided in a compound selected from Compound A-Compound L. In one non-limiting embodiment, the substitution of a hydrogen atom for a deuterium atom occurs within a group selected from any of R, $R^1$, $R^2$, $R^3$, $R^4$, and $R^5$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compounds of the present invention may form a solvate with solvents. Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. Additional non-limiting examples of solvents are dimethyl acetamide and N-methyl-2-pyrrolidine. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

As used herein, "pharmaceutically acceptable salt" is a derivative of the disclosed compound in which the parent compound is modified by making inorganic or organic, non-toxic, acid or base addition salts thereof. The salts of the present compounds can be synthesized from a parent compound that contains a basic or acidic moiety by conventional chemical methods.

Generally, such salts can be prepared by reacting free acid forms of these compounds with a stoichiometric amount of the appropriate base (such as Na, Ca, Mg, or K hydroxide, carbonate, bicarbonate, or the like), or by reactive free base forms of these compounds with a stoichiometric amount of the appropriate acid. Such reactions are typically carried out in a variety of solvents or solvent mixtures which are compatible with the compound. Generally, non-aqueous media like ether, ethyl acetate, ethanol, isopropanol, or acetonitrile are typical, where practical. Salts of the present compounds further include solvates of the compound and the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic organic acids. For example, conventional non-toxic acid salts include the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* $17^{th}$ ed., Mack Publishing Company, Easton, Pa., p. 1418 (1985).

II. COMPOUNDS OF THE PRESENT INVENTION

In one aspect of the present invention, a compound of Formula I or a pharmaceutically acceptable salt is provided:

(I)

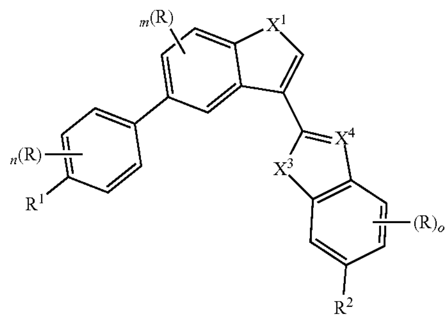

wherein:

m and o are independently selected from 0, 1, 2, or 3;

n is 0, 1, 2, 3, or 4;

X is O, S, or $NR^4$;

$X^3$ is independently at each occurrence selected from the group consisting of $C(R^3)_2$, O, S, and $NR^4$;

$X^4$ is independently at each occurrence selected from the group consisting of $CR^3$ and N;

$X^5$ is $C(R^3)_2$, O, or S;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$R^1$ and $R^2$ are independently at each occurrence selected from the group consisting of:

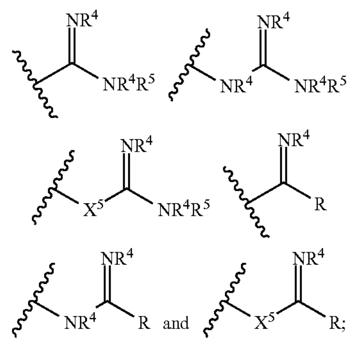

and $R^3$ is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, heteroaryl, aryl, heterocyclyl, —COOR, —C(O)R, fluorine, chlorine, bromine, and iodine; and $R^4$ and $R^5$ are independently at each occurrence selected from the group consisting of hydrogen, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, aryl, heteroaryl, heterocyclyl, —COOR, and —C(O)R.

In one embodiment, a compound is provided of Formula I or a pharmaceutically acceptable salt thereof, optionally in a pharmaceutically acceptable carrier, to form a pharmaceutical composition.

In one embodiment of Formula I, m is 0. In one embodiment of Formula I, m is 1. In one embodiment of Formula I, m is 2. In one embodiment of Formula I, m is 3.

In one embodiment of Formula I, n is 0. In one embodiment of Formula I, n is 1. In one embodiment of Formula I, n is 2. In one embodiment of Formula I, n is 3. In one embodiment of Formula I, n is 4.

In one embodiment of Formula I, o is 0. In one embodiment of Formula I, o is 1. In one embodiment of Formula I, o is 2. In one embodiment of Formula I, o is 3.

In one embodiment of Formula I, p is 0. In one embodiment of Formula I, p is 1. In one embodiment of Formula I, p is 2.

In one embodiment of Formula I, $X^1$ is O. In one embodiment of Formula I, $X^1$ is $NR^4$ and $R^4$ is hydrogen. In one embodiment of Formula I, $X^1$ is $NR^4$ and $R^4$ is $C_1$-$C_6$alkyl.

In one embodiment of Formula I, $X^2$ is O. In one embodiment of Formula I, $X^2$ is S. In one embodiment of Formula I, $X^2$ is $NR^4$ and $R^4$ is hydrogen. In one embodiment of Formula I, $X^2$ is $NR^4$ and $R^4$ is $C_1$-$C_6$alkyl.

In one embodiment of Formula I, $X^3$ is $C(R^3)_2$ and $R^3$ is hydrogen. In one embodiment of Formula I, $X^3$ is S. In one embodiment of Formula I, $X^3$ is $C(R^3)_2$ and $R^3$ is $C_1$-$C_6$alkyl. In one embodiment of Formula I, $X^3$ is $C(R^3)_2$ and one $R^3$ is hydrogen and the other is $C_1$-$C_6$alkyl.

In one embodiment of Formula I, $X^3$ is $C(R^3)_2$ and one $R^3$ is fluorine, chlorine, bromine iodine or $C_1$-$C_6$haloalkyl. In one embodiment of Formula I, $X^3$ is O. In one embodiment of Formula I, $X^3$ is $NR^4$ and $R^4$ is hydrogen. In one embodiment of Formula I, $X^3$ is $NR^4$ and $R^4$ is alkyl.

In one embodiment of Formula I, $X^4$ is N. In one embodiment of Formula I, $X^4$ is $CR^3$ and $R^3$ is hydrogen. In one embodiment of Formula I, $X^4$ is $CR^3$ and $R^3$ is $C_1$-$C_6$alkyl.

In one embodiment of Formula I, $X^4$ is $C(R^3)_2$ and $R^3$ is fluorine, chlorine, bromine, iodine or $C_1$-$C_6$haloalkyl.

In one embodiment of Formula I, $X^5$ is $C(R^3)_2$ and $R^3$ is hydrogen. In one embodiment of Formula I, $X^5$ is $C(R^3)_2$ and $R^3$ is $C_1$-$C_6$alkyl. In one embodiment of Formula I, $X^5$ is $C(R^3)_2$ and one $R^3$ is hydrogen and the other is alkyl, hydroxyl, fluorine, chlorine, bromine iodine or $C_1$-$C_6$haloalkyl. In one embodiment of Formula I, $X^5$ is O.

In one embodiment of Formula I, R is hydrogen, fluorine, chlorine, bromine, or iodine.

In one embodiment of Formula I, $R^1$ is

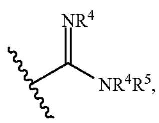

wherein $R^4$ and $R^5$ are independently hydrogen or $C_1$-$C_6$alkyl. In certain embodiments $R^1$ is

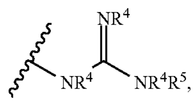

wherein $R^4$ and $R^5$ are independently hydrogen or $C_1$-$C_6$alkyl.

In one embodiment of Formula I, $R^2$ is

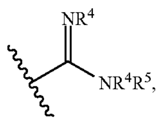

wherein $R^4$ and $R^5$ are independently hydrogen or alkyl. In certain embodiments $R^2$ is

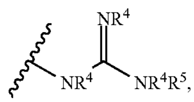

wherein $R^4$ and $R^5$ are independently hydrogen or $C_1$-$C_6$alkyl.

In one embodiment of Formula I, $R^1$ and $R^2$ are each

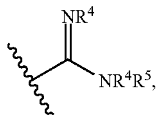

wherein $R^4$ and $R^5$ are independently hydrogen or $C_1$-$C_6$alkyl. In one embodiment of Formula I, $R^1$ and $R^2$ are each

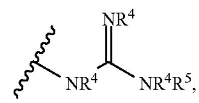

wherein $R^4$ and $R^5$ are independently hydrogen or $C_1$-$C_6$alkyl.

In one embodiment of Formula I,

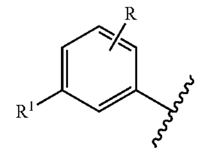

is selected from the group consisting of:

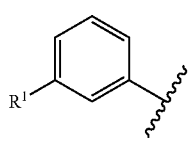
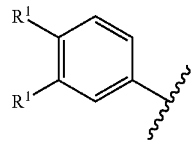
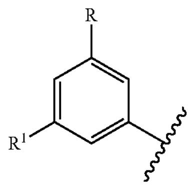
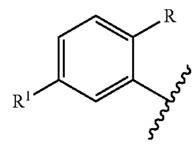
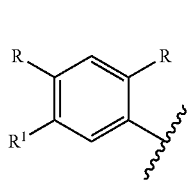
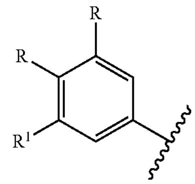
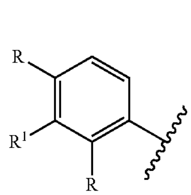
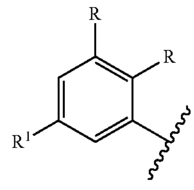
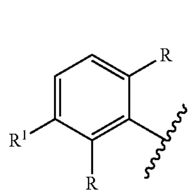
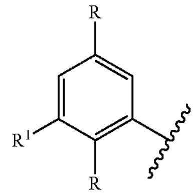
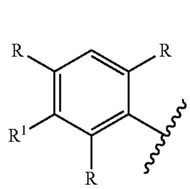
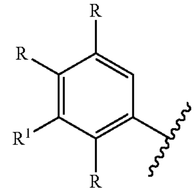

-continued
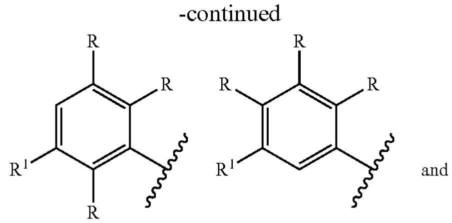
and
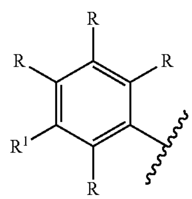
In one embodiment of Formula I,
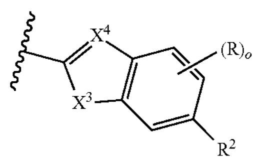
is selected from the group consisting of:
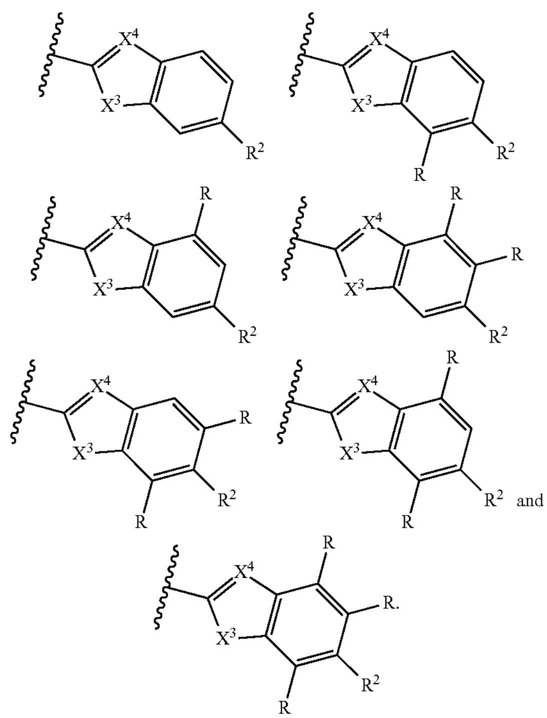
and
In one embodiment of Formula I,
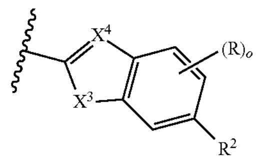
is selected from the group consisting of:
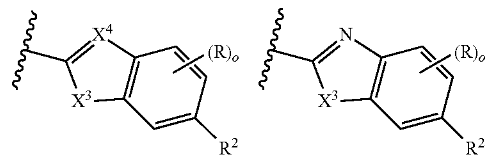
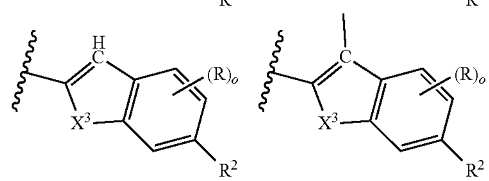
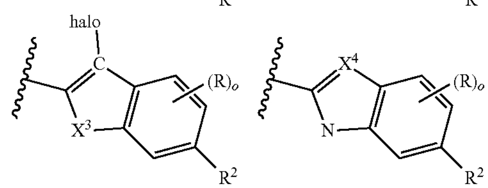
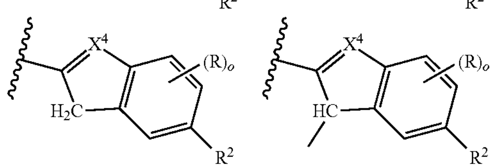
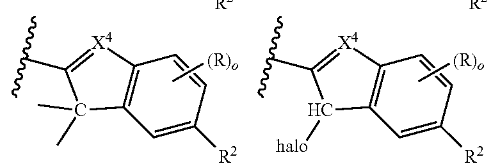
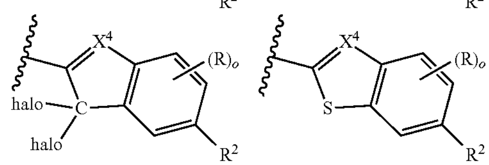
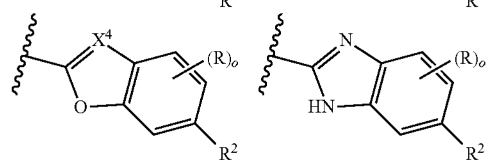
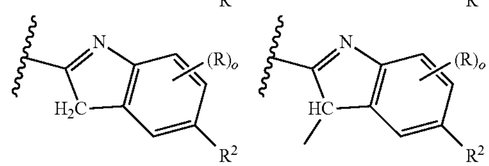
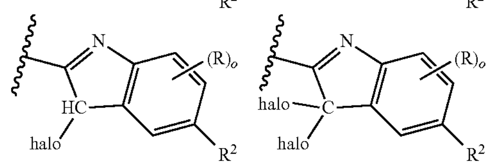

-continued
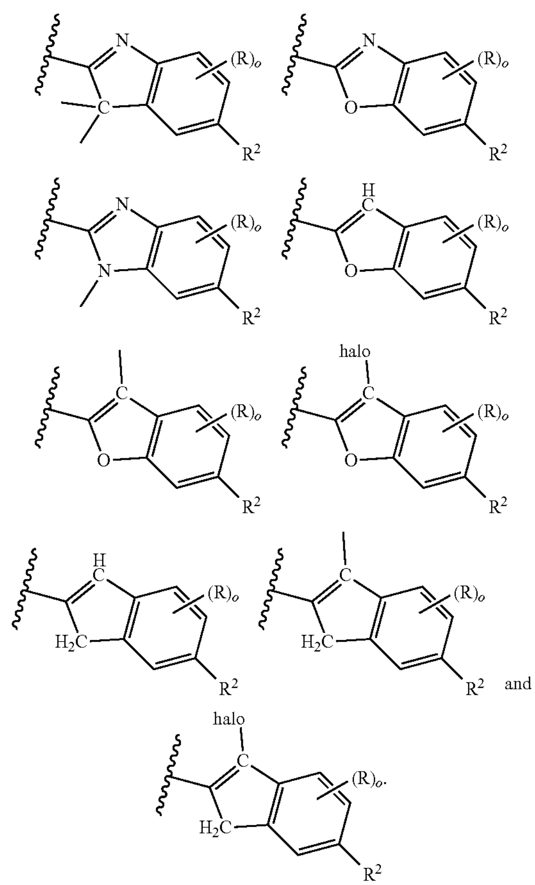
and
In one embodiment of Formula I,
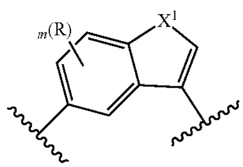
is selected from the group consisting of:
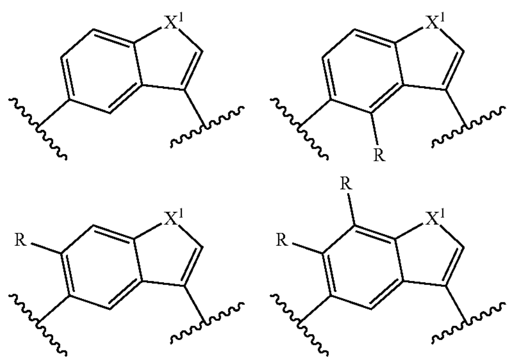
-continued
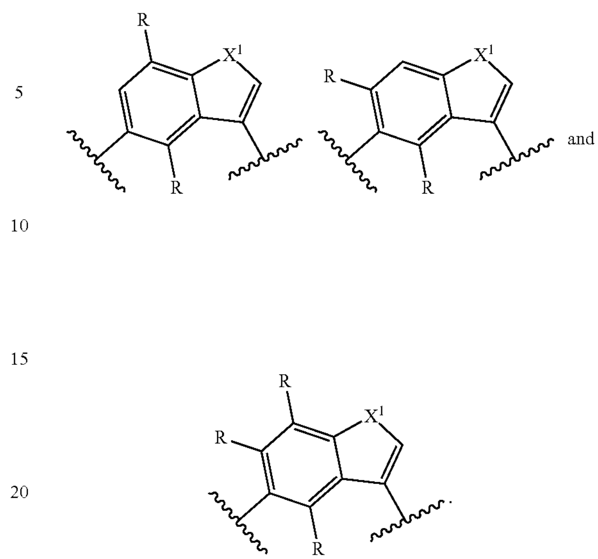
and
In one embodiment of Formula I,
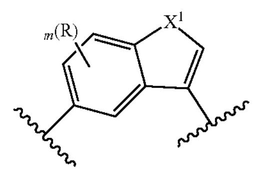
is selected from the group consisting of:
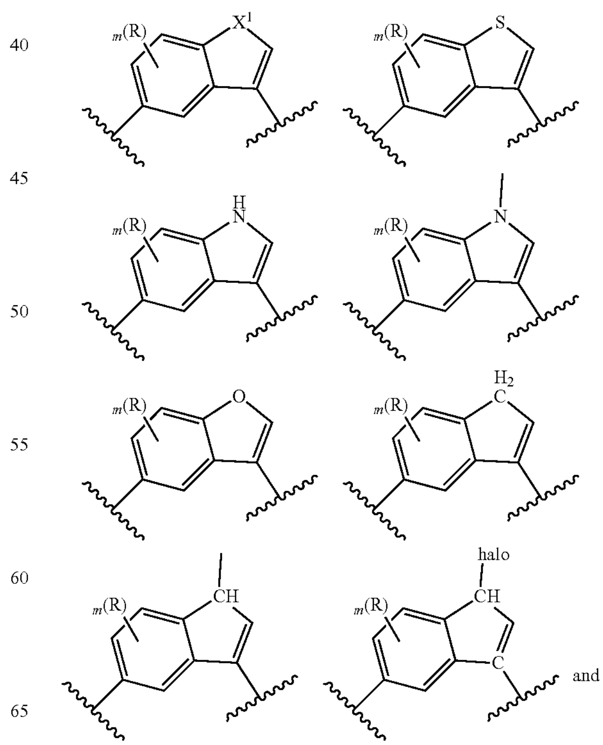
and -continued
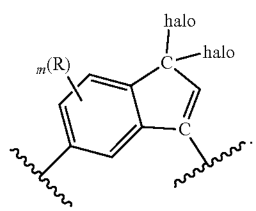
In certain embodiments, the compound of Formula I is a compound of the formula:
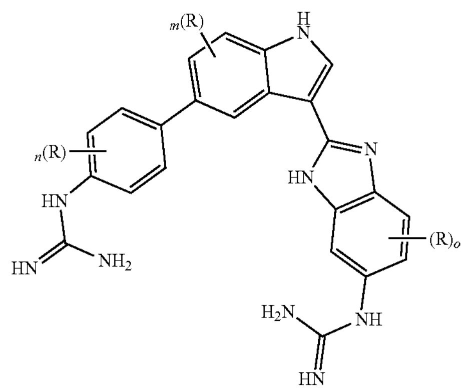
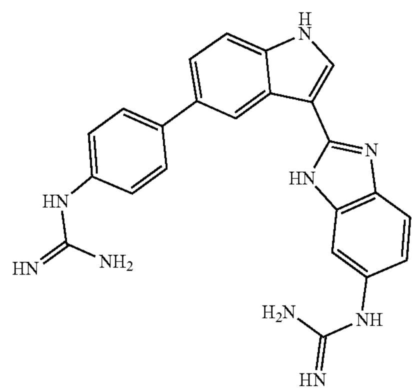
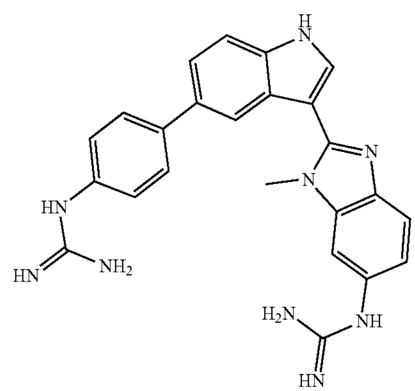
-continued
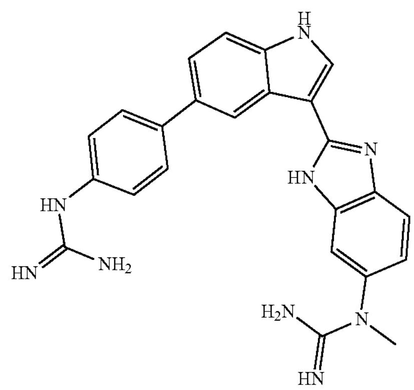
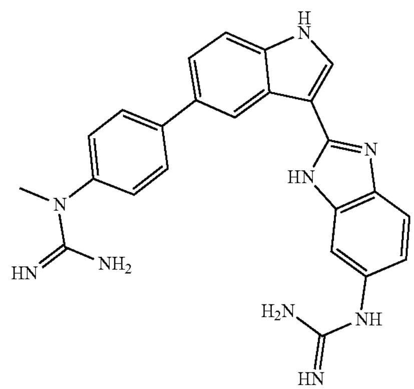
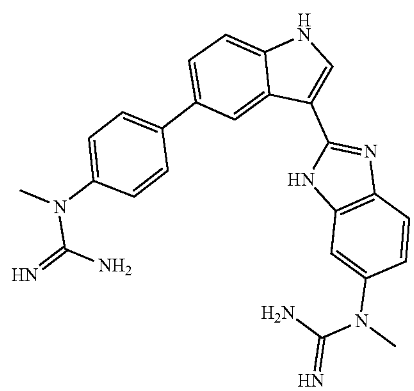
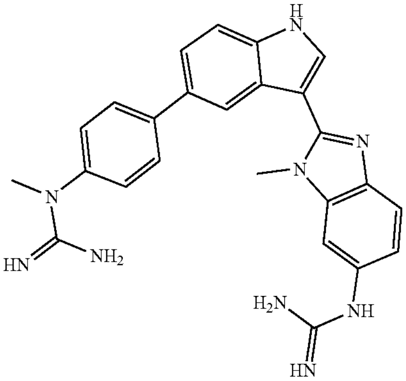

-continued
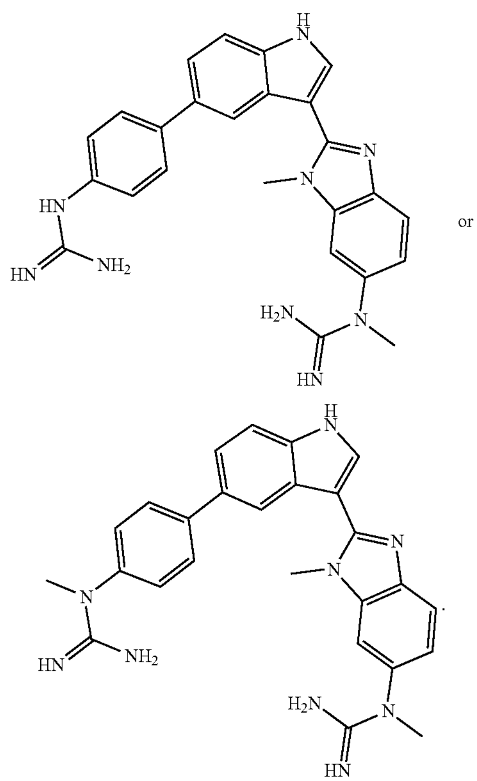
or
In certain embodiments, the compound of Formula I is a compound of the formula:
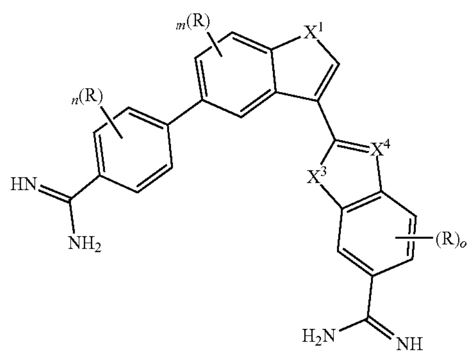
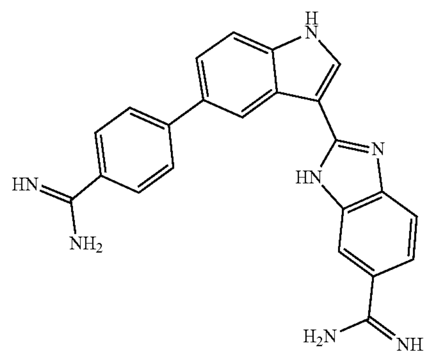
-continued
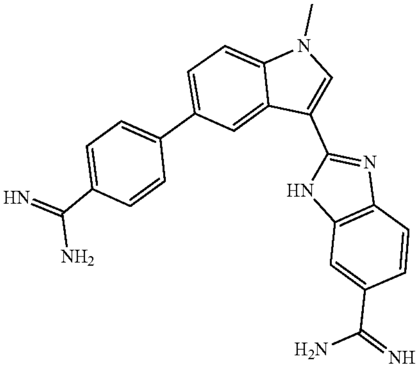
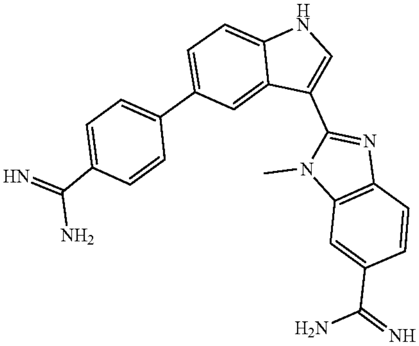
or
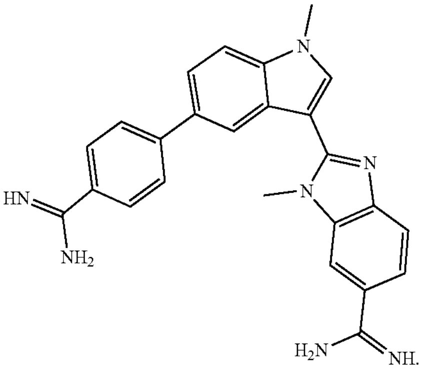
In certain embodiments, the corn und of Formula I is a compound of the formula:
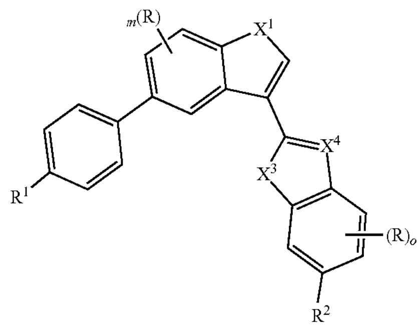

-continued
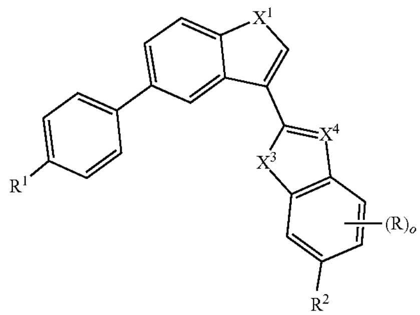
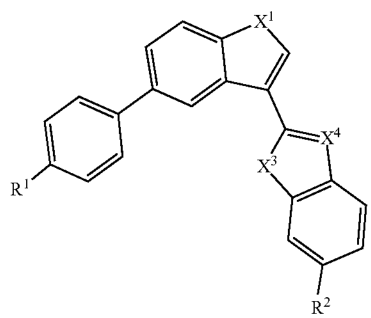
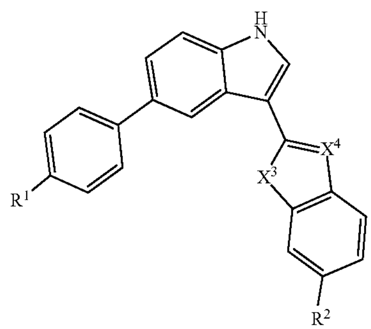
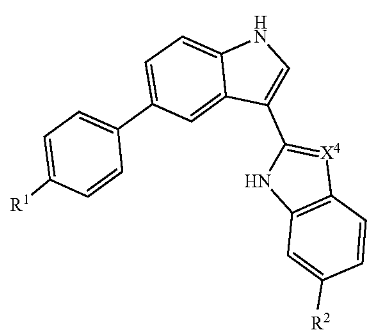
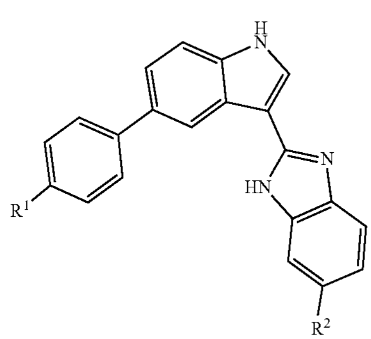
-continued
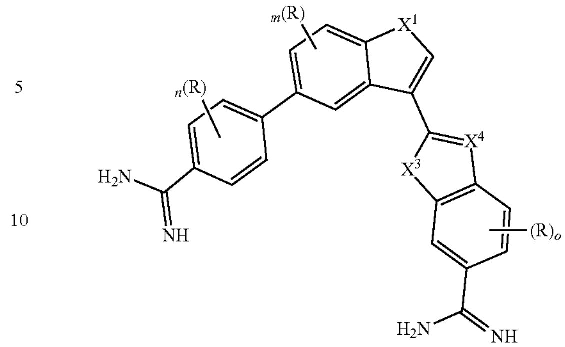
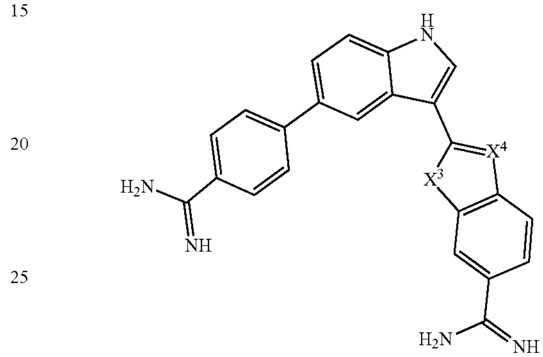
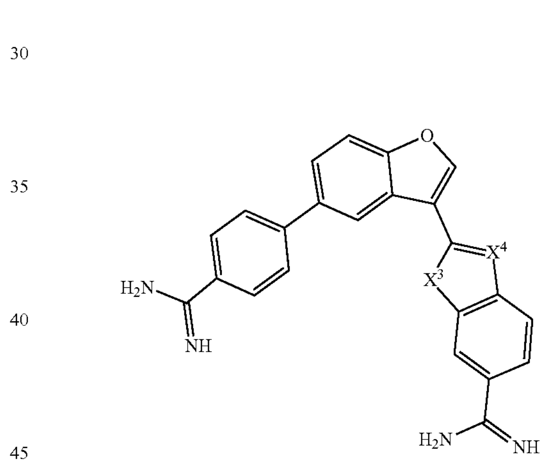
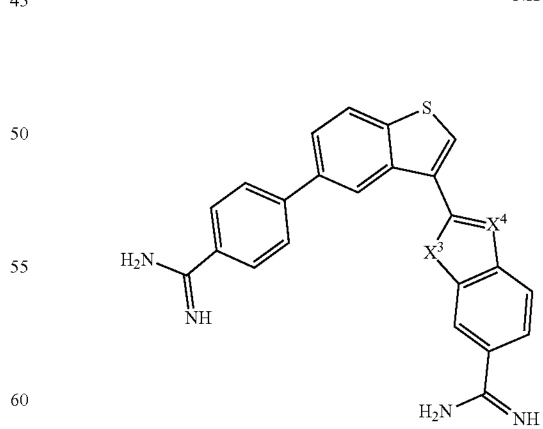
Non-limiting examples of compounds of Formula I include:

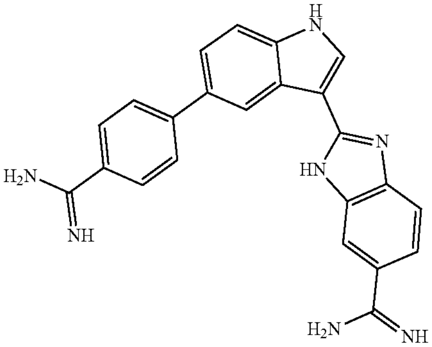
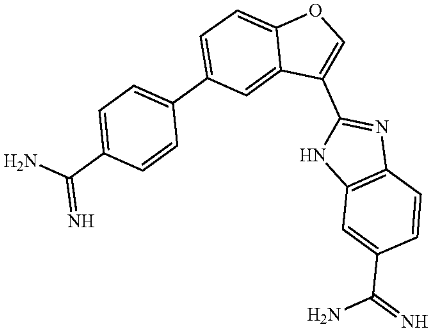
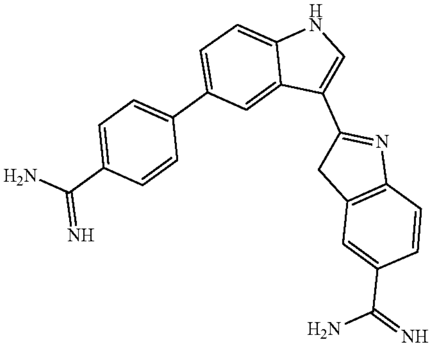
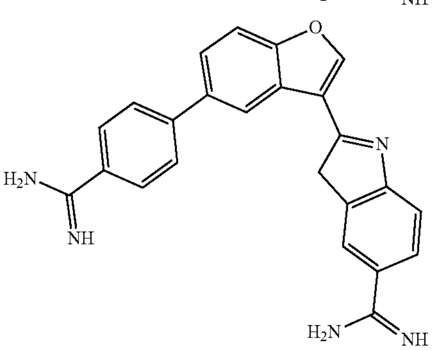
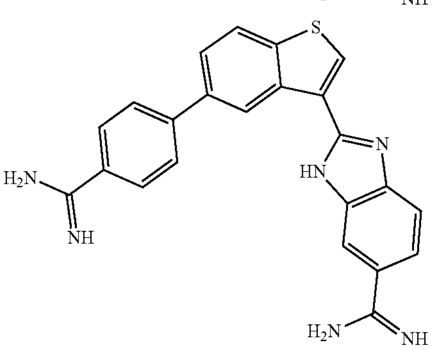
-continued
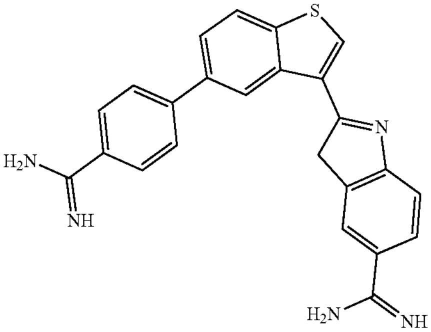
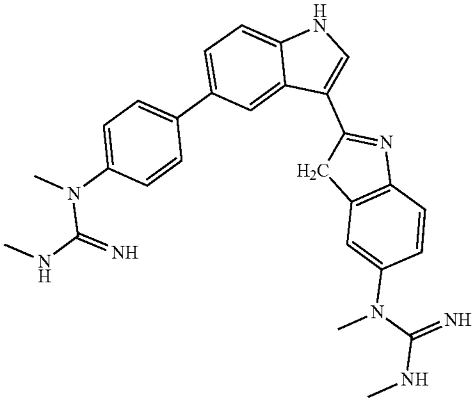
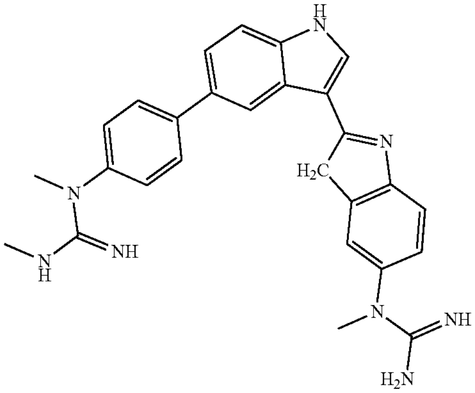
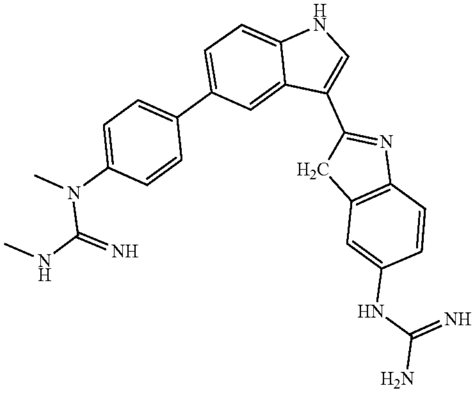

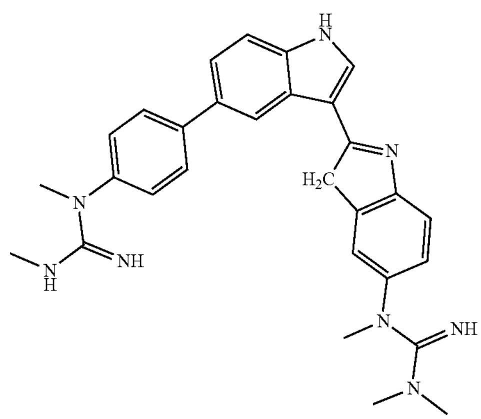
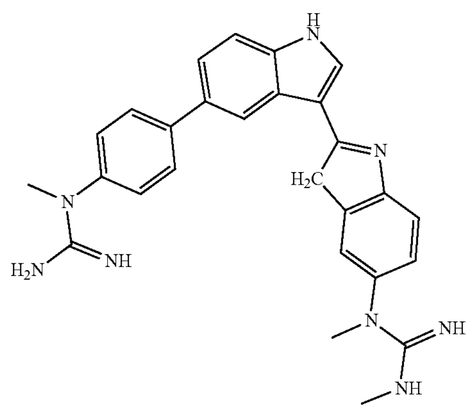
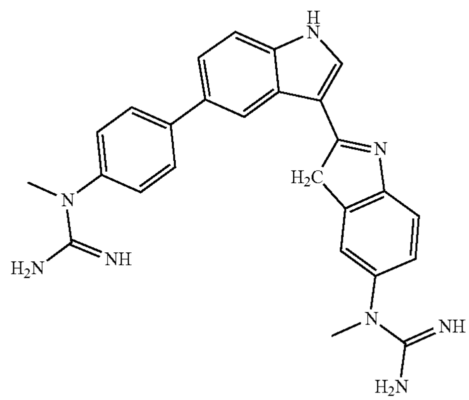
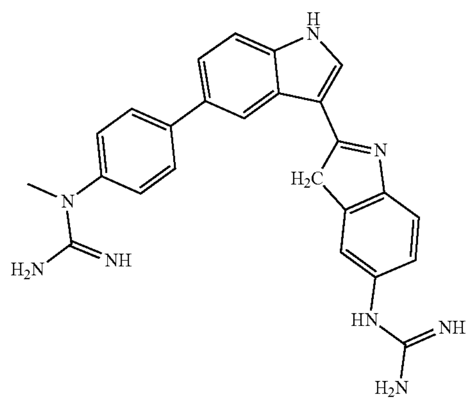
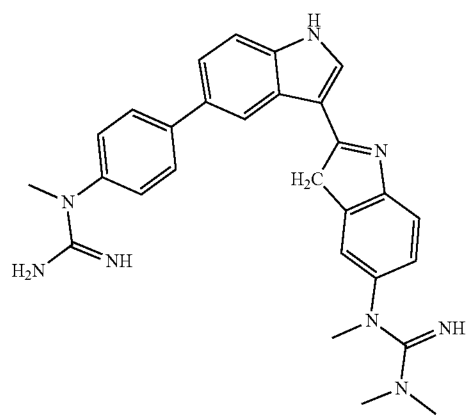
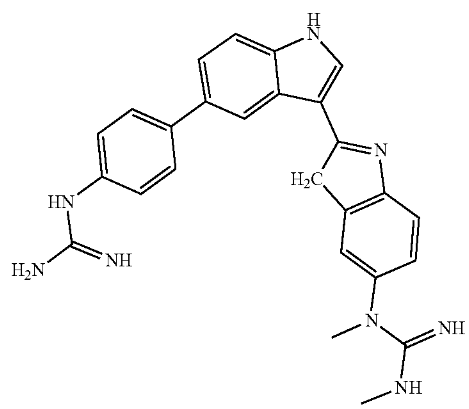
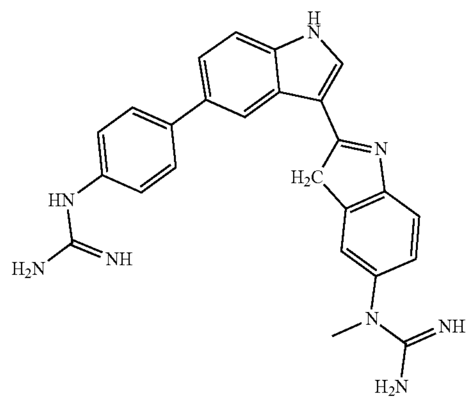
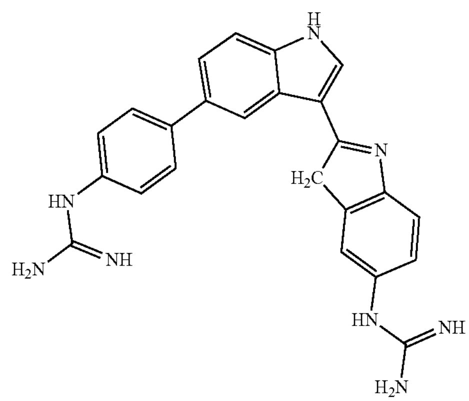

-continued
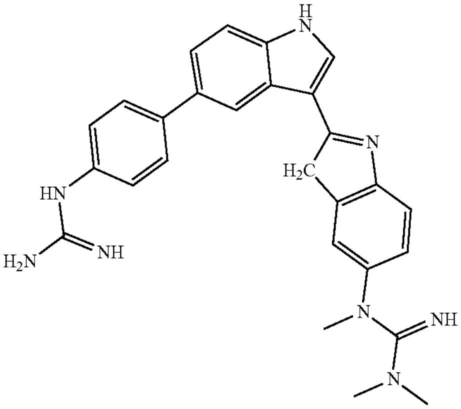
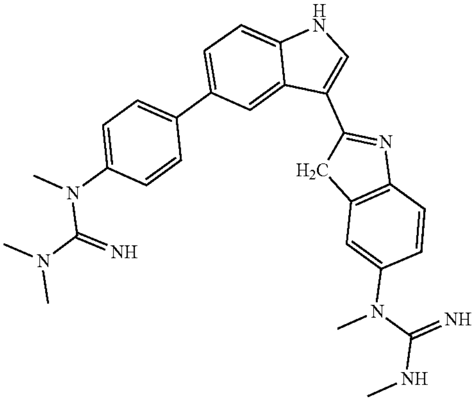
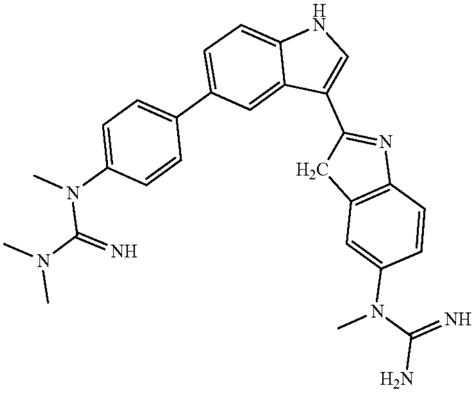
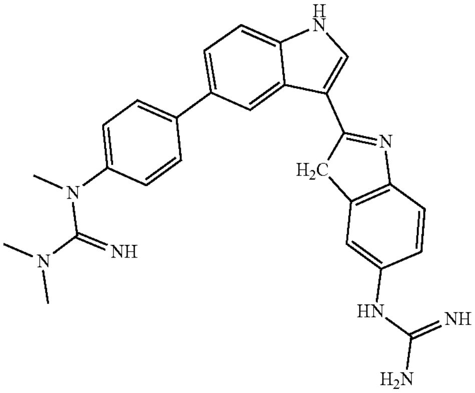
-continued
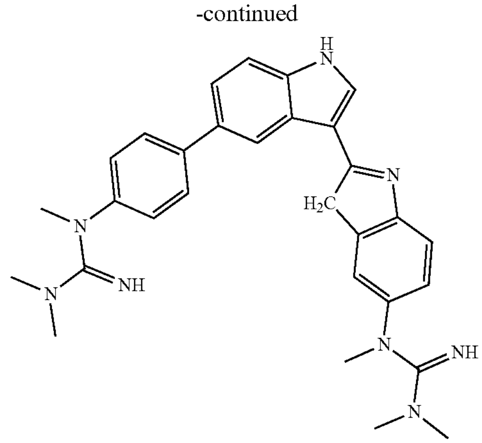
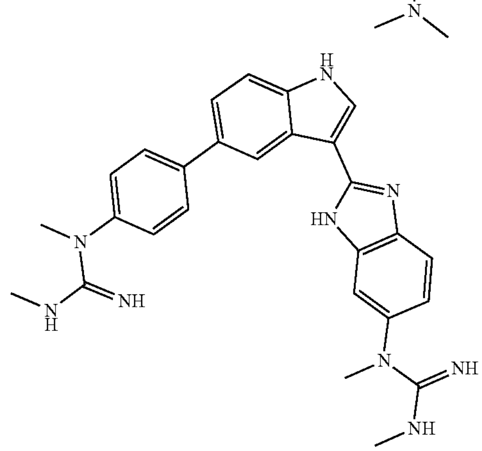
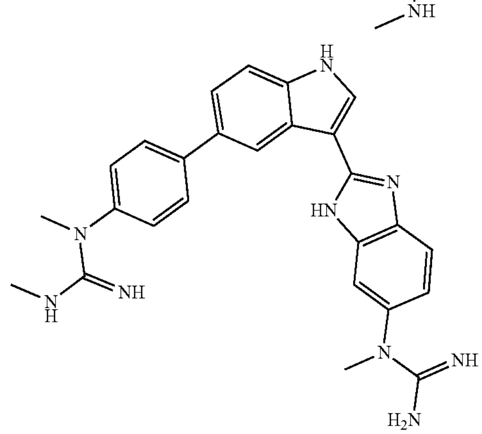
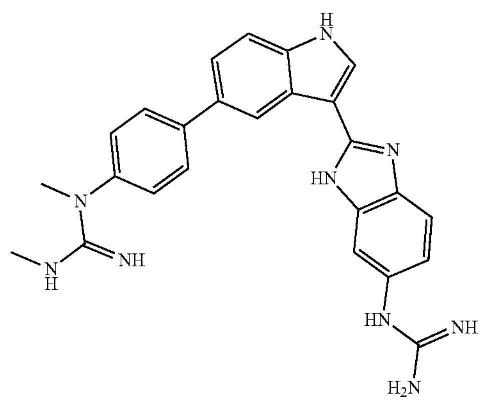

-continued
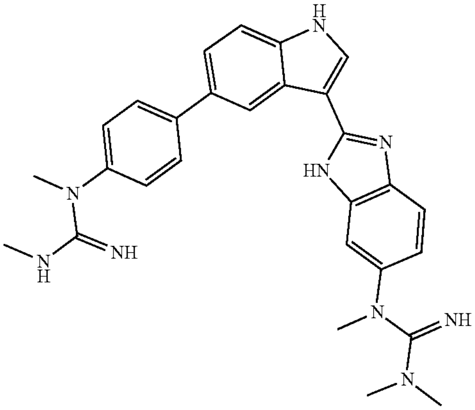
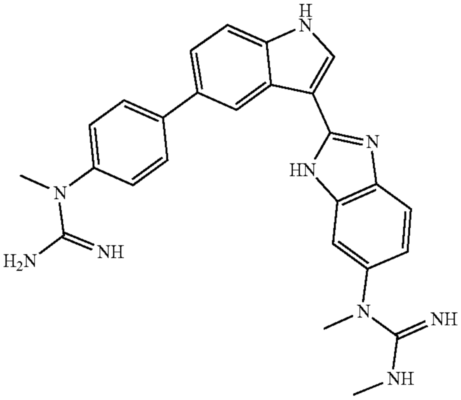
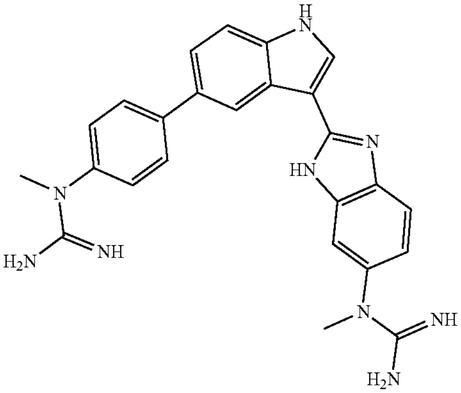
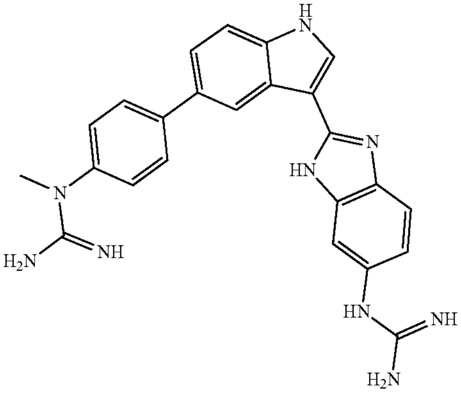
-continued
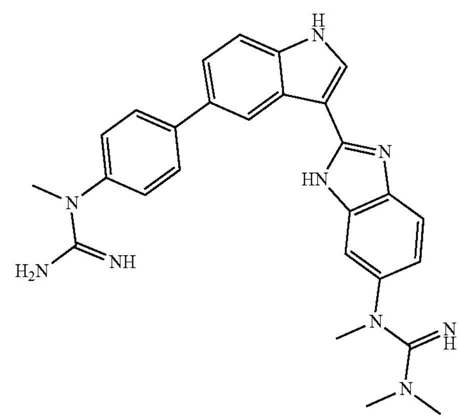
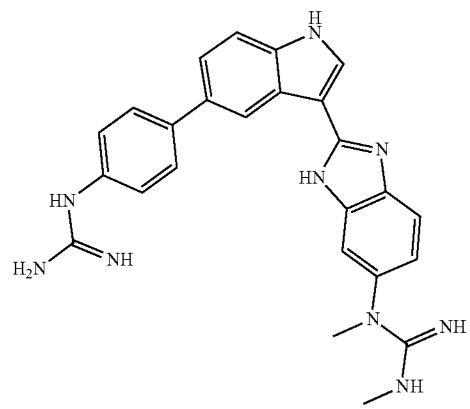
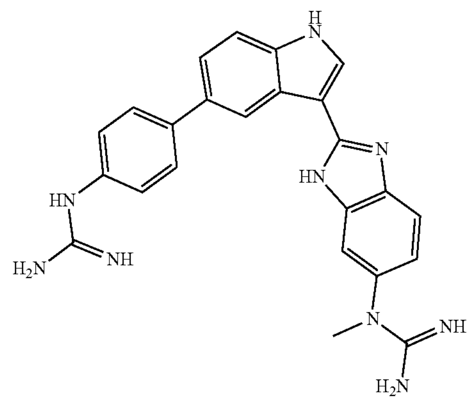
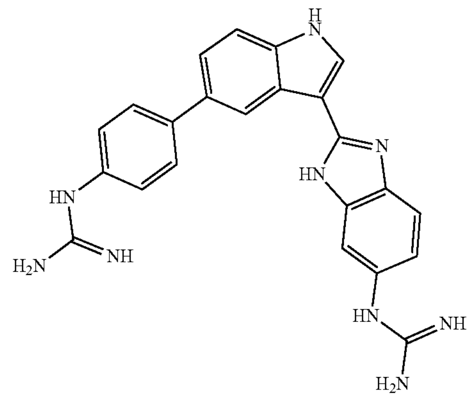

-continued
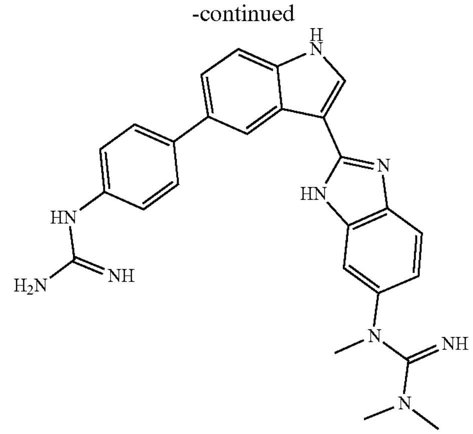
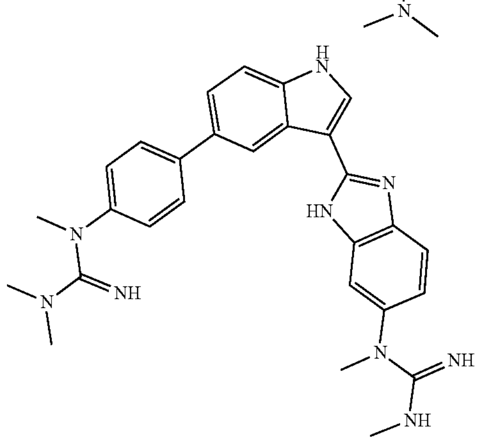
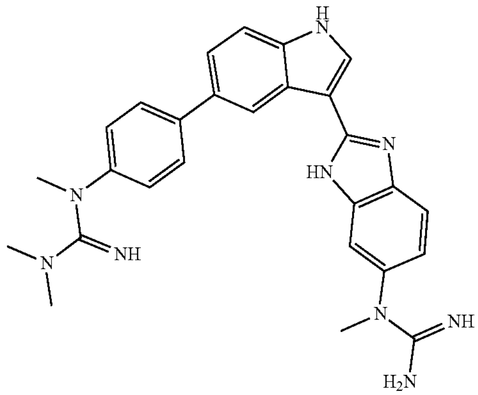
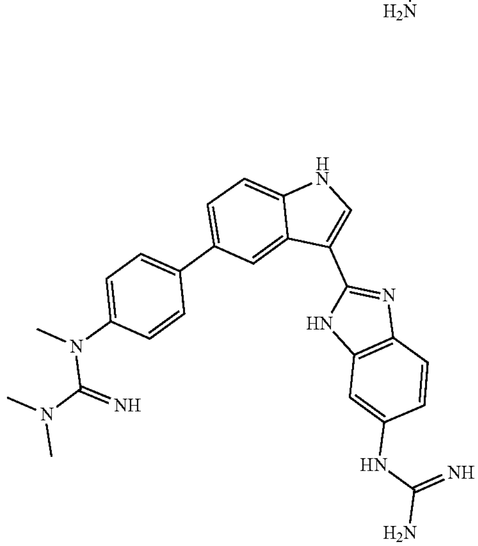
-continued
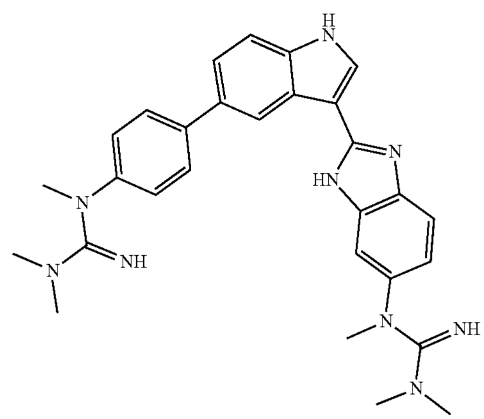
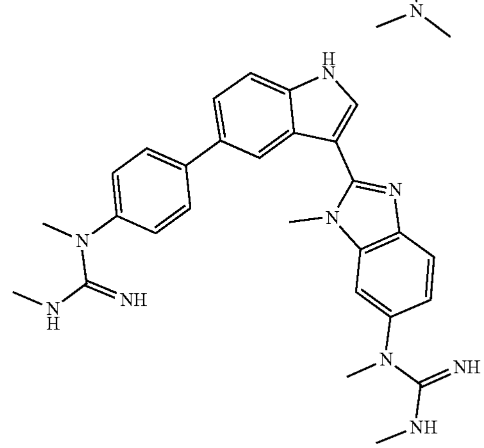
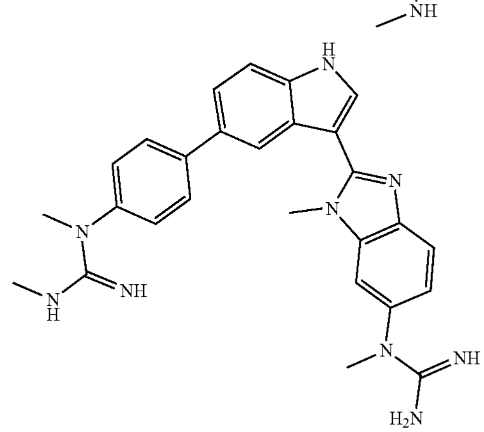
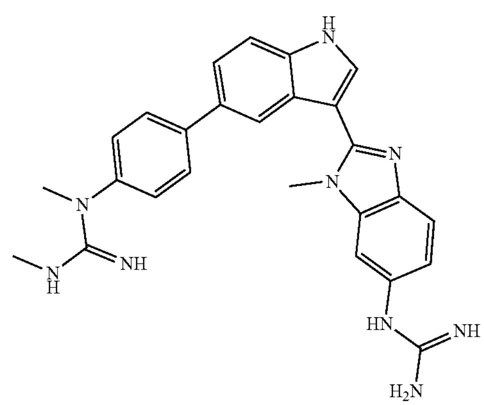

-continued
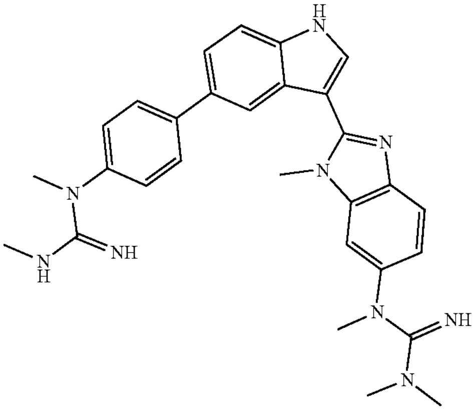
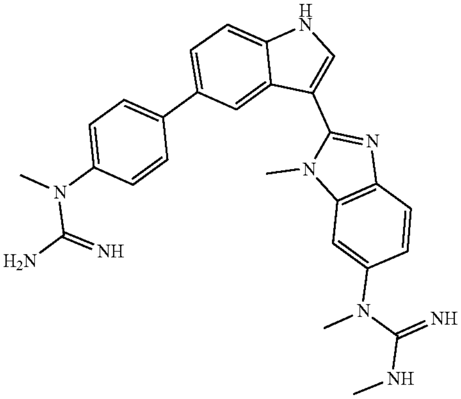
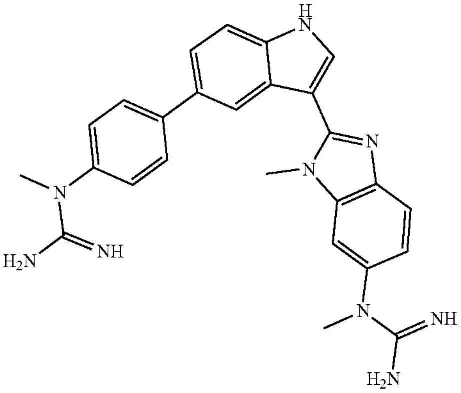
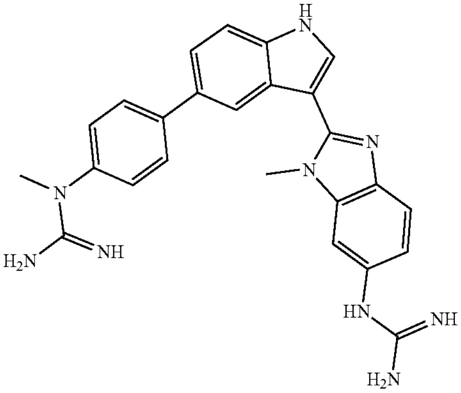
-continued
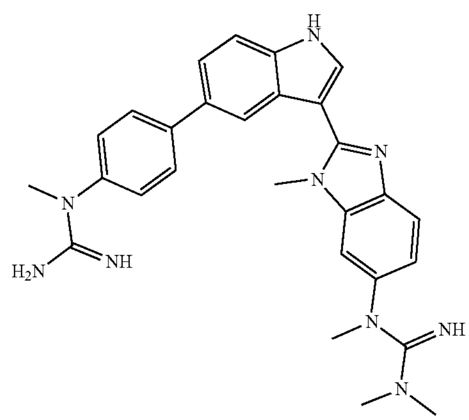
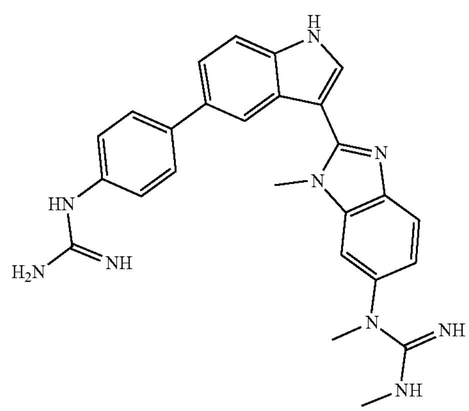
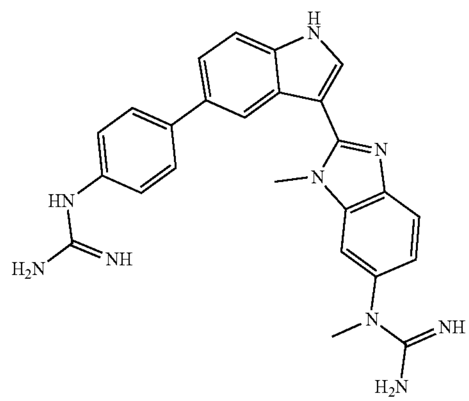
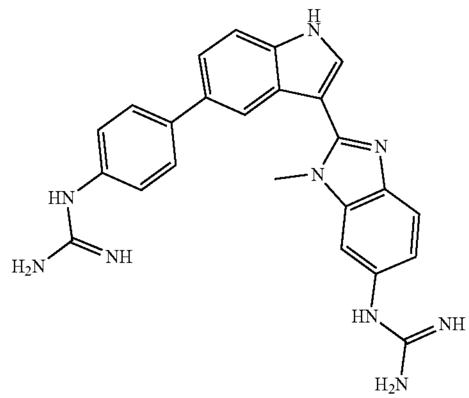

-continued
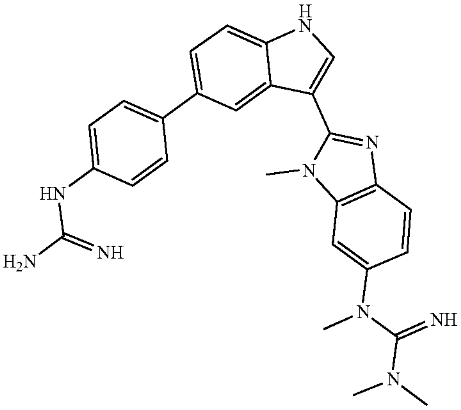
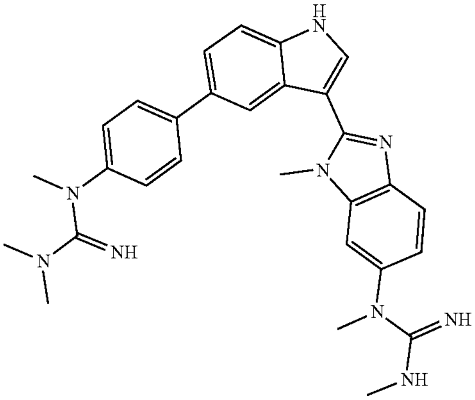
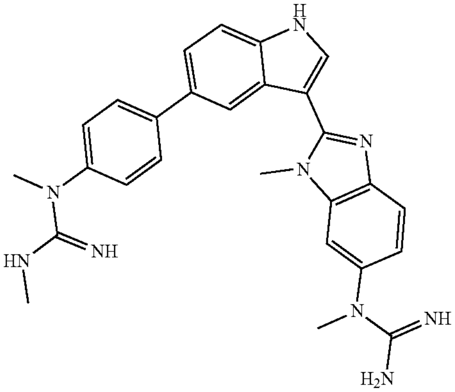
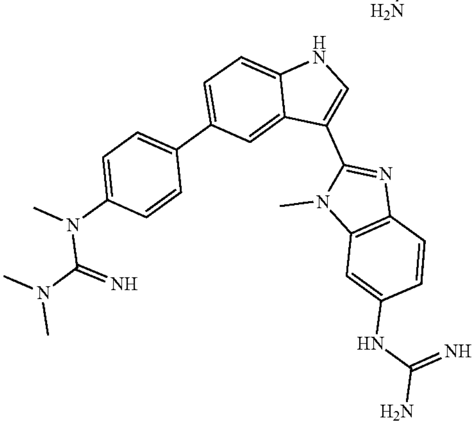
-continued
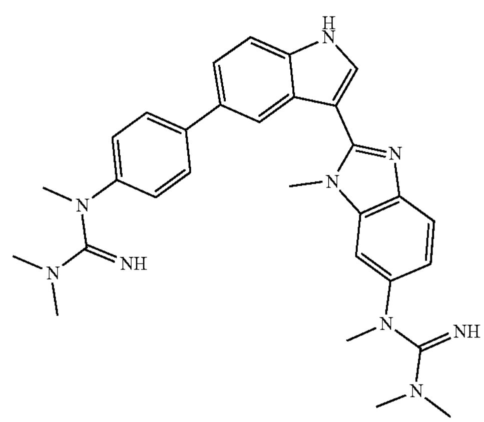
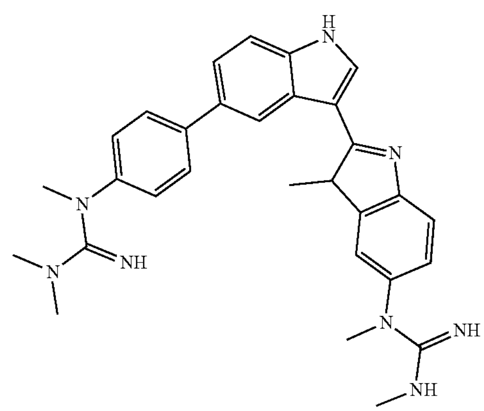
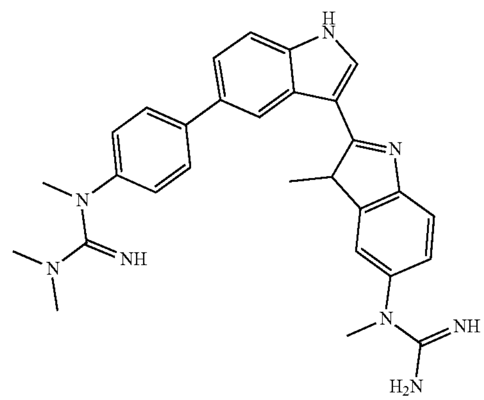
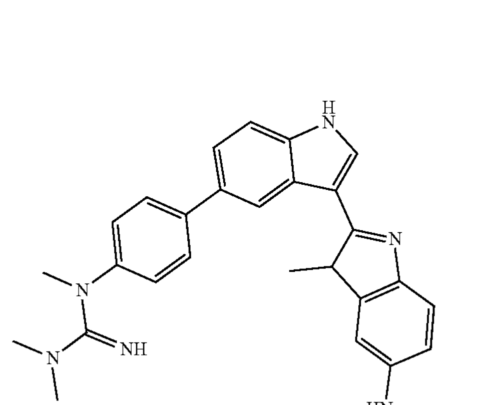
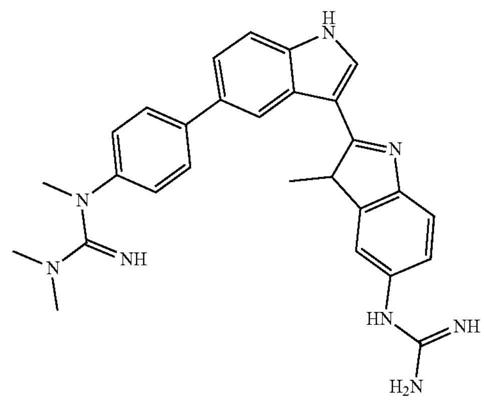

-continued

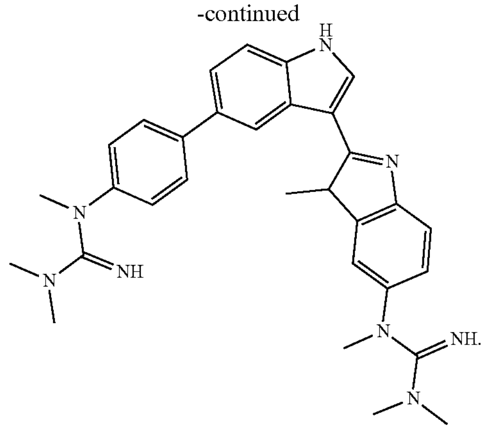

In another aspect, a method is provided for treating a bacterial infection comprising administering an effective amount of a compound of Formula II, Formula III, Formula IV, or Formula V or pharmaceutically acceptable salt thereof to a host in need thereof:

(II)

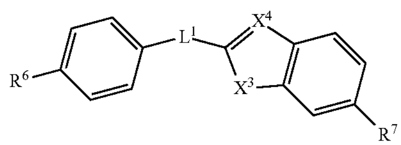

(III)

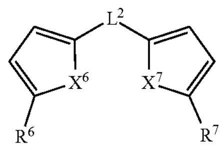

(IV)

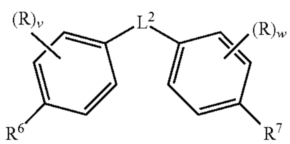

(V)

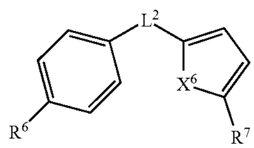

wherein $L^1$ is selected from

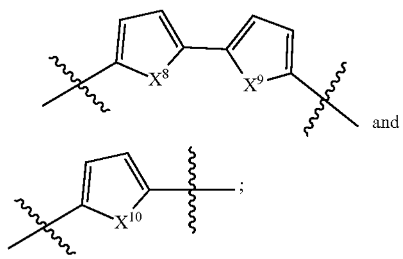

and

;

$L^2$ is selected from

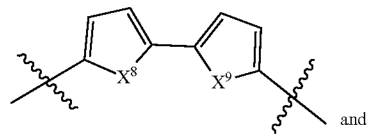

and

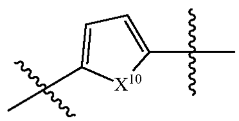

;

v and w are independently selected from 0, 1, 2, 3, and 4;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_{61}$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, — N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$X^6$, $X^7$, $X^8$, and $X^9$ are independently selected from O, S, NH, or Se;

$X^{10}$ is selected from Se, S, or NH;

$R^6$ and $R^7$ are independently at each occurrence selected from the group consisting of:

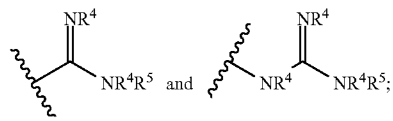

and

;

and

R, $R^1$, $R^2$, $R^4$, and $R^5$ are as defined herein.

In some embodiments of Formula II, Formula III, Formula IV, and/or Formula V, $X^{10}$ is not S.

In some embodiments of Formula II, Formula III, Formula IV, and/or Formula V, $X^{10}$ is not NH.

In some embodiments of Formula II, Formula III, Formula IV and/or Formula V, $L^2$ is not

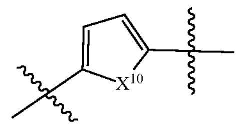

.

In some embodiments of Formula II, Formula III, Formula IV and/or Formula V, one or more of $X^6$, $X^7$, $X^8$, and $X^9$ is not NH.

In some embodiments of Formula II, the compound has a chemical structure selected from:

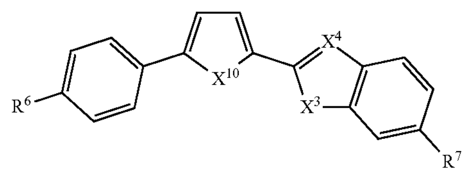

-continued
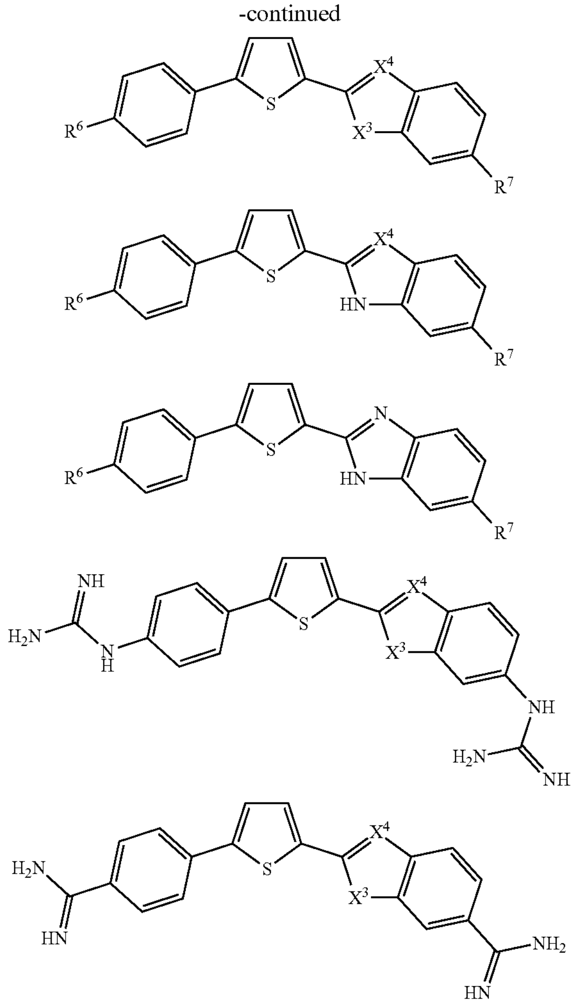
Non-limiting examples of compounds of Formula II include:
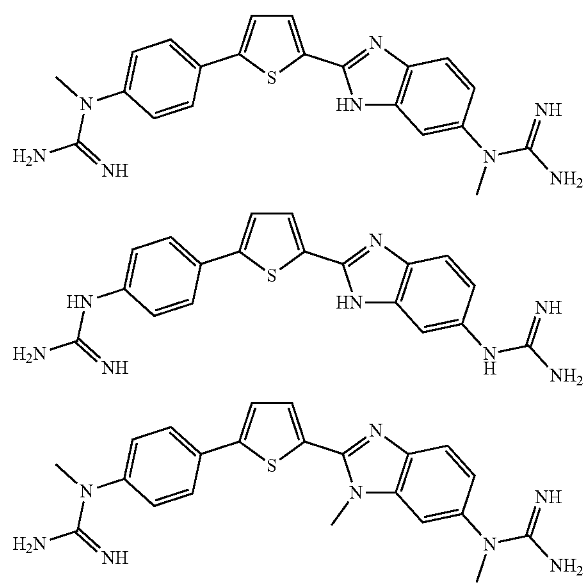
-continued
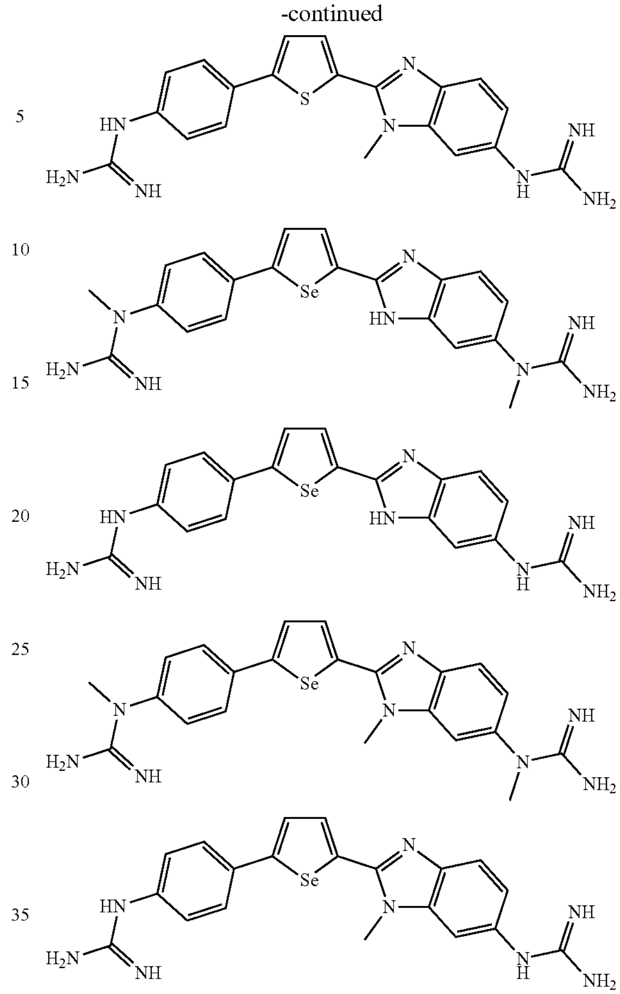
In some embodiments of Formula III, the compound has a chemical structure selected from:
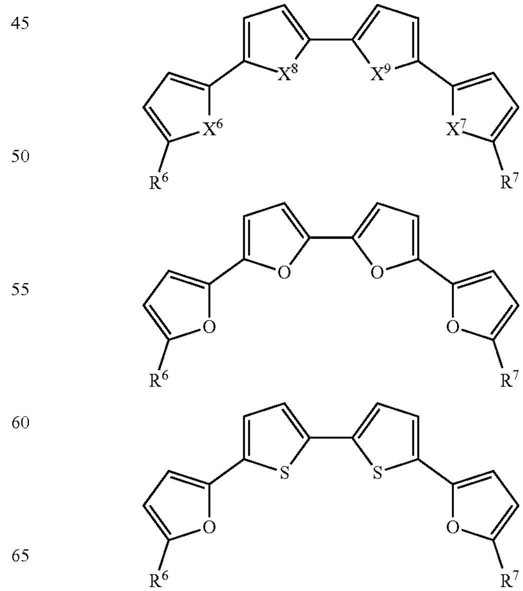

-continued
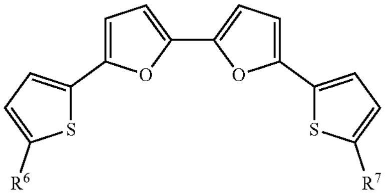
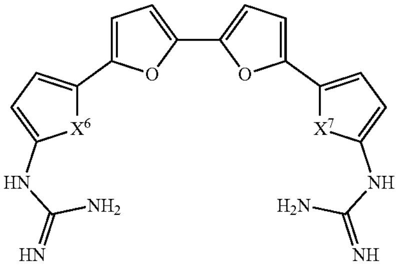
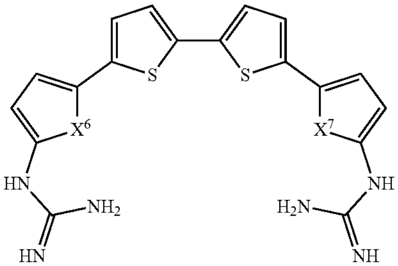
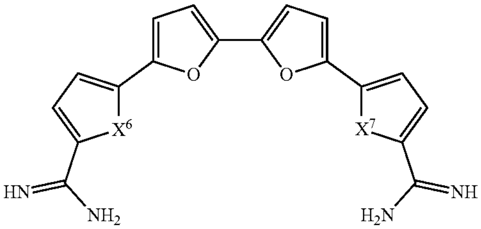
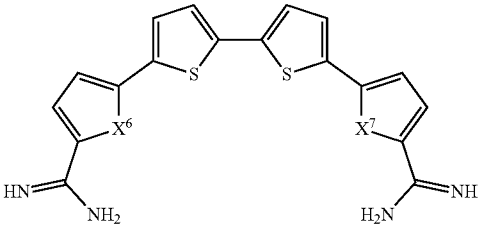
Non-limiting examples of compounds of Formula III include:
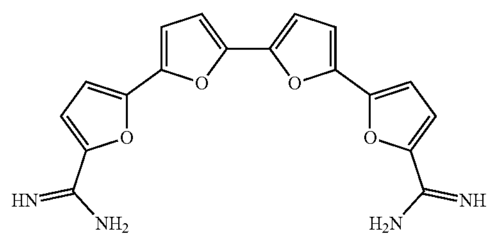
-continued
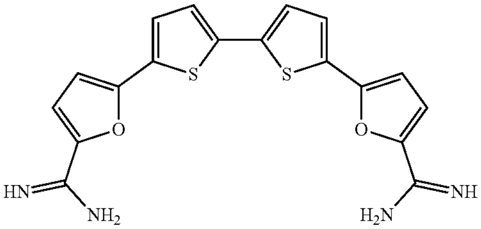
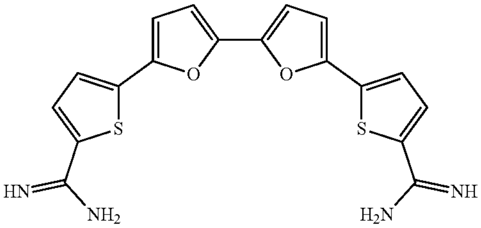
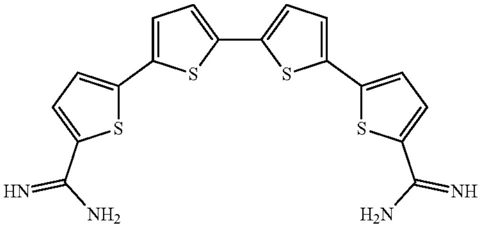
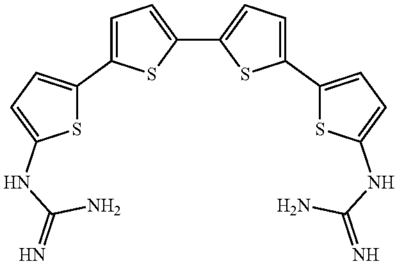
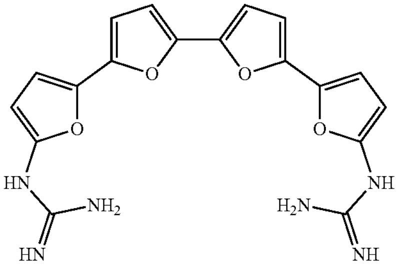
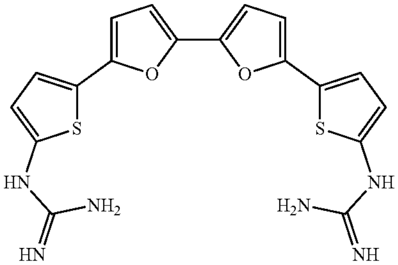

-continued
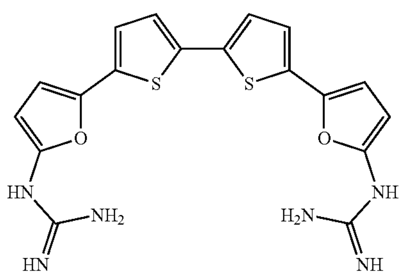
In some embodiments of Formula IV, the compound has a chemical structure selected from:
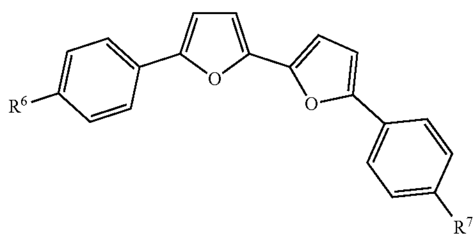
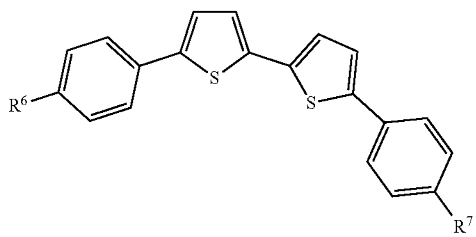
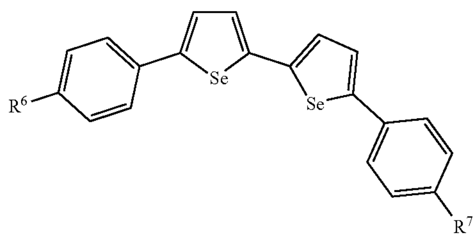
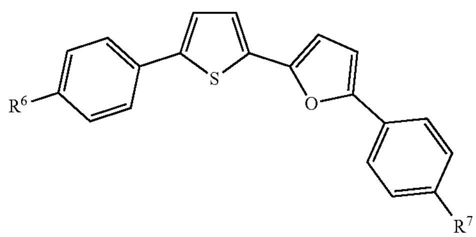
Non-limiting examples of compounds of Formula IV include:
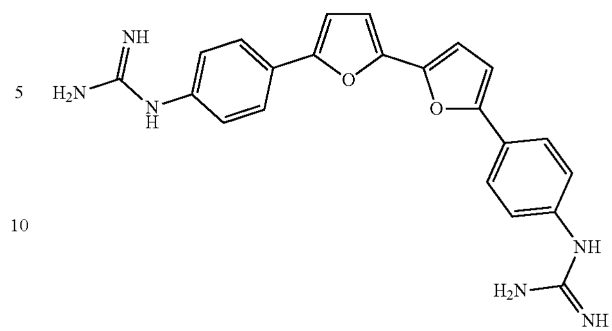
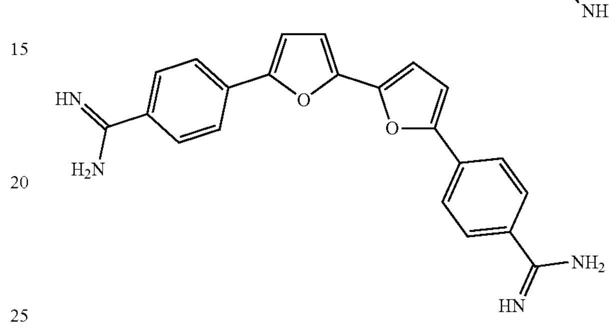
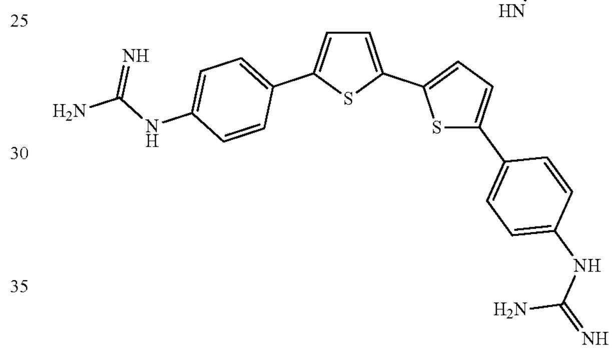
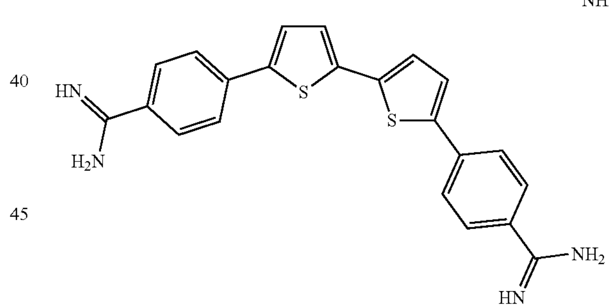
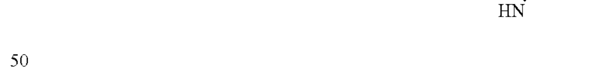
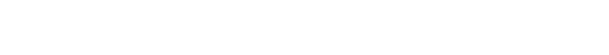
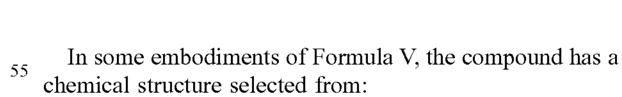
In some embodiments of Formula V, the compound has a chemical structure selected from:
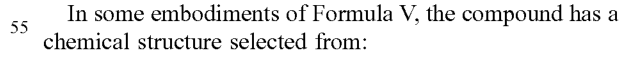
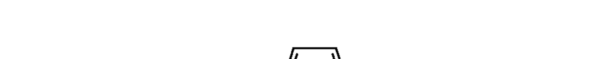
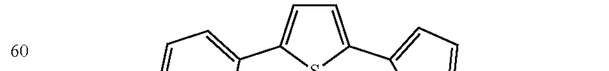
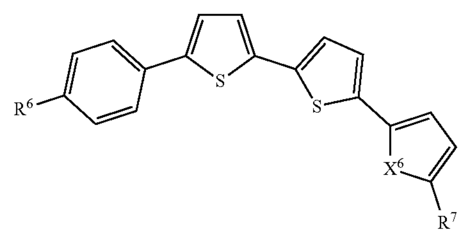
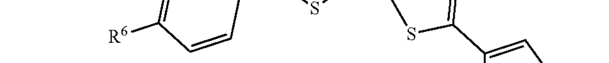
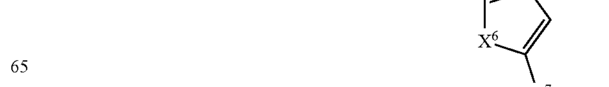
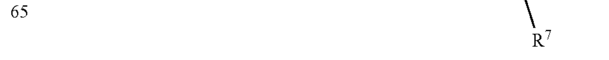
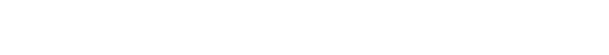
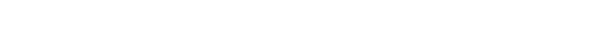

-continued
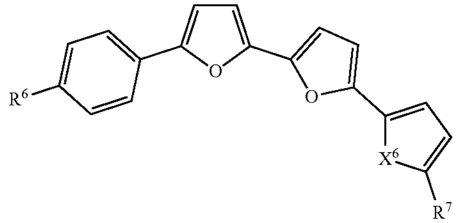
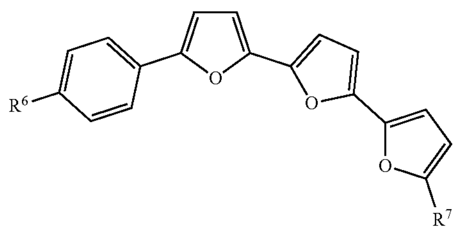
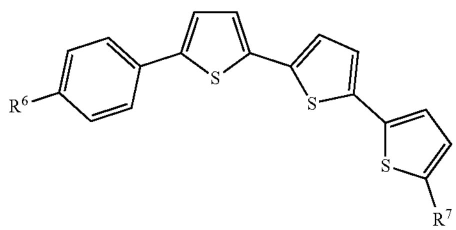
Non-limiting examples of compounds of Formula V include:
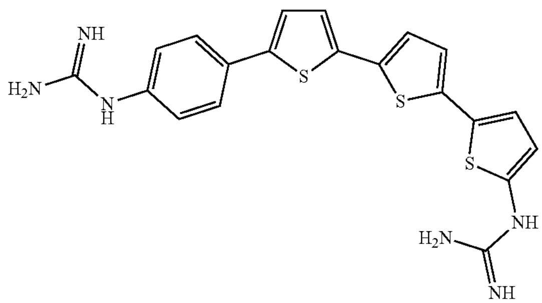
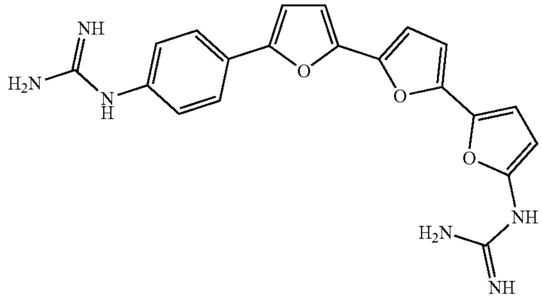
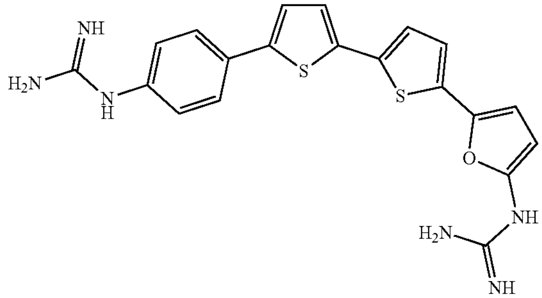
-continued
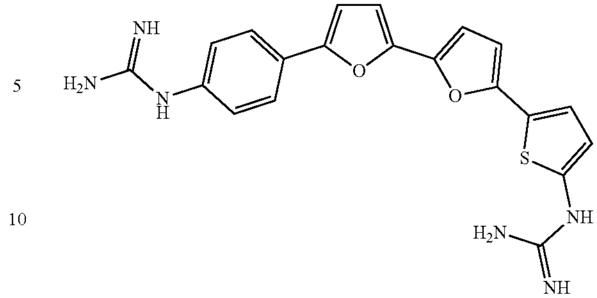
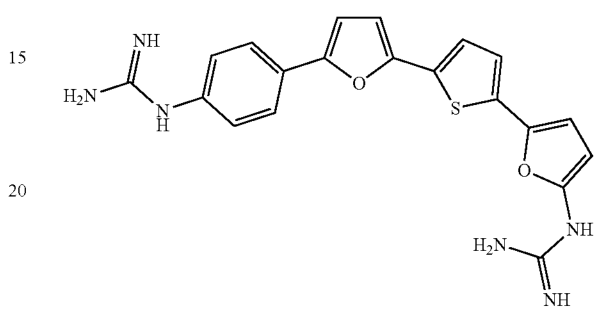
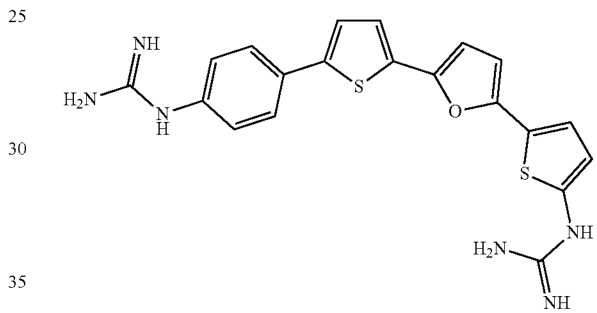
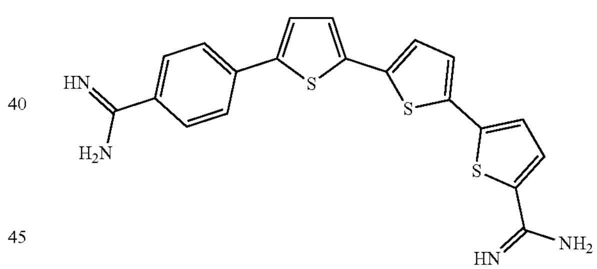
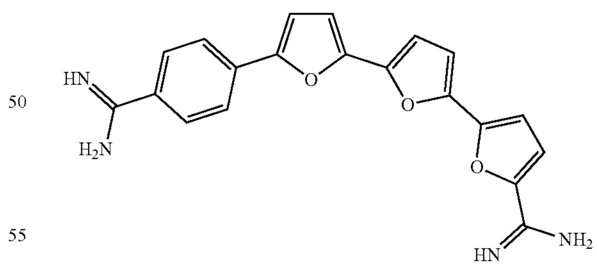
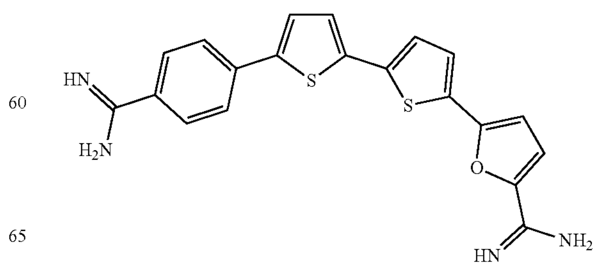

-continued

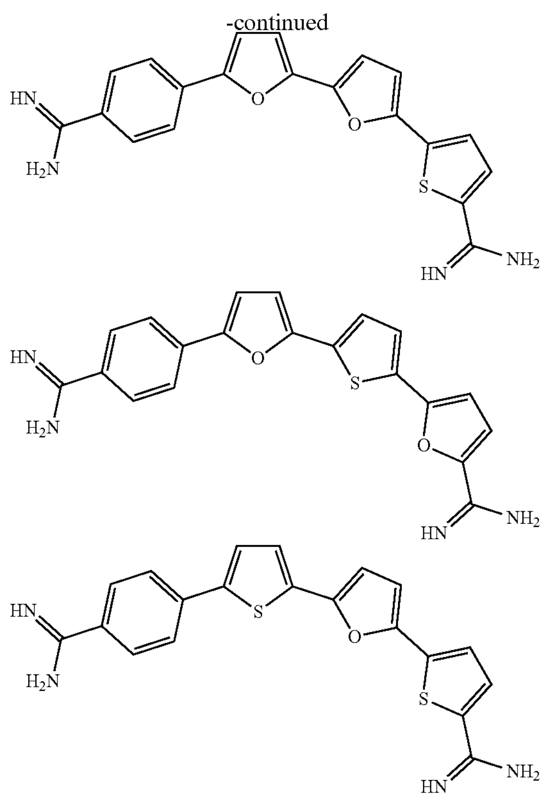

In another aspect, a method is provided for treating a gram-positive or a gram-negative bacterial infection comprising administering an effective amount of a compound of Formula VI:

(VI)

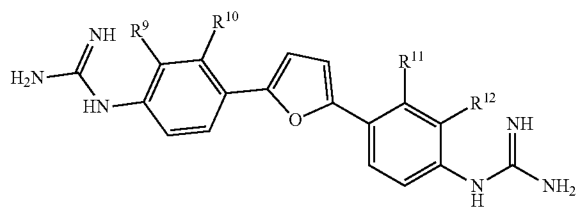

or a pharmaceutically acceptable salt thereof wherein $R^9$ and $R^{12}$ are independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl) $SO_2$alkenyl, —$NHSO_2$alkynyl, —N(alkyl)$SO_2$alkynyl, $NO_2$, —COOH, —$CONH_2$, —P(O)$(OH)_2$, —S(O)$R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano; and $R^{10}$ and $R^{11}$ are independently at each occurrence selected from the group consisting of hydroxyl, $C_1$-$C_6$alkanoyl, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl) $SO_2$alkynyl, $NO_2$, —COOH, —$CONH_2$—, —C(O)R, —P(O)$(OH)_2$, —S(O)$R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, bromine, iodine, thiol, and cyano.

In one embodiment, the compound of Formula VI is a compound of the Formula:

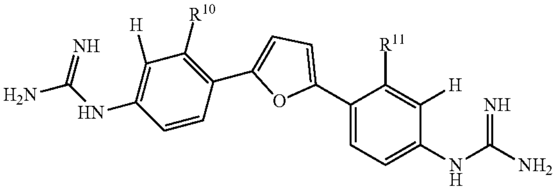

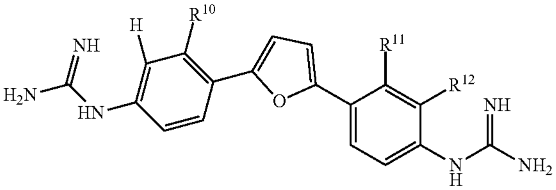

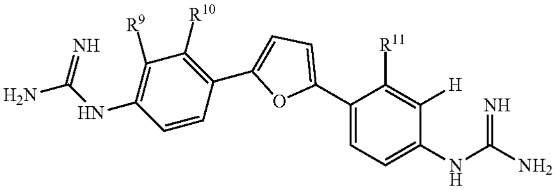

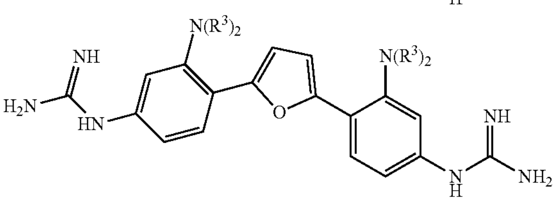

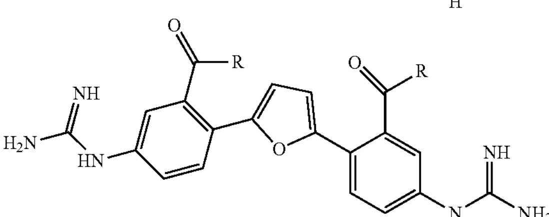

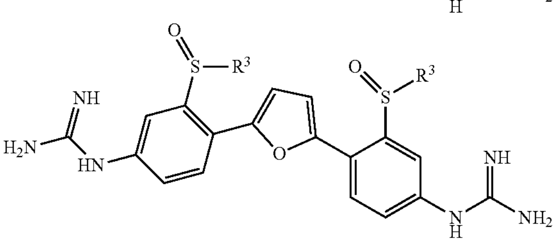

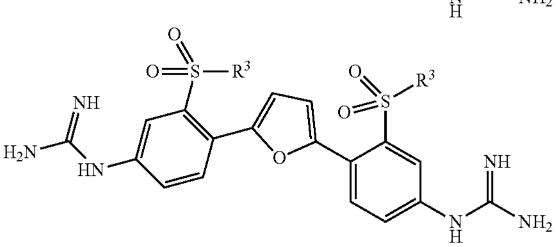

-continued

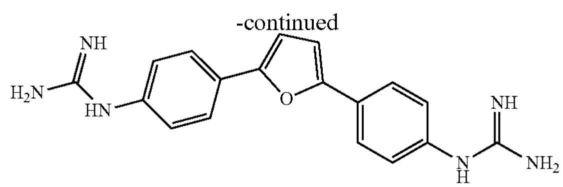

In one aspect, a compound of Formula VII or Formula VIII or a pharmaceutically acceptable salt is provided:

(VII)

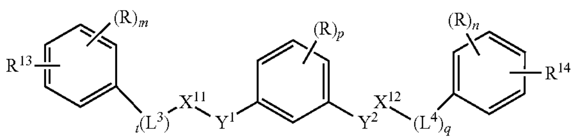

(VIII)

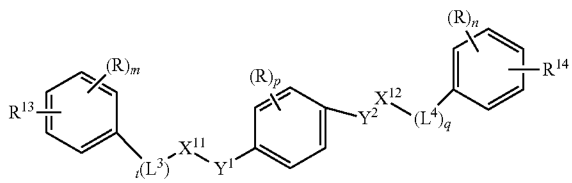

wherein:

m and n are independently selected from 1, 2, 3, or 4;

p is 0, 1, 2, or 3;

q and t are independently at each occurrence 0, 1, 2, 3, 4, 5, 6, 7, 8, 9, or 10;

$L^3$ and $L^4$ are each independently $C(R^3)_2$, O, or S;

R is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano;

$R^3$ is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, heteroaryl, aryl, heterocyclyl, —COOR, —C(O)R, fluorine, chlorine, bromine, and iodine;

$R^{13}$ and $R^{14}$ are independently selected from the group consisting of

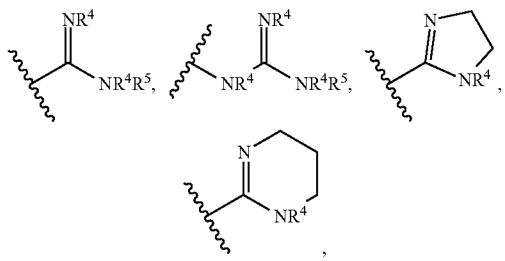

and —$C(R^3)NR^4R^5$ wherein $R^4$ and $R^5$ are independently at each occurrence selected from the group consisting of hydrogen and $C_1$-$C_6$alkyl and o is 0 to 10 (i.e., 0, 1, 2, 3, 4, 5, 6, 7, 8, 9, or 10);

$X^{11}$ and $X^{12}$ are each independently selected from the group consisting of $C(R^3)_2$, O, NH, or S, wherein $R^3$ is independently at each occurrence selected from a group as defined above;

$Y^1$ and $Y^2$ are each independently selected from the group consisting of $C(R^3)_2$, O, NH, or S, wherein $R^3$ is independently at each occurrence selected from a group as defined above; and Z is $CR^3$ or N, wherein $R^3$ is as defined above.

In some cases, a compound is provided of Formula VII or Formula VIII or a pharmaceutically acceptable salt thereof, optionally in a pharmaceutically acceptable carrier, to form a pharmaceutical composition.

In some cases of Formula VII or Formula VIII, $R^{13}$ is

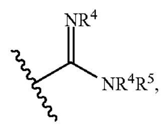

wherein $R^4$ and $R^5$ are independently hydrogen or $C_1$-$C_6$alkyl. In some cases of Formula VII or Formula VIII, $R^{13}$ is

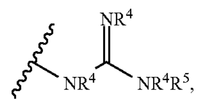

wherein $R^4$ and $R^5$ are independently hydrogen or $C_1$-$C_6$alkyl.

In some examples of Formula VII or Formula VIII, $R^4$ is

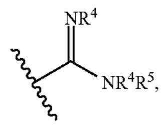

wherein $R^4$ and $R^5$ are independently hydrogen or alkyl. In some examples of Formula VII or Formula VIII, $R^{14}$ is

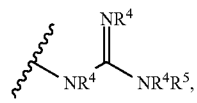

wherein $R^4$ and $R^5$ are independently hydrogen or $C_1$-$C_6$alkyl.

In some examples of Formula VII or Formula VIII, $R^{13}$ and $R^{14}$ are each

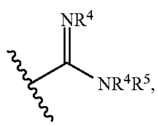

wherein $R^4$ and $R^5$ are independently hydrogen or $C_1$-$C_6$alkyl. In some examples of Formula VII or Formula VIII, $R^{13}$ and $R^{14}$ are each

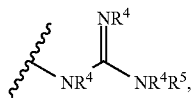

wherein $R^4$ and $R^5$ are independently hydrogen or $C_1$-$C_6$alkyl. In some cases, $R^4$ and $R^5$ are hydrogen.

Optionally, $X^{11}$ and $X^{12}$ are selected from the group consisting of O, $CH_2$, and S. In some cases, $X^{11}$ and $X^{12}$ are the same (e.g., $X^{11}$ and $X^{12}$ are each O, $X^{11}$ and $X^{12}$ are each $CH_2$, or $X^{11}$ and $X^{12}$ are each S).

Optionally, $Y^1$ and $Y^2$ are selected from the group consisting of O and $CH_2$. In some cases, $Y^1$ and $Y^2$ are the same (e.g., $Y^1$ and $Y^2$ are each O or $Y^1$ and $Y^2$ are each $CH_2$).

In some cases, each R is independently selected from the group consisting of hydrogen, $C_1$-$C_6$alkyl, $C_1$-$C_6$alkoxy, $C_1$-$C_6$haloalkyl, and fluorine is $C_1$-$C_6$alkyl, $C_1$-$C_6$alkoxy, or $C_1$-$C_6$haloalkyl.

In Formula VII, when t is 0, $L^3$ is absent and a direct bond is present between $X^{11}$ and the ring to which $L^3$ is connected in the structure. Similarly, in Formula VII, when q is 0, $L^4$ is absent and a direct bond is present between $X^{12}$ and the ring to which $L^4$ is connected in the structure. In some embodiments of Formula VII, both t and q are absent, resulting in a compound that has a chemical structure as shown below:

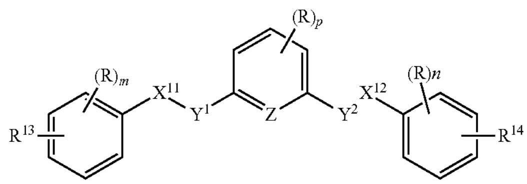

wherein m, n, p, R, $R^{13}$, $R^{14}$, $X^{11}$, $X^{12}$, $Y^1$, $Y^2$, and Z are as defined herein for Formula VII.

In Formula VIII, when t is 0, $L^3$ is absent and a direct bond is present between $X^{11}$ and the ring to which $L^3$ is connected in the structure. Similarly, in Formula VIII, when q is 0, $L^4$ is absent and a direct bond is present between $X^{12}$ and the ring to which $L^4$ is connected in the structure. In some embodiments of Formula VIII, both t and q are absent, resulting in a compound that has a chemical structure as shown below:

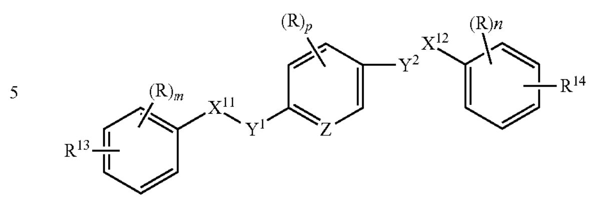

wherein m, n, p, R, $R^{13}$, $R^{14}$, $X^{11}$, $X^{12}$, $Y^1$, $Y^2$, and Z are as defined herein for Formula VIII.

In certain aspects, the compound of Formula VII is a compound of the following formula:

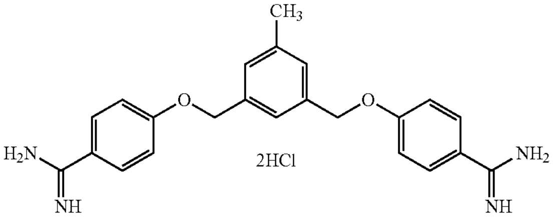

2HCl

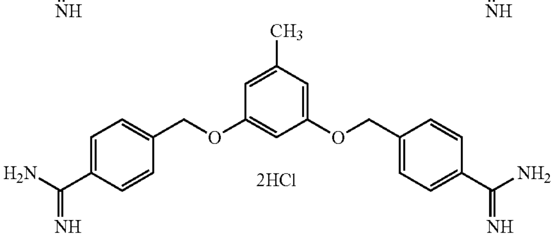

2HCl

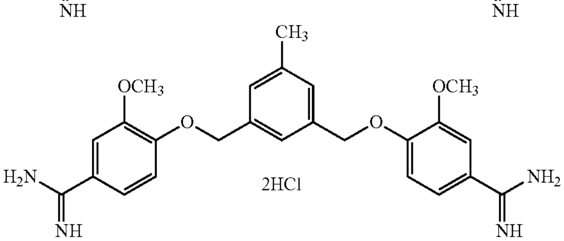

2HCl

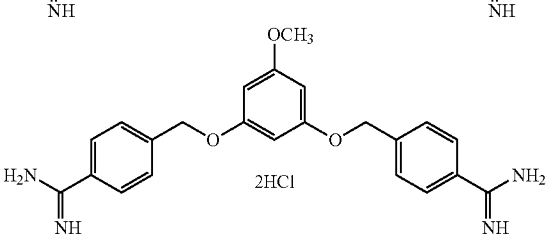

2HCl

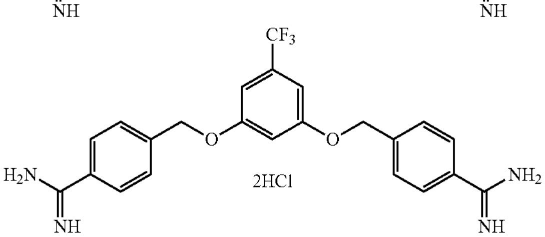

2HCl

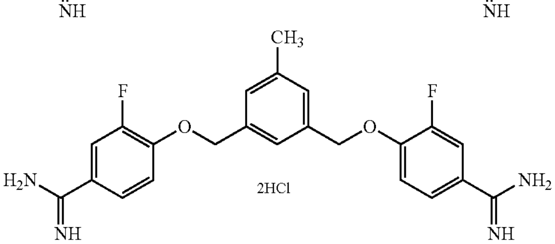

2HCl

-continued
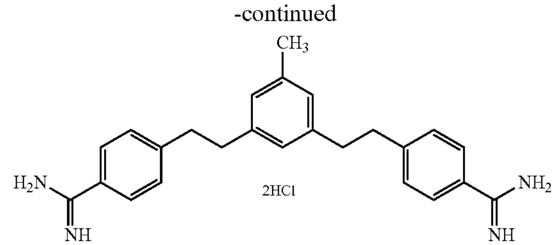
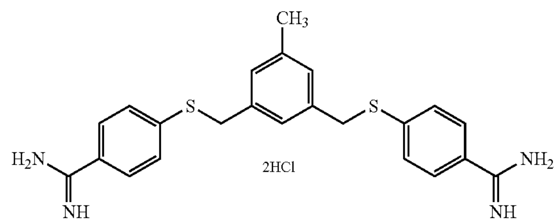
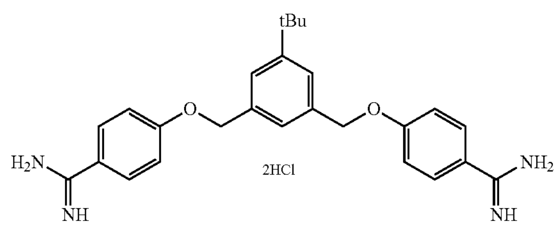
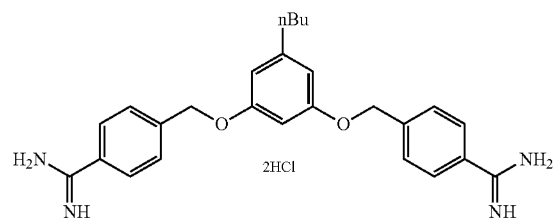
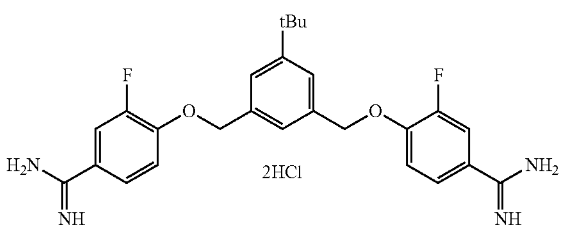
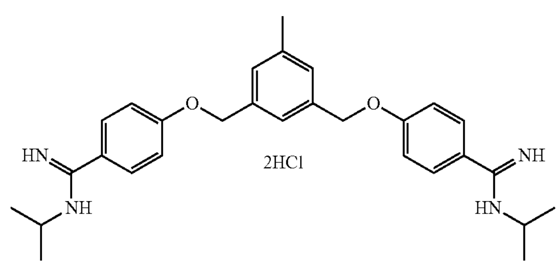
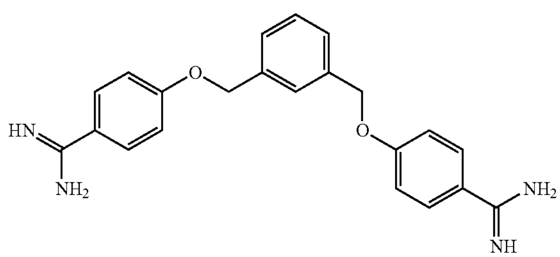
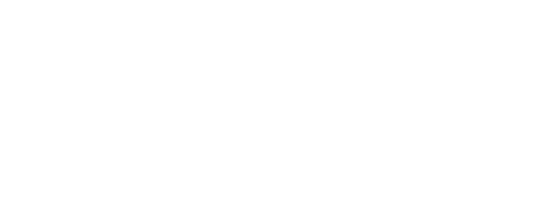
-continued
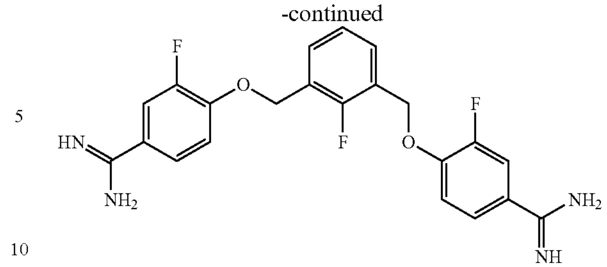
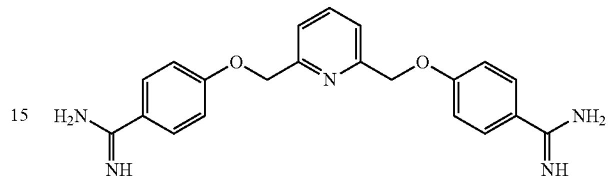
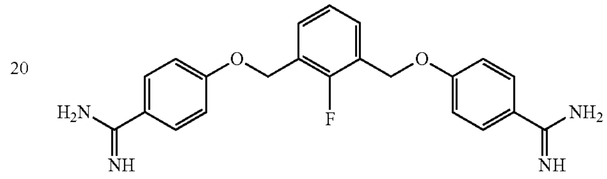
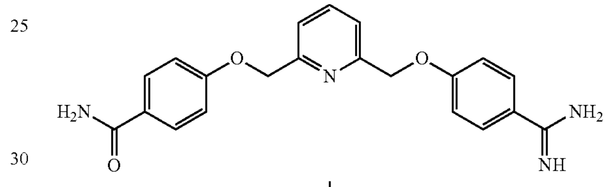
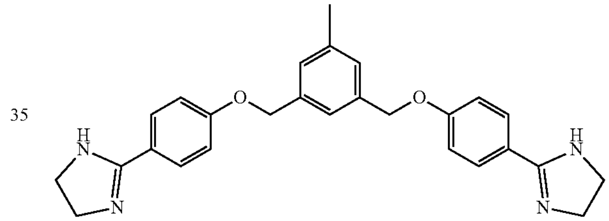
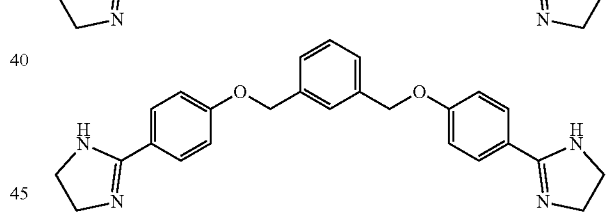
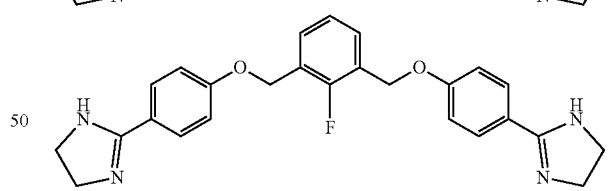
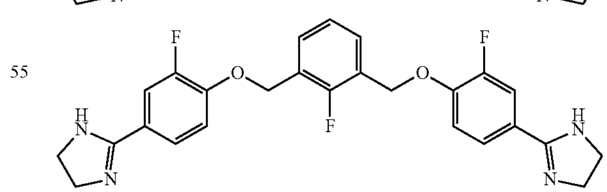
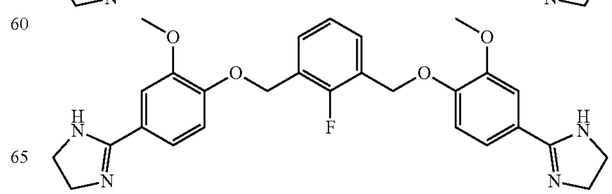
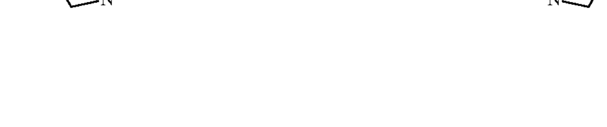

-continued
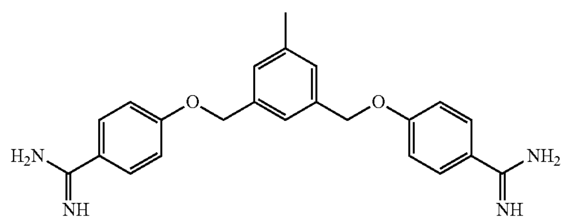
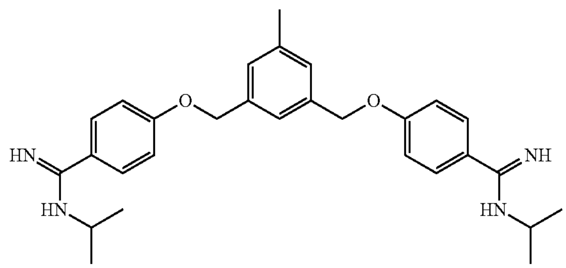
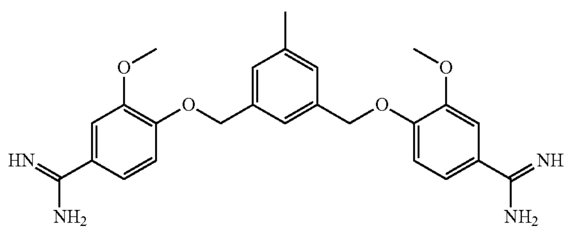
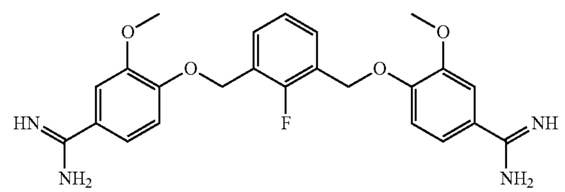
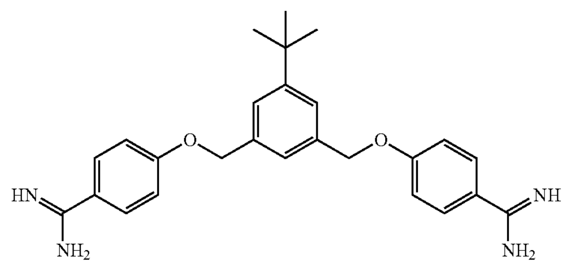
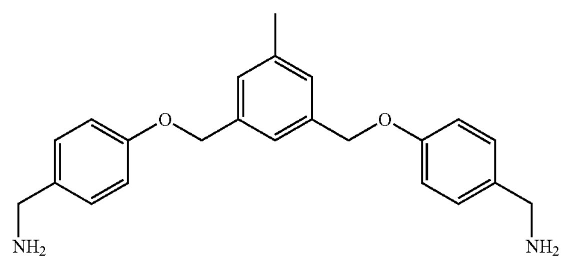
-continued
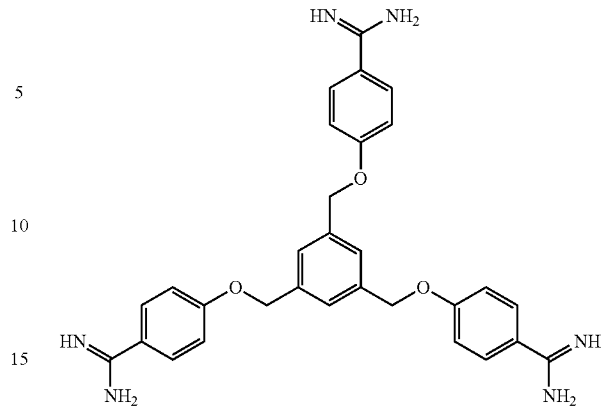
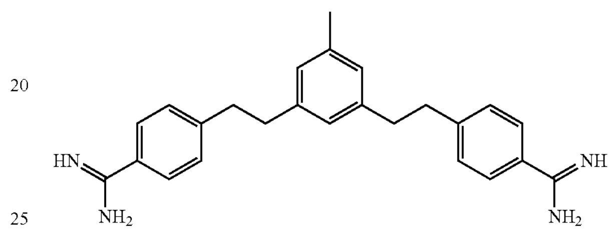
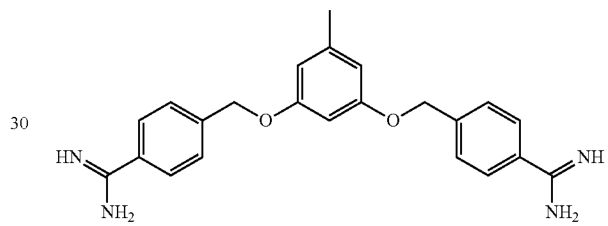
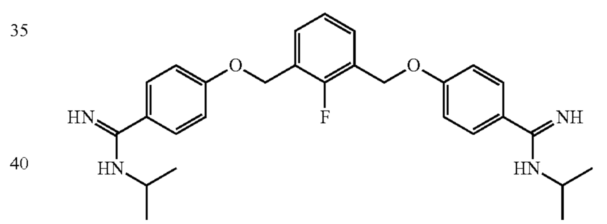
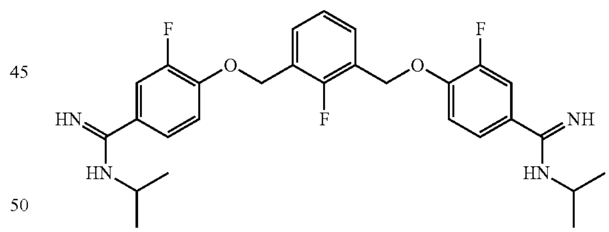
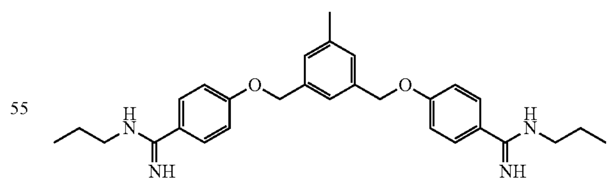
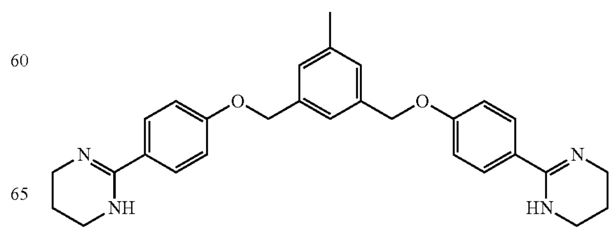

-continued
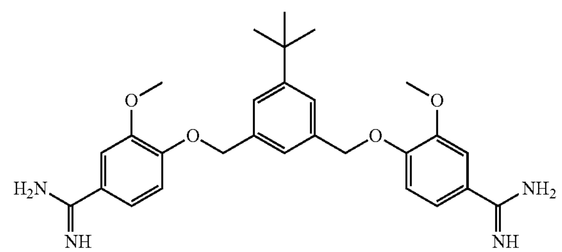
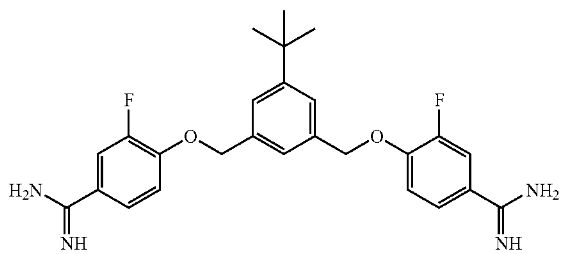
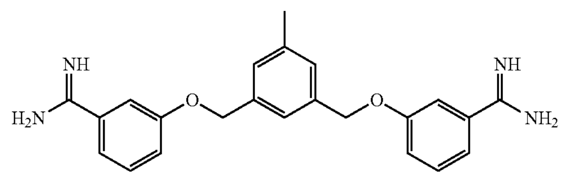
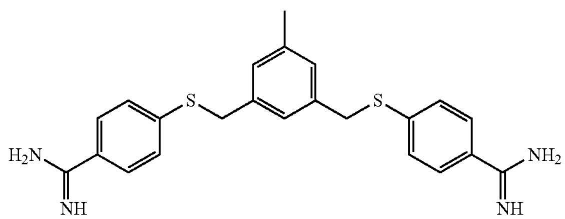
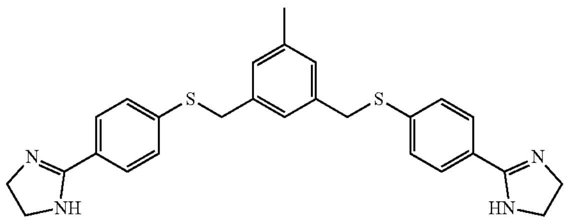
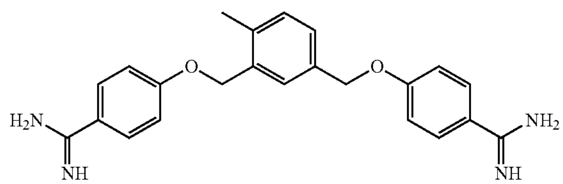
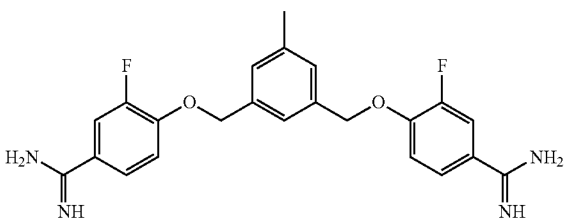
-continued
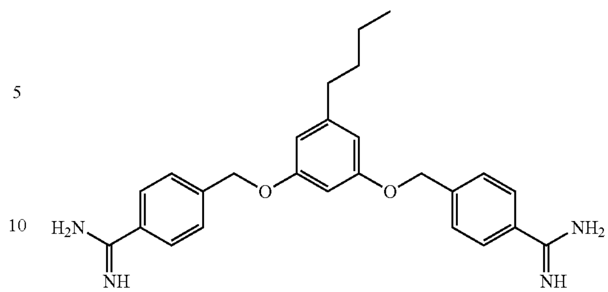
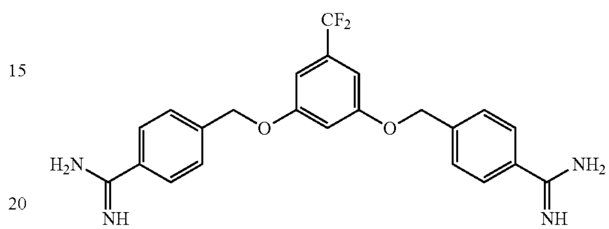
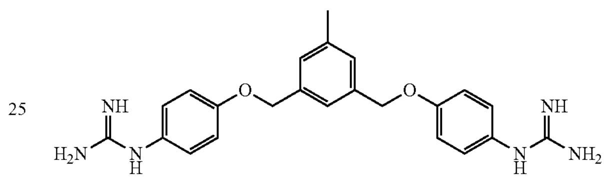
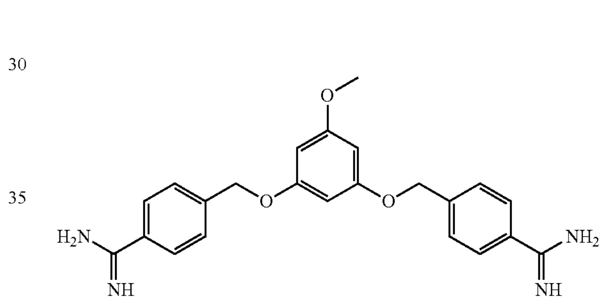
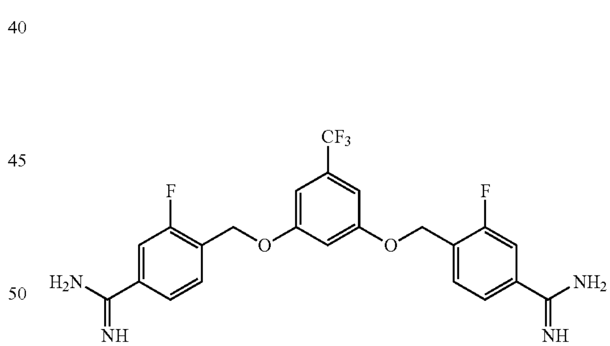
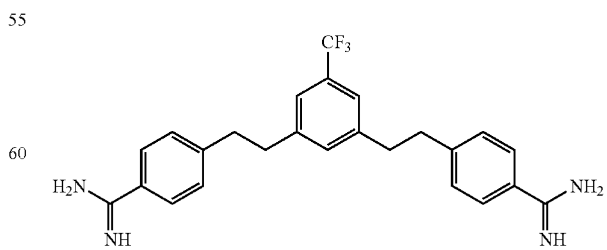
In certain aspects, the compound of Formula VIII is a compound of the following formula:

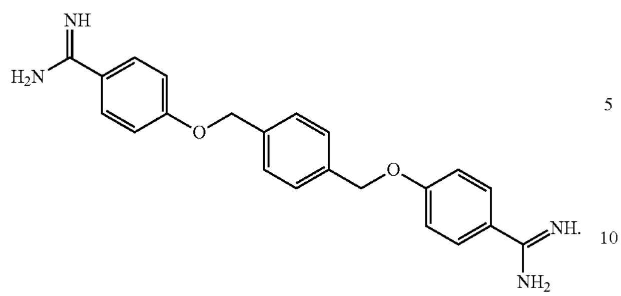
Additional compounds described herein include the following compounds. In some cases, the compounds are useful in the methods of treating bacterial infections as described herein.
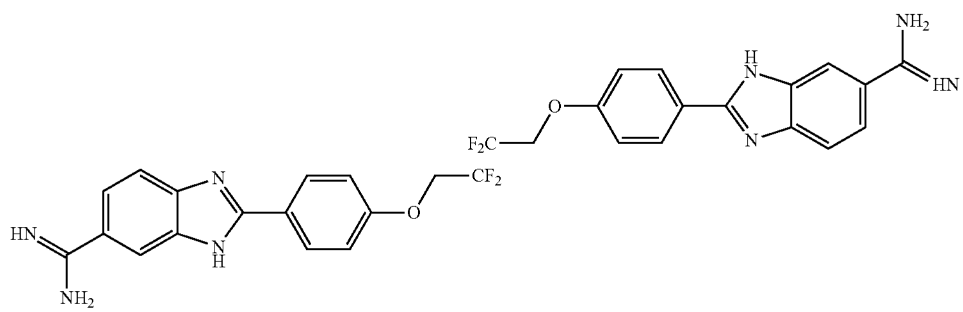
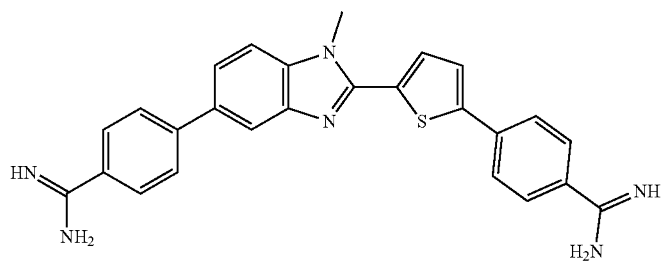
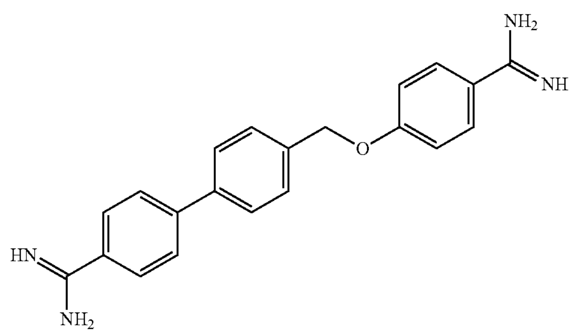
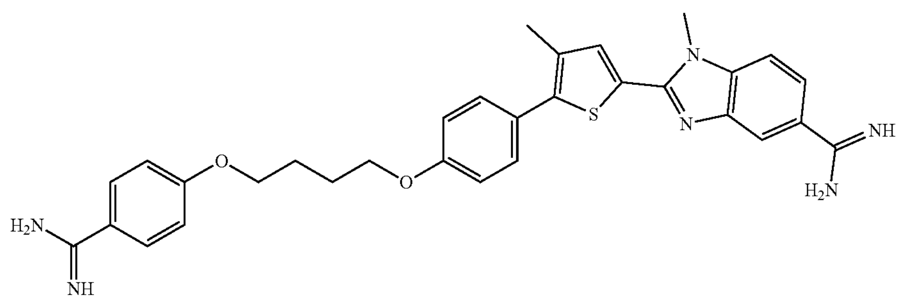

-continued

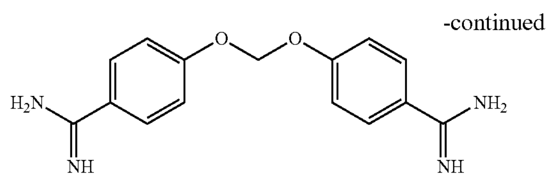

The compounds in any of the Formulas described herein may be in the form of a racemate, enantiomer, mixture of enantiomers, diastereomer, mixture of diastereomers, tautomer, N-oxide, or other isomer, such as a rotamer, as if each is specifically described unless specifically excluded by context Compound A-Compound L may be in the form of a racemate, enantiomer, mixture of enantiomers, diastereomer, mixture of diastereomers, tautomer, N-oxide, or other isomer, such as a rotamer, as if each is specifically described unless specifically excluded by context.

The present invention includes compounds of Formula I, Formula II, Formula III, Formula IV, Formula V, Formula VI, Formula VII, or Formula VIII with at least one desired isotopic substitution of an atom, at an amount above the natural abundance of the isotope, i.e. enriched. The present invention also includes a compound selected from Compound A-Compound L with at least one desired isotopic substitution of an atom, at an amount above the natural abundance of the isotope, i.e. enriched.

III. PHARMACEUTICAL COMPOSITIONS

An active compound as described herein can be administered to a host, for example, a human in need thereof in an effective amount as the neat chemical, but is more typically administered as a pharmaceutical composition that includes a pharmaceutically acceptable carrier suitable for the selected means of delivery. In one embodiment, the disclosure provides pharmaceutical compositions comprising an effective amount of compound or pharmaceutically acceptable salt thereof together with at least one pharmaceutically acceptable carrier for any of the uses described herein. The pharmaceutical composition may contain the compound or salt as the only active agent, or, in an alternative embodiment, the compound and at least one additional active agent.

Effective amount, when used to describe an amount of compound in a method, refers to the amount of a compound that achieves the desired pharmacological effect or other biological effect. For example, an effective amount can be a 10% reduction in a symptom or sign of a disease or condition as compared to a control. As used herein, control refers to the untreated condition (e.g., a subject or cell not treated with the compounds and compositions described herein). Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

An effective amount of the active compound as described herein, or the active compound described herein in combination or alternation with, or preceded by, concomitant with or followed by another active agent, can be used in an amount sufficient to (a) inhibit the progression of a bacterial infection; (b) cause a regression of a bacterial infection; (c) cause a cure of a bacterial infection; or (d) inhibit or prevent the development of a bacterial infection. The effective amount can be, for example, the concentrations of compounds at which a reduction in bacterial load is observed (e.g., a 10%, 20%, 30%, 40%, 50%, 60%, 70%, 80%, 90%, 100%, or any percent reduction in between 10% and 100% as compared to native or control levels).

A selected compound disclosed herein or used as described herein may be administered, for example, orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitoneal, subcutaneous, transnasal, sublingual, intrathecal, or rectal or by other means, in dosage unit formulations containing conventional pharmaceutically acceptable carriers.

For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The exact amount of the active compound or pharmaceutical composition described herein to be delivered to the host, typically a human, in need thereof, may be determined at the discretion of the health care provider to achieve the desired clinical benefit.

In certain embodiments the pharmaceutical composition is in a dosage form that contains from about 0.1 mg to about 1000 mg, from about 10 mg to about 750 mg, from about 100 mg to about 800 mg, or from about 200 mg to about 600 mg of the active compound and optionally from about 0.1 mg to about 2000 mg, from about 10 mg to about 750 mg, from about 100 mg to about 800 mg, or from about 200 mg to about 600 mg of an additional active agent in a unit dosage form.

Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or pharmaceutically acceptable salt thereof or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or pharmaceutically acceptable salt thereof. The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or pharmaceutically acceptable salt thereof, described herein. In one embodiment, the additional active agent is an antibiotic.

The pharmaceutical composition may be formulated as any pharmaceutically useful form, e.g., as a cream, a gel, a gel cap, a pill, a capsule, a microparticle, a nanoparticle, an injection or infusion solution, a capsule, a tablet, a syrup, as an aerosol, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert, or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils.

Examples of other matrix materials, fillers, or diluents include lactose, mannitol, xylitol, microcrystalline cellulose, calcium diphosphate, and starch.

Examples of surface-active agents include sodium lauryl sulfate and polysorbate 80. Examples of drug complexing agents or solubilizers include the polyethylene glycols, caffeine, xanthene, gentisic acid and cylodextrins.

Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth.

Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

In certain embodiments, the pharmaceutical composition for administration further includes a compound or salt described herein and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®980); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((D-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly(ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1, 3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment the particles are or include microparticles. In an alternative embodiment the particles are or include nanoparticles.

Common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method.

Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more In one embodiment an active compound as described herein is administered to a patient in need thereof as a spray dried dispersion (SDD). In another embodiment the present invention provides a spray dried dispersion (SDD) comprising a compound of the present invention and one or more pharmaceutically acceptable excipients as defined herein. In another embodiment the SDD comprises a compound of the present invention and an additional active agent. In a further embodiment the SDD comprises a compound of the present invention, an additional active agent, and one or more pharmaceutically acceptable excipients.

In another embodiment any of the described spray dried dispersions can be coated to form a coated tablet. In an alternative embodiment the spray dried dispersion is formulated into a tablet but is uncoated. Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

IV. METHODS OF TREATMENT

In one embodiment, an effective amount of a compound of Formula I through Formula V or a pharmaceutically acceptable salt or composition thereof or a compound of Formula VII or Formula VIII or a pharmaceutically acceptable salt or composition thereof is used to treat or to prevent a medical disorder which is caused by the presence of a bacterium, for example a bacterial infection. Optionally, the compound is MD-124 as described herein. In one embodiment, an effective amount of a compound selected from Compound A, Compound B, or Compound F-Compound L or a pharmaceutically acceptable salt or composition thereof is used to treat or to prevent a medical disorder which is mediated by the presence of a bacterium, for example a bacterial infection. In one embodiment, the compounds of the present invention may be used to treat a disorder, typically an infection, caused by a pathogenic bacterium. In one embodiment, a method is provided comprising administering an effective amount of a compound of Formula I through Formula V or a pharmaceutically acceptable salt or composition thereof or a compound of Formula VIII or a pharmaceutically acceptable salt or composition thereof to a subject, typically a human, to treat an infection caused by a pathogenic bacterium.

The compounds described herein are particularly effective in combination with antibiotics due to their potentiation of the antimicrobial effect of the antibiotic. In one embodiment, an active compound or its salt or composition as described herein may be used in combination or alternation with an antibiotic to potentiate the antibacterial effect of the antibiotic. Commonly used antibiotics include clindamycin, erythromycin, metronidazole, sulfacetamide, and tetracyclines such as doxycycline and minocycline. Other representative topical antibiotics include bacitracin, polymycin b, neomycin, retapamulin, mupirocin, pramoxine, gentamicin, mafenide, and ozenoxacin. In one embodiment, an active compound or its salt is formulated in combination with an antibiotic in a topical formulation as described herein.

In one embodiment, the compounds of the present invention may be used to treat a disorder, typically an infection, caused by a gram-positive bacterium. In one embodiment, a method is provided comprising administering an effective amount of a compound of Formula I through Formula VIII or a pharmaceutically acceptable salt or composition thereof to treat an infection caused by a gram-positive bacterium. In one embodiment, a method is provided comprising administering an effective amount of a compound selected from Compound A-Compound L or a pharmaceutically acceptable salt or composition thereof to treat an infection caused by a gram-positive bacterium.

Non-limiting examples of gram-positive bacteria which may be treated using the compounds of the present invention either alone or in combination with another therapeutic include: *Actinomyces* species including *Actinomyces israelii, Actinomyces naeslundii, Actinomyces viscosus, Actinomyces odontolyticus*, and *Actinomyces pyogenes; Bacillus* species including *Bacillus anthracis, Bacillus cereus*, and *Bacillus subtilis; Clostridium* species including *Clostridium botulinum, Clostridium difficile, Clostridium perfringens, Clostridium sordellii*, and *Clostridium tetani; Corynebacterium* species including *Corynebacterium diphtheriae, Corynebacterium jeikeium, Corynebacterium minutissimum, Corynebacterium mucifaciens, Corynebacterium pseudotuberculosis, Corynebacterium striatum, Corynebacterium tenuis*, and *Corynebacterium ulcerans; Enterococcus* species including *Enterococcus casseliflavus, Enterococcus faecalis, Enterococcus faecium, Enterococcus rafinosus*, and *Enterococcus hirae; Leuconostoc* species including *Leuconostoc pseudomesenteroides; Micrococcus* species such as *Microccocus luteus; Nocardia* species including *Nocardia asteroides; Propionibacterium* species including *Propionibacterium acnes; Staphylococcus* species including *Staphylococcus aureus, Staphylococcus capitis, Staphylococcus epidermidis, Staphylococcus haemolyticus, Staphylococcus hominis, Staphylococcus lugdunensis, Staphyloccocus pasteuri*, and *Staphyloccocus saprophyticus*; and *Streptococcus* species including *Streptococcus agalactiae, Streptococcus anginosus, Streptococcus bovis, Streptococcus dysgalactiae, Streptococcus mitis, Streptococcus mutans, Streptococcus pneumoniae, Streptococcus pyogenes, Streptococcus sanguinis, Streptococcus suis*, and *Streptococcus viridans.*

In one embodiment, the compounds of the present invention may be used to treat a disorder, typically an infection, caused by a gram-negative bacterium. In one embodiment, a method is provided comprising administering an effective amount of a compound of Formula I through Formula VIII or a pharmaceutically acceptable salt or composition thereof to treat an infection caused by a gram-negative bacterium. In one embodiment, a method is provided comprising administering an effective amount of a compound selected from Compound A-Compound L or a pharmaceutically acceptable salt or composition thereof to treat an infection caused by a gram-negative bacterium.

Non-limiting examples of gram-negative bacteria which may be treated using the compounds of the present invention either alone or in combination with another therapeutic include: *Acinetobacter* species including *Acinetobacter baumannii* and *Acinetobacter iwoffi; Aeromonas* species including *Aeromonas veronii* biovar *sobria* (previously *Aeromonas sobria*), *Aeromonas caviae*, and *Aeromonas hydrophila; Alcaligenes/Achromobacter* species including *Alcaligenes faecalis* and *Alcaligenes xylosoxidans; Bacteroides* species including *Bacteroides fragilis; Bartonella* species including *Bartonella bacilliformis, Bartonella clarridgeiae, Bartonella elizabethae, Bartonella henselae, Bartonella koehlerae, Bartonalla naantalienis, Bartonella quintana, Bartonella rochalimae, Bartonella vinsonii*, and *Bartonella washoensis; Bordetella* species including *Bordetella bronchispetica, Bordetella pertussis*, and *Bordetella parapertussis; Borrelia* species including *Borrelia afzelii, Borrelia burgdorferi, Borrelia crocidurae, Borrelia duttoni, Borrelia garinii, Borrelia hermsii, Borrelia hispanica, Borellia miyamotoi, Borrelia parkeri, Borrelia persica, Borrelia recurrentis, Borrelia turicatae*, and *Borrelia venezuelensis; Brevundimonas* species including *Brevundimonas diminuta* and *Brevundimonas vesicularis; Brucella* species including *Brucella abortus, Brucella canis, Brucella melitensis*, and *Brucella suis; Burkholderia* species including *Burkholderia cepacia, Burkholderia mallei*, and *Burkholderia pseudomallei; Campylobacter* species including *Campylobacter jejuni, Campylobacter coli, Campylobacter upsaliensis, Campylobacter lari*, and *Campylobacter coli; Chlamydia/Chlamidophila* species including *Chlamydophila pneumoniae, Chlamydophila psittaci, Chlamidophila pecorum*, and *Chlamydia trachomatis; Citrobacter* species including *Citrobacter amalonaticus, Citrobacter freundii, Citrobacter koseri*, and *Citrobacter diversus; Coxiella burnetti; Ehrlichia* species including *Ehrlichia canis* and *Ehrlichia chaffeensis; Enterobacter* species including *Enterobacter aerogenes* and *Enterobacter cloacae; Escherichia* species including *Escherichia coli; Francisella* species including *Francisella novicida, Francisella philomiragia*, and *Francisella tularensis; Haemophilus* species including *Haemophilus influenzae* and *Haemophilus ducreyi; Helicobacter* species including *Helicobacter pylori; Klebsiella* species including *Klebsiella granulomatis, Klebsiella oxytoca*, and *Klebsiella pneumoniae; Leclercia adecarboxylata; Legionella* species including *Legionella pneumophila; Leptospira* species including *Leptospira interrogans, Leptospira noguchii, Leptospira santarosai*, and *Leptospira weilii; Listeria* species including *Listeria monocytogenes; Moraxella* species including *Moraxella catarrhalis, Moraxella lacunata*, and *Moraxella bovis; Morganella* species including *Morganella morganii; Mycoplasma* species including *Mycoplasma amphoriforme, Mycoplasma buccale, Mycoplasma faucium, Mycoplasma fermentans, Mycoplasma genitalium, Mycoplasma hominis, Mycoplasma lipophilum, Mycoplasma orale, Mycoplasma penetrans, Mycoplasma pirum, Mycoplasma pneumoniae, Mycoplasma primatum, Mycoplasma salivarium*, and *Mycoplasma spermatophilum; Neisseria* species including *Neisseria meningitidis* and *Neisseria gonorrhoeae*; Orientia species including *Orientia isutsugamushi* and *Orientia chuto; Pantoea* species including *Pantoea agglomerans; Paracoccus* species including *Paracoccus yeei; Prevotella* species including *Prevotella intermedia* and *Prevotella melaninogenica; Proteus* species including *Proteus mirabilis, Proteus penneri*, and *Proteus vulgaris; Providencia* species including *Providencia rettgeri* and *Providencia stuartii; Pseudomonas* species including *Pseudomonas aeruginoas, Pseudomonas oryzihabitans, Pseudomonas plecoglossidica*, and *Pseudomonas stutzeri; Ralstonia* species including *Ralstonia pickettii* and *Ralstonia insidiosa; Rickettsia* species including *Rickettsia africae, Rickettsia akari, Rickettsia australis, Rickettsia conorii, Rickettsia felis, Rickettsia japonica, Rickettsia prowazekii, Rickettsia rickettsia, Rickettsia sibirica*, and *Rickettsia typhi; Roseomonas* species including *Roseomonas gilardii; Salmonella* species including *Salmonella bongori, Salmonella enterica, Salmonella paratyphi, Salmonella typhi*, and *Salmonella typhimurium; Serratia* species including *Serratia marcescens, Serratia liquefaciens, Serratia rubidaea*, and *Serratia odoriferae; Shigella* species including *Shigella dysenteriae* and *Shigella sonnei; Sphingomonas* species including *Sphingomonas mucosissima* and *Sphingomonas paucimobilus; Stenotrophomas* species including *Stenotrophomas maltophilia; Treponema* species including *Treponema carateum, Treponema paraluiscuniculi*, and *Treponema pallidum; Ureaplasma* species including *Ureaplasma urealyticum; Vibrio* species including *Vibrio cholera, Vibrio parahaemolyticus*, and *Vibrio vulnficus*; and *Yersinia* species including *Yersinia enterocolitica, Yersinia pestis*, and *Yersinia pseudotuberculosis.*

In one embodiment, the compounds of the present invention may be used to treat a disorder, typically an infection, caused by a mycobacterium. In one embodiment, a method is provided comprising administering an effective amount of a compound of Formula I through Formula V or a pharmaceutically acceptable salt or composition thereof to treat an infection caused by a mycobacterium. In one embodiment, a method is provided comprising administering an effective amount of a compound of Formula VII or Formula VIII or a pharmaceutically acceptable salt or composition thereof to treat an infection caused by a mycobacterium. In one embodiment, a method is provided comprising administering an effective amount of a compound selected from Compound A, Compound B, or Compound F-Compound L or a pharmaceutically acceptable salt or composition thereof to treat an infection caused by a mycobacterium.

Non-limiting examples of mycobacteria which may be treated using the compounds of the present invention either alone or in combination with another therapeutic include *Mycobacterium abcessus, Mycobacterium africanum, Mycobacterium agri, Mycobacterium aichiense, Mycobacterium alvei, Mycobacterium arabiense, Mycobacterium aromaticivorans, Mycobacterium arosiense, Mycobacterium arupense, Mycobacterium aquaticum, Mycobacterium asiaticum, Mycobacterium aubagnese, Mycobacterium aurum, Mycobacterium austroafricanum, Mycobacterium avium, Mycobacterium avium* paratuberculosis, *Mycobacterium avium silvaticum, Mycobacterium avium hominussuis, Mycobacterium bacteremicum, Mycobacterium barrassiae, Mycobacterium boenickei, Mycobacterium bohemicum, Mycobacterium bolletii, Mycobacterium botniense, Mycobacterium bovis, Mycobacterium branderi, Mycobacterium brisbanense, Mycobacterium brumae, Mycobacterium canariasense, Mycobacterium canettii, Mycobacterium caprae, Mycobacterium chimaera, Mycobacterium chelonae, Mycobacterium chitae, Mycobacterium chubuense, Mycobacterium colombiense, Mycobacterium conceptionense, Mycobacterium confluentis, Mycobacterium conspicuum, Mycobacterium cookii, Mycobacterium cosmeticum, Mycobacterium diernhoferi, Mycobacterium doricum, Mycobacterium duvalii, Mycobacterium elephantis, Mycobacterium fallax, Mycobacterium farcinogenes, Mycobacterium flavescens, Mycobacterium florentinum, Mycobacterium fortuitum, Mycobacterium frederikbergense, Mycobacterium gadium, Mycobacterium gastri, Mycobacterium genavense, Mycobacterium gilvum, Mycobacterium gordonae, Mycobacterium haemophilum, Mycobacterium hassiacum, Mycobacterium heidelbergense, Mycobacterium heckshornense; Mycobacterium hiberniae, Mycobacterium hodleri, Mycobacterium holsaticum, Mycobacterium hous-*

*tonense, Mycobacterium icosiumassilensis. Mycobacterium immunogenum, Mycobacterium indicus pranii, Mycobacterium intacellulare, Mycobacterium intracellulare, Mycobacterium interjectum, Mycobacterium intermedium, Mycobacterium iranicum, Mycobacterium kansasii, Mycobacterium komossense, Mycobacterium kubicae, Mycobacterium lentiflavum, Mycobacterium leprae, Mycobacterium lepraemurium, Mycobacterium lepromatosis, Mycobacterium liflandii, Mycobacterium llatzerense, Mycobacterium madagascariense, Mycobacterium mageritense, Mycobacterium malmoense, Mycobacterium marinum, Mycobacterium massiliense, Mycobacterium massilipolynesiensis, Mycobacterium microti, Mycobacterium monacense, Mycobacterium montfiorense, Mycobacterium morokaense, Mycobacterium mucogenicum, Mycobacterium mungi, Mycobacterium murale, Mycobacterium nebraskense, Mycobacterium neoaurum, Mycobacterium neworleansense, Mycobacterium nonchromogenicum, Mycobacterium obuense, Mycobacterium orygis, Mycobacterium palustre, Mycobacterium parascofulaceum, Mycobacterium parafortuitum, Mycobacterium perigrinum, Mycobacterium phlei, Mycobacterium phocaicum, Mycobacterium pinnipedii, Mycobacterium porcinum, Mycobacterium pseudoshottsii, Mycobacterium psychotolerans, Mycobacterium pulveris, Mycobacterium pyrenivorans, Mycobacterium saskatchewanense, Mycobacterium sediminis, Mycobacterium senegalense, Mycobacterium septicum, Mycobacterium shimoidei, Mycobacterium shottsii, Mycobacterium simiae, Mycobacterium smegmatis, Mycobacterium sphagni, Mycobacterium stephanolepidis, Mycobacterium suricattae, Mycobacterium szulgai, Mycobacterium talmoniae, Mycobacterium terrae, Mycobacterium thermoresistibile, Mycobacterium triplex, Mycobacterium triviale, Mycobacterium tuberculosis, Mycobacterium tusciae, Mycobacterium ulcerans, Mycobacterium vaccae, Mycobacterium vanbaalenii, Mycobacterium xenopi*, and *Mycobacterium yongonense.*

In one embodiment, an effective amount of an active compound or pharmaceutically acceptable salt thereof or composition as described herein is used to treat or to prevent a medical disorder which is mediated by the presence of an antibiotic-resistant bacterium. In one embodiment, the compounds of the present invention may be used to treat a disorder, typically an infection, caused by a pathogenic antibiotic-resistant bacterium.

In one embodiment, a method is provided comprising administering an effective amount of a compound or a pharmaceutically acceptable salt thereof or composition thereof described herein to a subject, typically a human, to treat an infection caused by a pathogenic antibiotic-resistant bacterium.

Non-limiting examples of gram-positive antibiotic-resistant bacteria include: antibiotic-resistant *Clostridium difficile*, drug-resistant *Streptococcus pneumoniae*, clindamycin-resistant Group B *Streptococcus*, erythromycin-resistant Group A *Streptococcus*, methicillin-resistant *Staphylococcus aureus* (MRSA), vancomycin-resistant *Staphylococcus aureus* (VRSA), and vancomycin-resistant *Enterococcus* (VRE).

Non-limiting examples of gram-negative antibiotic-resistant bacteria include: antibiotic-resistant *Burkholderia cepacia*, carbapenem-resistant Enterobacteriaceae (CRE) gut bacteria, drug-resistant *Campylobacter*, drug-resistant non-typhoidal *Salmonella*, drug-resistant *Shigella*, multi-drug-resistant *Acinetobacter*, multi-drug-resistant *Escherichia coli*, multi-drug-resistant *Klebsiella pneumoniae*, multi-drug-resistant *Neisseria Gonorrhoeae*. and multidrug-resistant *Pseudomonas aeruginosa.*

In one embodiment, an effective amount of a compound of Formula I through Formula V or a pharmaceutically acceptable salt or composition thereof is used to treat or to prevent a medical disorder which is mediated by the presence of an antibiotic-resistant mycobacterium. Optionally, an effective amount of a compound of Formula VII or Formula VIII or a pharmaceutically acceptable salt or composition thereof is used to treat or to prevent a medical disorder which is mediated by the presence of an antibiotic-resistant mycobacterium. In one embodiment, an effective amount of a compound selected from Compound A-Compound L or a pharmaceutically acceptable salt or composition thereof is used to treat or to prevent a medical disorder which is mediated by the presence of an antibiotic-resistant mycobacterium. In one embodiment, the compounds of the present invention may be used to treat a disorder, typically an infection, caused by a pathogenic antibiotic-resistant mycobacterium. In one embodiment, a method is provided comprising administering an effective amount of a compound as described herein or a pharmaceutically acceptable salt thereof or composition thereof described herein to a subject, typically a human, to treat an infection caused by a pathogenic antibiotic-resistant mycobacterium. In one embodiment, the antibiotic-resistant mycobacterium is multi-drug-resistant *Mycobacterium tuberculosis* (MDR-TB).

Non-limiting examples of disorders mediated by a bacterium that may be treated by the compounds of the present invention, either alone or in combination with another therapeutic, include actinomycosis, anaplasmosis, anthrax, bacillary angiomatosis, actinomycetoma, bacterial pneumonia, bacterial vaginosis, bacterial endocarditis, bartonellosis, botulism, boutenneuse fever, brucellosis, bejel, brucellosis spondylitis, bubonic plague, Buruli ulcer, Baimsdale ulcer, bacillary dysentery, campylobacteriosis, Carrion's disease, cat-scratch disease, cellulitis, chancroid, chlamydia, chlamydia conjunctivitis, clostridial myonecrosis, cholera, *Clostridium difficile* colitis, diphtheria, Daintree ulcer, donavanosis, dysentery, erhlichiosis, epidemic typhus, fried rice syndrome, five-day fever, floppy baby syndrome, Far East scarlet-like fever, gas gangrene, glanders, gonorrhea, granuloma inguinale, human necrobacillosis, hemolytic-uremic syndrome, human ewingii ehrlichiosis, human monocytic ehrlichiosis, human granulocytic anaplasmosis, infant botulism, Izumi fever, Kawasaki disease, Kumusi ulder, lymphogranuloma venereum, Lemierre's syndrome, Legionellosis, leprosy, leptospirosis, listeriosis, Lyme disease, lymphogranuloma venereum, Malta fever, Mediterranean fever, myonecrosis, mycoburuli ulcer, mucocutaneous lymph node syndrome, meliodosis, meningococcal disease, murine typhus, *Mycoplasma* pneumonia, mycetoma, neonatal conjunctivitis, nocardiosis, Oroya fever, ophthalmia neonatorum, ornithosis, Pontiac fever, peliosis hepatis, pneumonic plague, postanginal shock including sepsis, pasteurellosis, pelvic inflammatory disease, pertussis, plague, pneumococcal infection, pneumonia, psittacosis, parrot fever, pseudotuberculosis, Q fever, quintan fever, rabbit fever, relapsing fever, rickettsialpox, Rocky Mountain spotted fever, rat-bite fever, Reiter syndrome, rheumatic fever, salmonellosis, scarlet fever, sepsis, septicemic plague, Searls ulcer, shigellosis, soft chancre, syphilis, streptobacillary fever, scrub typhus, Taiwan acute respiratory agent, Trench fever, trachoma, tuberculosis, tularemia, typhoid fever, typhus, tetanus, toxic shock syndrome, undulant fever, ulcus molle, *Vibrio parahaemolyticus* enteritis, Whitmore's disease, walking pneumonia, Waterhouse-Friderichsen syndrome, yaws, and yersiniosis.

In one embodiment, the compounds of the present invention may be used to treat an inflammatory disorder caused by the presence of a bacterial infection. Non-limiting examples of such inflammatory disorders include adenoiditis, appendicitis, arteritis, ascending cholangitis, balanitis, blepharitis, bronchitis, bursitis, cellulitis, cerebral vasculitis, cervicitis, chemosis, cholecystitis, chondritis, choroioamnionitis, colitis, conjunctivitis, constrictive pericarditis, cryptitis, dacryoadenitis, dermatitis, duodenal lymphocytosis, encephalitis, endocarditis, endometritis, endotheliitis, enteritis, enterocolitis, eosinophilis fasciitis, epididymitis, esophagitis, folliculitis, gastritis, gingivitis, glomerulonephritis, glossitis, hepatitis, infectious arthritis, ileitis, intertrigo, keratitis, keratoconjunctivitis, labyrithitis, lymphadenitis, mastitis, mastoiditis, myocarditis, myopericarditis, myositis, necrotizing fasciitis, nephritis, omaphalitis, oophoritis, ophthalmitis, orchitis, osteitis, osteomyelitis, pancreatitis, paraproctitis, parotitis, pericarditis, perichondritis, perifolliculitis, periodontitis, peritonitis, pharyngitis, phlebitis, pleurisy, pneumonitis, pulmonitis, proctitis, prostatitis, pulpitis, pyelonephritis, pyomyositis, retinal vasculitis, rheumatic fever, rhinitis, scleritis, salpingitis, sialadenitis, sinusitis, stomatitis, synovitis, septicemia, tenosynovitis, thyroiditis, tonsillitis, tularemia, urethritis, uveitis, vaginitis, vasculitis, and vulvitus.

V. COMBINATION THERAPY

In one embodiment, an active compound of Formula I through Formula VIII or a pharmaceutically acceptable salt or composition thereof may be provided in combination or alternation with or preceded by, concomitant with or followed by, an effective amount of at least one additional active agent, for example, for treatment of a disorder listed herein. Non-limiting examples of additional active agents for such combination therapy are provided below.

In the described below and herein generally, whenever any of the terms referring to an active compound or pharmaceutically acceptable salt thereof or composition as described herein are used, it should be understood that pharmaceutically acceptable salt, prodrugs, or compositions are considered included, unless otherwise stated or inconsistent with the text.

In one embodiment, an active compound of Formula I through Formula VIII or a pharmaceutically acceptable salt or composition thereof as described herein may be used in combination or alternation with an antibiotic.

In one embodiment, a compound selected from Compound A-Compound L or a pharmaceutically acceptable salt or composition thereof as described herein may be used in combination or alternation with an antibiotic.

In one embodiment, the antibiotic is an aminoglycoside. In one embodiment, the antibiotic is selected from amikacin, gentamicin, kanamycin, neomycin, netilmicin, tobramycin, paromomycin, streptomycin, and spectinomycin.

In one embodiment, the antibiotic is an ansamycin. In one embodiment, the antibiotic is selected from geldanamycin, herbimycin, and rifaximin.

In one embodiment, the antibiotic is a carbapenem. In one embodiment, the antibiotic is selected from ertapenem, doripenem, imipenem, panipenem, biapenem, tebipenem, and meropenem.

In one embodiment, the antibiotic is a cephalosporin. In one embodiment, the antibiotic is selected from cefacetrile, cefadroxil, cephalexin, cefaloglycin, cefalonium, cefaloridine, cefalotin, cefapirin, cefatrizine, cefazaflur, cefazedone, cefazolin, cefradrine, cefroxadine, and ceftezole. In one embodiment, the antibiotic is selected from cefaclor, cefonicid, cefprozil, cefuroxime, cefuzonam, cefmetazole, cefotetan, cefoxitin, loracarbef, cefbuperazone, cefminox, cefoxitin, and cefotiam. In one embodiment, the antibiotic is selected from cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, and latamoxef. In one embodiment, the antibiotic is selected from cefclidine, cefepime, cefluprenam, cefoselis, cefozopran, cefpirome, cefquinome, and flomoxef. In one embodiment, the antibiotic is selected from ceftobiprole, ceftaroline, and ceftolozane.

In one embodiment, the antibiotic is a glycopeptide. In one embodiment, the antibiotic is selected from teicoplanin, vancomycin, telavancin, dalbavancin, ramoplanin, decaplanin, and oritavancin.

In one embodiment, the antibiotic is a lincosamide. In one embodiment, the antibiotic is selected from lincomycin, clindamycin, and pirlimycin. In one embodiment, the antibiotic is daptomycin.

In one embodiment, the antibiotic is a macrolide. In one embodiment, the antibiotic is selected from azithromycin, clarithromycin, erythromycin, fidaxomicin, telithromycin, carbomycin A, josamycin, kitasanmycin, midecamycin, oleandomycin, solithromycin, spiramycin, troleandomycin, tylosin, and roxithromycin.

In one embodiment, the antibiotic is a ketolide. In one embodiment, the antibiotic is selected from telithromycin, cethromycin, and solithromycin.

In one embodiment, the antibiotic is a monobactam.

In one embodiment, the antibiotic is selected from aztreonam. In one embodiment, the antibiotic is a nitrofuran. In one embodiment, the antibiotic is selected from diruazone, firazolidone, nifirfoline, nifuroxazide, nifurquinazol, nifirtoinol, nifurzide, nitrofural, and nitrofurantoin.

In one embodiment, the antibiotic is an oxazolidinone. In one embodiment, the antibiotic is selected from linezolid, posizolid, tedizolid, radezolid, torezolid, and cycloserine.

In one embodiment, the antibiotic is a penicillin. In one embodiment, the antibiotic is selected from penicillin G, penicillin K, penicillin N, penicillin O, and penicillin V. In one embodiment, the antibiotic is selected from meticillin, nafcillin, oxacillin, cloxacillin, dicloxacillin, and flucoxacillin. In one embodiment, the antibiotic is selected from ampicillin, amoxicillin, pivampicillin, hetacillin, bacampicillin, metampicillin, talampicillin, and epicillin.

In one embodiment, the antibiotic is selected from carbenicilin, ticarcillin, and temocillin. In one embodiment, the antibiotic is selected from mezlocillin and piperacillin. In one embodiment, the antibiotic is selected from clavulanic acid, sulbactam, and tazobactam.

In one embodiment, the antibiotic is a polypeptide antibiotic. In one embodiment, the antibiotic is selected from bacitracin, colistin, and polymyxin B.

In one embodiment, the antibiotic is a quinolone or fluoroquinolone antibiotic. In one embodiment, the antibiotic is selected from flumequine, oxolinic acid, rosoxacin, cinoxacin, nalidixic acid, and piromidic acid. In one embodiment, the antibiotic is selected from ciprofloxacin, fleroxacin, lomefloxacin, nadifloxacin, norfloxacin, ofloxacin, pefloxacin, rufloxacin, and enoxacin. In one embodiment, the antibiotic is selected from balofloxacin, grepafloxacin, levofloxacin, pazufloxacin, sparfloxacin, temafloxacin, and tosufloxacin. In one embodiment, the antibiotic is selected from clinafloxacin, gatifloxacin, moxifloxacin, sitafloxacin, prulifloxacin, besifloxacin, gemifloxacin, trovafloxacin, delafloxacin, and ozenoxacin.

In one embodiment, the antibiotic is a sulfonamide. In one embodiment, the antibiotic is selected from sulfacetamide, sulfadiazine, sulfadimidine, sulfafurazole, sulfisomidine, sulfadoxine, sulfamethoxazole, sulfamoxole, sulfanitran, sulfadimethoxine, sulfamethoxypyridazine, sulfametoxydiazine, sulfadoxine, sulfametopyrazine, terephtyl, mafenide, sulfanilamide, sulfasalazine, sulfisoxazole, and sulfonamicochrysoidine.

In one embodiment, the antibiotic is a tetracycline. In one embodiment, the antibiotic is selected from tetracycline, chlortetracycline, oxytetracycline, demeclocycline, lymecycline, meclocycline, metacycline, minocycline, and rolitetracycline. In one embodiment, the antibiotic is selected from clofazimine, dapsone, capreomycin, cycloserine, ethambutol, ethionamide, isoniazid, pyrazinamide, rifampicin, rifabutin, rifapentine, and streptomycin. In another embodiment, the antibiotic is selected from arsphenamide, chloramphenicol, fosfomycin, fusidic acid, metronidazole, mupirocin, platensimycin, quinupristin, dalfopristin, thiamphenicol, tigecycline, and trimethoprim.

VI. TOPICAL FORMULATIONS FOR THE TREATMENT OF ACNE VULGARIS

Acne vulgaris is a skin disease caused in part by excessive outgrowth of *Propionibacterium acnes* bacteria and inflammation induced in response to the *P. acnes* bacteria. Acne, a common skin disease, occurs when hair follicles become clogged with dead skin cells and oil from the skin. Acne develops due to blockages that occur through increased sebum production influenced by androgens, excessive deposition of keratin in the hair follicle leading to comedo formation. The earliest pathological change involves the formation of a microcomedone due to the accumulation of skin cells in the hair follicle, which mix with oily sebum to block the follicle, a process further exacerbated by the presence of the *P. acnes* biofilm. If the microcomedone is superficial, melanin within the plug oxidizes upon exposure to air, forming a blackhead or open comedo. If the microcomedone is deeper within the hair follicle, a whitehead or closed comedo forms.

*Propionibacterium acnes* (reclassified as *Cutibacterium acnes* in 2016) is a Gram-positive bacterium (rod) linked to acne that belongs to the *Cutibacterium* Genus and the Propionibacteriaceae Family. Typically, slow growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately live deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris. While less common, *Staphylococcus epidermidis* can also cause acne. It is a Gram-positive bacterium belonging to the *Staphylococcus* Genus and the Staphylococcaceae Family that is part of the normal human flora and typically skin flora or mucosal flora. It is a facultative anaerobic bacterium and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

The presence of *P. acnes* induces skin inflammation due to the bacteria's ability to bind to toll-like receptors (TLRs), especially TLR2 and TLR4 and by altering the fatty composition of the oily sebum by oxidizing squalene. The subsequent inflammatory cascades lead to the formation of inflammatory acne lesions such as papules, pustules, or nodules. If the inflammatory reaction is very severe, the follicle will break into the dermis and subcutaneous tissue as a deep nodule, leading to local tissue destruction and scarring.

Traditionally, acne is classified as either non-inflammatory (open/closed comedones) or inflammatory (papules, pustules, or nodules). Mounting evidence indicates that inflammation exists throughout the entire duration of the acne lesion lifecycle, establishing the critical role of inflammation in the pathology of acne. In the earliest stages of acne lesion development, CD3+ T cell, CD4+ T cell, and macrophage populations are elevated, while the levels of the pro-inflammatory cytokine interleukin-1 are also upregulated. Initiation of inflammatory events have been documented even before clinical detection of acne lesions.

An active compound described herein can be administered to a human in need thereof as a neat chemical or as a topical formulation that includes an effective amount of a compound described herein, or its pharmaceutically acceptable salt, for a human in need of treatment of acne vulgaris. Thus, in one embodiment, the disclosure provides topical formulations comprising an effective amount of a compound described herein, or its pharmaceutically acceptable salt, together with at least one topically acceptable carrier for any of the uses described herein. The topical formulation may contain a compound or salt as the only active ingredient, or, in an alternative embodiment, the compound and at least one additional active agent.

An effective amount of a compound as described herein, or a compound described herein in combination or alternation with, or preceded by, concomitant with or followed by another active agent, can be used in an amount sufficient to (a) inhibit the progression of acne vulgaris; (b) cause a regression of acne vulgaris; (c) cause a cure of acne vulgaris; or inhibit or prevent the development of acne vulgaris. Accordingly, an effective amount of a compound or pharmaceutically acceptable salt thereof or composition described herein will provide a sufficient amount of the agent when administered to human to provide a desired benefit.

Topical formulations are classified into three major categories: solid forms (such as dusting powders); liquid forms (such as lotions and liniments); and semi-liquid forms (such as ointments, pastes, creams, and gels). Additives or excipients are used as inactive ingredients in topical formulations for structuring. The main use of topical formulation additives is to control the extent of absorption of the active compound, maintaining the viscosity, improving the stability and organoleptic properties, and increasing the bulk of the formulation. The main goal of topical formulations is to confine the desired effect to the skin or within the skin. Such formulations are preferred because they are protective, emollient, and deliver the active agent to exert local activity when applied to the skin or mucous membranes.

In one embodiment, the topical formulation is a solid formulation such as a dusting powder. A dusting powder is a finely divided insoluble powder containing ingredients used on skin especially for allaying irritation or absorbing moisture, discouraging bacterial growth and providing lubricant properties. Easy powder flow ability and spreadability are important parameters that are considered in the manufacture and evaluation of a dusting powder formulation. The dusting powder should adhere to the skin, provide good coverage and skin adsorption, should be free of irritant properties, and should protect the skin from drying and irritation. Representative examples of excipients that can be used in dusting powder formulations include, but are not limited to, talc, starch (such as corn starch, wheat starch, or potato starch), kaolin, zinc stearate, zinc oxide, aluminum chlorohydrate, aluminum zirconium chlorhydrex, micronized wax, and chlorhexidine (as the acetate, gluconate, or hydrochloride salt).

In one embodiment, the topical formulation is a cream formulation. Creams are semisolid emulsion formulation for application to the skin or mucous membranes. Creams may be formulated as water in oil (w/o) emulsions or as oil in water (o/w) emulsions. Water in oil emulsion creams are less greasy and provide good spreadability compared to ointments. Oil in water emulsion creams, often called vanishing creams, readily rub into the skin and are easily removed by water.

Water in oil emulsion formulations typically consist of a hydrophilic component, e.g. water or other hydrophilic diluent, and a hydrophobic component, e.g. a lipid, oil, or oily material. The hydrophilic component is typically dispersed, i.e. exists as small particles and droplets, within the hydrophobic component. Water in oil emulsions typically comprise from about 1% to about 98% of the dispersed hydrophilic phase and from about 1% to about 50% of the hydrophobic phase. Additives commonly used in water in oil emulsion formulations include wool fat (containing sterols, cholesterol, oxycholesterol, triterpene, or aliphatic alcohols), waxes, bivalent soaps, sorbitan esters, borax, and oleic acid. In some embodiments, the water in oil emulsion refers to a water in silicone emulsion.

Oil in water emulsion formulations typically consist of a hydrophilic component, e.g. water or other hydrophilic diluent, and a hydrophobic component, e.g. a lipid, oil, or oily material. The hydrophobic component is typically dispersed, i.e. exists as small particles and droplets, within the hydrophilic component. Water in oil emulsions typically comprise from about 1% to about 98% of the hydrophilic phase and from about 1% to about 50% of the dispersed hydrophobic phase. Additives commonly used in oil in water emulsion formulations include polysorbates (such as Tween 80, Tween 21, and Tween 40), methylcellulose, acacia, tragacanth, triethanolamine oleate, arachis oil, and cetostearyl alcohol.

In one embodiment, the topical formulation is an ointment formulation. Ointments are greasy semisolid preparations of a dissolved or dispersed active compound. Ointment bases often influence topical drug bioavailability due to their occlusive properties of the stratum corneum, which enhances the flux of drug across the skin and affects drug dissolution or partitioning within and from the ointment to the skin. Ointments usually are moisturizing and are good for dry skin, as well as having a low risk of sensitization or irritation due to having few ingredients beyond the base oil or fat. The vehicle for an ointment formulation, known as an ointment base, may be an oleaginous base, an absorption base, or a water-soluble base.

Oleaginous bases are composed entirely of lipophilic materials. They are anhydrous, insoluble in water, and not easily removable with water. Oleaginous bases are inexpensive, non-reactive, nonirritating, are good emollients, have protective and occlusive properties, and are not water washable. Representative examples of oleaginous bases include hydrocarbons (such as petrolatum, paraffin wax, liquid paraffin, microcrystalline wax, plastibase, or Ceresi), vegetable oils and animal fat (such as coconut oil, bees wax, olive oil, lanolin, peanut oil, spermacetic wax, sesame oil, or almond oil), hydrogenated and sulfated oils (such as hydrogenated castor oil, hydrogenated cotton seed oil, hydrogenated soya bean oil, hydrogenated corn oil, or hydrogenated sulfated castor oils), alcohols/acids/esters (such as cetyl alcohol, stearic acid, stearyl alcohol, oleic acid, olelyl alcohol, palmitic acid, lauryl alcohol, lauraic acid, myristyl alcohol, ethyl oleate, isopropyl myristicate, or ethylene glycol), and silicones (such as dimethylpropylsiloxanes, methyl phenyl polysiloxanes, and steryl esters of dimethyl polysiloxanes).

Absorption bases are known to take up several times their own weights in water but not permit absorption of medicament form the base. The advantages of absorption bases are their protective, occlusive, and emollient properties, their ability to absorb liquids, and that they do not wash off easily, so they hold the incorporated compound with sufficient contact with the skin. Representative examples of absorption bases include hydrophilic petrolatum and anhydrous lanolin.

Water-soluble bases, also known as greaseless ointment bases, consists of water-soluble ingredients such as polyethylene glycol polymer (carbowax). Polyethylene glycol is water soluble, nonvolatile, and inert. Other water-soluble bases include glyceryl monostearate, cellulose derivatives, sodium alginate, bentonite, and carbopol 934.

In one embodiment, the topical formulation is a gel formulation. Gels are transparent or translucent semisolid preparations of one or more active ingredients in suitable hydrophilic or hydrophobic bases. Gels may be clear or opaque, and polar hydroalcoholic or nonpolar. Gels are prepared by either a fusion process or a special procedure necessitated by the gelling agents, humectants, and preservatives. Gelling agents exhibit pseudoplastic properties that give the formulation a thixotropic consistency. Gelling agents are typically used in concentrations of 0.5-10% to allow for easy addition of the active drug before the gel is formed. Representative examples of agents used in gel formulations include tragacanth, fenugreek mucilage, methyl cellulose, hydroxy ethyl cellulose, hydroxy propyl cellulose, hydroxy propyl methyl cellulose, carboxy methylcellulose, carbopol, pectin, poloxamers, alginates (such as sodium, potassium, or ammonium alginates), gelatin, starch, polyvinyl alcohol, povidone, propylene glycol, and ethyldiamine tetraacetic acid.

In one embodiment, the topical formulation is a paste formulation. Pastes are stiff preparations containing a high proportion of a finely powdered solid such as starch, zinc oxide, calcium carbonate, or talc. Pastes are often less greasy than ointment formulations.

In one embodiment, the topical formulation is a lotion formulation. Lotions are low-to medium-viscosity preparations intended for application to unbroken skin. Lotions are applied to external skin with bare hands, a clean cloth, cotton wool or gauze. Lotions provide cooling effects to the skin by the evaporation of solvents formulated therein. Typical additives in lotion formulations include bentonite, sodium carboxymethylcellulose, alcohols, and glycerin.

In one embodiment, the topical formulation is a liniment formulation. Liniments are liquid or semiliquid preparations meant for application to the skin with friction or rubbing. They act as a rubefacient, soother, or stimulant. Typical vehicles for liniment formulations are alcohol, oil, or soap based. Typical additives in a liniment formulation include castor oil, cotton seed oil, peanut oil, sesame oil, and oleic acid.

A wide variety of optional components/ingredients may be included in the topical formulations including, but not limited to, absorbents, abrasives, anticaking agents, antifoaming agents, antimicrobial agents, binders, biological actives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, antioxidants and/or radical scavengers, chelating agents, oil/sebum control agents, sweat control agents, sequestrants, anti-inflammatory agents, anti-androgens, depilation agents, desquamation agents/exfoliants, organic hydroxy acids, vitamins and derivatives thereof, and natural extracts.

An effective amount of a compound of Formula I through Formula VIII or a pharmaceutically acceptable salt or composition thereof can also be used to treat or prevent acne vulgaris in a human, due to any bacteria that causes such acne, including *P. acnes* and *S. epidermis.*

An effective amount of a compound selected from Compound A-Compound L or a pharmaceutically acceptable salt or composition thereof can also be used to treat or prevent acne vulgaris in a human, due to any bacteria that causes such acne, including *P. acnes* and *S. epidermis*. In one embodiment, a method is provided comprising administering to a human an effective amount of a compound described herein or its pharmaceutically acceptable salt thereof or composition either alone or in combination with an effective amount of an additional active agent, for example an antibiotic or anti-inflammatory agent, to treat acne vulgaris.

Acne vulgaris severity may be classified as mild, moderate, or severe. Mild acne is classically defined by the presence of clogged skin follicle (known as comedones) limited to the face with occasional inflammatory lesions. Moderate acne occurs when a higher number of inflammatory papules and pustules occur on the face, with some being found on the trunk of the body. Severe acne occurs when nodules are the characteristic facial lesions and involvement of the trunk is extensive.

The present method includes identifying a target portion of skin affected with acne vulgaris and in need of treatment and applying a compound of Formula I through Formula VIII or a pharmaceutically acceptable salt or composition thereof to the target portion of skin. In some instances, the target portion of skin may not appear to be suffering from acne vulgaris, i.e. the compound Formula I through Formula VIII or a pharmaceutically acceptable salt or composition as described herein may be used as a preventative therapy for acne vulgaris. The compound of Formula I through Formula VIII or a pharmaceutically acceptable salt or composition as described herein, may be applied to the target skin portion and, if desired, to the surrounding skin at least once a day, twice a day, or on a more frequent daily basis during the treatment period. Typically, the compound described herein or pharmaceutically acceptable salt thereof or composition is applied in the morning and/or in the evening before bed.

The treatment period is ideally sufficient time for the active compound to reduce or eliminate the appearance of acne vulgaris on the target portion of skin. The treatment period may last for at least 1 week, about two weeks, about 4 weeks, about 8 weeks, or about 12 weeks. The treatment period may extend over multiple months (about 3-12 months) or multiple years. The step of applying a compound described herein or a pharmaceutically acceptable salt or composition may be accomplished by localized application, i.e. by applying to the targeted area while minimizing delivery to skin surfaces where treatment is not desired, or by applying more generally or broadly to one or more skin surfaces. *Propionibacterium acnes* (reclassified as *Cutibacterium acnes* in 2016) is a Gram-positive bacterium (rod) linked to acne that belongs to the *Cutibacterium* Genus and the Propionibacteriaceae Family. Typically, slow growing, it is aerotolerant anaerobe, meaning that it can tolerate the presence of oxygen, but does not utilize oxygen for its growth. While the bacteria is involved in the maintenance of healthy skin, it can also cause many common skin disorders such as acne vulgaris. The bacteria predominately live deep within follicles and pores, where it uses sebum, cellular debris, and metabolic byproducts from surrounding skin tissue as a source of energy and nutrients. Elevated production of sebum or blockage of follicles can cause the bacteria to grow and this rapid growth can trigger inflammation that can led to the symptoms of common skin disorders, such as folliculitis and acne vulgaris.

*Staphylococcus epidermidis* is a Gram-positive bacterium belonging to the *Staphylococcus* Genus and the Staphylococcaceae Family that is part of the normal human flora and typically skin flora or mucosal flora. It is a facultative anaerobic bacterium and can therefore grow with or without oxygen. It is usually not pathogenic, but in patients with comprised immune systems, the bacteria can cause an infection. *Staphylococcus epidermidis* has ability to form biofilms on plastic and its infections are generally related to catheters or surgical implants.

In one embodiment, a compound of Formula I through Formula VIII or a pharmaceutically acceptable salt or composition thereof may be used in combination or alternation with benzoyl peroxide. In the skin follicle, benzoyl peroxide kills *P. acnes* by oxidizing its proteins through the formation of oxygen free radicals and benzoic acid. These radicals are believed to interfere with the bacterium's metabolism and ability to make proteins. Additionally, benzoyl peroxide is mildly effective at breaking down comedones and inhibiting inflammation. In one embodiment, a compound of Formula I through Formula VIII or a pharmaceutically acceptable salt is formulated in combination with benzoyl peroxide in a topical formulation as described herein.

In one embodiment, a compound of Formula I through Formula VIII or a pharmaceutically acceptable salt or composition as described herein may be used in combination or alternation with a retinoid. Retinoids are medications which reduce inflammation, normalize the follicle cell life cycle, and reduce sebum production. They are structurally related to vitamin A. The retinoids appear to influence the cell life cycle in the follicle lining; this helps prevent the accumulation of skin cells within the hair follicle that can create a blockage. Frequently used topical retinoids include adapalene, isotretinoin, retinol, tazarotene, and tretinoin. In one embodiment, a compound of Formula I through Formula VIII or a pharmaceutically acceptable salt thereof is formulated in combination with a retinoid in a topical formulation as described herein.

In one embodiment, a compound of Formula I through Formula VIII or a pharmaceutically acceptable salt or composition as described herein may be used in combination or alternation with an antibiotic. Antibiotics are frequently applied to the skin or taken orally to treat acne and are thought to work due to their antimicrobial activity against *P. acnes* and their ability to reduce inflammation. Commonly used antibiotics include clindamycin, erythromycin, metronidazole, sulfacetamide, and tetracyclines such as doxycycline and minocycline. Other representative topical antibiotics include bacitracin, polymycin b, neomycin, retapamulin, mupirocin, pramoxine, gentamicin, mafenide, and ozenoxacin. The antibiotics described herein can be applied to the skin, taken orally, or administered in any other suitable way as determined by one of skill in the art. The compounds described herein are particularly effective in combination with antibiotics due to their potentiation of the antimicrobial effect of the antibiotic. In one embodiment, a compound of Formula I through Formula VIII or a pharmaceutically acceptable salt thereof, is formulated in combination with an antibiotic in a topical formulation as described herein.

In one embodiment, a compound of Formula I through Formula VIII or a pharmaceutically acceptable salt or composition as described herein may be used in combination or alternation with azelaic acid. Azelaic acid is thought to be an effective acne treatment due to its ability to reduce skin cell accumulation in the follicle, along with its antibacterial and anti-inflammatory properties. In one embodiment, a compound of Formula I through Formula VIII or a pharmaceutically acceptable salt thereof is formulated in combination with an antibiotic in a topical formulation as described herein.

In one embodiment, a compound of Formula I through Formula VIII or a pharmaceutically acceptable salt thereof or composition as described herein may be used in combination or alternation with salicyclic acid. Salicyclic acid is a topically applied beta-hydroxy acid that has keratolytic properties in addition to stopping bacterial reproduction. In one embodiment, a compound of Formula I through Formula VIII or a pharmaceutically acceptable salt thereof is formulated in combination with salicyclic acid in a topical formulation as described herein.

In one embodiment, a compound of Formula I through Formula VIII or a pharmaceutically acceptable salt thereof or composition as described herein may be used in combination or alternation with niacinamide. Niacinamide can improve acne by decreasing inflammation, suppressing sebum production, and promoting wound healing. In one embodiment, a compound of Formula I through Formula VIII or a pharmaceutically acceptable salt thereof is formulated in combination with salicyclic acid in a topical formulation as described herein.

VII. GENERAL SYNTHESIS

The compounds described herein can be prepared by methods known to those skilled in the art. In one non-limiting example, the disclosed compounds can be made using the routes provided below.

Compounds of the present invention with stereocenters may be drawn without stereochemistry for convenience. One skilled in the art will recognize that pure enantiomers and diastereomers can be prepared by methods known in the art. Example of methods to obtain optically active materials include at least the following.

i. physical separation of crystals—a technique whereby macroscopic crystals of the individual enantiomers are manually separated. This technique can be used if crystals of the separate enantiomers exist, i.e., the material is a conglomerate, and the crystals are visually distinct;

ii. simultaneous crystallization—a technique whereby the individual enantiomers are separately crystallized from a solution of the racemate, possible only if the enantiomer is a conglomerate in the solid state;

iii. enzymatic resolutions—a technique whereby partial or complete separation of a racemate by virtue of differing rates of reaction for the enantiomers with an enzyme;

iv. enzymatic asymmetric synthesis—a synthetic technique whereby at least one step in the synthesis uses an enzymatic reaction to obtain an enantiomerically pure or enriched synthetic precursor of the desired enantiomer;

v. chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi. diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii. first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii. kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix. enantiospecific synthesis from non-racemic precursors—a synthetic technique whereby the desired enantiomer is obtained from non-chiral starting materials and where the stereochemical integrity is not or is only minimally compromised over the course of the synthesis;

x. chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi. chiral gas chromatography—a technique whereby the racemate is volatilized and enantiomers are separated by virtue of their differing interactions in the gaseous mobile phase with a column containing a fixed non-racemic chiral adsorbent phase;

xii. extraction with chiral solvents—a technique whereby the enantiomers are separated by virtue of preferential dissolution of one enantiomer into a particular chiral solvent;

xiii. transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through; and xiv. simulated moving bed chromatography is used in one embodiment. A wide variety of chiral stationary phases are commercially available.

VIII. EXAMPLES

Example 1. Synthesis of Representative Examples of the Present Invention

The synthesis of representative compounds of the present invention are described in Arafa et. Al., "Novel linear triaryl guanidines, N-substituted guanidines and potential prodrugs as antiprotozal agents", European Journal of Medicinal Chemistry, 2008, 43, 2901-2908 (Compound A); Wang et al. "Evaluation of the Influence of Compound Structure on Stacked-Dimer Formation in the DNA Minor Groove" *Biochemistry,* 2001, 40, 2511 (Compound B); WO2002/055025, Scheme 1 and page 22, paragraph 120 (Compound D); Giordani et al. "Green Fluorescent Diamidine as Diagnostic Probes for Trypanosomes" Antimicrobial Agents and Chemotherapy 2014, 58:1793 (Compound M, Compound N, Compound P, Compound Q); Ismail M A, Boykin D W, and Stephens C E, "An efficient synthesis of 2,5'-diarylbichalcophenes", Tetrahedron Letters, 2006, 47, pg. 795-797 (Compound O); WO2009/051796, Example 1, Scheme 1 on page 40 and 41 (Compound R); Gonzalez et. al., "Synthesis and antiparasitic evaluation of bis-2,5-[4-guanidinophenyl] thiophenes", European Journal of Medicinal Chemistry, 2007, 42, 552-557 (Compound C); EP1726589, Example 3, Scheme 4 on page 27, and paragraph 142 (Compound T).

Synthesis of Compound U

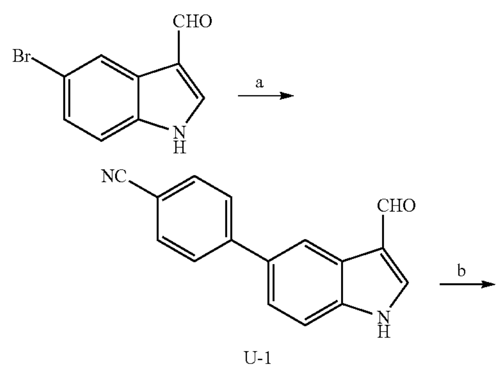

U-1

-continued

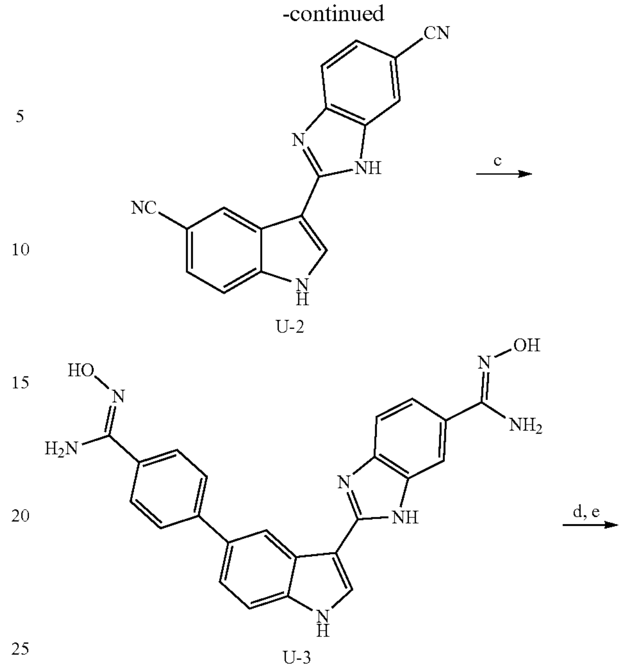

U-2

U-3

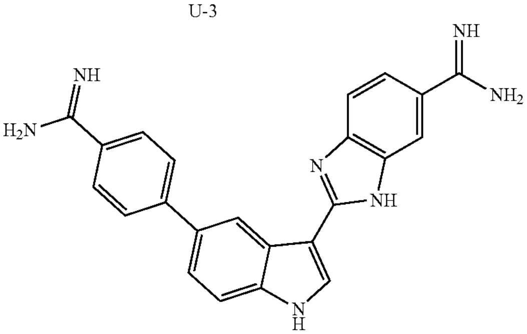

Compound U a) 3,4-diaminobenzonitrile 4-cyanobenzeneboronic acid, Pd(PPh3)4, reflux, overnight;
b) 3,4-diaminobenzonitrile, sodium bisulfite, DMF, reflux, overnight;
c) hydroxylamine hydrochloride, potassium t-butoxide, DMSO, rt, overnight;
d) glacial acetic acid, acetic anhydride, 2h;
e) $H_2$, Pd/C.

5-(4-Cyanophenyl)indole-3-carbaldehyde (U-1)

To a solution of 5-bromoindole-3-carbaldehyde (1.12 g, 5.0 mmol) and $Pd(PPh_3)_4$ (0.30 g, 0.26 mmol) in 20 mL of toluene under a nitrogen atmosphere was added 10 mL of 2M aqueous $NaHCO_3$ and 0.74 g (5.0 mmol) of 4-cyanobenzeneboronic acid in 5 mL of methanol. The mixture was vigorously stirred and heated under reflux overnight. The mixture was cooled and extracted with dichloromethane. The organic layer was dried and concentrated to dryness under reduced pressure to afford 1.0 g (81%) of product, mp 248-250° C. 1H-NMR (DMSO-$d_6$) δ 10.98 (d, 1H, J=2), 8.40 (d, 1H, J=2), 7.87 (dd, 4H, J=8 and J=2), 7.62 (s, 1H); 13C-NMR (DMSO-d6) δ 185.2, 145.7, 139.4, 137.2, 132.8, 132.7, 127.6, 124.9, 122.9, 119.4, 119.0, 118.4, 113.2, 109.3. Anal. calcd. $C_{16}H_{10}N_2O$: C, 78.03; H, 4.09. Found: C, 77.73; H, 4.17.

3-(5-Cyanobenzimidazol-2-yl)-5-(4-cyanophenyl)indole (U-2)

A solution of 5-(4-cyanophenyl)indole-3-carbaldehyde (0.80 g, 3.25 mmol), 3,4-diaminobenzonitrile (0.44 g, 3.3 mmol) and sodium bisulfite (0.40 g, 3.9 mmol) in 5 mL DMF was heated under reflux overnight. After cooling, the mixture was poured onto chipped ice. The solid was collected by filtration and washed with aqueous sodium bicarbonate (2.5%) and water to yield 1.0 g (85%) of an off white solid, mp 311-313° C. $^1$H-NMR (DMSO-$d_6$) δ 8.82 (s, 1H), 8.28 (s, 1H), 7.93 (s, 4H), 7.61 (m, 4H); $^{13}$C-NMR (DMSO-$d_6$) δ 152.3, 146.3, 136.8, 132.9, 131.4, 128.7, 125.7, 125.2, 122.0, 120.4, 119.1, 113.0, 109.1, 106.3, 103.0; HRMS (FAB) calcd. mass for $C_{23}H_{13}N_5$ (M+H): 360.383; observed mass, 360.125.

3-(5-Hydroxyamidinobenzimidazol-2-yl)-5-(4-hydroxyamidinophenyl)indole (U-3)

To a solution of hydroxylamine hydrochloride (0.72 g, 10.3 mmol) in 5 mL of DMSO, potassium t-butoxide (1.16 g, 10.3 mmol) was added in portions under nitrogen. After stirring the mixture for 30 minutes, 0.37 g (1.01 mmol) of 3-(5-cyanobenzimidazol-2-yl)-5-(4-cyanophenyl)indole was added and the mixture was stirred at room temperature overnight. The mixture was poured into ice water and filtered to yield the expected 3-(5-hydroxyamidinobenzimidazol-2-yl)-5-(4-hydroxyamidinophenyl)indole as a white solid, 0.43 g (98%); mp 370° C. (decomp.); $^1$H-NMR (DMSO-$d_6$) δ 9.71 (s, 1H), 9.60 (s, 1H), 8.79 (s, 1H), 8.23 (d, 1H, J=2.7), 7.84 (d, 2H, J=8.4), 7.76 (d, 2H, J=8.4), 7.60 (m, 5H), 5.98 (s, 2H), 5.91 (s, 4H); $^{13}$C-NMR (DMSO-$d_6$) δ 172.1, 152.3, 150.8, 150.4, 142.3, 136.3, 132.5, 131.5, 127.4, 126.6, 126.4, 126.0, 125.7, 121.7, 119.5, 119.4, 112.6, 106.9. Anal. calcd. for $C_{23}H_{19}N_7O_2 \cdot 2.3H_2O$: C, 59.17; H, 5.09. Found: C, 59.11; H, 4.99.

3-(5-Acetoxyamidinobenzimidazol-2-yl)-5-(4-acetoxyamidinophenyl)indole

The above amidoxime (0.35 g, 2.0 mmol) was dissolved in glacial acetic acid (5 mL) and acetic anhydride (0.5 mL, 6.5 mmol) was added. The mixture was allowed to stir for 2 hours and the solvent was evaporated. The product was used in the next step without further characterization.

3-(5-Amidinobenzimidazol-2-yl)-5-(4-amidinophenyl)indole acetate salt (Compound U)

Crude 3-(5-acetoxyamidinobenzimidazol-2-yl)-5-(4-acetoxyamidinophenyl)indole was submitted to catalytic hydrogenation in the presence of Pd/C to afford 0.25 g (43% yield) of Compound L, mp >228° C. $^1$H-NMR (DMSO-$d_6$) δ 8.86 (s, 1H), 8.37 (s, 1H), 8.12 (s, 1H), 7.93 (m, 4H), 7.62 (m, 4H), 5.99 (br, 1H), 1.82 (s, 11H); 13C-NMR (DMSO-$d_6$) δ 175.5, 166.7, 165.9, 152.5, 146.5, 136.9, 131.5, 128.8, 128.4, 127.1, 127.0, 125.9, 121.9, 121.4, 120.9, 119.9, 112.9, 106.6, 24.0; HRMS (FAB) calcd. mass for $C_{23}H_{19}N_6$ (M+H): 394.450; observed mass, 394.178. Anal. calcd. for $C_{23}H_{19}N_6 \cdot 3.5CH_3COOH \cdot 3.0H_2O$: C, 54.78, H, 5.97; N, 14.90. Found: C, 54.83, H, 5.79; N, 14.81.

General Methods for the Synthesis of Diamidine Compounds

Diamidine compounds were synthesized from dinitrile compounds, either through method B or method C. Substituted amidine or cyclized amidine compounds (MD-102, MD-112, MD-113 and MD-129) were synthesized from dinitrile compounds through method D.

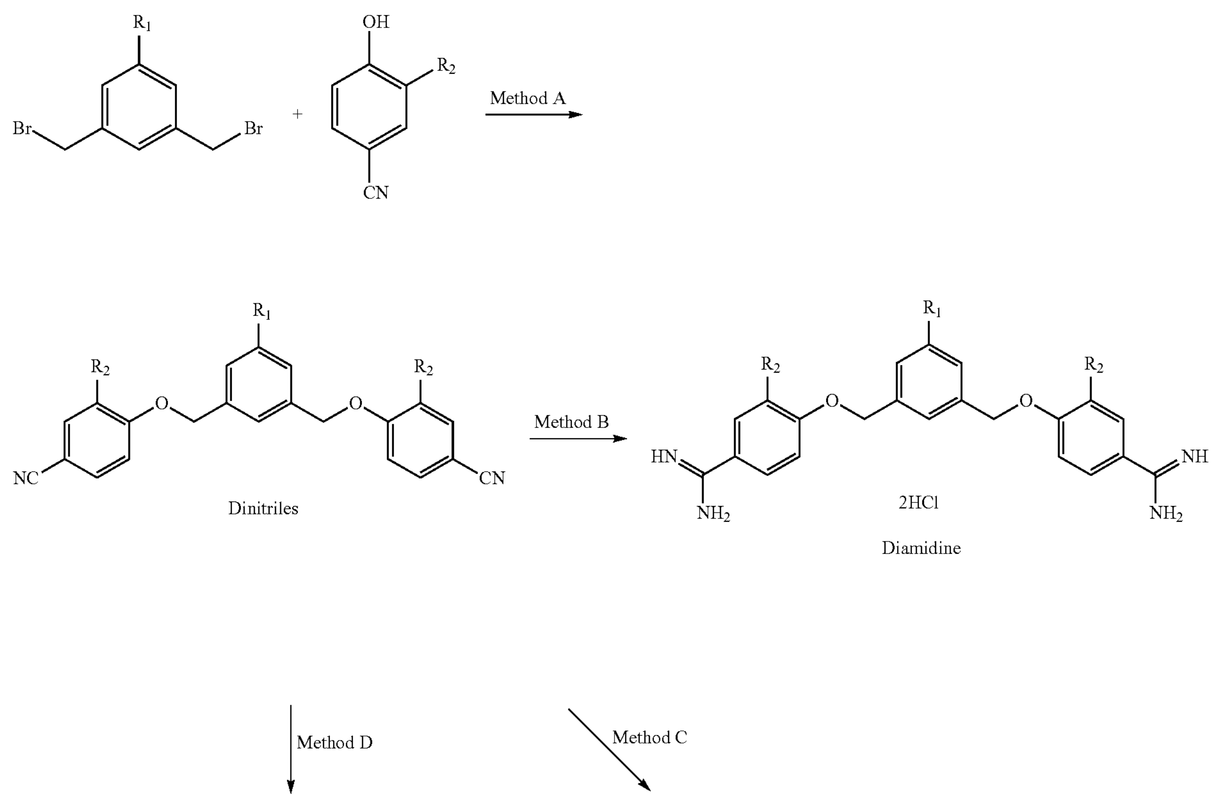

-continued

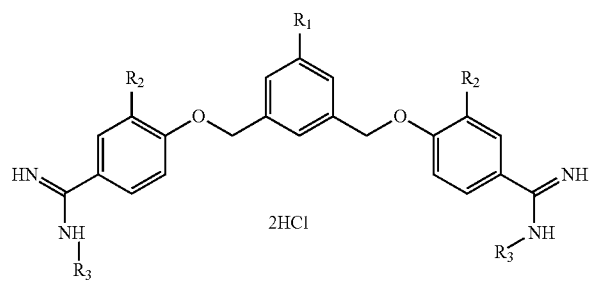

Substituted or cyclized Diamidine

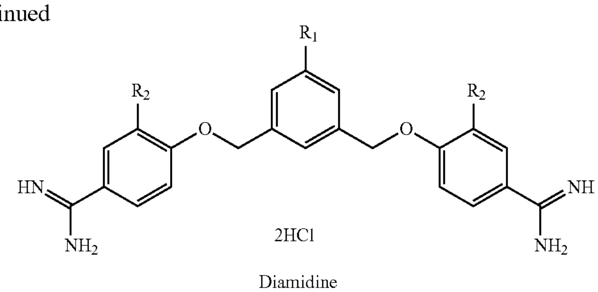

Diamidine

General Procedures for the Preparation of Dinitriles (Method A)

A mixture of 1,3-bis (bromomethyl)-benzene/substituted benzene (5 mmol), 4-hydroxybenzonitrile or 4-hydroxy substituted benzonitrile (10 mmol) and anhydrous $K_2CO_3$ (2.07 g, 15 mmol) in 10 mL DMF was heated at 45° C. for 4 hours. Then the reaction mixture was diluted with ice water (70 mL) and stirred for 30 minutes. The white precipitate was filtered, washed with water, and dried in air. Then the white solid was dissolved in organic solvent (75 mL) (DCM, methanol or THF). The organic phase was dried over anhydrous $MgSO_4$. $MgSO_4$ was then filtered and the supernatant was concentrated with rotavapor to afford crude product. The crude product was then triturated with hexane, filtered and dried in vacuum to yield white solid in 80-90% yield.

General Procedure for Diamidines as Dihydrochloride Salt (Method B)

To a cold and stirred suspension of dinitrile (1 mmol) in 15 mL dry THF was added 6.0 mL (6 mmol) of $LiN(TMS)_2$ (1M in THF). The reaction was stirred for 24 hours at room temperature. Then the mixture was cooled and acidified with saturated ethanolic-HCl to form a white solid. The mixture was stirred for 2 hours, after which all solvents were removed under vacuum to afford a crude product. The crude product was then diluted with ether and the mixture was filtered to obtain a white solid. The white solid was then diluted with 10 mL ice water and basified with 2M NaOH to afford a white precipitate. The white precipitate was then filtered, washed with water and dried in air. The solid was suspended in anhydrous ethanol (15 mL) and 5 mL saturated ethanolic HCl for 6 hours. Then ethanol was distilled off and the product was triturated with dry ether and filtered. The solid was dried in vacuum at 80° C. for 12 hours to yield (65-75%) diamidine dihydrochloride as white solid.

General Procedure for Diamidines as Dihydrochloride Salt (Method C)

Dinitrile (1 mmol) was added to anhydrous ethanol (EtOH) saturated with hydrogen chloride (20 mL) at 0° C. in a dry flask. The reaction mixture was then sealed, slowly warmed to ambient temperature, and stirred for 7 days. Ethanol was removed using rotary evaporator. Anhydrous diethyl ether (20 mL) was added to the reaction mixture and the precipitated imidate ester dihydrochloride was filtered off and dried under high vacuum. Ammonia gas (using a cylinder) was passed through imidate ester in EtOH (10 mL) and stirred for a day. The reaction mixture was concentrated in vacuum. Then anhydrous ether was added, and the product was filtered and dried under vacuum. The diamidine was converted to its dihydrochloride salt by stirring the diamidine with saturated ethanolic HCl (2 mL) for 2-3 hours. The solvent was removed, and the solid was dried in vacuum at 80° C. for 12 hours to yield final product (65-75%).

General Procedure for the Preparation of Substituted Diamidine or Cyclized Diamidine as Dihydrochloride Salts (Method D)

The nitrile compound was added to anhydrous EtOH saturated with hydrogen chloride at 0° C. in a dry flask. The reaction mixture was then sealed, slowly warmed to ambient temperature, and stirred until the nitrile compound was no longer detectable by TLC. The reaction mixture was diluted with anhydrous ether. The precipitated imidate ester dihydrochloride was filtered off under nitrogen and dried under high vacuum. The imidate was then reacted immediately with 2.5 equivalents of the appropriate amine in EtOH for 24 hours. The reaction mixture was concentrated in vacuum. Then ether was added, and the product was filtered. The solid was suspended in 10 mL ice-water and basified with 2M NaOH. The resulting white precipitate was filtered, washed with water, and air dried. The free base was converted to its dihydrochloride salt using saturated ethanolic HCl as white solid, which was dried in vacuum at 80° C. for 12 hours to yield final product (65-75%).

Synthesis of MD-100

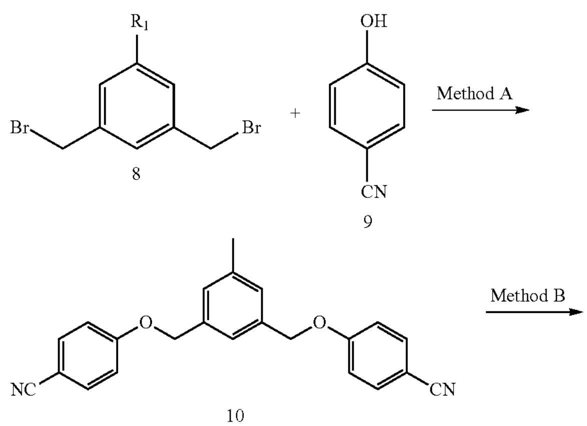

8 9 10

-continued

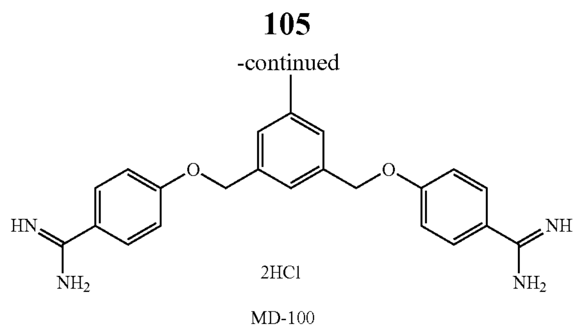

MD-100

Synthesis of 4,4'-((5-methyl-1,3-phenylene)bis(methylene))bis(oxy))dibenzonitrile (10). Reaction of 1,3-bis (bromomethyl)-5-methylbenzene (8, 1.38 g, 5 mmol) and 4-hydroxybenzonitrile (9, 1.19 g, 10 mmol) in the presence of anhydrous $K_2CO_3$ (2.07 g, 15 mmol) in 10 mL DMF yielded 1, 3-bis (4-cyano-phenoxy methyl)-5-methyl-benzene as white solid (10, 1.58 g, 90%) using method A. $^1$H NMR ($CDCl_3$): δ 7.59 (d, J=8.8 Hz, 4H), 7.26 (s, 1H), 7.22 (s, 2H), 7.02 (d, J=8.8 Hz, 4H), 5.09 (s, 4H), 2.40 (s, 3H). $^{13}$C NMR ($CDCl_3$): δ 161.9, 139.3, 136.4, 134.1, 128.3, 123.7, 119.2, 115.6, 104.3, 70.1, 21.4. HRMS calcd for $C_{23}H_{18}N_2O_2Na$ $[M+Na]^+$: 377.1266, found: 377.1269.

Synthesis of 4,4'-(((5-methyl-1,3-phenylene)bis(methylene))bis(oxy))dibenzimidamide dihydrochloride (MD-100). 10 (0.354 g, 1 mmol) was converted to MD-100 as brown solid following method B (MD-100, 0.33 g, 71%). $^1$H NMR (DMSO-$d_6$): δ 9.24 (s, 4H), 8.90 (s, 4H), 7.82 (d, J=8.8 Hz, 4H), 7.34 (s, 1H), 7.25 (s, 2H), 7.20 (d, J=8.8 Hz, 4H), 5.18 (s, 4H), 2.32 (s, 3H). $^{13}$C NMR (DMSO-$d_6$): δ 165.0, 162.9, 138.6, 136.9, 130.5, 128.5, 124.6, 120.0, 115.5, 69.9, 21.2. HRMS calcd for $C_{23}H_{25}N_4O_2$ $[M+H]^+$: 389.1972, found: 389.1976.

1, 4-Bis [(4-amidino)-phenoxy methyl]benzene dihydrochloride (MD-101)

Reaction of 1,4-bis (bromomethyl)lbenzene (1.32 g, 5 mmol) and 4-hydroxybenzonitrile (1.19 g, 10 mmol) yielded 1, 4-bis (4-cyano-phenoxy methyl) benzene as white solid (1.74 g, 78%), using method A; $^1$H NMR ($CDCl_3$): 7.59 (d, 4H, J=8.9 Hz), 7.45 (s, 4H), 7.02 (d, J=8.9 Hz, 4H), 5.13 (s, 4H); $^{13}$C NMR ($CDCl_3$): 161.82, 136.01, 134.07, 127.86, 119.10, 115.57, 104.45, 69.88; MS: HRMS-ESI-POS.: calc. for $C_{22}H_{17}N_2O_2$ m/z 341.1285 ($M^+$+1), found m/z 341.1283. Dinitrile (0.340 g, 1 mmol) was converted to 1, 4-bis (4-amidino (phenoxy methyl))benzene dihydrochloride as pale yellow solid following Method B (0.33 g, 76%). $^1$H NMR (DMSO-$d_6$): 9.25 (s, 4H), 9.02 (s, 4H), 7.85 (d, J=8.9 Hz, 4H), 7.51 (s, 4H), 7.23 (d, J=9.0 Hz, 4H), 5.26 (s, 4H); $^{13}$C NMR (DMSO-$d_6$): 165.16, 163.12, 136.67, 130.67, 128.49, 120.12, 115.64, 69.79; MS: HRMS-ESI-POS.: calc. for $C_{22}H_{24}N_4O_2$ m/z 188.0944 ($M/2^+$+2), found m/z 188.0936.

Synthesis of MD-102

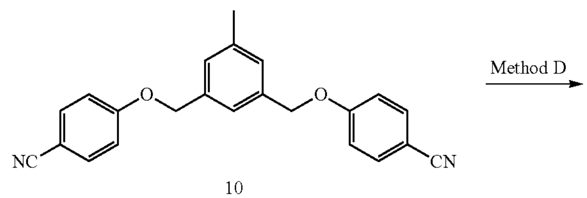

10

-continued

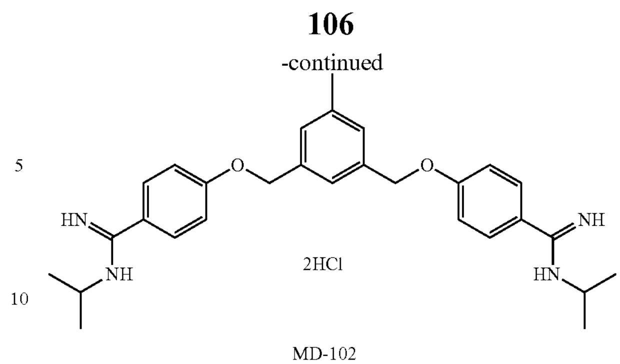

MD-102

Synthesis of 4,4'-(((5-methyl-1,3-phenylene)bis(methylene))bis(oxy))bis(N-isopropylbenzimidamide) dihydrochloride (MD-102). Dinitrile (10, 0.35 g, 1 mmol) was converted to MD-102 by the reaction with isopropyl amine (0.15 g, 2.5 mmol) in ethanol (10 mL) at room temperature for 24 hours as a pale yellow solid using general method D (MD-102, 0.27 g, 50%). $^1$H NMR (DMSO-$d_6$): δ 9.43 (d, J=8.0 Hz, 2H), 9.33 (s, 2H), 8.99 (s, 2H), 7.73 (d, J=8.8 Hz, 4H), 7.36 (s, 1H), 7.27 (s, 2H), 7.21 (d, J=8.8 Hz, 4H), 5.20 (s, 4H), 4.09-4.04 (m, 2H), 2.34 (s, 3H), 1.26 (d, J=6.4 Hz, 12H). $^{13}$C NMR (DMSO-$d_6$): δ 162.1, 161.2, 138.1, 136.7, 130.3, 128.1, 124.3, 121.2, 114.9, 69.5, 54.9, 44.9, 21.3, 21.0. HRMS calcd for $C_{29}H_{38}N_4O_2$ $[M+2H]^{2+}/2$: 237.1492, found 237.1482.

Synthesis of MD-103

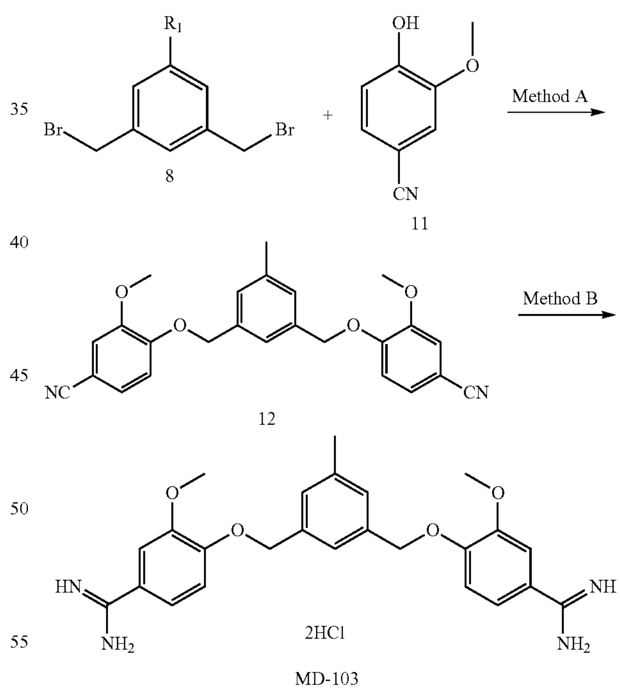

8

11

12

MD-103

Synthesis of 4,4'-(((5-methyl-1,3-phenylene)bis(methylene))bis(oxy))bis(3-methoxybenzonitrile) (12). Reaction of 1,3-bis (bromomethyl)-5-methylbenzene (8, 1.4 g, 5 mmol) and 4-hydroxy-2-methoxybenzonitrile (11, 1.37 g, 10 mmol) in the presence of anhydrous $K_2CO_3$ (2.07 g, 15 mmol) in 10 mL DMF yielded 4,4'-(((5-methyl-1,3-phenylene)bis(methylene))bis(oxy))bis(3-methoxybenzonitrile) as white solid (12, 1.57 g, 76%) following method A. $^1$H NMR (DMSO-$d_6$): δ 7.41-7.39 (m, 4H), 7.30 (s, 1H), 7.24 (s, 2H), 7.18 (d, J=8.8 Hz, 2H), 5.15 (s, 4H), 3.80 (s, 6H), 2.33 (s, 3H). $^{13}C$ NMR (DMSO-$d_6$): δ 151.8, 149.2, 138.0, 136.5, 128.5, 126.3, 124.6, 119.2, 114.7, 113.4, 102.9, 69.9, 56.0, 21.0. HRMS calcd for $C_{25}H_{23}N_2O_4$ $[M+H]^+$: 415.1652, found 415.1643.

Synthesis of 4,4'-(((5-methyl-1,3-phenylene)bis(methylene))bis(oxy))bis(3-methoxybenzimidamide) dihydrochloride (MD-103). Dinitrile (12, 0.41 g, 1 mmol) was converted to yield 4,4'-(((5-methyl-1,3-phenylene)bis(methylene))bis(oxy))bis(3-methoxybenzimidamide) dihydrochloride as brown solid following method B (MD-103, 0.39 g, 76%). $^1H$ NMR (DMSO-$d_6$): δ 9.27 (s, 4H), 8.97 (s, 4H), 7.49-7.48 (m, 4H), 7.33 (s, 1H), 7.26-7.24 (m, 4H), 5.18 (s, 4H), 3.86 (s, 6H), 2.34 (s, 3H). $^{13}C$ NMR (DMSO-$d_6$): δ 164.7, 152.3, 148.81, 138.1, 136.7, 128.5, 124.7, 121.9, 119.5, 112.8, 111.6, 70.0, 56.1, 21.0. HRMS calcd for $C_{25}H_{30}N_4O_4$ $[M+2H]^{2+}/2$: 225.1128, found 225.1119.

1, 4-Bis [((4-amidino)-2-methoxy)-phenoxy methyl] 2-fluorobenzene dihydrochloride (MD-104)

Dinitrile (0.41 g, 1 mmol) was converted to 1, 4-Bis [((4-amidino)-2-methoxy)-phenoxy methyl]2-fluorobenzene dihydrochloride as a brown solid following Method B (0.37 g, 72%). $^1H$_NMR (DMSO-$d_6$): 9.32 (s, 4H), 9.04 (s, 4H), 7.61 (t, 2H, J=7.2 Hz), 7.53 (m, 4H), 7.39-7.28 (m, 4H), 5.27 (s, 4H), 3.863 (s, 6H); $^{13}C$ NMR (DMSO-$d_6$): 165.30, 159.29 (d, $J_{C-F}$=250 Hz), 152.58, 149.19, 131.86 (d, $J_{C-F}$=2.9 Hz), 125.03 (d, $J_{C-F}$=3.6 Hz), 123.88 (d, $J_{C-F}$=14.7 Hz), 122.23, 120.32, 113.18, 111.99, 64.79 (d, $J_{C-F}$=3.2 Hz), 56.40; MS: HRMS-ESI-POS.: calc. for $C_{24}H_{27}FN_4O_4$ m/z 237.1003 ($M/2^+ +2$), found m/z 237.0995.

Synthesis of MD-105

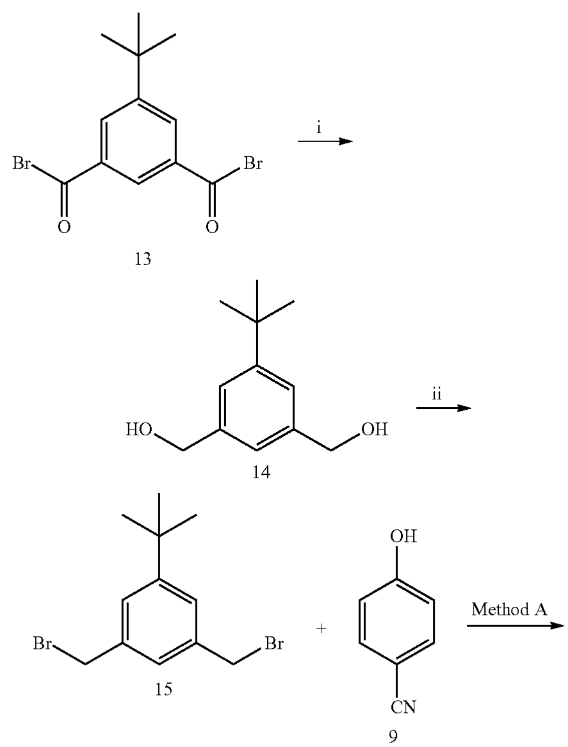

13

14

15

9

-continued

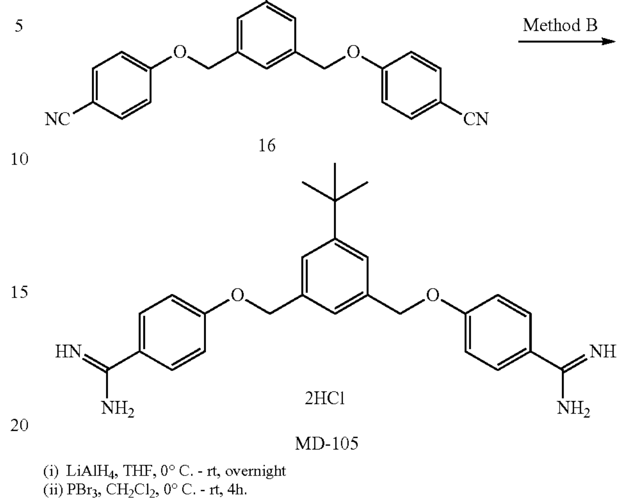

16

2HCl

MD-105

Synthesis of diol (5-(tert-butyl)-1,3-phenylene)dimethanol (14). 5-tert-butylisophthalic acid (13, 4 g, 18 mmol) in THF (100 mL) was added dropwise under ice-bath condition to a solution of lithium aluminium hydride (1.5 g, 38 mmol) in THF (100 mL). The reaction was stirred for 1 hour at 0° C., after which the reaction was heated at 60° C. for 24 hours. The reaction was monitored by TLC. Upon completion, the reaction mixture was cooled to 0° C. and quenched with methanol and water. The quenched reaction was filtered through celite and washed with EtOAc (100 mL). The combined organic solvent was removed under reduced pressure and was extracted with EtOAc (3×100 mL), dried over $MgSO_4$ and concentrated to give the required diol (5-(tert-butyl)-1,3-phenylene)dimethanol (14, 3.2 g, 94%). $^1H$ NMR ($CDCl_3$): δ 7.32 (s, 2H), 7.19 (s, 1H), 4.69 (s, 4H), 1.33 (s, 6H). $^{13}C$ NMR ($CDCl_3$): δ 152.2, 141.1, 123.6, 123.1, 65.7, 34.9, 31.5. HRMS calcd for $C_{12}H_{17}O$ $[M-H_2O]^+$: 177.1274, found 177.1274.

Synthesis of 1, 3-bis (4-cyano-phenoxy methyl)-5-(tert-butyl)benzene (16). $PBr_3$ (2.5 mL, 26 mmol) was added dropwise to a solution of diol (5-(tert-butyl)-1,3-phenylene) dimethanol (14, 2.3 g, 11.8 mmol) in DCM at 0° C. The reaction mixture was stirred at room temperature for 4 hours and then quenched with ice water. The solution was extracted with $CH_2Cl_2$ (3×100 mL), dried over $MgSO_4$ and concentrated to give the required dibromo compound (1,3-bis(bromomethyl)-5-(tert-butyl)benzene) as a white solid (15, 3.4 g, 90%). Reaction of 1,3-bis(bromomethyl)-5-(tert-butyl)benzene (15, 1.6 g, 5 mmol) and 4-hydroxybenzonitrile (9, 1.19 g, 10 mmol) yielded dinitrile compound as white solid (16, 1.54 g, 78%) using method A. $^1H$ NMR (DMSO-$d_6$): δ 7.79-7.78 (m, 4H), 7.48 (s, 2H), 7.36 (s, 1H), 7.20-7.18 (m, 4H), 5.20 (s, 4H), 1.29 (s, 9H). $^{13}C$ NMR ($CDCl_3$): δ 161.8, 151.3, 136.1, 134.2, 124.8, 119.1, 115.9, 103.0, 69.9, 34.5, 31.1. HRMS calcd for $C_{26}H_{25}N_2O_2$ $[M+H]^+$: 397.1911, found 397.1912.

Synthesis of 4,4'-(((5-(tert-butyl)-1,3-phenylene)bis(methylene))bis(oxy))dibenzimidamide dihydrochloride (MD-105). 1, 3-bis (4-cyano-phenoxy methyl)-5-(tert-butyl) benzene (16, 0.370 g, 1 mmol) was converted to yielded 4,4'-(((5-(tert-butyl)-1,3-phenylene)bis(methylene))bis(oxy))dibenzimidamide dihydrochloride as brown solid following method B (MD-105, 0.35 g, 70%). $^1H$ NMR (DMSO-$d_6$): δ 9.42 (s, 4H), 9.21 (s, 4H), 7.94 (d, J=8.4 Hz, 4H), 7.49 (s, 2H), 7.39 (s, 1H), 7.23 (d, J=8.4 Hz, 4H), 5.23 (s, 4H), 1.28 (s, 9H). $^{13}C$ NMR (DMSO-$d_6$): δ 165.7, 163.5, 152.5, 137.0, 131.0, 125.6, 120.3, 116.1, 70.7, 35.2, 31.8. HRMS calcd for $C_{26}H_{31}N_4O_2$ $[M+H]^+$: 431.2442, found 431.2425.

Synthesis of MD-106

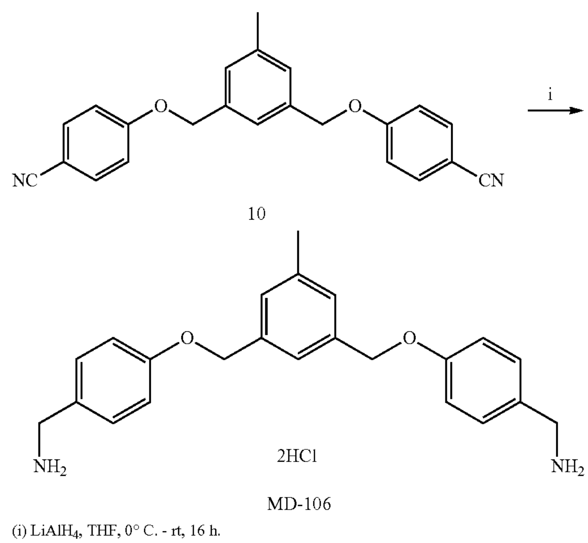

10

MD-106

Synthesis of ((((S-methyl-1,3-phenylene)bis(methylene)) bis(oxy))bis(4,1-phenylene))dimethanamine dihydrochloride (MD-106). A solution of 1, 3-bis (4-cyano-phenoxy methyl)-5-methyl-benzene (10, 1.0 g, 2.8 mmol) in THF (20 mL) was added dropwise to a suspension of $LiAlH_4$ (0.32 g, 7.4 mmol) in THF under argon gas at 0° C. and the mixture was stirred at room temperature for 16 hours. The reaction was quenched with the addition of $H_2O$ (5 mL) at 0° C. followed by addition of 16% NaOH solution (2 mL). The mixture was stirred at room temperature for around 2 hours after which it was filtered through celite. The solution was then concentrated in vacuo to obtain the free diamine. The product residue was then dissolved in ethanol followed by addition of HCl in ethanol (2 mL) for salt formation. The reaction mixture was evaporated in vacuo followed by ether precipitation to obtain the product as a green solid. (MD-106, 1.0 g, 87%). $^1H$ NMR (DMSO-$d_6$): δ 8.45 (s, 6H), 7.43 (d, J=8.4 Hz, 4H), 7.32 (s, 1H), 7.22 (s, 2H), 7.03 (d, J=8.4 Hz, 4H), 5.09 (s, 4H), 2.32 (s, 3H). 15 $^{13}C$ NMR (DMSO-$d_6$): δ 158.4, 137.9, 137.2, 130.5, 127.8, 126.2, 124.3, 114.8, 69.2, 41.6, 21.0. HRMS calcd for $C_{23}H_{27}N_2O_2$ $[M+H]^+$: 363.2079, found 363.2067.

Synthesis of MD-107

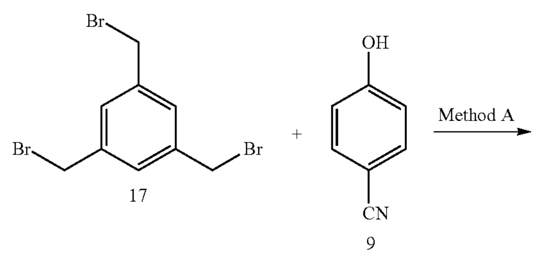

17 9

-continued

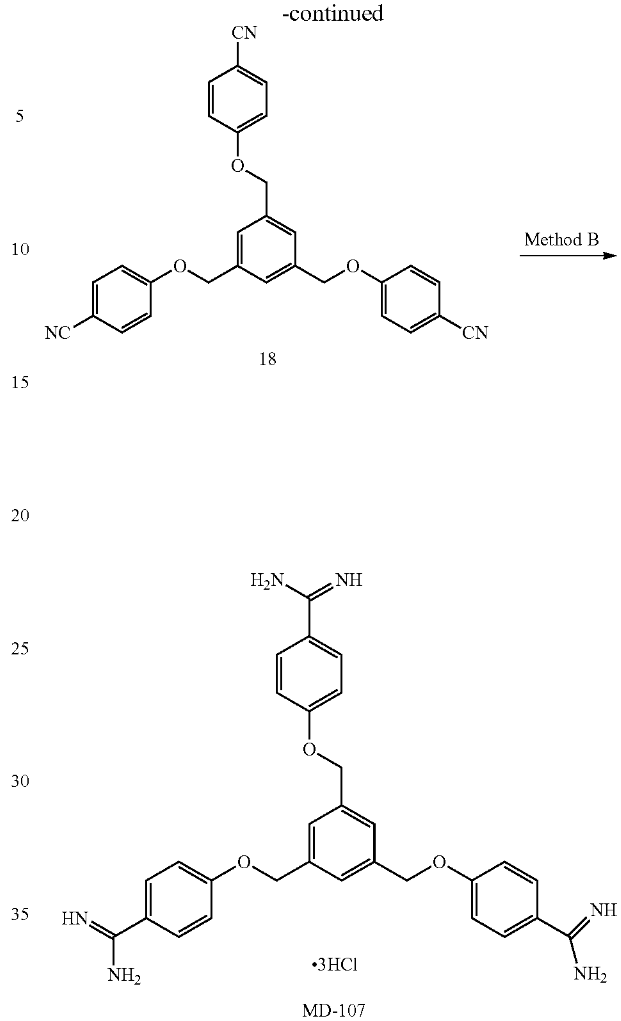

18

MD-107

Synthesis of 4,4',4"-((benzene-1,3,5-triyltris(methylene)) tris(oxy))tribenzonitrile (18). Reaction of 1,3,5-tris (bromomethyl)benzene (17, 1.54 g, 4.3 mmol) and 4-hydroxy-benzonitrile (9, 1.64 g, 14 mmol) the presence of anhydrous $K_2CO_3$ (2.35 g, 17 mmol) in 10 mL DMF yielded 4,4',4"-((benzene-1,3,5-triyltris(methylene))tris(oxy))tribenzonitrile as a white solid (18, 1.69 g, 84%), using method A. $^1H$ NMR (DMSO-$d_6$): δ 7.77 (d, J=9.2 Hz, 6H), 7.53 (s, 3H), 7.18 (d, J=9.2 Hz, 6H), 5.24 (s, 6H). $^{13}C$ NMR (DMSO-$d_6$): δ 161.7, 137.0, 134.2, 126.9, 119.1, 115.9, 103.2, 69.3. HRMS calcd for $C_{30}H_{21}N_3O_3Na$ $[M+Na]^+$: 494.1481, found 494.1481.

Synthesis of 4,4',4"-((benzene-1,3,5-triyltris(methylene)) tris(oxy))tribenzimidamide trihydrochloride (MD-107). Trinitrile (18, 0.56 g, 1.2 mmol) was converted to 4,4',4"-((benzene-1,3,5-triyltris(methylene))tris(oxy))tribenzimidamide trihydrochloride (MD-107) as brown solid using method B (MD-107, 0.58 g, 78%). $^1H$ NMR (DMSO-$d_6$): δ 9.45 (s, 6H), 9.25 (s, 6H), 7.95 (d, J=8.4 Hz), 7.56 (s, 3H), 7.22 (d, J=8.4 Hz, 6H), 5.27 (s, 6H). $^{13}C$ NMR (DMSO-$d_6$): δ 164.7, 162.6, 137.1, 130.3, 126.9, 119.6, 115.1, 69.4. HRMS calcd for $C_{30}H_{32}N_6O_3$ $[M+2H]^{2+}/2$: 262.1262, found 262.1258.

Synthesis of MD-108

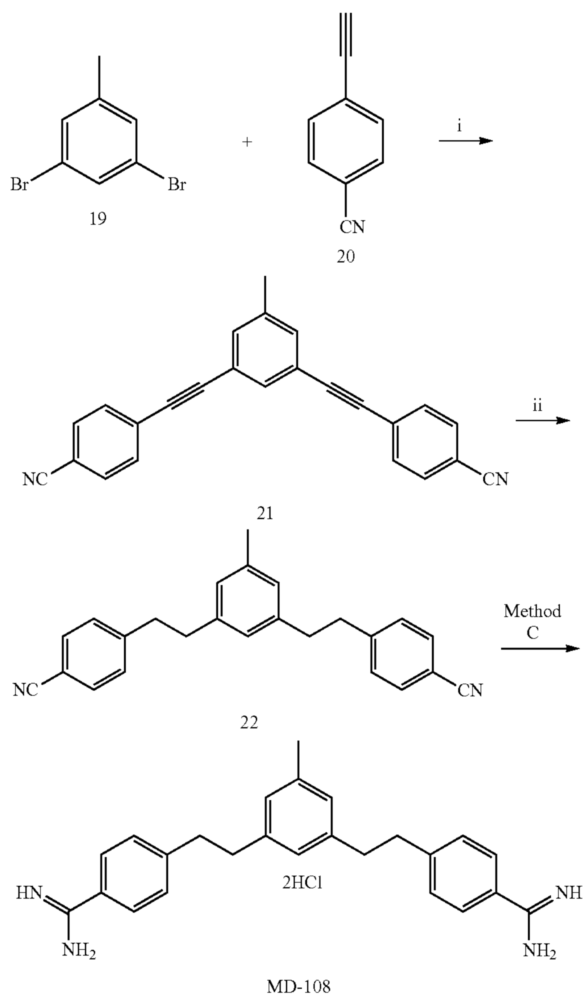

19 20 21 22

MD-108

(i) 3 mol % Pd(PPh3)$_4$, 6 mol % sodium ascorbate, 1 mol % $CuSO_4$, 1:1 $Et_3N$; DMSO
(ii) $H_2$, Pd/C MeOH, overnight.

Synthesis of 4,4'-((5-methyl-1,3-phenylene)bis(ethyne-2, 1-diyl))dibenzonitrile (21). 3,5-dibromotoluene (19, 0.98 g, 3.9 mmol) was dissolved with 1:1 DMF-$Et_3N$ (6 mL). To this solution, 3 mole % $Pd(PPh_3)_4$ and 4-ethynylbenzonitrile (1 g, 7.8 mmol) were added and the mixture was stirred for 5 minutes. Further, 6 mol % sodium ascorbate solution, 1 mol % $CuSO_4$ solution in DMF were added to the reaction mixture and stirred for 4 h at 80° C. The reaction mixture was extracted with ethyl acetate followed by ammonium chloride and brine wash. The combined organic layer was dried over anhydrous $Na_2SO_4$ and then concentrated in vacuo. The product was purified using column chromatography and obtained using 5:1 hexane:ethyl acetate system as a white solid (21, 0.67 g, 50%). 1 $^1$H NMR ($CDCl_3$): δ 7.66-7.59 (m, 8H), 7.55 (s, 1H), 7.38 (s, 2H), 2.38 (s, 3H). $^{13}$C NMR ($CDCl_3$): δ 38.9, 133.1, 132.3, 132.2, 128.1, 122.8, 118.6, 111.9, 92.9, 88.3, 21.2. HRMS-calcd for $C_{25}H_{14}N_2Na$ $[M+Na]^+$: 365.1055 found 365.1068.

Synthesis of 4,4'-((5-methyl-1,3-phenylene)bis(ethane-2, 1-diyl))dibenzonitrile (22). To 10% Pd/C in THF (30 mL) under argon gas was added 4,4'-((5-methyl-1,3-phenylene) bis(ethyne- 2,1-diyl))dibenzonitrile (21, 0.5 g, 1.46 mmol). The argon gas was exchanged for $H_2$ gas and the reaction mixture was stirred overnight. The reaction mixture was quenched with $CH_2Cl_2$ and filtered through celite. Extraction was carried out with $CH_2Cl_2$ followed by washing with $H_2O$. The combined organic layer was dried over anhydrous $Na_2SO_4$ and then concentrated under vacuum to give the product as a pale-yellow solid (22, 0.45 g, 87.6%). $^1$H NMR ($CDCl_3$): δ 7.56 (d, J=8.4 Hz, 4H), 7.24 (d, J=8.4 Hz, 4H), 6.81 (s, 2H), 6.67 (s, 1H), 2.95-2.90 (m, 4H), 2.85-2.81 (m, 4H), 2.29 (s, 3H). $^{13}$C NMR ($CDCl_3$): δ 147.5, 141.0, 138.4, 132.3, 129.4, 127.3, 125.8, 119.2, 110.0, 38.1, 37.3, 21.5. HRMS calcd for $C_{25}H_{23}N_2$ $[M+H]^+$: 351.1856 found 351.1846.

Synthesis of 4,4'-((5-methyl-1,3-phenylene)bis(ethane-2, 1-diyl))dibenzimidamide dihydrochloride (MD-108). Dinitrile compound (21, 0.35 g, 1 mmol) was converted to 4,4'-((5-methyl-1,3-phenylene)bis(ethane-2,1-diyl))dibenzimidamide dihydrochloride (MD-108) as a white solid following method B (MD-108, 0.32 g, 70%). $^1$H NMR (DMSO-$d_6$): δ 9.34 (s, 4H), 9.12 (s, 4H), 7.78 (d, J=8.4 Hz, 4H), 7.49 (d, J=8.4 Hz, 4H), 6.94 (s, 1H), 6.90 (s, 2H), 2.98-2.94 (m, 4H), 2.85-2.81 (m, 4H), 2.24 (s, 3H). $^{13}$C NMR (DMSO-$d_6$): δ 165.5, 148.4, 141.0, 137.3, 129.1, 128.2, 126.9, 125.6, 125.5, 36.9, 36.6, 21.1. HRMS calcd for $C_{25}H_{30}N_4$ $[M+2H]^{2+}/2$: 193.1230, found 193.1222.

Synthesis of MD-109

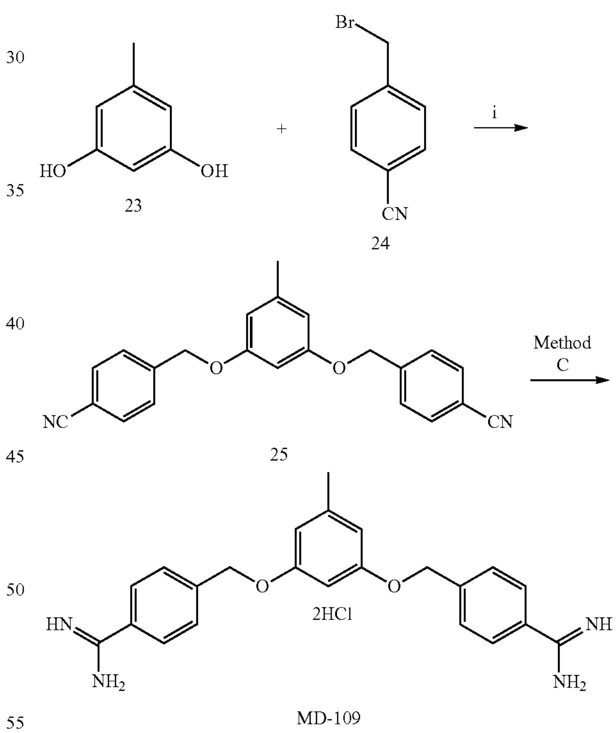

23 24 25

MD-109 i) $K_2CO_3$, DMF, rt, overnight.

Synthesis of 4,4'-(((5-methyl-1,3-phenylene)bis(oxy))bis (methylene))dibenzonitrile (25). A mixture of orcinol (23, 0.5 g, 4.1 mmol), 4-cyanobenzyl bromide (24, 1.65 g, 8.4 mmol) and anhydrous $K_2CO_3$ (1.66 g, 12 mmol) in 10 mL DMF was stirred at room temperature overnight. Then the reaction mixture was diluted with ice water (70 mL) and stirred for 30 minutes. The yellow precipitate was filtered, washed with water, and dried in air. Then the yellow solid was dissolved in a dichloromethane (100 mL), dried over anhydrous $MgSO_4$, filtered and concentrated with rotavapor. The crude product was triturated with hexane and the precipitate was filtered, which was then dried in vacuo to yield 4,4'-(((5-methyl-1,3-phenylene)bis(oxy))bis(methylene))dibenzonitrile as a yellow solid (25, 0.97 g, 66.5%). $^1H$ NMR ($CDCl_3$): δ 7.68 (d, J=8.4 Hz, 4H), 7.53 (d, J=8.4 Hz, 4H), 6.43 (d, J=2.0 Hz, 2H), 6.39 (t, J=2.0 Hz, 1H), 5.08 (s, 4H), 2.30 (s, 3H). $^{13}C$ NMR ($CDCl_3$): δ 159.5, 142.5, 140.9, 132.5, 127.7, 118.8, 111.9, 108.7, 99.5, 69.0, 22.0. HRMS calcd for $C_{23}H_{18}N_2O_2Na$ $[M+Na]^+$: 377.1266, found 377.1283.

Synthesis of 4,4'-(((5-methyl-1,3-phenylene)bis(oxy))bis(methylene))dibenzimidamide dihydrochloride (MD-109). Dinitrile (25, 0.33 g, 0.93 mmol) was converted to 4,4'-(((5-methyl-1,3-phenylene)bis(oxy))bis(methylene))dibenzimidamide dihydrochloride as white solid following method C (MD-109, 0.3 g, 75%). $^1H$ NMR (DMSO-$d_6$): δ 9.45 (s, 4H), 9.25 (s, 4H), 7.86 (d, J=7.6 Hz, 4H), 7.64 (d. J=8.0 Hz, 4H), 6.50 (s, 1H), 6.48 (s, 2H), 5.20 (s, 4H), 2.23 (s, 3H). $^{13}C$ NMR (DMSO-$d_6$): δ 165.5, 159.1, 143.4, 140.0, 128.4, 127.6, 127.3, 108.3, 99.3, 68.3, 21.5. HRMS calcd for $C_{23}H_{25}N_4O_2$ $[M+H]^+$: 389.1978, found 389.1960.

1, 3-Bis{(4-isopropylamidino)-phenoxy methyl}-2-fluorobenzene dihydrochloride (MD-110)

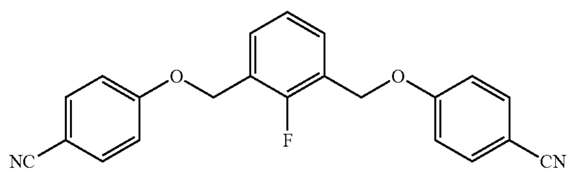 [SMILES: N#Cc1ccc(OCc2cccc(COc3ccc(C#N)cc3)c2F)cc1]

Reaction of 1,3-bis (bromomethyl)-2-fluorobenzene (1.4 g, 5 mmol) and 4-hydroxybenzonitrile (1.19 g, 10 mmol) yielded 1, 3-bis (4-cyano-phenoxy methyl)-2-fluorobenzene as white solid (2.53 g, 70%), following method A; mp 173-5° C.; $^1H$ NMR (DMSO-$d_6$): 7.78 (d, 4H, J=8.4 Hz), 7.59 (t, 2H, J=7.2 Hz), 7.29 (t, 1H, J=7.2 Hz), 7.23 (d, 4H, J=8.4 Hz), 5.3 (s, 4H); $^{13}C$ NMR (DMSO-$d_6$): 161.4, 158.4 (d, $J_{C-F}$=248 Hz), 134.0, 130.7 (d, $J_{C-F}$=4.1 Hz), 124.2 (d, $J_{C-F}$=4.1 Hz), 123.1 (d, $J_{C-F}$=13.5 Hz), 118.7, 115.6, 103.3, 63.8 (d, $J_{C-F}$=3.3 Hz); MS: HRMS-ESI-POS.: calc. for $C_{22}H_{15}FN_2O_2Na$ m/z 381.1015 ($M^+$+Na), found m/z 381.1005.

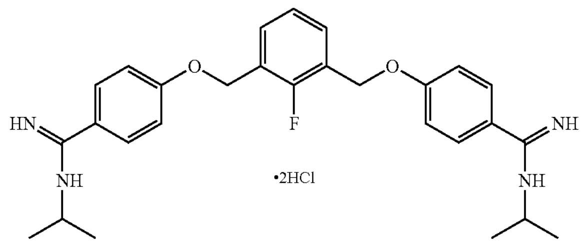 [SMILES: CC(C)NC(=N)c1ccc(OCc2cccc(COc3ccc(C(=N)NC(C)C)cc3)c2F)cc1]

Dinitrile (0.35 g, 0.97 mmol) was converted to 1, 3-bis {4-isopropylamidino (phenoxy methyl)-2-fluorobenzene dihydrochloride as white solid following Method D (0.38 g, 73%) with isopropylamine (0.17 g, 2.92 mmol); mp. 269-70° C.; $^1H$ NMR (DMSO-$d_6$): 9.48 (d, 2H, J=8.0 Hz), 9.37 (s, 2H), 9.06 (s, 2H), 7.76 (d, 4H, J=8.7 Hz), 7.62 (t, 2H, J=7.2 Hz), 7.30 (t, 1H, J=7.6 Hz), 7.25 (d, 4H, J=8.7 Hz), 5.30 (s, 4H), 4.10 (dd, 2H, J=13.6, 6.6 Hz), 1.27 (d, 12H, J=6.3 Hz); $^{13}C$ NMR (DMSO-$d_6$): 162.31, 161.55, 159.23 (d, $J_{C-F}$=249.7 Hz), 131.66 (d, $J_{C-F}$=3.4 Hz), 130.85, 125.01 (d, $J_{C-F}$=3.6 Hz), 123.93 (d, $J_{C-F}$=14.6 Hz), 121.86, 115.28, 64.45 (d, $J_{C-F}$=3.5 Hz), 45.42, 21.76; MS: HRMS-ESI-POS.: calc. for $C_{28}H_{34}FN_4O_2$ m/z 477.2660 ($M^+$+1), found m/z 477.2643; analysis calc. for $C_{28}H_{34}FN_4O_2 \cdot 2HCl \cdot 1.19H_2O$): C, 58.79; H, 6.76; N, 9.79. Found: C, 58.49; H, 6.05; N, 9.85.

1, 3-Bis {(4-isopropylamidino-2-fluoro)-phenoxy methyl}-2-fluorobenzene dihydrochloride (MD-111)

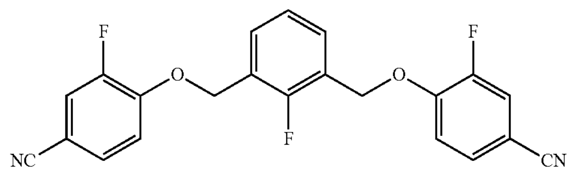 [SMILES: N#Cc1ccc(OCc2cccc(COc3ccc(C#N)cc3F)c2F)c(F)c1]

Reaction of 1,3-bis(bromomethyl)-2-fluorobenzene (1.4 g, 5 mmol) and 2-fluoro-4-hydroxybenzonitrile (1.37 g, 10 mmol) following Method A yielded 1, 3-bis (2-fluoro-4-cyano-phenoxymethyl)-2-fluorobenzene as white solid (2.8 g, 71%); mp 185-7° C.; $^1H$ NMR (DMSO-$d_6$): 7.88 (d, 2H, J=8.4 Hz), 7.72 (d, 8.4 Hz), 7.64 (t, 2H, J=7.6 Hz), 7.54 (t, 2H, J=7.6 Hz), 7.33 (t, 1H, J=7.6 Hz), 7.23 (d, 4H, J=8.4 Hz), 5.37 (s, 4H); $^{13}C$ NMR (DMSO-$d_6$): 158.50 (d, $J_{C-F}$=250 Hz), 151.0 (d, $J_{C-F}$=248 Hz), 150.1 (d, $J_{C-F}$=11.0 Hz), 131.1 (d, $J_{C-F}$=4.4 Hz), 130.1 (d, $J_{C-F}$=3.75 Hz), 124.4 (d, $J_{C-F}$=4.28 Hz), 122.7 (d, $J_{C-F}$=15.4 Hz), 119.6 (d, $J_{C-F}$=21.4 Hz), 117.6 (d, $J_{C-F}$=3.4 Hz), 115.91 (d, $J_{C-F}$=2.25 Hz), 103.3 (d, $J_{C-F}$=8.73 Hz), 64.84 (d, $J_{C-F}$=4.21 Hz); MS: HRMS-ESI-POS.: calc. for $C_{22}H_{13}F_3N_2O_2Na$ m/z 417.0827 ($M^+$+Na), found m/z 417.0832.

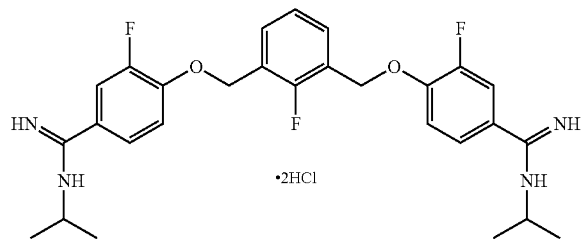 [SMILES: CC(C)NC(=N)c1ccc(OCc2cccc(COc3ccc(C(=N)NC(C)C)cc3F)c2F)c(F)c1]

Dinitrile (0.32 g, 0.81 mmol) was converted to 1, 3-bis (4-isopropylamidino-2-fluoro-phenoxy methyl)-2-fluorobenzene dihydrochloride as white solid following (Method D) (0.28 g, 70%) using isopropylamine (0.14 g, 2.43 mmol); mp. 193-5° C.; $^1H$ NMR (DMSO-$d_6$): 9.50 (s, 2H), 9.21 (s, 2H), 7.77 (dd, 2H, J=11.9, 2.2 Hz), 7.69-7.62 (m, 4H), 7.57 (t, 2H, J=8.6 Hz), 7.33 (t, 1H, J=7.6 Hz), 5.39 (s, 4H), 4.10 (dt, 2H, J=13.0, 6.5 Hz), 1.27 (d, 12H, J=6.4 Hz); $^{13}C$ NMR (DMSO-$d_6$): 160.01, 158.90 (d, $J_{C-F}$=250.6 Hz), 151.95, 149.85, 149.63 (d, $J_{C-F}$=24.1 Hz), 131.56 (d, $J_{C-F}$=2.5 Hz), 125.91 (d, $J_{C-F}$=2.9 Hz), 124.68 (d, $J_{C-F}$=3.8 Hz), 123.08 (d, $J_{C-F}$=14.5 Hz), 121.60 (d, $J_{C-F}$=7.2 Hz), 116.63 (d, $J_{C-F}$=20.9 Hz), 114.91, 64.89 (d, $J_{C-F}$=3.7 Hz), 45.13, 21.25, MS: HRMS-ESI-POS.: calc. for $C_{28}H_{32}F_3N_4O_2$ m/z 513.2472 ($M^+$+1), found m/z 513.2450; analysis calc. for $C_{22}H_{19}F_3N_4O_2 \cdot 2HCl \cdot 1.25H_2O$; C, 55.31; H, 5.88; N, 9.21. Found: C, 55.39; H, 5.85; N, 8.95.

Synthesis of MD-112

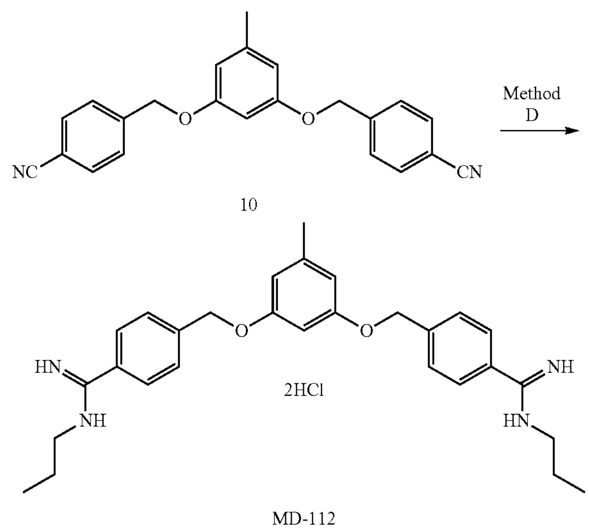

10

MD-112

Synthesis of 4,4'-(((5-methyl-1,3-phenylene)bis(oxy))bis(methylene))bis(N-propylbenzimidamide) dihydrochloride (MD-112). Dinitrile (10, 0.35 g, 0.98 mmol) was converted to 4,4'-(((5-methyl-1,3-phenylene)bis(oxy))bis(methylene))bis(N-propylbenzimidamide) dihydrochloride (MD-112) by the reaction with n-propylamine (0.14 g, 2.45 mmol) in ethanol (10 mL) at 49° C. for 24 h as white solid following method D (0.37 g, 70%). $^1$H NMR (DMSO-$d_6$): δ 9.90 (s, 2H), 9.53 (s, 2H), 9.18 (s, 2H), 7.79 (d, J=8.4 Hz, 4H), 7.63 (d. J=8.4 Hz, 4H), 6.50-6.48 (m, 3H), 5.19 (s, 4H), 3.41-3.36 (m, 2H), 2.23 (s, 3H), 1.68-1.63 (m, 4H), 0.95 (t, J=7.2 Hz, 6H). $^{13}$C NMR (DMSO-$d_6$): δ 162.5, 159.1, 142.7, 140.2, 128.5, 128.3, 127.6, 108.3, 99.7, 68.3, 44.2, 21.5, 20.9, 11.2. HRMS-calcd for $C_{29}H_{37}N_4O_2$ [M+H]$^+$: 473.2917, found 473.2940.

Synthesis of MD-113

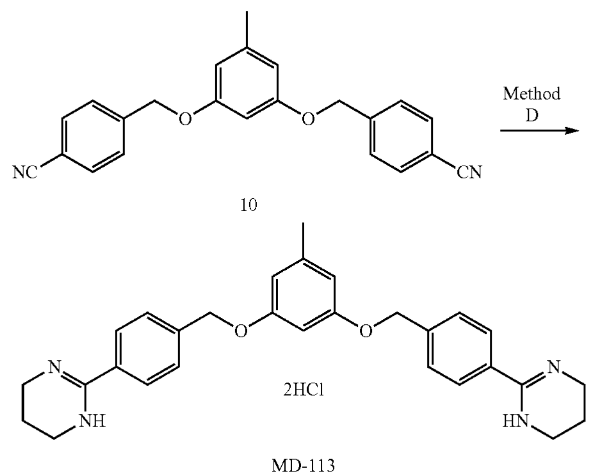

10

MD-113

Synthesis of 2,2'-((((5-methyl-1,3-phenylene)bis(methylene))bis(oxy))bis(4,1-phenylene))bis(1,4,5,6-tetrahydropyrimidine) dihydrochloride (MD-113). Dinitrile (10, 0.4 g, 1.12 mmol) was converted to 2,2'-((((5-methyl-1,3-phenylene)bis(methylene))bis(oxy))bis(4,1-phenylene))bis(1,4,5,6-tetrahydropyrimidine) dihydrochloride (MD-113) by the reaction with 1,3-diaminopropane (0.25 g, 3.4 mmol) in ethanol (10 mL) at 140° C. as white solid following method D (MD-113, 0.48 g, 75%). $^1$H NMR (DMSO-$d_6$): δ 10.23 (s, 4H), 7.82 (d, J=8.0 Hz, 4H), 7.63 (d, J=8.0 Hz, 4H), 6.51 (s, 1H), 6.48 (s, 2H), 5.19 (s, 4H), 3.48-3.37 (M, 8H), 2.23 (s, 3H), 1.98-1.95 (M, 4H). $^{13}$C NMR (DMSO-$d_6$): δ 159.1, 158.5, 142.6, 139.9, 128.0, 127.6, 127.6, 108.3, 99.2, 68.3, 38.7, 21.4, 17.7. HRMS calcd for $C_{29}H_{33}N_4O_2$ [M+H]$^+$: 469.2604, found 469.2617.

1, 3-Bis {[4-amidino-2-methoxy)-phenoxy methyl]}-5-(tert-butyl)benzene dihydrochloride (MD-114)

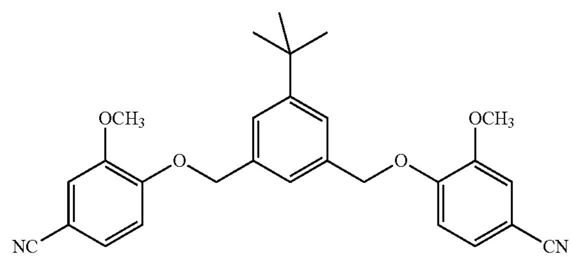 [SMILES: COc1cc(C#N)ccc1OCc1cc(COc2ccc(C#N)cc2OC)cc(C(C)(C)C)c1]

Reaction of 1,3-bis(bromomethyl)-5-(tert-butyl)benzene (1.2 g, 3.75 mmol) and 2-methoxy-4-hydroxybenzonitrile (1.2 g, 7.5 mmol) yielded 1, 3-bis (2-methoxy-4-cyano-phenoxy methyl)-5-(tert-butyl)benzene as white solid (1.35 g, 79%) following Method A. $^1$H NMR ($CDCl_3$): 7.41 (s, 2H), 7.31 (s, 1H), 7.23 (dd, J=8.3, 1.5 Hz, 2H), 7.11 (d, J=1.4 Hz, 2H), 6.93 (d, J=8.4 Hz, 2H), 5.19 (s, 4H), 3.90 (s, 6H), 1.32 (s, 9H); $^{13}$C NMR ($CDCl_3$): 152.36, 152.05, 149.70, 136.07, 126.26, 124.48, 123.58, 119.18, 114.46, 113.45, 104.31, 71.17, 56.21, 34.81, 31.29; MS: HRMS-ESI-POS.: calc. for $C_{28}H_{28}N_2O_4Na$ m/z 479.1947 (M$^+$+Na), found m/z 479.1942.

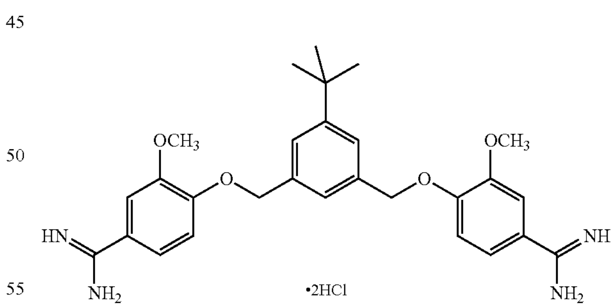

Dinitrile (0.35 g, 0.76 mmol) was converted to yielded 1, 3-bis (2-methoxy-4-cyano-phenoxy methyl)-5-(tert-butyl) benzene dihydrochloride as white solid following Method B (0.30 g, 72%); $^1$H NMR (DMSO-$d_6$): 9.33 (s, 4H), 9.04 (s, 4H), 7.55-7.46 (m, 6H), 7.35 (s, 1H), 7.28 (d, J=9.2 Hz, 2H), 5.21 (s, 4H), 3.86 (s, 6H), 1.29 (s, 9H); $^{13}$C NMR (DMSO-$d_6$): 165.11, 152.79, 151.78, 149.26, 136.74, 125.39, 122.29, 119.97, 113.35, 111.94, 70.80, 56.45, 34.91, 31.55; MS: HRMS-ESI-POS.: calc. for $C_{28}H_{35}N_4O_4$ m/z 479.1947 (M$^+$+1) 491.2658, found m/z 491.2645.

Synthesis of BW-MD-115

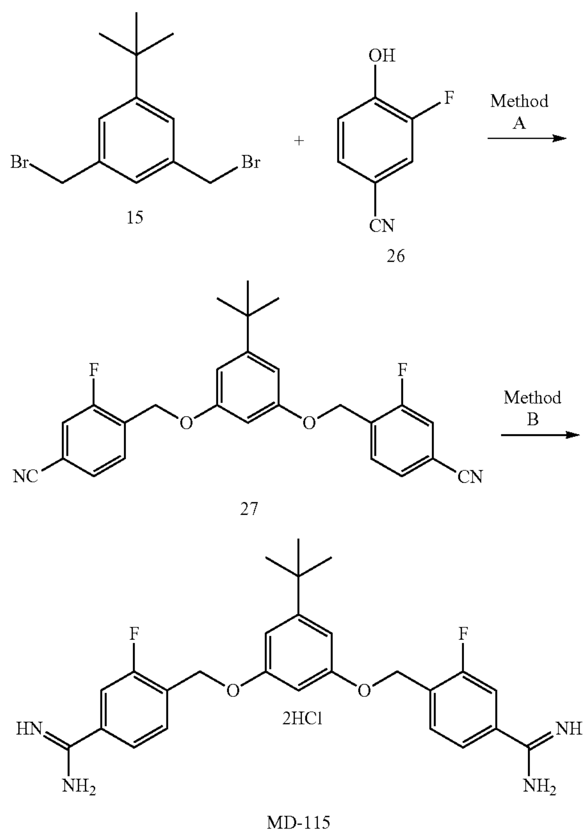

15

26

27

MD-115

Synthesis of 4,4'-(((5-(tert-butyl)-1,3-phenylene)bis(methylene))bis(oxy))bis(3-fluorobenzonitrile) (27). Reaction of 1,3-bis(bromomethyl)-5-(tert-butyl)benzene (15, 1.5 g, 4.7 mmol) and 2-fluoro-4-hydroxybenzonitrile (26, 1.3 g, 9.4 mmol) yielded 4,4'-(((5-(tert-butyl)-1,3-phenylene)bis(methylene))bis(oxy))bis(3-fluorobenzonitrile) as white solid (27, 1.52 g, 75%) using method A. $^1$H NMR (DMSO-$d_6$): δ 7.85 (dd, J=11.2, 1.6 Hz, 2H), 7.68-7.66 (m, 2H), 7.50 (s, 2H), 7.44 (t, J=8.8 Hz, 2H), 7.36 (s, 1H), 5.29 (s, 4H), 1.29 (s, 9H). $^{13}$C NMR (DMSO-$d_6$): δ 153.4, 151.8 (d, $J_{C-F}$=186 Hz), 151.0, 135.6, 129.7 (d, $J_{C-F}$=4 Hz), 125.0, 123.9, 120.0 (d, $J_{C-F}$=21 Hz), 118.0 (d, $J_{C-F}$=3 Hz), 115.4 (d, $J_{C-F}$=3 Hz), 104.6 (d, $J_{C-F}$=9 Hz), 71.5, 35.0, 31.4. HRMS calcd for $C_{26}H_{22}F_2N_2O_2Na$ [M+Na]$^+$: 455.1547, found 455.1541.

Synthesis of 4,4'-(((5-(tert-butyl)-1,3-phenylene)bis(methylene))bis(oxy))bis(3-fluorobenzimidamide) dihydrochloride (MD-115). Dinitrile (27, 0.35 g, 0.8 mmol) was converted to 4,4'-(((5-(tert-butyl)-1,3-phenylene)bis(methylene))bis(oxy))bis(3-fluorobenzimidamide) dihydrochloride (MD-115) as brown solid following method B (0.30 g, 70.1%). $^1$H NMR (DMSO-$d_6$): δ 9.49 (s, 4H), 9.26 (s, 4H), 7.90 (dd, J=12.4, 2.4 Hz, 2H), 7.81-7.79 (m, 2H), 7.52-7.50 (m, 4H), 7.39 (s, 1H), 5.31 (s, 4H), 1.28 (s, 9H). $^{13}$C NMR (DMSO-$d_6$): δ 164.0, 152.3, 151.0 (d, $J_{C-F}$=11 Hz), 150.8 (d, $J_{C-F}$=177 Hz), 136.0, 126.0 (d, $J_{C-F}$=3 Hz), 125.2, 124.9, 120.0 (d, $J_{C-F}$=7 Hz), 116.3 (d, $J_{C-F}$=20 Hz), 115.3, 70.9, 34.6, 31.2. HRMS calcd for $C_{26}H_{29}F_2N_4O_2$ [M+H]$^+$: 467.2272, found 467.2271.

Synthesis of MD-116

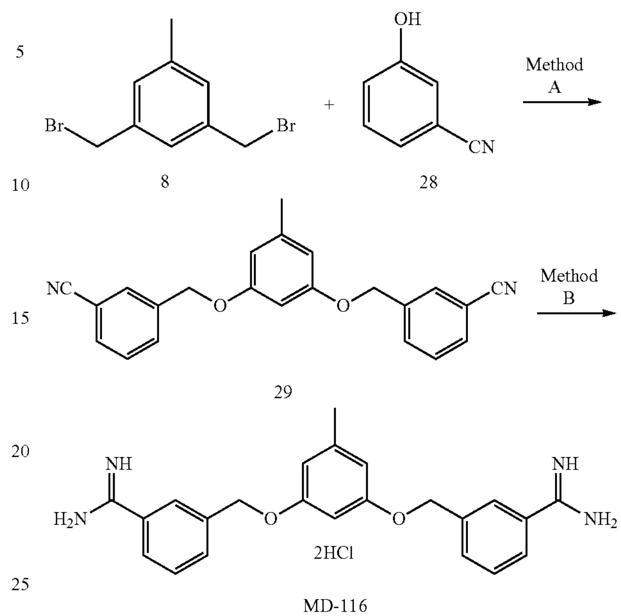

8

28

29

MD-116

Synthesis of 3,3'-(((5-methyl-1,3-phenylene)bis(methylene))bis(oxy))dibenzonitrile (29). Reaction of 1,3-bis (bromomethyl)-5-methylbenzene (8, 2.13 g, 7.7 mmol) and 3-cyanophenol (28, 2.05 g, 17 mmol) yielded 3,3'-(((5-methyl-1,3-phenylene)bis(methylene))bis(oxy))dibenzonitrile as white solid (29, 2.6 g, 91%) using method A. $^1$H NMR ($CDCl_3$): δ 7.38-7.36 (m, 2H), 7.27-7.25 (m, 3H), 7.22-7.19 (m, 6H), 5.06 (s, 4H), 2.41 (s, 3H). $^{13}$C NMR ($CDCl_3$): δ 158.8, 139.3, 136.6, 130.6, 128.3, 125.0, 123.6, 120.2, 118.8, 117.9, 113.4, 70.2, 21.5. HRMS calcd for $C_{23}H_{18}N_2O_2Na$ [M+Na]$^+$: 377.1266, found 377.1250.

Synthesis of 3,3'-(((5-methyl-1,3-phenylene)bis(methylene))bis(oxy))dibenzimidamide dihydrochloride (MD-116). Dinitrile (29, 0.32 g, 0.9 mmol) was converted to 3,3'-(((5-methyl-1,3-phenylene)bis(methylene))bis(oxy))dibenzimidamide dihydrochloride (MD-116) as white solid using method B (0.32 g, 76%). $^1$H NMR (DMSO-$d_6$): δ 9.40 (s, 4H), 9.07 (s, 4H), 7.53 (t, J=8.0 Hz, 2H), 7.47 (s, 2H), 7.41-7.34 (m, 5H), 7.26 (s, 2H), 5.16 (s, 4H), 2.33 (s, 3H). $^{13}$C NMR (DMSO-$d_6$): δ 165.6, 158.7, 138.5, 137.0, 130.8, 129.5, 128.5, 124.6, 120.7, 120.5, 114.5, 69.9, 21.2. HRMS calcd for $C_{23}H_{25}N_4O_2$ [M+H]$^+$: 389.1978, found 389.1980.

Synthesis of MD-117

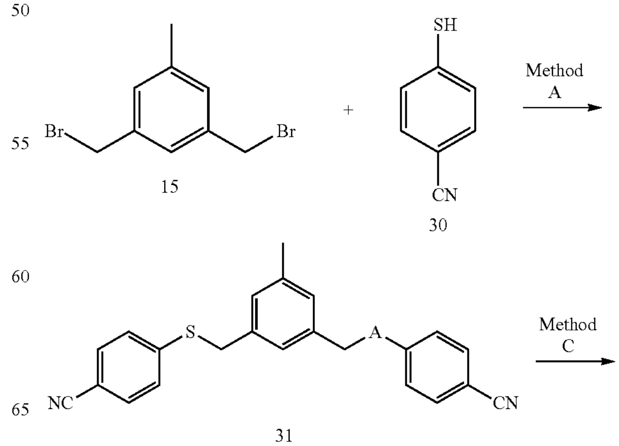

15

30

31

-continued

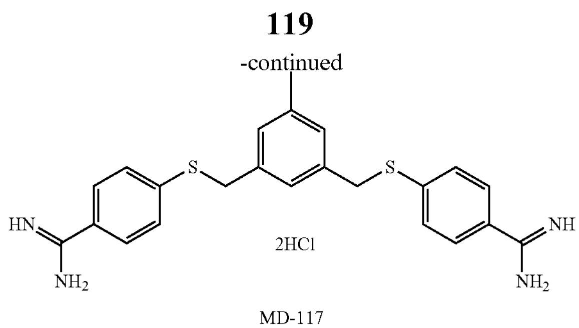

MD-117

Synthesis of 4,4'-(((5-methyl-1,3-phenylene)bis(methylene))bis(sulfanediyl))dibenzonitrile (31). Reaction of 1,3-bis (bromomethyl)-5-methylbenzene (8, 0.93 g, 3.3 mmol) and 4-mercaptobenzonitrile (30, 1.0 g, 7.3 mmol) yielded 4,4'-(((5-methyl-1,3-phenylene)bis(methylene))bis(sulfanediyl))dibenzonitrile as white solid (1.12 g, 85%), using method A. $^1$H NMR ($CDCl_3$): δ 7.50 (d, J=8.4 Hz, 4H), 7.28 (d, J=8.4 Hz, 4H), 7.14 (s, 1H), 7.08 (s, 2H), 4.13 (s, 4H), 2.32 (s, 3H). $^{13}$C NMR (DMSO-$d_6$): δ 144.3, 139.0, 136.2, 132.1, 128.9, 127.1, 126.1, 118.7, 108.4, 36.7, 21.2. HRMS calcd for $C_{23}H_{19}N_2S_2$ $[M+H]^+$: 387.0984, found 387.1003.

Synthesis of 4,4'-(((5-methyl-1,3-phenylene)bis(methylene))bis(sulfanediyl)) dibenzimidamide dihydrochloride (MD-117). Dinitrile (31, 0.30 g, 0.74 mmol) was converted to 4,4'-(((5-methyl-1,3-phenylene)bis(methylene))bis(sulfanediyl))dibenzimidamide dihydrochloride (MD-117) as green solid following method C (MD-117, 0.19 g, 50%). $^1$H NMR (DMSO-$d_6$): δ 9.30 (s, 4H), 9.03 (s, 4H), 7.74 (d, J=8.4 Hz, 4H), 7.51 (d, J=8.4 Hz, 4H), 7.31 (s, 1H), 7.16 (s, 2H), 4.33 (s, 4H), 2.26 (s, 3H). $^{13}$C NMR (DMSO-$d_6$): δ 164.9, 144.8, 138.1, 136.8, 128.6, 128.5, 126.5, 126.3, 124.1, 35.0, 20.9. HRMS calcd for $C_{23}H_{25}N_4S_2$ $[M+H]^+$: 421.1521, found 421.1532.

1, 3-Bis {(4-(2-imidazolino))-thiophenoxy methyl}-5-methylbenzene dihydrochloride (MD-118)

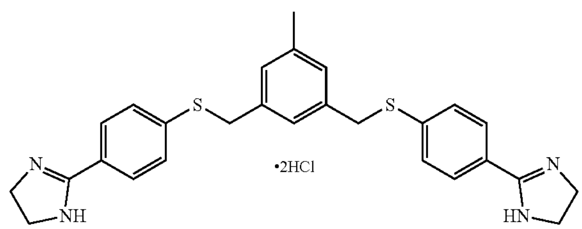 [SMILES: Cc1cc(CSc2ccc(C3=NCCN3)cc2)cc(CSc2ccc(C3=NCCN3)cc2)c1]

Dinitrile (0.386 g, 1 mmol) was converted to 1, 3-Bis {(4-(2-imidazolino))-thiophenoxy methyl}-5-methylbenzene dihydrochloride as a brown solid following Method D (0.39 g, 72%) by refluxing imidate ester with 1,2 diaminoethane. $^1$H NMR (DMSO-$d_6$): 10.73 (s, 4H), 7.96 (d, 4H, J=8.6 Hz), 7.54 (d, 4H, J=8.6 Hz), 7.32 (s, 1H), 7.16 (s, 2H), 4.36 (s, 4H), 3.98 (s, 8H), 2.26 (s, 3H); $^{13}$C NMR (DMSO-$d_6$): 164.00, 145.86, 138.05, 136.70, 129.01, 128.61, 126.32, 118.23, 44.19, 34.77, 20.88; MS:HRMS-ESI-POS.: calc. for $C_{27}H_{29}N_4S_2$ m/z 473.1834 ($M^+$+1), found m/z 473.1842.

1, 3-Bis {(4-amidino)-phenoxy methyl}-6-methylbenzene dihydrochloride (BW-MD-119)

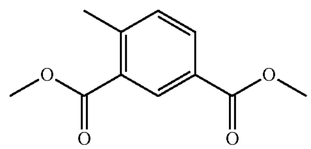

3-bromo-4 methylbenzoic acid (5 g, 23.25 mmol) was added to 50 ml dry THF in a three neck round bottom flask under Ar gas atmosphere. The temperature of this reaction mixture was cooled to 0° C. and a solution of 3.0 M methyl magnesium bromide (8.5 ml, 25.57 mmol) was added to it and stirred for 2 hrs. The temperature was further lowered to −65° C. and 1.6M n-butyl lithium solution (29 mL, 46.5 mmol) in hexane was added to it with constant stirring. After 4 h of reaction time, dry ice was added to the reaction mixture, sealed and stirred overnight. On completion of reaction, mixture was acidified and then filtered. This residue was taken with catalytic amounts of conc. $H_2SO_4$ in methanol and refluxed overnight to form the methyl ester. The reaction mixture was cooled to room temperature on completion, 10 ml water was added to it and extracted with ethyl acetate (3×50 mL). The organic layer was dried with anhydrous $Na_2SO_4$ and concentrated in vacuo to yield Dimethyl 4-methylisophthalate as white solid (3.92 g, 81%). $^1$H NMR ($CDCl_3$): 8.57 (d, J=1.7 Hz, 1H), 8.04 (dd, J=8.0, 1.8 Hz, 1H), 7.33 (d, J=8.0 Hz 1H), 3.92 (d, J=3.2 Hz, 6H), 2.66 (s, 3H); $^{13}$C NMR ($CDCl_3$): 167.34, 166.50, 145.73, 132.79, 132.12, 132.04, 129.90, 128.11, 52.36, 52.20, 22.03; MS: HRMS-ESI-POS.: calc. for $C_{11}H_{12}O_4$ m/z 231.0633 ($M^+$+Na), found m/z 231.0642.

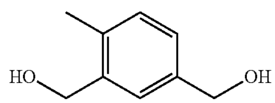

Dimethyl 4-methylisophthalate (1 g, 4.8 mmol) in THF (20 ml) was added dropwise under ice-bath condition in a solution of lithium aluminium hydride (0.73 g, 19.2 mmol) in THF (30 ml). The reaction was stirred for 1 h at 0° C. following which the reaction was stirred overnight at room temperature. The reaction was monitored by TLC. On completion, the reaction mixture was cooled to 0° C. and quenched with methanol and water. The quenched reaction was filtered through Celite and washed with EtOAc (50 mL). The solvent was removed under reduced pressure and was extracted with EtOAc (3×50 mL), dried over $MgSO_4$ and concentrated to give the required diol (4-methyl-1,3-phenylene)dimethanol (0.62 g, 85%) as a white solid. %). $^1$H NMR ($CDCl_3$): 7.32 (s, 1H), 7.14 (d, J=1.8 Hz, 2H), 4.60 (d, J=14.4 Hz, 4H), 2.29 (s, 3H); $^{13}$C NMR ($CDCl_3$): 139.13, 138.71, 135.34, 130.50, 126.45, 126.24, 65.14, 63.21, 18.45; MS: HRMS-ESI-POS.: calc. for $C_9H_{12}O_2$ m/z 175.0735 ($M^+$+Na), found m/z 175.0730.

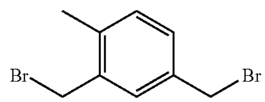

PBr$_3$ (0.7 mL, 7.38 mmol) was added dropwise to a solution of diol (0.511 g, 3.35 mmol) in DCM maintained at 0° C. The reaction mixture was stirred at room temperature for 4 h and then quenched with ice water. The solution was extracted with $CH_2Cl_2$ (3×25 mL), dried over $MgSO_4$ and concentrated to give the required dibromo compound as a white solid (0.93 g, 90%). $^1$H NMR ($CDCl_3$): 7.34 (d, J=1.6 Hz, 1H), 7.28-7.24 (m, 1H), 7.17 (d, J=7.8 Hz, 1H), 4.48 (d, J=12.6 Hz, 4H), 2.41 (s, 3H); $^{13}$C NMR ($CDCl_3$): 137.81, 136.37, 136.10, 131.47, 130.64, 129.66, 33.10, 31.82, 18.70;

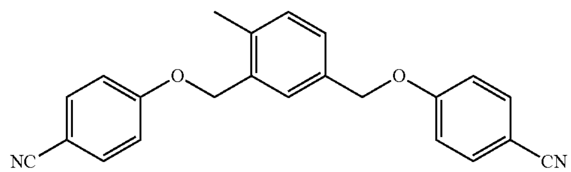 [SMILES: Cc1ccc(COc2ccc(C#N)cc2)cc1COc1ccc(C#N)cc1]

Reaction of 2,4-bis(bromomethyl)-1-methylbenzene (0.9 g, 3.2 mmol) and 4-hydroxybenzonitrile (0.84 g, 7 mmol) yielded 1, 3-bis (4-cyano-phenoxy methyl)-6-methyl-benzene as white solid (0.81 g, 72%), using method A; $^1$H NMR ($CDCl_3$): 7.59 (dd, J=11.2, 8.9 Hz, 4H), 7.44 (s, 1H), 7.36-7.27 (m, 2H), 7.08-6.96 (m, 4H), 5.09 (d, J=1.6 Hz, 4H), 2.38 (s, 3H); $^{13}$C NMR ($CDCl_3$): 162.05, 162.01, 137.10, 134.28, 134.21, 134.15, 133.81, 131.18, 128.02, 127.87, 119.24, 115.68, 115.59, 104.59, 104.44, 70.08, 68.74, 18.83; MS: HRMS-ESI-POS.: calc. for $C_{23}H_{18}N_2O_2$ m/z 377.1266 ($M^+$+Na), found m/z 377.1256.

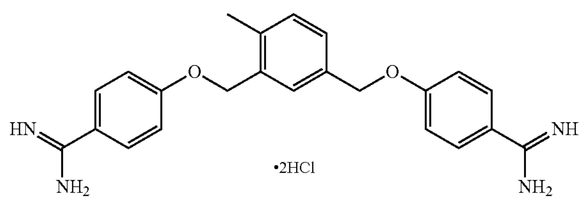 [SMILES: Cc1ccc(COc2ccc(C(=N)N)cc2)cc1COc1ccc(C(=N)N)cc1]

Dinitrile (0.35 g, 1 mmol) was converted to 1, 3-bis {4-amidino (phenoxy methyl)-6-methyl-benzene dihydrochloride as brown solid following Method B (0.32 g, 70%); H NMR (DMSO-d$_6$):9.33 (d, J=9.8 Hz, 4H), 9.14 (d, J=6.6 Hz, 4H), 7.90 (dd, J=12.8, 8.9 Hz, 4H), 7.55 (s, 1H), 7.41-7.35 (m, 1H), 7.31-7.18 (m, 5H), 5.23 (d, J=7.0 Hz, 4H), 2.34 (s, 3H); $^{13}$C NMR (DMSO-d$_6$): 164.73, 162.73, 162.61, 136.74, 134.52, 133.87, 130.45, 130.24, 130.20, 128.21, 127.95, 119.70, 119.59, 115.15, 115.08, 69.45, 68.36, 18.29; MS: HRMS-ESI-POS.: calc. for $C_{23}H_{24}N_4O_2$ m/z 389.1978 ($M^+$+1), found m/z 389.1971.

Synthesis of MD-120

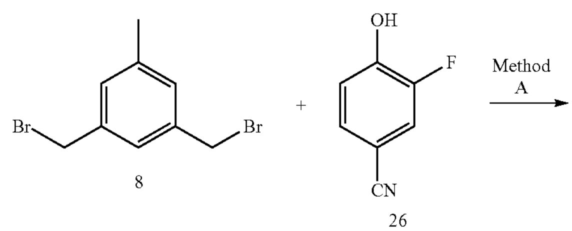

8

26

-continued

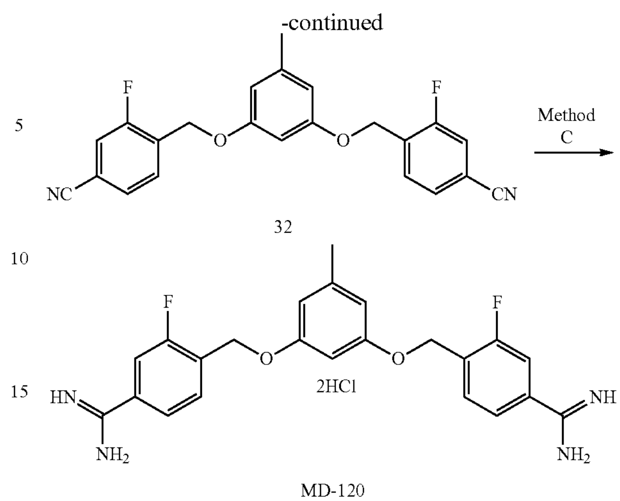

32

MD-120

Synthesis of 4,4'-(((5-methyl-1,3-phenylene)bis(methylene))bis(oxy))bis(3-fluorobenzonitrile) (32). Reaction of 1,3-bis (bromomethyl)-5-methylbenzene (8, 0.99 g, 3.6 mmol) and 3-fluoro-4-hydroxybenzonitrile (26, 1.1 g, 7.9 mmol) yielded 4,4'-(((5-methyl-1,3-phenylene)bis(methylene))bis(oxy))bis(3-fluorobenzonitrile) as white solid (32, 1.12 g, 80%), using method A. $^1$H NMR ($CDCl_3$): δ 7.40-7.37 (m, 4H), 7.28 (s, 1H), 7.23 (s, 2H), 7.04 (t, J=8.4 Hz, 2H), 5.17 (s, 4H), 2.40 (s, 3H). $^{13}$C NMR ($CDCl_3$): δ 152.2 (d, $J_{C-F}$=242 Hz), 150.9 (d, $J_{C-F}$=4 Hz), 139.5, 135.9, 129.7 (d, $J_{C-F}$=4 Hz), 128.5, 123.6, 120.0 (d, $J_{C-F}$=21 Hz), 118.0 (d, $J_{C-F}$=2 Hz), 115.3 (d, $J_{C-F}$=2 Hz), 104.6 (d, $J_{C-F}$=8 Hz), 71.1, 21.5. HRMS calcd for $C_{23}H_{16}F_2N_2O_2Na$ $[M+Na]^+$: 413.1078, found 413.1087.

Synthesis of 4,4'-(((5-methyl-1,3-phenylene)bis(methylene))bis(oxy))bis(3-fluorobenzimidamide) dihydrochloride (MD-120). Dinitrile (32, 0.35 g, 0.9 mmol) was converted to 4,4'-(((5-methyl-1,3-phenylene)bis(methylene))bis(oxy))bis(3-fluorobenzimidamide) dihydrochloride as white solid following method B (MD-120, 0.32 g, 72%). $^1$H NMR (DMSO-d$_6$): δ 9.42 (s, 4H), 9.24 (s, 4H), 7.90 (dd, J=12.0, 2.0 Hz, 2H), 7.78-7.76 (m, 2H), 7.49 (t, J=8.8 Hz, 2H), 7.38 (s, 1H), 7.29 (s, 2H), 5.30 (s, 4H), 2.35 (s, 3H). $^{13}$C NMR (DMSO-d$_6$): δ 163.8, 150.9 (d, $J_{C-F}$=244 Hz), 150.6 (d, $J_{C-F}$=10 Hz), 138.3, 136.2, 128.5, 125.8 (d, $J_{C-F}$=3 Hz), 124.5, 119.8 (d, $J_{C-F}$=7 Hz), 116.1 (d, $J_{C-F}$=21 Hz), 151.0, 70.3, 20.9. HRMS calcd for $C_{23}H_{23}F_2N_4O_2$ $[M+H]^+$: 425.1789, found 425.1777.

Synthesis of MD-123

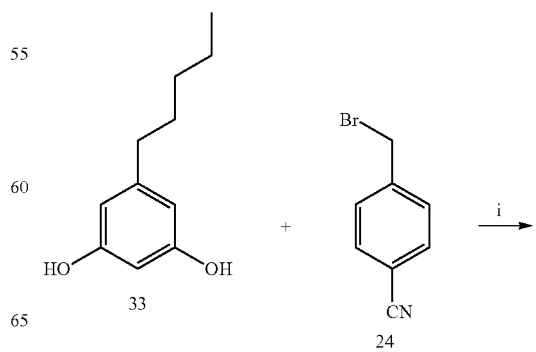

33

24

-continued

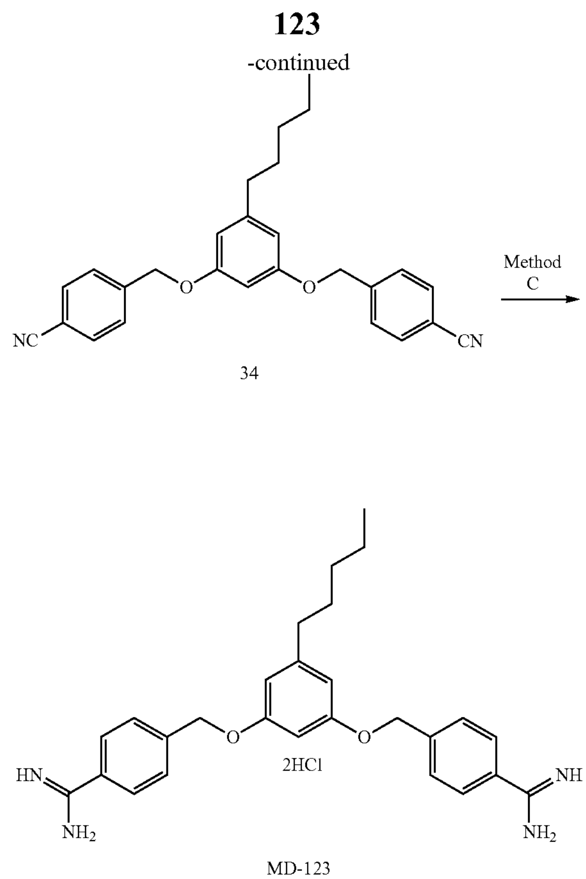

34

MD-123 i) $K_2CO_3$, DMF, rt, overnight.

Synthesis of MD-124

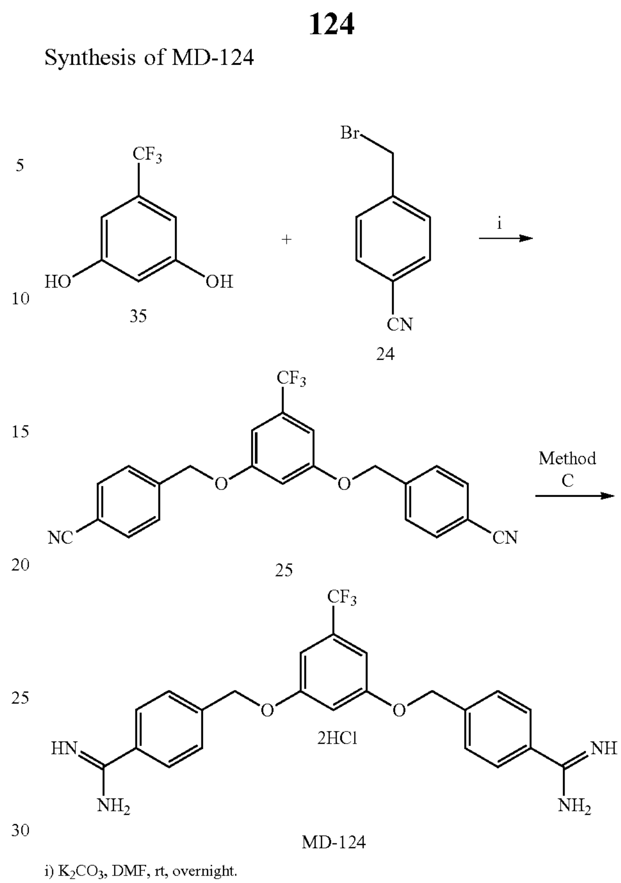

35

24

25

MD-124 i) $K_2CO_3$, DMF, rt, overnight.

Synthesis of 4,4'-(((5-butyl-1,3-phenylene)bis(oxy))bis(methylene))dibenzonitrile (34). A mixture of olivetol (33, 1.4 g, 8.2 mmol), 4-cyanobenzyl bromide (24, 3.53 g, 18 mmol) and anhydrous $K_2CO_3$ (3.4 g, 24.6 mmol) in 100 mL DMF was stirred at room temperature overnight. Then the reaction mixture was diluted with ice water (50 mL) and extracted with ethyl acetate (3×100 mL) followed by water and brine wash. The combined organic layer is dried over anhydrous $Na_2SO_4$, filtered, concentrated in vacuum to yield 4,4'-(((5-butyl-1,3-phenylene)bis(oxy))bis(methylene)) dibenzonitrile (34) as an orange solid (34, 3.2 g, 95.0%). $^1H$ NMR ($CDCl_3$): δ 7.67 (d, J=8.4 Hz, 4H), 7.53 (d, J=8.4 Hz, 4H), 6.44 (d, J=2.0 Hz, 2H), 6.40 (t, J=2.0 Hz, 1H), 5.09 (s, 4H), 2.56-2.52 (m, 2H), 1.60-1.57 (m, 2H), 1.33-1.27 (m, 4H), 0.89 (t, J=7.2 Hz, 3H). $^{13}C$ NMR ($CDCl_3$): δ 59.4, 146.0, 142.5, 132.5, 127.7, 118.8, 111.8, 108.0, 99.5, 69.0, 36.3, 31.5, 31.0, 22.6, 14.1. HRMS calcd for $C_{27}H_{26}N_2O_2Na$ $[M+Na]^+$: 433.1892, found 433.1873.

Synthesis of 4,4'-((5-pentyl-1,3-phenylene)bis(ethane-2,1-diyl))dibenzimidamide dihydrochloride (MD-123). Dinitrile (34, 0.32 g, 0.78 mmol) was converted to 4,4'-((5-pentyl-1,3-phenylene)bis(ethane-2,1-diyl)) dibenzimidamide dihydrochloride (MD-123) as white solid following method C (MD-123, 0.32 g, 80%). $^1H$ NMR (DMSO-$d_6$): δ 9.47 (s, 4H), 9.28 (s, 4H), 7.87 (d, J=8.4 Hz, 4H), 7.65 (d, J=8.4 Hz, 4H), 6.51 (t, J=2.0 Hz, 1H), 6.48 (d, J=2.0 Hz, 2H), 5.20 (s, 4H), 2.50-2.46 (m, 2H), 1.55-1.52 (m. 2H), 1.29-1.20 (m, 4H), 0.84 (t, J=6.8 Hz, 3H). $^{13}C$ NMR (DMSO-$d_6$): δ 165.4, 159.1, 145.0, 143.4, 128.3, 127.7, 127.3, 107.6, 99.6, 68.3, 35.4, 30.9, 30.4, 22.0, 14.0. HRMS calcd for $C_{27}H_{33}N_4O_2$ $[M+H]^+$: 445.2604, found 445.2624.

Synthesis of 4,4'-(((5-(trifluoromethyl)-1,3-phenylene)bis(oxy))bis(methylene)) dibenzonitrile (36). A mixture of 5-(Trifluoromethyl)-1,3-diol (35, 0.7 g, 4.2 mmol), 4-cyanobenzyl bromide (24, 1.80 g, 9.21 mmol) and anhydrous $K_2CO_3$ (1.73 g, 12.6 mmol) in 20 mL DMF was stirred at room temperature overnight. Then the reaction mixture was diluted with ice water (50 mL) and stirred for 30 min. The grey precipitate was filtered, washed with water, and dried in air. Then the yellow solid was dissolved in a dichloromethane (100 mL), dried over anhydrous $Na_2SO_4$, filtered, concentrated in vacuum to afford crude product. The crude product was triturated with hexane, filtered and dried in vacuum to yield 4,4'-(((5-(trifluoromethyl)-1,3-phenylene) bis(oxy))bis(methylene))dibenzonitrile (36) as a grey solid (36, 1.48 g, 87.0%). $^1H$ NMR ($CDCl_3$): δ 7.70 (d, J=8.4 Hz, 4H), 7.54 (d, J=8.4 Hz, 4H), 6.85 (d, J=2.0 Hz, 2H), 6.71 (t, J=2.0 Hz, 1H), 5.13 (s, 4H). $^{13}C$ NMR ($CDCl_3$): 159.8, 141.5, 132.7, 127.8, 118.7, 112.3, 105.4, 104.9, 104.8, 69.4. HRMS-calcd for $C_{23}H_{15}N_2O_2F_3Na$ $[M+Na]^+$: 431.0961, found 431.0983.

Synthesis of 4,4'-(((5-(trifluoromethyl)-1,3-phenylene)bis(oxy))bis(methylene)) dibenzimidamide dihydrochloride (MD-124). Dinitrile (36, 0.35 g, 0.85 mmol) was converted to 4,4'-(((5-(trifluoromethyl)-1,3-phenylene)bis(oxy))bis(methylene))dibenzimidamide dihydrochloride as pale-yellow solid following method C (MD-124, 0.3 g, 70%). $^1H$ NMR (DMSO-$d_6$): 9.43 (s, 4H), 9.20 (s, 4H), 7.87 (d, J=8.4 Hz, 4H), 7.68 (d, J=8.4 Hz, 4H), 7.03 (s, 1H), 6.99 (s, 2H), 5.32 (s, 4H). $^{13}C$ NMR (DMSO-$d_6$): δ 165.4, 159.7, 142.5, 131.1 (q, $J_{C-F}$=32 Hz), 128.4, 127.8, 127.6 (q, $J_{C-F}$=240 Hz), 122.4, 105.9, 104.2, 68.9. HRMS calcd for $C_{23}H_{22}F_3N_4O_2$ $[M+H]^+$: 443.1695, found 443.1687.

Synthesis of MD-125

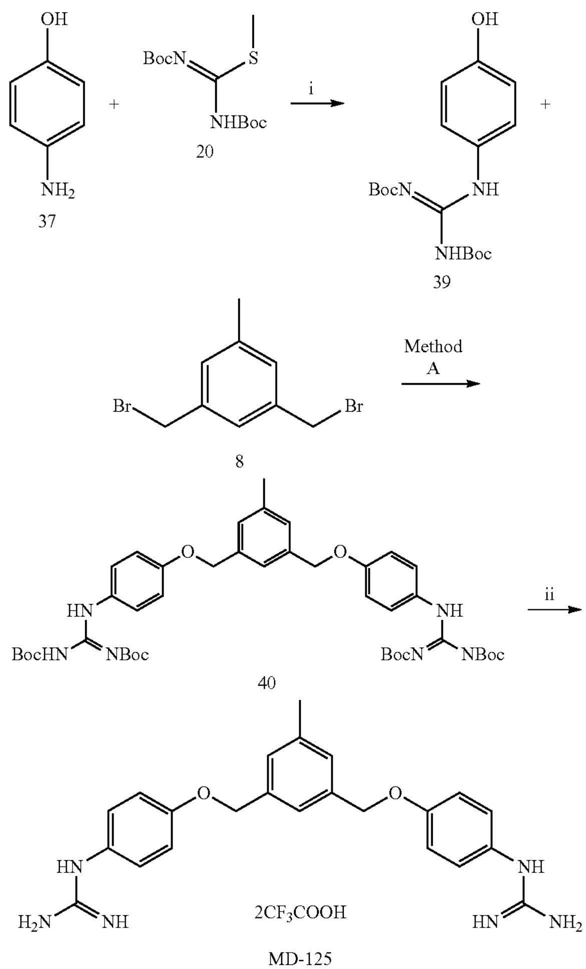

37 20 39 8 40 MD-125

Synthesis of p-[N', N"-Di(Boc)guanidino]phenol (39). p-aminophenol (37, 1.64 g, 15.0 mmol) and N,N'-Di(Boc)-S-methylisothiourea (38, 2.90 g, 10.0 mmol) were stirred in THF (100 mL) for 10 minutes after which the reaction was cooled to 0° C. $HgCl_2$ (2.99 g, 11.0 mmol) was added slowly to this solution and stirred for 20 h. The reaction mixture was concentrated and purified with column chromatography using 5:1 Hexane:EA as eluant to give p-[N', N"-Di(Boc) guanidino]phenol (39) as a white solid (3.16 g, 60%). [2] $^1$H NMR ($CDCl_3$): δ 11.61 (s, 1H), 9.96 (s, 1H), 7.01 (d, J=8.8 Hz, 2H), 6.58 (d, J=8.8 Hz, 2H), 1.53 (s, 9H), 1.44 (s, 9H). $^{13}$C NMR ($CDCl_3$): δ 156.1, 155.7, 153.3, 126.7, 116.4, 84.0, 80.4, 28.3, 28.2. HRMS calcd for $C_{17}H_{26}N_3O_5$ $[M+H]^+$: 352.1872, found 352.1863.

Synthesis of 1,1'-((((5-methyl-1,3-phenylene)bis(methylene))bis(oxy))bis(4,1-phenylene)) diguanidine di(trifluoroacetate). Reaction of 1,3-bis (bromomethyl)-5-methylbenzene (0.36 g, 1.3 mmol), p-[N',N"-Di(Boc)guanidino]phenol (39, 1.0 g, 2.84 mmol) and $K_2CO_3$ (0.54 g, 3.9 mmol) yielded 1, 3-Bis[2]-5-methylbenzene (40) as white solid (40, 0.74 g, 70%) using method A. Compound 40 (32 mg, 0.039 mmol) in DCM (2 mL) was treated with TFA (1 mL) for 2 h The solvent was removed in vacuo to yield 1, 3-Bis[2]-5-methylbenzene di(trifluoroacetate) (MD-125) salt as a white solid (MD-125, 20 mg, 80%). $^1$H NMR (MeOD): δ 7.33 (s, 1H), 7.23 (s, 2H), 7.22-7.20 (m, 4H), 7.09-7.07 (m, 4H), 5.09 (s, 4H), 2.36 (s, 3H). $^{13}$C NMR (MeOD): δ 159.8, 158.5, 139.8, 138.7, 128.8, 128.8, 128.6, 124.8, 117.2, 71.1, 21.4. HRMS calcd for $C_{23}H_{27}N_6O_2$ $[M+H]^+$: 419.2195, found 419.2212.

Synthesis of MD-126

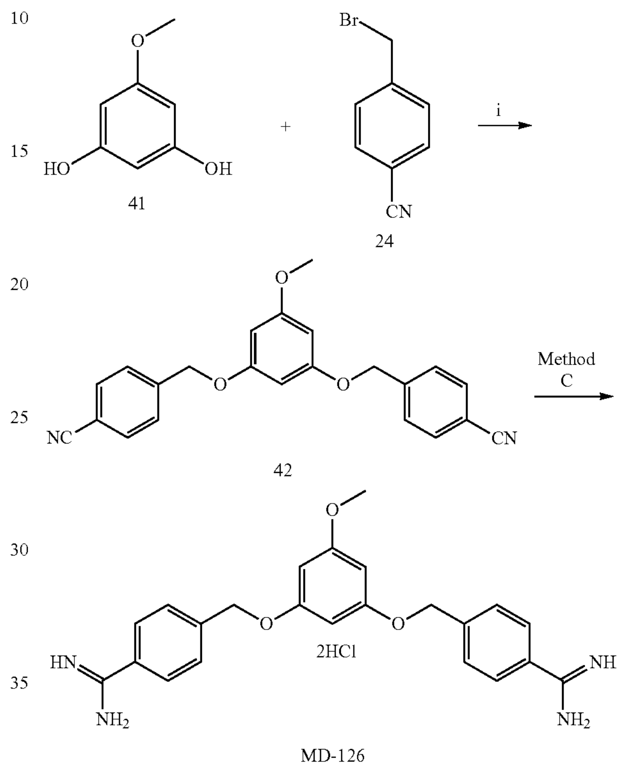

41 24 42 MD-126

Synthesis of 4,4'-(((5-methoxy-1,3-phenylene)bis(oxy)) bis(methylene))dibenzonitrile (42). A P125, mixture of 5-methoxyresorcinol (41, 1.22 g, 8.7 mmol), 4-cyanobenzyl bromide (24, 3.74 g, 18 mmol) and anhydrous $K_2CO_3$ (3.6 g, 26.02 mmol) in 100 mL DMF was stirred at room temperature overnight. Then the reaction mixture was diluted with ice water (50 mL) and extracted with ethyl acetate (3×100 mL) followed by water and brine wash. The combined organic layer is dried over anhydrous $Na_2SO_4$, filtered, concentrated with rotavapor and purified with column chromatography using 5:1 hexane:EA as elution buffer to yield of 4,4'-(((5-methoxy-1,3-phenylene)bis(oxy))bis (methylene))dibenzonitrile (42) as a white solid (42, 2.94 g, 71.0%). $^1$H NMR ($CDCl_3$): δ 7.64 (d, J=8.4 Hz, 4H), 7.51 (d, J=8.4 Hz, 4H), 6.18 (t, J=2.0 Hz, 1H), 6.16 (d J=2.0 Hz, 2H), 5.06 (s, 4H), 3.75 (s, 3H). $^{13}$C NMR ($CDCl_3$): δ 161.8, 160.3, 142.3, 132.6, 127.7, 118.8, 111.9, 94.7, 94.5, 69.11, 55.6. HRMS calcd for $C_{23}H_{18}N_2O_3Na$ $[M+Na]^+$: 393.1215, found 393.1201.

Synthesis of 4,4'-(((5-methoxy-1,3-phenylene)bis(oxy)) bis(methylene))dibenzimidamide dihydrochloride (MD-126). Dinitrile (42, 0.37 g, 0.99 mmol) was converted to 4,4'-(((5-methoxy-1,3-phenylene)bis(oxy))bis(methylene)) dibenzimidamide dihydrochloride as yellow solid following method C (MD-126, 0.35 g, 75%) using ammonia gas. $^1$H NMR (DMSO-$d_6$): δ 9.44 (s, 4H), 9.23 (s, 4H), 7.86 (d, J=8.0 Hz, 4H), 7.65 (d, J=8.0 Hz, 4H), 6.31 (s, 1H), 6.22 (s, 2H), 5.21 (s, 4H), 3.70 (s, 3H). $^{13}$C NMR (DMSO-$d_6$): δ 165.4, 161.2, 159.8, 143.2, 128.3, 127.6, 94.7, 94.1, 68.4, 55.3. HRMS calcd for $C_{23}H_{25}N_4O_3$ [M+H]$^+$: 405.1927, found 405.1923.

1, 3-Bis {(4-amidino-2-fluoro)-benzyloxy}-5-(methoxy)benzene dihydrochloride (MD-127)

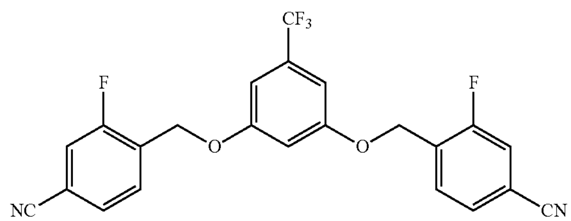 [SMILES: N#Cc1ccc(COc2cc(OCc3ccc(C#N)cc3F)cc(C(F)(F)F)c2)c(F)c1]

A mixture of 5-(Trifluoromethyl)-1,3-diol (0.42 g, 2.4 mmol), 4-cyano2-fluorobenzyl bromide (1.07 g, 5.04 mmol) and anhydrous $K_2CO_3$ (0.99 g, 7.2 mmol) in 20 ml DMF was stirred at 45° C. for 4 h [TLC (Hex:EtOAc 4:1) monitored]. Then the reaction mixture was diluted with ice water (30 ml) and stirred for 30 min. The white precipitate was filtered, washed with water, and dried in air. Then the grey white was dissolved in a dichloromethane (50 ml), dried over anhydrous $Na_2SO_4$, filtered, concentrated with rotavapor and dried in vacuum to yield 1, 3-Bis {(4-cyano 2-fluoro)-benzyloxy}-5-trifluoromethylbenzene as a white solid (0.73 g, 70%); $^1$H NMR ($CDCl_3$): 7.67 (t, J=7.5 Hz, 2H), 7.51 (s, 2H), 7.42 (d, J=9.3 Hz, 2H), 6.89 (s, 2H), 6.75 (s, 1H), 5.19 (s, 4H); $^{13}$C NMR (DMSO-$d_6$): 159.53 (d, $J_{C-F}$=251.1 Hz), 159.45, 130.13 (d, $J_{C-F}$=4.4 Hz), 129.29 (d, $J_{C-F}$=14.0 Hz), 128.54 (d, $J_{C-F}$=4.1 Hz), 119.16 (d, $J_{C-F}$=24.4 Hz), 117.30 (d, $J_{C-F}$=2.8 Hz), 113.58 (d, $J_{C-F}$=9.4 Hz), 105.06, 104.97 (d, $J_{C-F(CF3)}$=4.0 Hz), 63.42 (d, $J_{C-F}$=4.4 Hz); MS: HRMS-ESI-POS.: calc. for $C_{23}H_{13}N_2O_2F_5Na$ m/z 467.077 (M$^+$+Na), found m/z 467.0468.

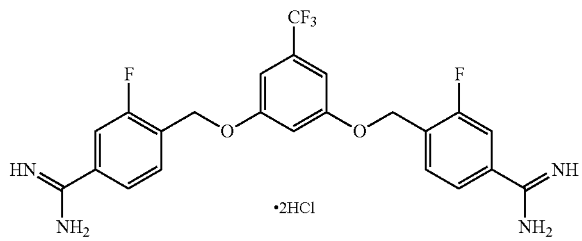 [SMILES: N=C(N)c1ccc(COc2cc(OCc3ccc(C(=N)N)cc3F)cc(C(F)(F)F)c2)c(F)c1]

Dinitrile (0.30 g, 0.68 mmol) was added to anhydrous EtOH saturated with hydrogen chloride (20 mL) at 0° C. in a dry flask. The reaction mixture was then sealed, slowly warmed to ambient temperature, and stirred for 7 days. Ethanol was removed using rotary evaporator. Anhydrous diethyl ether (20 mL) was added to the reaction mixture and the precipitated imidate ester dihydrochloride was filtered off and dried under high vacuum. Ammonia gas (using a cylinder) was passed through imidate ester in EtOH (10 mL) and stirred for a day. The reaction mixture was concentrated in vacuum. Then anhydrous ether was added, and the product was filtered and dried in the oil pump. The free base was converted to its dihydrochloride salt by stirring the diamidine with saturated ethanolic HCl (2 mL) for 2-3 h. The solvent was removed thoroughly and the obtained product was dried in vacuum at 80° C. for 12 h to yield 1, 3-Bis {(4-amidino2-fluoro)-benzyloxy}-5-trifluoromethylbenzene dihydrochloride as a white solid (0.3 g, 60%). $^1$H NMR (DMSO-$d_6$); $^1$H NMR (DMSO-$d_6$): 9.42 (s, 4H), 9.23 (s, 4H), 7.83 (t, J=7.2 Hz, 4H), 7.76 (d, J=10.5 Hz, 2H), 7.70 (d, J=7.9 Hz, 2H), 7.08 (s, 1H), 7.04 (s, 2H), 5.35 (s, 4H); MS: HRMS-ESI-POS.: calc. for $C_{23}H_{20}N_4O_2F_5$ m/z 479.1506 (M$^+$+1), found m/z 479.1512.

1,3-Bis {(4-amidino)-phenethyl}-5-trifluoromethylbenzene dihydrochloride (MD-128)

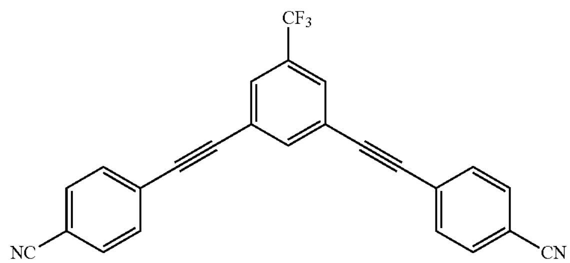 [SMILES: N#Cc1ccc(C#Cc2cc(C#Cc3ccc(C#N)cc3)cc(C(F)(F)F)c2)cc1]

To 3,5-dibromobenzotrifluoride (1.57 g, 5.2 mmol) was added 1:1 DMF-$Et_3N$ (10 ml). To this solution, 3 mole % $Pd(PPh_3)_4$ and 4-Ethynylbenzonitrile (1.32 g, 10.4 mmol) were added and stirred for 5 minutes. Further, 6 mol % Na ascorbate solution, 1 mol % $CuSO_4$ solution in DMF were added to the reaction mixture and stirred for 4 h at 80° C. The reaction mixture was extracted with ethyl acetate followed by ammonium chloride and brine wash. The combined organic layer was dried over anhydrous $Na_2SO_4$ and then concentrated in vacuo. The product was purified using column chromatography and obtained using 5:1 Hexane: Ethyl acetate system as a white solid (1.23 g, 60%). H NMR ($CDCl_3$) 7.88 (s, 1H), 7.79 (s, 2H), 7.70-7.61 (m, 8H); $^{13}$C NMR ($CDCl_3$): δ 137.70, 132.39, 132.36, 128.79, 127.19, 124.06, 118.40, 112.55, 90.90, 90.03; MS: HRMS-ESI-POS.: calc. for $C_{25}H_{111}N_2F_3Na$ m/z 419.0772 (M$^+$+Na), found m/z 419.0771.

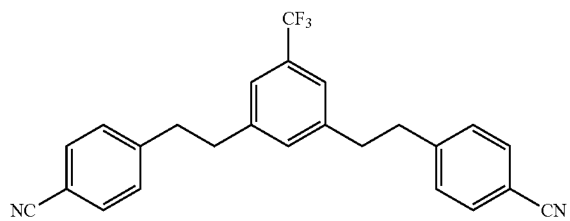 [SMILES: N#Cc1ccc(CCc2cc(CCc3ccc(C#N)cc3)cc(C(F)(F)F)c2)cc1]

To 10% Pd//0C in THF (30 ml) under argon gas was added 4,4'-((5-trifluoromethyl-1,3-phenylene)bis(ethyne-2,1-diyl))dibenzonitrile (1.23 g, 3.1 mmol). The argon gas was exchanged for $H_2$ gas and the reaction mixture was stirred overnight. The reaction mixture was quenched with $CH_2Cl_2$ and filtered through celite. Extraction was carried out with $CH_2Cl_2$ followed by water wash. The combined organic layer was dried over anhydrous $Na_2SO_4$ and then concentrated in vacuo to give the product as a white solid (1.22 g, 97.3%). $^1$H NMR ($CDCl_3$) δ 7.58 (d, J=8.2 Hz, 4H), 7.22 (d, J=8.3 Hz, 6H), 7.00 (s, 1H), 2.94 (s, 8H); $^{13}$C NMR (DMSO-$d_6$): 146.56, 141.85, 132.40, 132.18, 129.40, 123.38 (dd, $J_{C-F(CF3)}$=7.7, 3.5 Hz), 123.19, 123.15, 123.12, 119.04, 110.30, 37.78, 37.03); MS: HRMS-ESI-POS.: calc. for $C_{25}H_{19}N_2F_3Na$ m/z 427.1377 ($M^+$+Na), found m/z 427.1398.

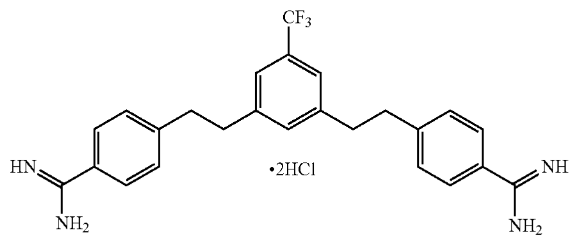 [SMILES: N=C(N)c1ccc(CCc2cc(CCc3ccc(C(=N)N)cc3)cc(C(F)(F)F)c2)cc1]

Dinitrile (0.31 g, 0.76 mmol) was added to anhydrous EtOH saturated with hydrogen chloride (20 mL) at 0° C. in a dry flask. The reaction mixture was then sealed, slowly warmed to ambient temperature, and stirred for 7 days. Ethanol was removed using rotary evaporator. Anhydrous diethyl ether (20 mL) was added to the reaction mixture and the precipitated imidate ester dihydrochloride was filtered off and dried under high vacuum. Ammonia gas (using a cylinder) was passed through imidate ester in EtOH (10 mL) and stirred for a day. The reaction mixture was concentrated in vacuum. Then anhydrous ether was added, and the product was filtered and dried in the oil pump. The free base was converted to its dihydrochloride salt by stirring the diamidine with saturated ethanolic HCl (2 mL) for 2-3 h. The solvent was removed thoroughly and the obtained product was dried in vacuum at 80° C. for 12 h to yield 1, 3-Bis {(4-amidino)-benzyloxy}-5-trifluoromethylbenzene dihydrochloride as a white solid (0.31 g, 62%). $^1$H NMR (DMSO-$d_6$): $^1$H NMR (DMSO-$d_6$) δ 9.24 (s, 4H), 9.12 (s, 4H), 7.76 (d, J=8.2 Hz, 4H), 7.51 (m, 5H), 7.46 (s, 2H), 2.99 (s, 8H); NMR ($CDCl_3$) δ 7.58 (d, J=8.2 Hz, 4H), 7.22 (d, J=8.3 Hz, 6H), 7.00 (s, 1H), 2.94 (s, 8H); $^{13}$C NMR (DMSO-$d_6$):165.40, 147.92, 142.59, 132.70, 129.05, 128.13, 125.75, 122.75, 36.46, 56.13; MS: HRMS-ESI-POS.: calc. for $C_{25}H_{26}N_4F_3$ m/z 439.2110 ($M^+$+1), found m/z 439.2111.

1, 3-Bis {(4-amidino)-phenoxy methyl}-benzene dihydrochloride (DB 2559)

A mixture of 1,3-bis (bromomethyl)-benzene (1.30 g, 5 mmol) and 4-hydroxybenzonitrile (1.19, 10 mmol) used reacted using Method A, yielding 1, 3-bis {(4-cyano)-phenoxy methyl}-benzene as white solid (2.6 g, 76%); $^1$H NMR (DMSO-$d_6$): 7.78 (d, 4H, J=8.8 Hz), 7.55 (s, 1H), 7.45 (s, 3H), 7.19 (d, 4H, J=8.8 Hz), 5.23 (s, 4H); $^{13}$C NMR (DMSO-$d_6$): 161.7, 136.5, 134.2, 128.8, 127.6, 127.2, 119.1, 115.9, 103.1, 69.5; MS: HRMS-ESI-POS.: calc. for $C_{22}H_{22}N_4O_2Na$ m/z 363.1109 ($M^+$+Na), found m/z 363.1105.

Dinitrile (0.34 g, 1 mmol) was converted to 1, 3-bis {(4-amidino) phenoxy methyl}-benzene dihydrochloride as white solid (0.35 g, 74%) following Method B; mp 168-70° C.; $^1$H NMR (DMSO-$d_6$): 9.35 (s, 4H), 9.18 (s, 4H), 7.91 (d, 4H, J=8.8 Hz), 7.59 (s, 1H), 7.46 (s, 3H), 7.23 (d, 4H, J=8.8 Hz), 5.27 (s, 4H); $^{13}$C NMR (DMSO-$d_6$): 164.7, 162.5, 136.7, 130.2, 128.8, 127.6, 127.1, 119.7, 115.1, 69.5; MS: HRMS-ESI-POS.: calc. for $C_{22}H_{23}N_4O_2$ m/z 375.1816 ($M^+$+1), found m/z 375.1816; analysis calc. for $C_{22}H_{22}N_4O_2 \cdot 2HCl \cdot 1.25H_2O$: C, 56.23; H, 5.68; N, 11.92. Found: C, 56.48; H, 5.66; N, 11.85.

1, 3-Bis {(4-(2-imidazolino))-phenoxy methyl}-benzene dihydrochloride (DB 2538)

Dinitrile (0.34 g, 10 mmol) was converted to imidate dihydrochloride, which was reacted with 1,2-diamino ethane to yield diimidazoline dihydrochloride as white solid (0.36 g, 72%) following Method D; mp 245-7° C.; $^1$H NMR (DMSO-$d_6$): 10.73 (s, 4H), 8.12 (d, 4H, J=8.4 Hz), 7.58 (s, 1H), 7.46 (s, 3H), 7.26 (d, 4H, J=8.4 Hz), 5.28 (s, 4H), 3.96 (s, 8H); $^{13}$C NMR (DMSO-$d_6$): 163.9, 162.9, 136.6, 131.0, 128.8, 127.7, 127.2, 115.4, 114.3, 69.5, 44.0; MS: HRMS-ESI-POS.: calc. for $C_{26}H_{27}N_4O_2$ m/z 427.2148 ($M^+$+1), found m/z 427.2134; analysis calc. for $C_{26}H_{26}N_4O_2 \cdot 2HCl \cdot 0.75H_2O$: C, 60.97; H, 5.81; N, 10.97. Found: C, 60.88; H, 5.89; N, 10.90.

1, 3-Bis {(4-(2-imidazolino))-phenoxy methyl}-5-methylbenzene dihydrochloride (MD-129)

Dinitrile (0.354 g, 1 mmol) was converted to 1, 3-bis {4-(2-imidazolino)-phenoxy methyl-5-methylbenzene dihydrochloride as white solid following Method C (0.38 g, 72%), mp 274-6° C.; $^1$H NMR (DMSO-$d_6$): 10.9 (s, 4H), 8.09 (d, 4H, J=8.0 Hz), 7.68 (d, 4H, J=8.0 Hz), 6.52 (s, 1H), 6.49 (s, 2H), 5.22 (s, 4H), 4.0 (s, 8H), 2.42 (s, 3H); $^{13}$C NMR (DMSO-$d_6$): 164.4, 159.0, 144.1, 128.9, 127.7, 121.4, 108.3, 99.3, 68.2, 44.2, 21.4; MS: HRMS-ESI-POS.: calc. for $C_{27}H_{29}N_4O_2$ m/z 441.2291 ($M^+$+1), found m/z 441.2292; analysis calc. for $C_{27}H_{24}N_4O_2 \cdot 2HCl \cdot 1.55H_2O$: C, 60.09; H, 6.17; N, 10.39. Found: C, 60.38; H, 5.99; N, 10.33.

1, 3-Bis{(4-amidino)-phenoxy methyl}-2-fluorobenzene dihydrochloride (DB 2573)

Reaction of 1,3-bis (bromomethyl)-2-fluorobenzene (1.4 g, 5 mmol) and 4-hydroxybenzonitrile (1.19 g, 10 mmol) yielded 1, 3-bis (4-cyano-phenoxy methyl)-2-fluorobenzene as white solid (2.53 g, 70%), following method A; mp 173-5° C.; $^1$H NMR (DMSO-$d_6$): 7.78 (d, 4H, J=8.4 Hz), 7.59 (t, 2H, J=7.2 Hz), 7.29 (t, 1H, J=7.2 Hz), 7.23 (d, 4H, J=8.4 Hz), 5.3 (s, 4H); $^{13}$C NMR (DMSO-$d_6$): 161.4, 158.4 (d, $J_{C-F}$=248 Hz), 134.0, 130.7 (d, $J_{C-F}$=4.1 Hz), 124.2 (d, $J_{C-F}$=4.1 Hz), 123.1 (d, $J_{C-F}$=13.5 Hz), 118.7, 115.6, 103.3, 63.8 (d, $J_{C-F}$=3.3 Hz); MS: HRMS-ESI-POS.: calc. for $C_{22}H_{15}FN_2O_2Na$ m/z 381.1015 ($M^+$+Na), found m/z 381.1005.

Dinitrile (0.358 g, 1 mmol) was converted to 1, 3-bis {4-amidino (phenoxy methyl)-2-fluorobenzene dihydrochloride as white solid following Method B (0.36 g, 71%); mp. 175-7° C.; $^1$H NMR (DMSO-$d_6$): 9.22 (s, 4H), 8.95 (s, 4H), 7.87 (d, 4H, J=9.2 Hz), 7.64 (t, 2H, J=7.6 Hz), 7.31 (t, 1H, J=7.6 Hz), 7.29 (d, 4H, J=9.2 Hz), 5.31 (s, 4H); $^{13}$C NMR (DMSO-$d_6$): 164.7, 162.4, 158.8 (d, $J_{C-F}$=248 Hz), 131.2 (d, $J_{C-F}$=3.7 Hz), 130.3, 124.6 (d, $J_{C-F}$=3.7 Hz), 123.4 (d, $J_{C-F}$=14.5 Hz), 119.9, 115.0, 64.1 (d, $J_{C-F}$=2.98 Hz), MS: HRMS-ESI-POS.: calc. for $C_{22}H_{22}FN_4O_2$ m/z 393.1721 ($M^+$+Na), found m/z 393.1707; analysis calc. for $C_{22}H_{21}FN_4O_2 \cdot 2HCl \cdot 1.5H_2O$. $0.2C_4H_{10}O$ 9ether): C, 54.07; H, 5.57; N, 11.07. Found: C, 54.38; H, 5.27; N, 10.89.

1, 3-Bis {(4-(2-imidazolino))-phenoxy methyl}-2-fluorobenzene dihydrochloride (DB 2510)

Dinitrile (0.358 g, 1 mmol) was converted to di-imidazoline dihydrochloride as white solid following Method D (0.38 g, 70%); mp. 250-2° C.; $^1$H NMR (DMSO-$d_6$): 10.81

(s, 4H), 8.15 (d, 4H, J=7.6 Hz), 7.64 (t, 2H, J=7.2 Hz), 7.33-7.30 (m, 5H, J=7.6 Hz), 5.23 (s, 4H), 3.39 (s, 8H); $^{13}C$ NMR (DMSO-$d_6$): 163.8, 162.7, 154.6 (d, $J_{C-F}$=248 Hz), 130.0 (d, $J_{C-F}$=4.2 Hz), 124.4 (d, $J_{C-F}$=2.25 Hz), 123.2 (d, $J_{C-F}$=15.2 Hz), 115.2, 114.4, 64.5 (d, $J_{C-F}$=3.5 Hz), 43.9; MS: HRMS-ESI-POS.: calc. for $C_{26}H_{26}FN_4O_2$ m/z 445.2034 ($M^+$+Na), found m/z 440.2047; analysis calc. for $C_{26}H_{25}FN_4O_2·2HCl·1.75H_2O$: C, 56.88; H, 5.60; N, 10.20. Found: C, 58.99; H, 5.63; N, 10.41.

1, 3-Bis {(4-amidino-2-fluoro)-phenoxy methyl}-2-fluorobenzene dihydrochloride (DB 2558)

Reaction of 1,3-bis(bromomethyl)-2-fluorobenzene (1.4 g, 5 mmol) and 2-fluoro-4-hydroxybenzonitrile (1.37 g, 10 mmol) following Method A yielded 1, 3-bis (2-fluoro-4-cyano-phenoxymethyl)-2-fluorobenzene as white solid (2.8 g, 71%); mp 185-7° C.; $^1H$ NMR (DMSO-$d_6$): 7.88 (d, 2H, J=8.4 Hz), 7.72 (d, 8.4 Hz), 7.64 (t, 2H, J=7.6 Hz), 7.54 (t, 2H, J=7.6 Hz), 7.33 (t, 1H, J=7.6 Hz), 7.23 (d, 4H, J=8.4 Hz), 5.37 (s, 4H); $^{13}C$ NMR (DMSO-$d_6$): 158.50 (d, $J_{C-F}$=250 Hz), 151.0 (d, $J_{C-F}$=248 Hz), 150.1 (d, $J_{C-F}$=11.0 Hz), 131.1 (d, $J_{C-F}$=4.4 Hz), 130.1 (d, $J_{C-F}$=3.75 Hz), 124.4 (d, $J_{C-F}$=4.28 Hz), 122.7 (d, $J_{C-F}$=15.4 Hz), 119.6 (d, $J_{C-F}$=21.4 Hz), 117.6 (d, $J_{C-F}$=3.4 Hz), 115.91 (d, $J_{C-F}$=2.25 Hz), 103.3 (d, $J_{C-F}$=8.73 Hz), 64.84 (d, $J_{C-F}$=4.21 Hz); MS: HRMS-ESI-POS.: calc. for $C_{22}H_{13}F_3N_2O_2Na$ m/z 417.0827 ($M^+$+Na), found m/z 417.0832.

Dinitrile (0.394 g, 1 mmol) was converted to 1, 3-bis (4-amidino-2-fluoro-phenoxy methyl)-2-fluorobenzene dihydrochloride as white solid following (Method B)(0.303 g, 71%); mp. 2255-7° C.; $^1H$ NMR (DMSO-$d_6$): 9.27 (br, 8H), 7.88 (dd, 2H, J=2.4 Hz, J=12.0 Hz), 7.78 (dd, 2H, 2H, J=1.6 Hz, J=8.4 Hz), 7.66 (t, 2H, 2H, J=7.6 Hz), 7.61 (d, 2H, J=8.8 Hz), 7.34 (d, 1H, J=7.6 Hz), 5.40 (s, 4H); $^{13}C$ NMR (DMSO-$d_6$): 164.3, 159.35 (d, $J_{C-F}$=249 Hz), 151.31 (d, $J_{C-F}$=245 Hz), 150.88 (d, $J_{C-F}$=11.0 Hz), 152.1 (d, $J_{C-F}$=4.5 Hz), 126.33 (d, $J_{C-F}$=3.0 Hz), 125.14 (d, $J_{C-F}$=3.0 Hz), 123.44 (d, $J_{C-F}$=14.0 Hz), 120.65 (d, $J_{C-F}$=7 Hz), 116.71 (d, $J_{C-F}$=21.0 Hz), 115.5, 65.42 (d, $J_{C-F}$=2.98 Hz), MS: HRMS-ESI-POS.: calc. for $C_{22}H_{20}F_3N_4O_2$ m/z 429.1533 ($M^+$+1), found m/z 429.1536; analysis calc. for $C_{22}H_{19}F_3N_4O_2·2HCl·0.75H_2O$; C, 51.32; H, 4.40; N, 10.88. Found: C, 51.47; H, 4.39; N, 10.69.

1, 3-Bis {4-(2-imidazolino)-2-fluoro)-phenoxy methyl}-2-fluorobenzene dihydrochloride (DB 2554)

Dinitrile (0.394 g, 1 mmol) was converted to di-imidazoline dihydrochloride as white solid following Method D (0.4 g, 70%); mp. 218-20° C.; $^1H$ NMR (DMSO-$d_6$): 10.78 (br, 4H), 8.12 (d, 2H, J=12.0 Hz), 8.02 (d, 2H, J=9.2 Hz), 7.63 (t, 2H, J=7.6 Hz), 7.58 (t, 2H, J=8.4 Hz), 7.32 (t, 1H, J=7.6 Hz), 5.43 (s, 4H), 3.99 (s, 8H); $^{13}C$ NMR (DMSO-$d_6$): 164.2, 159.12 (d, $J_{C-F}$=250 Hz), 151.68 (d, $J_{C-F}$=247 Hz), 151.3 (d, $J_{C-F}$=10.5 Hz), 131.74 (d, $J_{C-F}$=4.5 Hz), 126.6 (d, $J_{C-F}$=3.3 Hz), 124.91 (d, $J_{C-F}$=4.5 Hz), 123.18 (d, $J_{C-F}$=14.5 Hz), 116.61 (d, $J_{C-F}$=21.0 Hz), 116.3, 115.18 (d, $J_{C-F}$=7.5 Hz), 65.73 (d, $J_{C-F}$=4.0 Hz), MS: HRMS-ESI-POS.: calc. for $C_{26}H_{24}F_3N_4O_2$ m/z 481.1846 ($M^+$+1), found m/z 481.1857; analysis calc. for $C_{26}H_{23}F_3N_4O_2·2HCl·1.1H_2O$; C, 54.47; H, 4.78; N, 9.77. Found: C, 54.10; H, 4.76; N, 9.65.

1, 3-Bis {[4-(2-imidazolyl)-2-methoxy)-phenoxy methyl]}-2-fluorobenzene dihydrochloride (DB 2555)

Reaction of 1,3-bis (bromomethyl)-2-fluorobenzene (1.4 g, 5 mmol) and 4-hydroxy-2-methoxybenzonitrile (1.37 g, 10 mmol) following Method A yielded 1, 3-Bis {(4-cyano-2-methoxy)-phenoxy methyl}-2-fluorobenzene as white solid (2.8 g, 71%); mp 185-7° C.; $^1H$ NMR (DMSO-$d_6$): 7.59 (t, 2H, J=7.2 Hz), 7.45-7.41 (m, 4H), 731-7.27 (m 3H), 5.25 (s, 4H), 3.82 (s, 6H); $^{13}C$ NMR (DMSO-$d_6$): 159.2 (d, $J_{C-F}$=247 Hz), 152.01, 149.59, 131.91 (d, $J_{C-F}$=3 Hz) 126.74, 125.02 (d, $J_{C-F}$=4.0 Hz), 123.77 (d, $J_{C-F}$=14 Hz), 119.64, 115.22, 113.88, 103.69, 64.76, 56.41; MS: HRMS-ESI-POS.: calc. for $C_{24}H_{19}FN_2O_4Na$ m/z 441.1226 ($M^+$+Na), found m/z 441.1237.

Dinitrile (0.418 g, 1 mmol) was converted to di-imidazoline dihydrochloride as white solid (0.43 g, 70%) following Method D; mp. 237-9° C.; $^1H$ NMR (DMSO-$d_6$): 10.79 (s, 4H), 7.84 (d, 2H, J=2.0 Hz), 7.77 (dd, 2H, J=2.0 Hz, J=8.4 Hz), 7.62 (t, 2H, J=7.6 Hz), 7.40 (d, J=8.4 Hz), 7.32 (t, 1H, J=7.6 Hz), 5.29 (s, 4H), 3.97 (s, 8H), 3.86 (s, 6H); $^{13}C$ NMR (DMSO-$d_6$): 164.1, 159.01 (d, $J_{C-F}$=250 Hz), 152.4, 148.9, 131.5 (d, $J_{C-F}$=3.0 Hz), 124.9 (d, $J_{C-F}$=4.0 Hz), 123.0 (d, $J_{C-F}$=15.0 Hz), 122.8, 114.4, 112.8, 112.1, 64.4 (d, $J_{C-F}$=3.5 Hz), 56.2, 44.1; MS: HRMS-ESI-POS.: calc. for $C_{28}H_{30}FN_4O_4$ m/z 505.2246 ($M^+$+1), found m/z 505.2248; analysis calc. for $C_{28}H_{29}F3N_4O_4·2HCl·1.85H_2O$; C, 54.83; H, 5.83; N, 8.90. Found: C, 55.01; H, 5.67; N, 9.02.

Example 2. Antibacterial Activity Against *E. coli*

The sensitization fold of select compounds of the present invention was determined. *E. coli* bacteria were cultured in nutrient broth at 37° C. overnight prior to treatment. Bacteria were then incubated with various concentrations of erythromycin with or without the compounds shown below for 20 hours. Bacterial density was measured based on $OD_{600}$. Magnitude of the sensitization (sensitization fold) was calculated based on the $IC_{90}$ of erythromycin using the following formula:

Sensitization fold (SF)=$IC_{90}$ of erythromycin without compounds/$IC_{90}$ of erythromycin with compounds The cytotoxicity in H9c2 (ATCC®CRL-1446™) cells was also determined. The H9c2 cells were maintained in DMEM (Dulbecco's Modified Eagle's Medium) supplemented with 10% fetal bovine serum (MidSci; S01520HI) and 1% penicillin-streptomycin (Sigma-Aldrich; P4333) at 37° C. with 5% $CO_2$. The H9c2 cells were seeded in 96-well plate one day before the experiment. Different concentrations of di-amidine compounds were added into the H9c2 cells. The cells were then incubated with the compounds for 24 hours at 37° C. with 5% $CO_2$. The cell viability was tested by the CCK-8. Specifically, after 24 hour incubation, 10 μL CCK-8 was added to each well. After 3 hours incubation at 37° C., the absorbance at 450 nm was recorded by a plate reader. The results for the sensitization fold and cytotoxicity are shown in Table 1.

TABLE 1

| MIC Sensitization Activity on *E. coli* | | | |
|---|---|---|---|
| Compd ID | Structure | Sensitization ability | Cytotoxicity ($IC_{50}$) |
| A | 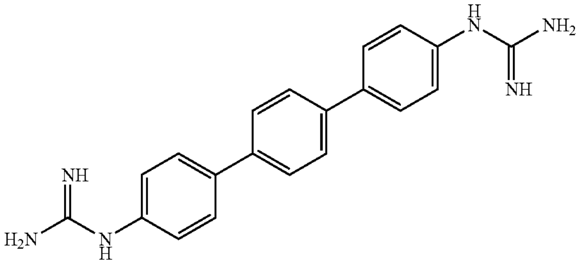 [SMILES: N=C(N)Nc1ccc(-c2ccc(-c3ccc(NC(=N)N)cc3)cc2)cc1] | At 25 μM, sensitize *E. coli* towards rifampicin for 256-fold; | 50 μM |
| B | 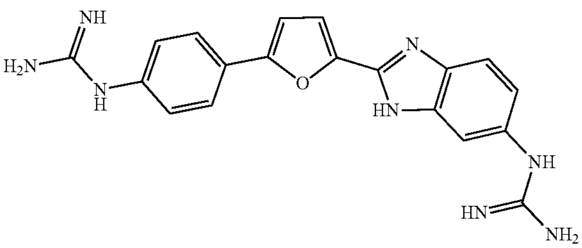 [SMILES: N=C(N)Nc1ccc(-c2ccc(-c3nc4ccc(NC(=N)N)cc4[nH]3)o2)cc1] | At 25 μM, sensitize *E. coli* towards rifampicin for 16-fold; | 100 μM |
| C | 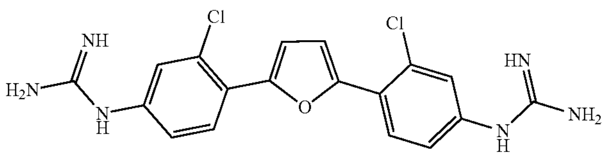 [SMILES: N=C(N)Nc1ccc(-c2ccc(-c3ccc(NC(=N)N)cc3Cl)o2)c(Cl)c1] | At 4 μM, sensitize *E. coli* towards rifampicin for 516-fold; | 50 μM |
| D | 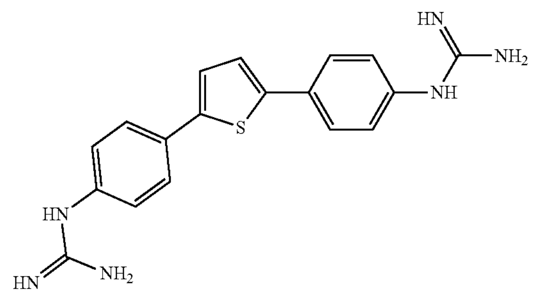 [SMILES: N=C(N)Nc1ccc(-c2ccc(-c3ccc(NC(=N)N)cc3)s2)cc1] | At 15 μM, sensitize *E. coli* towards rifampicin for 32-fold; | >100 μM |
| M | 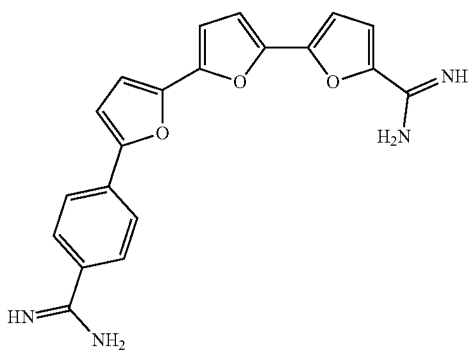 [SMILES: N=C(N)c1ccc(-c2ccc(-c3ccc(-c4ccc(C(=N)N)o4)o3)o2)cc1] | At 25 μM, sensitize *E. coli* towards rifampicin for 516-fold; At 15 μM, sensitize *E. coli* towards rifampicin for 32-fold. | 100 μM |

TABLE 1-continued

| MIC Sensitization Activity on *E. coli* | | | |
|---|---|---|---|
| Compd ID | Structure | Sensitization ability | Cytotoxicity ($IC_{50}$) |
| N | 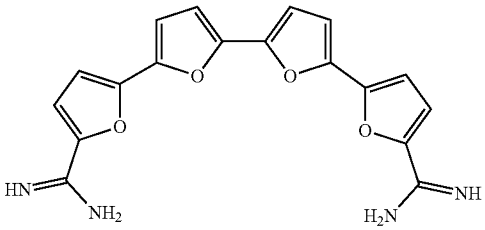 [SMILES: N=C(N)c1ccc(-c2ccc(-c3ccc(-c4ccc(C(=N)N)o4)o3)o2)o1] | At 25 μM, sensitize *E. coli* towards rifampicin for 64-fold. | 100 μM |
| O | 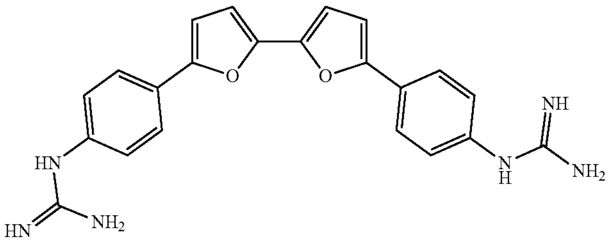 [SMILES: N=C(N)Nc1ccc(-c2ccc(-c3ccc(-c4ccc(NC(=N)N)cc4)o3)o2)cc1] | At 10 μM, sensitize *E. coli* towards rifampicin for 256-fold. | >100 μM |
| P | 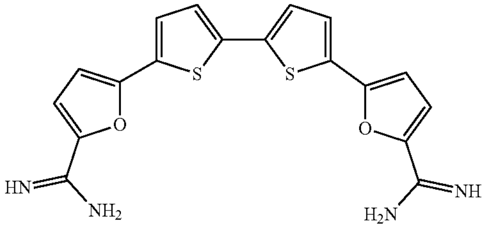 | At 25 μM, sensitize *E. coli* towards rifampicin for 32-fold; | 50 μM |
| Q | 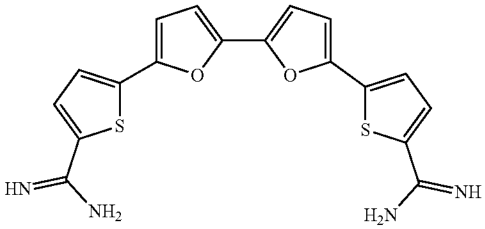 | At 25 μM, sensitize *E. coli* towards rifampicin for 32-fold; | 50 μM |
| R | 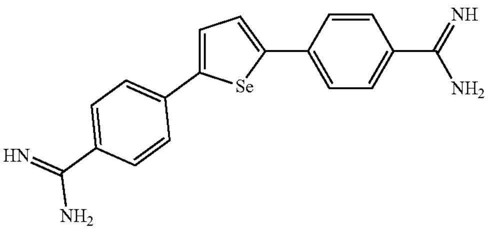 | At 25 μM, sensitize *E. coli* towards rifampicin for 32-fold; | >100 μM |
| T | 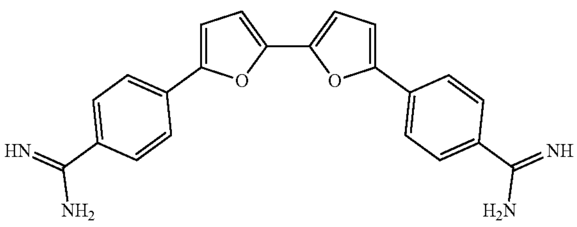 [SMILES: N=C(N)c1ccc(-c2ccc(-c3ccc(-c4ccc(C(=N)N)cc4)o3)o2)cc1] | At 25 μM, sensitize *E. coli* towards rifampicin for 32-fold; | >100 μM |

TABLE 1-continued

| MIC Sensitization Activity on *E. coli* | | | |
|---|---|---|---|
| Compd ID | Structure | Sensitization ability | Cytotoxicity ($IC_{50}$) |
| U | 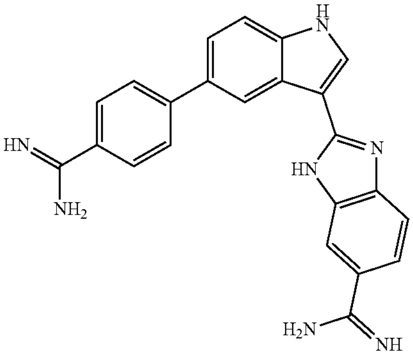 [SMILES: N=C(N)c1ccc(-c2ccc3[nH]cc(-c4nc5ccc(C(=N)N)cc5[nH]4)c3c2)cc1] | At 10 μM, sensitize *E. coli* towards rifampicin for 32-fold; | 100 μM |

Example 3. Sensitization of *Escherichia Coil* (Gram Negative Bacterium) to Clarithromycin The minimum inhibitory concentration (MIC) of clarithromycin on *E. coli* is 50 mcg/ml. Bacteria were cultured with clarithromycin at various concentrations in the presence or absence of the bacterial sensitizer, Compound D, for 24 hours at 37° C. Then bacterial growth density was determined by measuring $OD_{600}$ and the results are shown in Table 2.

Compound D

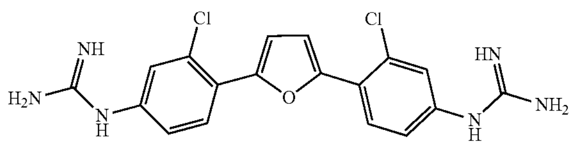

TABLE 2

| MIC of clarithromycin on *E. coli* with different concentrations. | | |
|---|---|---|
| Conc of Compound D (mcg/ml) | Sensitization fold | MIC (mcg/ml) |
| 0.5 | 2 | 25 |
| 1 | 16 | 3.2 |
| 1.5 | 32 | 1.6 |
| 2.0 | 64 | 0.8 |
| 2.5 | 512 | 0.1 |
| 3 | >512 | <0.1 |
| 3.5 | >512 | <0.1 |

Example 4. Sensitization of *Escherichia Coil* (Gram Negative Bacterium) to Novobiocin The minimum inhibitory concentration (MIC) of novobiocin on *E. coli* is 100 mcg/ml. Bacteria were cultured with novobiocin at various concentrations in the presence or absence of bacterial sensitizer, Compound D, for 24 hours at 37° C. Then bacterial growth density was determined by measuring $OD_{600}$ and the results are shown in Table 3.

Compound D

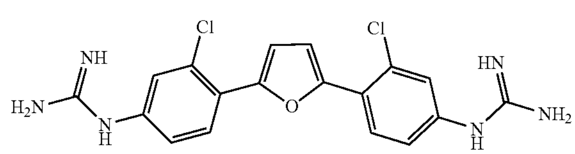

TABLE 3

| MIC of novobiocin on *E. coli* with different concentrations. | | |
|---|---|---|
| Conc of Compound D (mcg/ml) | Sensitization fold | MIC (mcg/ml) |
| 0.5 | 2 | 50 |
| 1 | 8 | 12.5 |
| 1.5 | 64 | 1.6 |
| 2.0 | 128 | 0.8 |
| 2.5 | 512 | 0.2 |
| 3 | >512 | <0.2 |
| 3.5 | >512 | <0.2 |

Example 5. Sensitization of *Escherichia Coil* (Gram Negative Bacterium) to Rifampicin The minimum inhibitory concentration (MIC) of rifampicin on *A. baumannii* is 5 mcg/ml. Bacteria were cultured with the antibiotic at various concentrations in the presence or absence of bacterial sensitizer, Compound D, for 24 hours at 37° C. Then bacterial growth density was determined by measuring $OD_{600}$ and the results are shown in Table 4.

Compound D

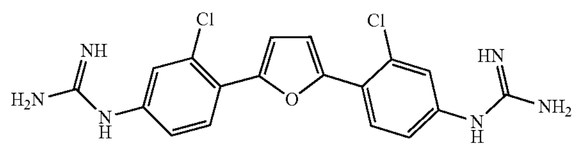

TABLE 4

MIC of rifampicin on *A. baumannii* with different concentrations.

| Conc of Compound D (mcg/ml) | Sensitization fold | MIC (mcg/ml) |
|---|---|---|
| 0.5 | 4 | 1.25 |
| 1 | 32 | 0.16 |
| 1.5 | 256 | 0.02 |
| 2.0 | 512 | 0.01 |
| 2.5 | >512 | <0.01 |
| 3 | >512 | <0.01 |
| 3.5 | >512 | <0.01 |

Example 6: Highly Potent Small Molecule Sensitizers of Gram-Negative Bacteria Towards Existing Antibiotics Instruments and reagents. All solvents were of reagent grade and were purchased from Fisher Scientific and Aldrich. Reagents and antibiotics were purchased from Aldrich, Oakwood, or VWR. The stationary phase of chromatographic purification is silica (230×400 mesh, Sorbtech). Silica gel TLC plate was purchased from Sorbtech. $^1$H-NMR (400 MHz) and $^{13}$C-NMR (100 MHz) spectra were recorded on a Bruker Avance 400 MHz NMR spectrometer. Mass spectral analyses were performed on an ABI API 3200 (ESI-Triple Quadruple). HPLC was performed on a Shimadzu Prominence UFLC (column: Waters C18 3.5 μM, 4.6×100 mm). $OD_{600}$ and fluorescence intensity was recorded on Perkin Elmer Enspire UV/Vis/Fluorescence plate reader Bacteria strains: *E. coli* (ATCC 25922), *A. baumannii* (ATCC 17978), *K. pneumoniae* (43816), *S. maltophilia* (ATCC 31559), *S. typhimurium* (ATCC 14028), *C. werkmanii* (ATCC 51114), *S. aureus* (ATCC 12600) and methicillin-resistant *Staphylococcus aureus* (MRSA, ATCC 33592) strains were purchased from ATCC. NR698 was provided.

Bacteria culture and MICs determination: Gram-negative bacteria were cultured in Mueller Hinton II cation-adjusted broth. Gram-positive bacteria were cultured in LB broth. *Mycobacterium smegmatis* was cultured in Middlebrook 7H9 Broth. MICs of antibiotics itself were determined by performing two-fold serial dilutions of antibiotics. MICs of antibiotics in the presence of bacterial sensitizers were determined by performing two-fold serial dilutions of antibiotics with or without a constant concentration of bacterial sensitizers. The MICs tests were performed on 96-well plates with a final volume of 200 μl Mueller Hinton II cation-adjusted broth in each well. Each well was inoculated with $5\times10^5$ CFU/ml bacteria and was incubated for 24 h at 37° C. with continuous shaking of 200 rpm. The bacterial density was then determined by $OD_{600}$. Bacterial growth %=$OD_{600}$ of antibiotic treatment group/$OD_{600}$ of antibiotic non-treatment group. MICs was determined as the concentrations that inhibit more than 90% of bacteria growth.

Sensitization fold determination and FIC index calculations: Sensitization fold=MIC of antibiotic only/MIC of antibiotic with bacterial sensitizer. For example, the MIC of rifampin on *E. coli* is 10 μg/ml, the MIC of rifampicin in the presence of 5 μg/ml MD-124 is measured to be 0.019 μg/ml, so the sensitization fold of 5 μg/ml MD-124 on *E. coli* towards rifampicin is 10 μg/ml/0.019 μg/ml=512-fold. Since the MICs were determined by performing two-fold serial dilutions of antibiotic, so the sensitization fold can is the times of 2.

FIC index between compound a and b was calculated according to the formula below:

$$FIC = FICa + FICb = \frac{MIC \text{ of } a \text{ in combination}}{MIC \text{ of } a \text{ alone}} + \frac{MIC \text{ of } b \text{ in combination}}{MIC \text{ of } b \text{ alone}}$$

FIC≤0.5: Synergy; FIC between 0.5 and 1: Additive; FIC between 1 and 2: no interaction; FIC >4: antagonism.

Bacterial resistance frequency study: *E. coli* was grown overnight in Mueller Hinton II cation-adjusted broth medium and concentrated to ~$5\times10^9$ CFUs/ml in Mueller Hinton II cation-adjusted broth. Then a 200 μl volume of ~$5\times10^9$ CFUs/ml (equal to $1\times10^9$ CFUs) was then transferred onto solid Mueller Hinton agar plates (100 mm Petri dishes) containing antibiotic 2- to 6-times the MIC, with or without 10 μg/ml MD-124. Then the plates were incubated at 37° C. for 48 h. Then the colonies formed on the plate were recorded and resistant frequency was calculated. Resistance frequency towards antibiotics or MD-124 and antibiotics combination were calculated by dividing the number of colonies formed after a 48 h by total CFUs inoculated on the plates initially.

The resistance frequency calculation towards MD-124: For trovafloxacin and MD-124 combination, 2, 3 and 4 times of MIC of trovafloxacin was used and each combination has 3 replicates. So, for trovafloxacin and MD-124 combination, it is 3 combination conditions with each condition having 3 replicates, and the amount of CFUs tested is: $10^9$ CFUs per agar plates 5×3 replicates per combination condition×3 combination conditions=$9\times10^9$ CFUs. The amount of CFUs tested for the novobiocin/MD-124 and clindamycin/MD-124 combination is the same. So, together $2.7\times10^{10}$ CFUs were tested in the MD-124 and antibiotics combination. There are colonies that were resistant MD-124 and antibiotic combination. To find out whether those resistant strains are resistant to MD-124 or antibiotics, those colonies were then subjected to another antibiotic combination: MD-124 and rifampicin. It turned out that MD-124 was still able to sensitize those resistant strains towards rifampicin with the same potency on wild-type *E. coli*, which demonstrated those 6 combinational therapy resistant strains are not resistant to MD-124. No strain was found to be resistant to 10 μg/ml MD-124 out of $2.7\times10^{10}$ CFUs.

The resistance frequency towards MD-124 was calculated to be:

$$\frac{<1}{2.7\times10^{10}} < 3.7\times10^{-11}$$

Lysozyme assay to evaluate the disruption of Gram-negative bacteria out membrane by bacterial sensitizers. Lysozyme assay was performed based on literature reported method. *E. coli* was cultured in Mueller Hinton II cation-adjusted broth for overnight, centrifuged at 3000 g for 10 min, washed with HEPES buffer (pH=7.2) and then centrifuged again to obtain bacteria pallet. The pallet was then gently resuspended in HEPES buffer with 5 mM NaCN to obtain an *E. coli* suspension with $OD_{600}$ between 0.8~1.0. On a 96-well plate, each well was supplied with 100 μl lysozyme solution (100 μg/ml) containing 50 or 100 μg/ml bacterial sensitizers in HEPES buffer. To each well was added 100 μl *E. coli* suspension. The final concentration of lysozyme was 50 μg/ml. The plate was incubated at room temperature for 10 min and the $OD_{600}$ was recorded. *E. coli* was also incubated with bacterial sensitizers in the absence of lysozyme to test if bacterial sensitizers would directly induce bacterial lysis. *E. coli* that was incubated with lysozyme alone or *E. coli* without any treatment were also used as negative control.

Evaluation of the influence of exogenous LPS and $Mg^{2+}$ on bacterial sensitizer. The MICs of bacterial sensitizer and antibiotic combination in the presence of LPS (ranging from 0 to 40 μM) or $Mg^{2+}$ (ranging from 0 to 20 mM) was determined as described above (Bacteria culture and MICs determination section).

Construction of MCR-1 and NDM-1 expressing *E. coli* strain. *E. coli* (ATCC 25922) was transformed with pGDP2 MCR-1 (Addgene, pGDP2 MCR-1, plasmid #118404) to generate colistin resistant strains. *E. coli* (ATCC 25922) was transformed with pGDP1 NDM-1 (Addgene, plasmid #112883, pGDP1 NDM-1) to generate strains that are resistant to a broad range of β-lactam antibiotics. The successful construction of the MCR-1 and NDM-1 over-expression *E. coli* strains were validated by their increased resistance towards polymyxin B and β-lactam antibiotics (ampicillin, ceftazidime and meropenem) respectively.

Direct comparison of the antibiotic uptake in the presence and absence of MD-100 through HPLC study. *E. coli* (ATCC 25922) was cultured in Mueller Hinton II cation-adjusted broth for overnight at 37° C. to reach a density of $OD_{600}$ of 0.8 to 1.0. To 20 ml fresh Mueller Hinton II cation-adjusted broth was added 50 μl *E. coli* stock, 200 μl 5 mg/ml O—$CH_3$ novobiocin and 100 μl 10 mM MD-100. In the other group, the same amount of *E. coli* stock, O—$CH_3$ novobiocin was used in the absence of MD-100. Then *E. coli* was incubated for 20 h at 37° C. with continuous shaking of 200 rpm. After, the *E. coli* suspension was centrifuged at 3000 g for 10 min and the culture media was removed to obtain bacteria pallet. The pallets from the two groups was re-suspended in PBS to reach the same $OD_{600}$ of 2.0. To this *E. coli* suspension was spiked with 10 μM internal standard. 1 ml *E. coli* from each group in PBS was lysed by sonication on ice for 15 min, followed by adding 2 ml MeOH, the mixture was then centrifuged at 3000 g for 5 min and the supernatant was analyzed by HPLC. 20 μl of each sample was injected into Shimadzu Prominence UFLC (column: Waters C18, 3.5 μM, 4.6×100 mm, injection loop volume: 20 μl). The mobile phase was acetonitrile (ACN)/$H_2O$ (with 0.05% trifluoroacetic acid in the aqueous) with ratios defined as: 20%~55% ACN, 0~10 min; 55%~65% ACN, 10~20 min; 65%~20% ACN, 20~25 min. The internal standard used here is novobiocin because novobiocin have a very similar structure and chemical property compared with the analyte O—$CH_3$ novobiocin.

Dansyl-PMBN displacement assay. Dansyl-PMBN was synthesized according to literature procedure. Dansyl-PMBN was dissolved in $H_2O$ to make 500 μM stock. Bacterial sensitizers were dissolved in ethanol to make 10 mM stock solutions. *E. coli* (ATCC 25922) was cultured in Mueller Hinton II cation-adjusted broth for overnight 37° C. The *E. coli* stock was centrifuged at 3000 g for 10 min, washed with HEPES buffer (pH=7.2) and then centrifuged again to obtain bacteria pallet. The pallet was then gently resuspended in HEPES buffer to obtain a *E. coli* suspension with $OD_{600}$ about 0.3. The experiment was performed on 96-well plates. Each well was supplied with 100 μl coli suspension with 10 μM Dansyl-PMBN, then to each well, different concentrations of bacterial sensitizers were added to achieve a final concentration ranging from 0 to 200 μM. Then the mixture was incubated at room temperature for 3 min and the fluorescence intensities with different concentration of bacterial sensitizers were recorded (Ex=340 nm; Em=520 nm).

Cytotoxicity test of bacterial sensitizers on mammalian cells. Cell viability was assessed by using Cell Counting Kit-8 (CCK-8, Dojindo, Japan). HEK293 or NIH3T3 cells were seeded in a 96-well plate one day before the experiment to reach 80% confluency. Cells were then incubated with various concentration of bacterial sensitizers at 37° C. with 5% $CO_2$ for 24 h, then 10 μL of CCK-8 solution was added to each well, and the plate was incubated for an additional at 37° C. 2 h with 5% $CO_2$. The optical density at 450 nm was recorded by plate reader; and the results were calculated as a percentage of viability compared with the untreated control.

Development of Gram-Negative Bacteria Sensitizers

Compounds were synthesized and tested for their ability of sensitizing *E. coli* towards narrow-spectrum antibiotics (Tables 5A and 5B). Table 5A shows the structures of the compounds and Table 5B shows the activities, sensitization, and cytotoxicity of compounds.

TABLE 5A

| Compound ID | Structure |
| --- | --- |
| DB2514 | 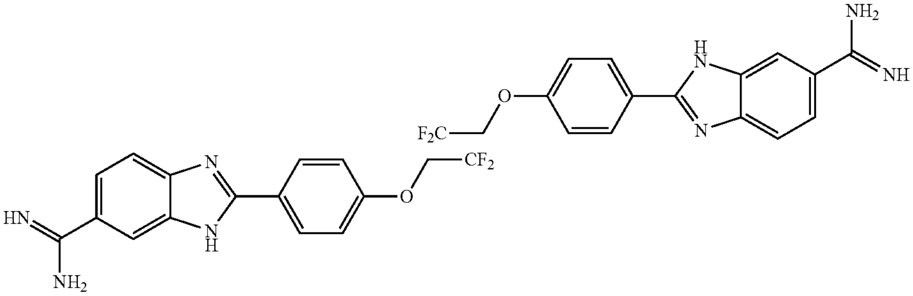 |

TABLE 5A-continued
| Compound ID | Structure |
| --- | --- |
| DB2457 | 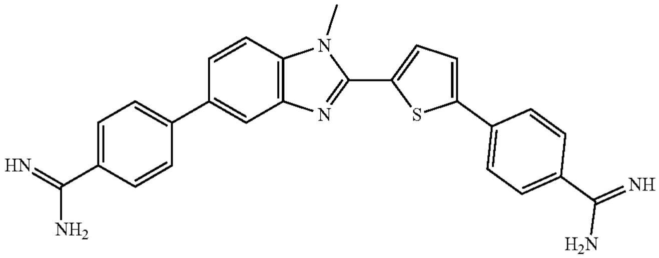 [SMILES: Cn1c(-c2ccc(-c3ccc(C(=N)N)cc3)s2)nc2cc(-c3ccc(C(=N)N)cc3)ccc21] |
| DB2542 | 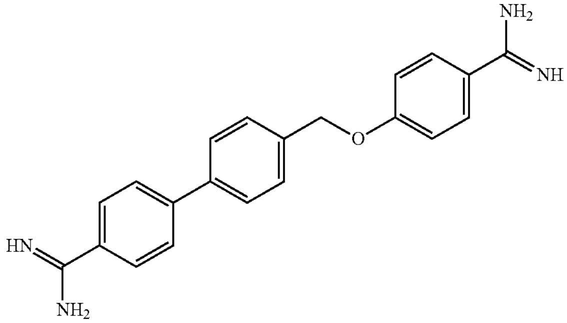 [SMILES: N=C(N)c1ccc(OCc2ccc(-c3ccc(C(=N)N)cc3)cc2)cc1] |
| DB2559 | 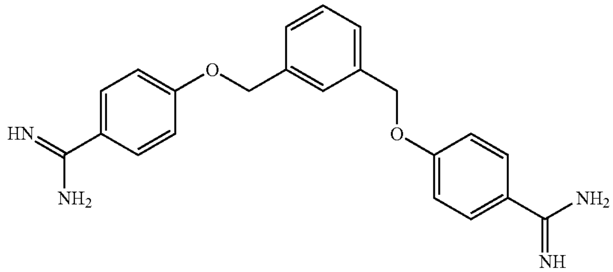 [SMILES: N=C(N)c1ccc(OCc2cccc(COc3ccc(C(=N)N)cc3)c2)cc1] |
| DB2558 | 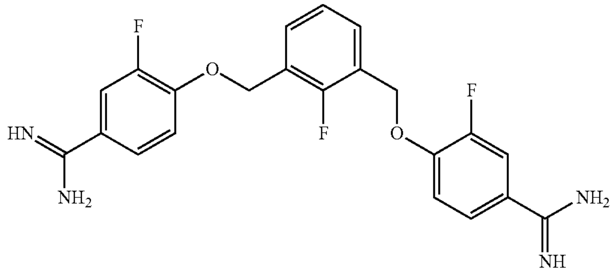 [SMILES: N=C(N)c1ccc(OCc2cccc(COc3ccc(C(=N)N)cc3F)c2F)c(F)c1] |
| DB2583 | 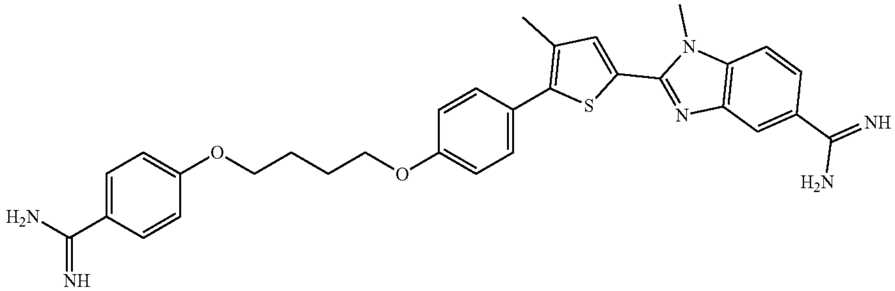 [SMILES: Cc1cc(-c2nc3cc(C(=N)N)ccc3n2C)sc1-c1ccc(OCCCCOc2ccc(C(=N)N)cc2)cc1] |

TABLE 5A-continued
| Compound ID | Structure |
| --- | --- |
| DB2447 | 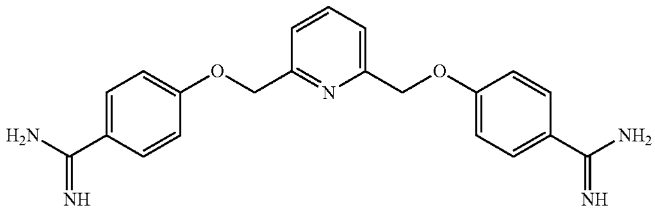 [SMILES: N=C(N)c1ccc(OCc2cccc(COc3ccc(C(=N)N)cc3)n2)cc1] |
| DB1824 | 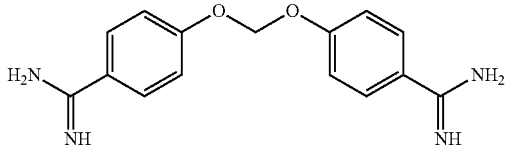 [SMILES: N=C(N)c1ccc(OCOc2ccc(C(=N)N)cc2)cc1] |
| DB2573 | 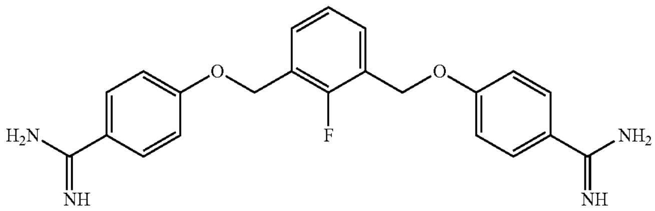 [SMILES: N=C(N)c1ccc(OCc2cccc(COc3ccc(C(=N)N)cc3)c2F)cc1] |
| DB2449 | 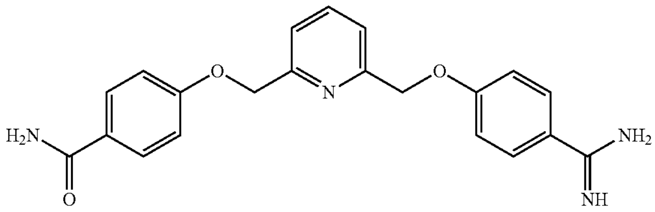 [SMILES: N=C(N)c1ccc(OCc2cccc(COc3ccc(C(N)=O)cc3)n2)cc1] |
| DB2362 | 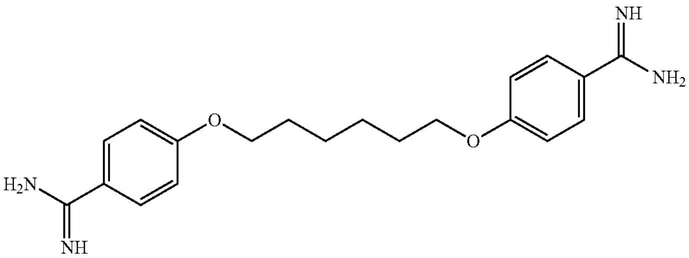 [SMILES: N=C(N)c1ccc(OCCCCCCOc2ccc(C(=N)N)cc2)cc1] |
| MD-129 | 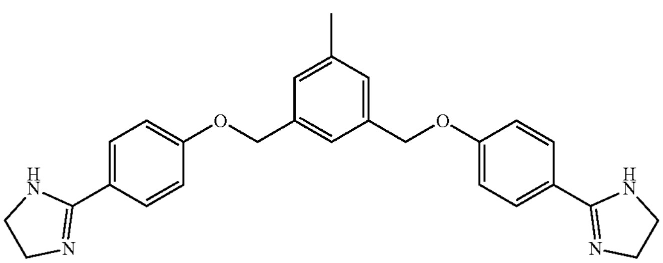 [SMILES: Cc1cc(COc2ccc(C3=NCCN3)cc2)cc(COc2ccc(C3=NCCN3)cc2)c1] |
| DB2538 | 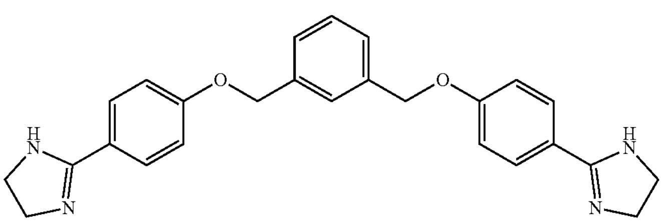 [SMILES: c1cc(COc2ccc(C3=NCCN3)cc2)cc(COc2ccc(C3=NCCN3)cc2)c1] |

TABLE 5A-continued
| Compound ID | Structure |
|---|---|
| DB2510 | 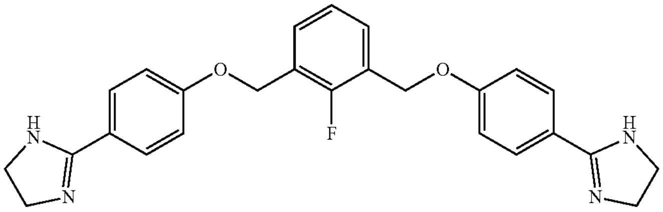 [SMILES: Fc1c(COc2ccc(C3=NCCN3)cc2)cccc1COc1ccc(C2=NCCN2)cc1] |
| DB2554 | 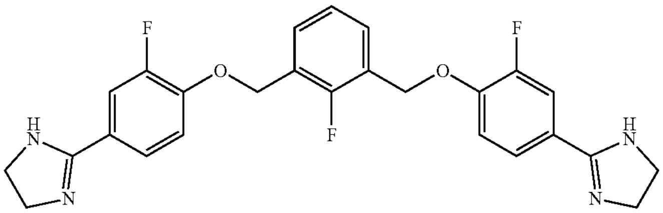 [SMILES: Fc1cc(C2=NCCN2)ccc1OCc1cccc(COc2ccc(C3=NCCN3)cc2F)c1F] |
| DB2555 | 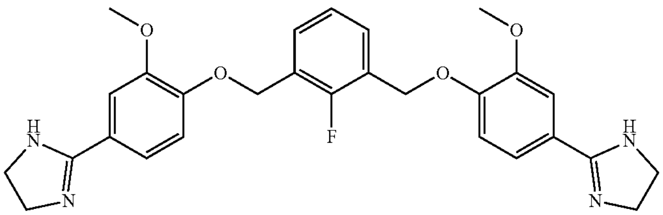 [SMILES: COc1cc(C2=NCCN2)ccc1OCc1cccc(COc2ccc(C3=NCCN3)cc2OC)c1F] |
| MD-100 | 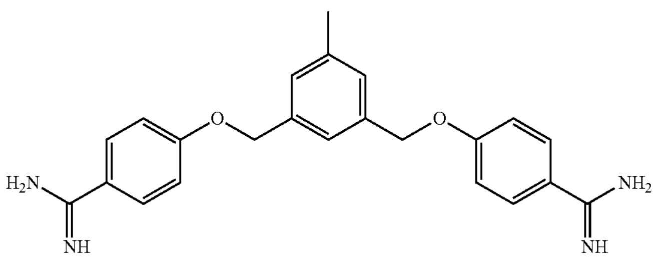 [SMILES: Cc1cc(COc2ccc(C(=N)N)cc2)cc(COc2ccc(C(=N)N)cc2)c1] |
| MD-101 | 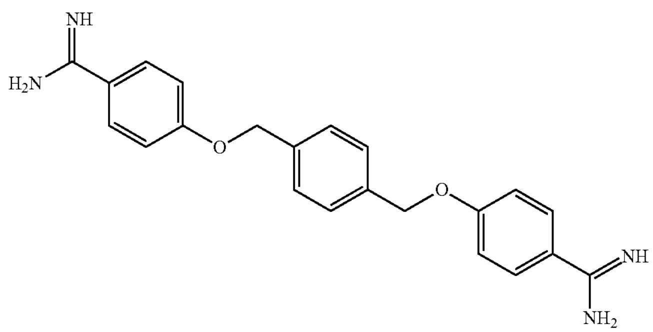 [SMILES: N=C(N)c1ccc(OCc2ccc(COc3ccc(C(=N)N)cc3)cc2)cc1] |
| MD-102 | 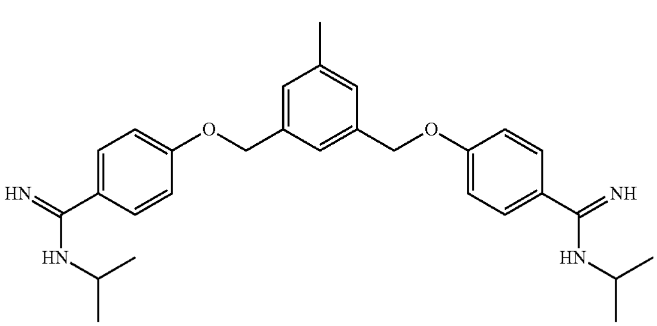 [SMILES: Cc1cc(COc2ccc(C(=N)NC(C)C)cc2)cc(COc2ccc(C(=N)NC(C)C)cc2)c1] |

TABLE 5A-continued
| Compound ID | Structure |
| --- | --- |
| MD-103 | 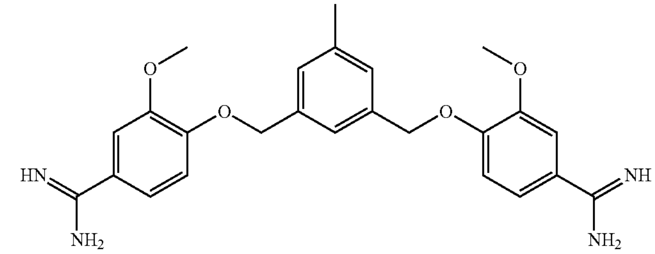 [SMILES: COc1cc(C(=N)N)ccc1OCc1cc(C)cc(COc2ccc(C(=N)N)cc2OC)c1] |
| MD-104 | 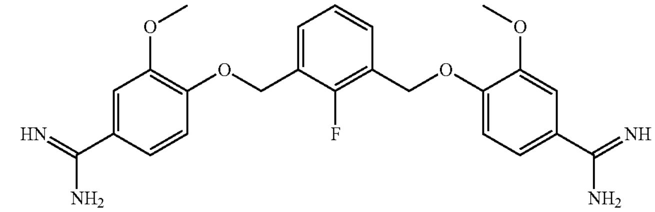 [SMILES: COc1cc(C(=N)N)ccc1OCc1cccc(COc2ccc(C(=N)N)cc2OC)c1F] |
| MD-105 | 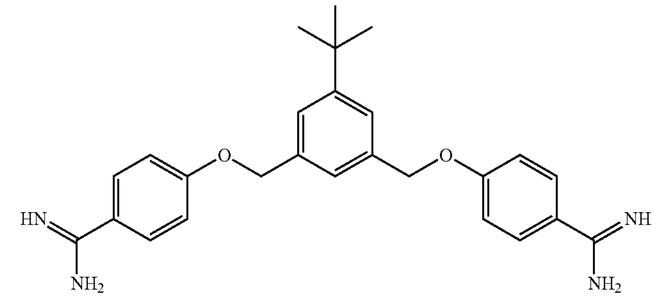 [SMILES: CC(C)(C)c1cc(COc2ccc(C(=N)N)cc2)cc(COc2ccc(C(=N)N)cc2)c1] |
| MD-106 | 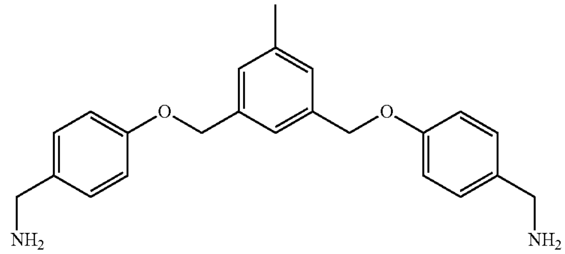 [SMILES: Cc1cc(COc2ccc(CN)cc2)cc(COc2ccc(CN)cc2)c1] |
| MD-107 | 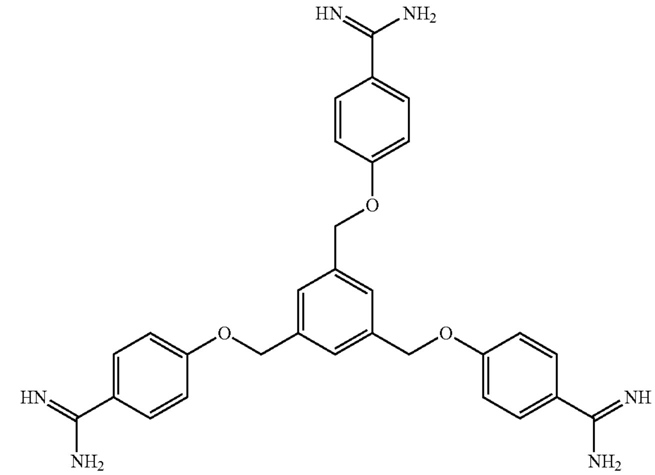 [SMILES: N=C(N)c1ccc(OCc2cc(COc3ccc(C(=N)N)cc3)cc(COc3ccc(C(=N)N)cc3)c2)cc1] |

TABLE 5A-continued
| Compound ID | Structure |
| --- | --- |
| 108 | 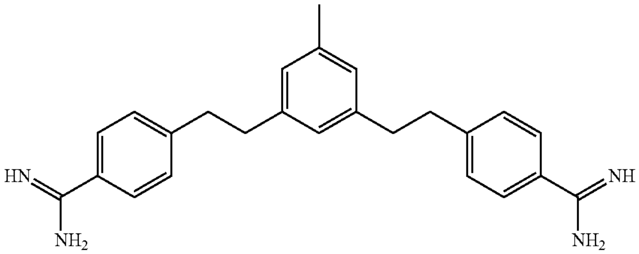 [SMILES: Cc1cc(CCc2ccc(C(=N)N)cc2)cc(CCc2ccc(C(=N)N)cc2)c1] |
| 109 | 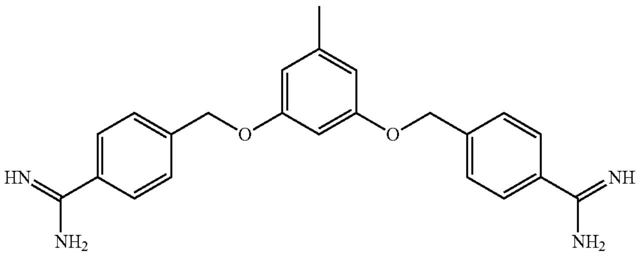 [SMILES: Cc1cc(OCc2ccc(C(=N)N)cc2)cc(OCc2ccc(C(=N)N)cc2)c1] |
| MD-110 | 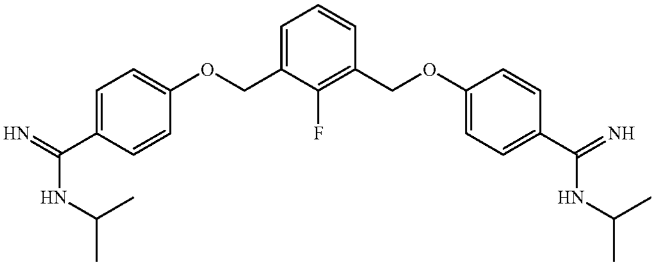 [SMILES: CC(C)NC(=N)c1ccc(OCc2cccc(COc3ccc(C(=N)NC(C)C)cc3)c2F)cc1] |
| MD-111 | 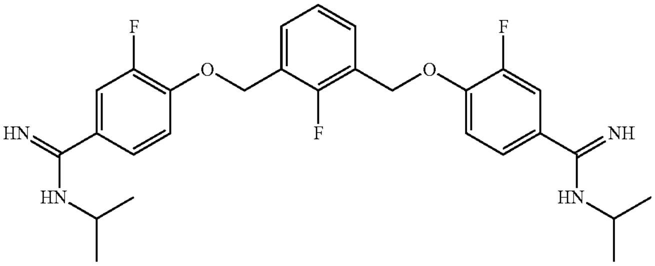 [SMILES: CC(C)NC(=N)c1ccc(OCc2cccc(COc3ccc(C(=N)NC(C)C)cc3F)c2F)c(F)c1] |
| MD-112 | 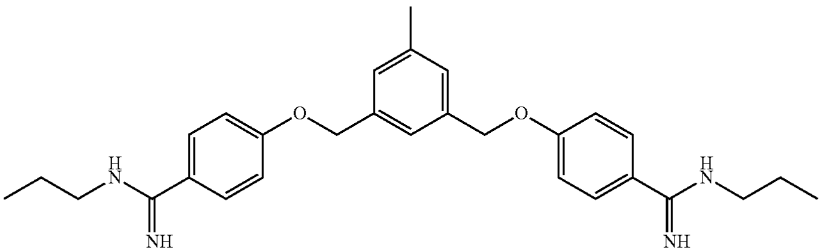 [SMILES: CCCNC(=N)c1ccc(OCc2cc(C)cc(COc3ccc(C(=N)NCCC)cc3)c2)cc1] |
| MD-113 | 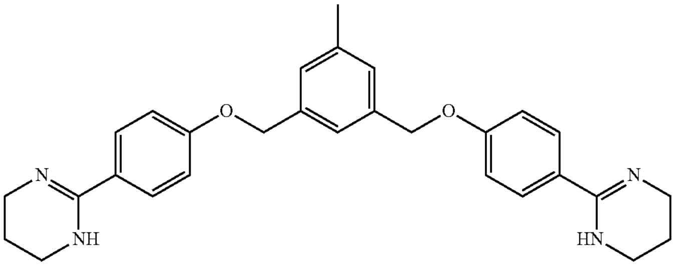 [SMILES: Cc1cc(COc2ccc(C3=NCCCN3)cc2)cc(COc2ccc(C3=NCCCN3)cc2)c1] |

TABLE 5A-continued
| Compound ID | Structure |
| --- | --- |
| MD-114 | 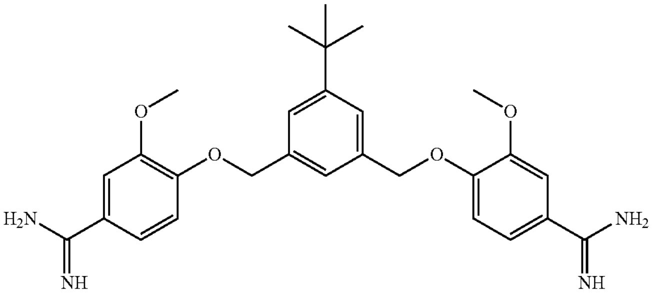 [SMILES: COc1cc(C(=N)N)ccc1OCc1cc(COc2ccc(C(=N)N)cc2OC)cc(C(C)(C)C)c1] |
| MD-115 | 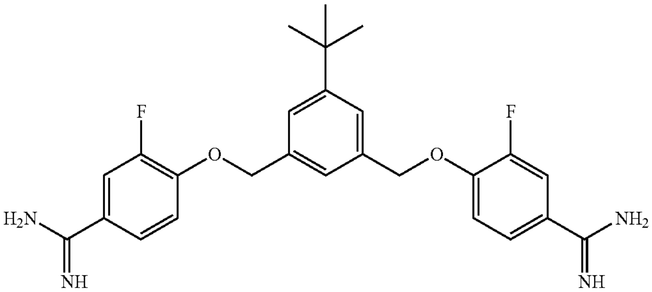 [SMILES: CC(C)(C)c1cc(COc2ccc(C(=N)N)cc2F)cc(COc2ccc(C(=N)N)cc2F)c1] |
| MD-116 | 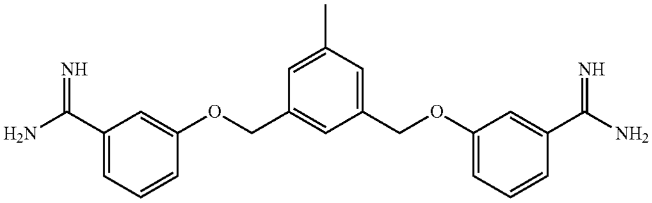 [SMILES: Cc1cc(COc2cccc(C(=N)N)c2)cc(COc2cccc(C(=N)N)c2)c1] |
| MD-117 | 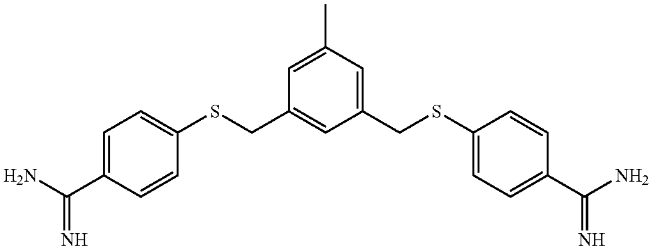 [SMILES: Cc1cc(CSc2ccc(C(=N)N)cc2)cc(CSc2ccc(C(=N)N)cc2)c1] |
| MD-118 | 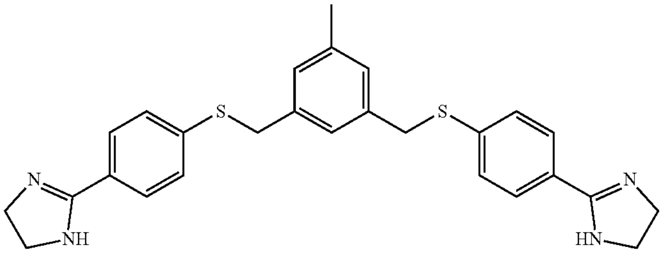 [SMILES: Cc1cc(CSc2ccc(C3=NCCN3)cc2)cc(CSc2ccc(C3=NCCN3)cc2)c1] |
| MD-119 | 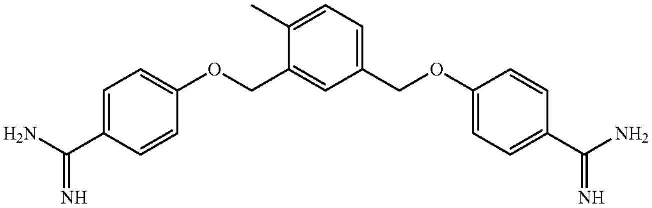 [SMILES: Cc1ccc(COc2ccc(C(=N)N)cc2)cc1COc1ccc(C(=N)N)cc1] |

TABLE 5A-continued
| Compound ID | Structure |
| --- | --- |
| MD-120 | 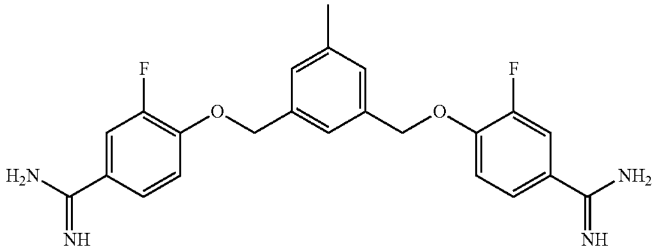 [SMILES: Cc1cc(COc2ccc(C(=N)N)cc2F)cc(COc2ccc(C(=N)N)cc2F)c1] |
| MD-123 | 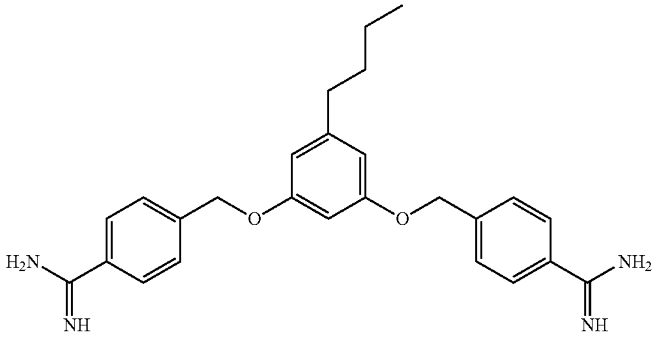 [SMILES: CCCCc1cc(OCc2ccc(C(=N)N)cc2)cc(OCc2ccc(C(=N)N)cc2)c1] |
| MD-124 | 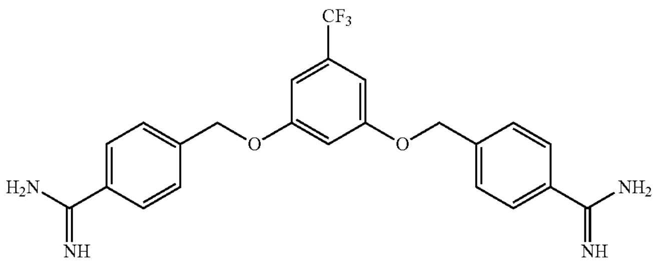 [SMILES: N=C(N)c1ccc(COc2cc(OCc3ccc(C(=N)N)cc3)cc(C(F)(F)F)c2)cc1] |
| MD-125 | 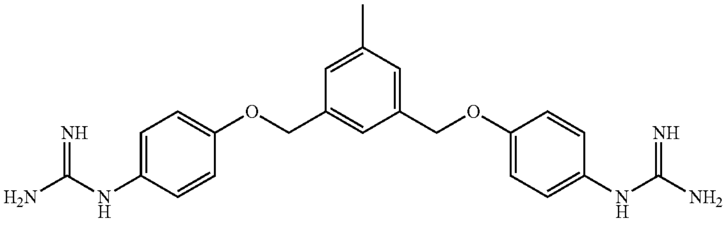 [SMILES: Cc1cc(COc2ccc(NC(=N)N)cc2)cc(COc2ccc(NC(=N)N)cc2)c1] |
| MD-126 | 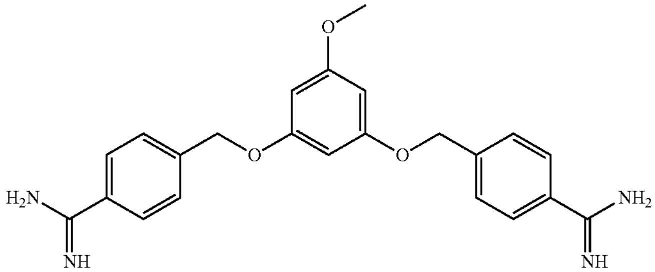 [SMILES: COc1cc(OCc2ccc(C(=N)N)cc2)cc(OCc2ccc(C(=N)N)cc2)c1] |

TABLE 5A-continued

| Compound ID | Structure |
|---|---|
| MD-127 | 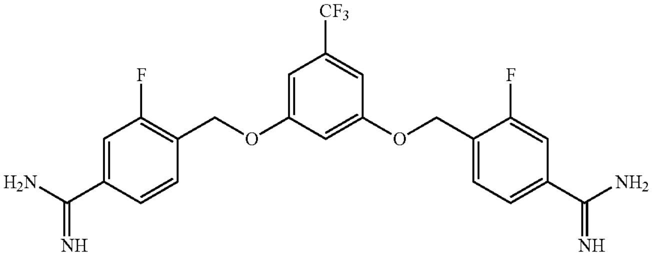 [SMILES: N=C(N)c1ccc(COc2cc(OCc3ccc(C(=N)N)cc3F)cc(C(F)(F)F)c2)c(F)c1] |
| MD-128 | 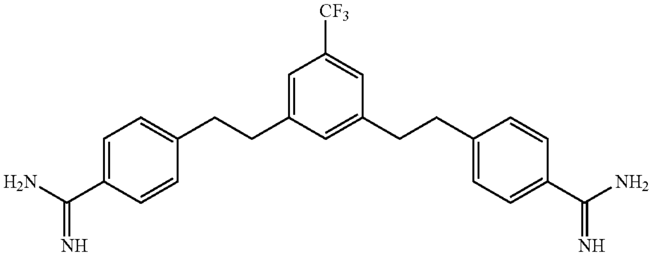 [SMILES: N=C(N)c1ccc(CCc2cc(CCc3ccc(C(=N)N)cc3)cc(C(F)(F)F)c2)cc1] |

Bacteria strains (as indicated in Table 5B) were cultured with rifampicin at various concentrations in the presence or absence of 10 μM of the indicated compound for 20 h at 37° C. The MIC, sensitization, cytotoxicity, and MIC on mycobacteria were tested according to methods described herein. As described herein, the sensitization fold refers to the ability of the compound to lower the MIC of the antibiotic (e.g., rifampicin or erythromycin) on certain bacteria strains. The sensitization activities of compounds on *B. subtilis* were tested using erythromycin. The sensitization activities of compounds on MRSA were tested using rifampicin. The sensitization activities of compounds on *E. coli* were tested using rifampicin. The results are shown in Table 5B.

TABLE 5B

| Compound ID | Results | | |
|---|---|---|---|
| DB2514 | MIC on *M. smegmatis* is 3 μM. | | |
| | | Strain | μM |
| DB2457 | MIC | *B. subtilis* | 12 |
| | MIC on mycobacteria | *M. smegmatis* | 6 |
| DB2542 | MIC | *E. coli* | 50 |
| | | *B. subtilis* | 12.5 |
| | | MRSA | |
| | | Cell line | $CC_{50}$ (μM) |
| | Cytotoxicity | H9c2 | 100 |
| | | Strain | μM |
| | MIC on mycobacteria | *M. smegmatis* | 6 |
| | | Strain | μM |
| DB2559 | MIC | *E. coli* | 100 |
| | | *B. subtilis* | 25 |

TABLE 5B-continued

| Compound ID | Results | | |
|---|---|---|---|
| | | Strain | Sensitization fold |
| | Sensitization | *E. coli* | 16-fold at 50 μM; |
| | | | 8-fold at 25 μM; |
| | | *B. subtilis* | 8-fold at 12 μM; |
| | | | 4-fold at 6 μM |
| | | MRSA | |
| | | Cell line | $CC_{50}$ (μM) |
| | Cytotoxicity | H9c2 | 100 |
| | | Strain | μM |
| | MIC on mycobacteria | *M. smegmatis* | 12 |
| | | Strain | μM |
| DB2558 | MIC | *E. coli* | 50 |
| | | *B. subtilis* | 12.5 |
| | | Strain | Sensitization fold |
| | Sensitization | *E. coli* | 8-fold at 25 μM; |
| | | | 4-fold at 12 μM. |
| | | Cell line | $CC_{50}$ (μM) |
| | Cytotoxicity | H9c2 | 50 |
| | | HEK293 | 100 |
| | | 3T3 | 100 |
| | | Strain | μM |
| | MIC on mycobacteria | *M. smegmatis* | 6-12 |
| | | Strain | μM |
| DB2583 | MIC | *E. coli* | 100 |
| | | *B. subtilis* | 25 |

TABLE 5B-continued

| Compound ID | Results | | |
|---|---|---|---|
| | | Strain | Sensitization fold |
| | Sensitization | *E. coli*<br>*B. subtilis* | No effect up to 25 μM<br>16-fold at 12 μM |
| | | Cell line | $CC_{50}$ (μM) |
| | Cytotoxicity | H9c2 | 12.5 |
| | | Strain | μM |
| | MIC on mycobacteria | *M. smegmatis* | 3-6 |
| | | Strain | μM |
| DB2447 | MIC | *E. coli*<br>*B. subtilis* | 100<br>12.5 |
| | | Strain | Sensitization fold |
| | Sensitization | *E. coli*<br>*B. subtilis*<br>MRSA | No effect up to 25 μM<br>No effect at 2 μM. |
| | | Cell line | $CC_{50}$ (μM) |
| | Cytotoxicity | H9c2 | No toxicity at 100 |
| | | Strain | μM |
| | MIC on mycobacteria | *M. smegmatis* | 12 |
| | | Strain | μM |
| DB1824 | MIC | *E. coli*<br>*B. subtilis*<br>MRSA | >100<br>12.5 |
| | | Strain | Sensitization fold |
| | Sensitization | *E. coli*<br>*B. subtilis*<br>MRSA | No effect up to 25 μM<br>2-fold at 12.5 μM, |
| | | Cell line | $CC_{50}$ (μM) |
| | Cytotoxicity | H9c2 | No toxicity at 100 |
| | | Strain | μM |
| DB2573 | MIC | *E. coli*<br>*B. subtilis* | 25<br>25 |
| | | Strain | Sensitization fold |
| | Sensitization | *E. coli*<br>*B. subtilis* | 32-fold at 12 μM<br>4-fold at 12 μM |
| | | Cell line | $CC_{50}$ (μM) |
| | Cytotoxicity | H9c2 | 50 |
| | | Strain | μM |
| | MIC on mycobacteria | *M. smegmatis* | 12 |
| | | Strain | μM |
| DB2449 | MIC | *E. coli*<br>*B. subtilis*<br>MRSA | >100<br>>50 |

TABLE 5B-continued

| Compound ID | Results | | |
|---|---|---|---|
| | | Strain | Sensitization fold |
| | Sensitization | *E. coli*<br>*B. subtilis* | No effect up to 25 μM<br>No effect up to 25 μM |
| | | Cell line | $CC_{50}$ (μM) |
| | Cytotoxicity | H9c2 | No toxicity at 100 |
| | | Strain | μM |
| DB2362 | MIC | *E. coli*<br>*B. subtilis* | 50<br>12 |
| | | Strain | Sensitization fold |
| | Sensitization | *E. coli*<br>*B. subtilis* | 8-fold at 25 μM;<br>4-fold at 6 μM |
| | | Cell line | $CC_{50}$ (μM) |
| | Cytotoxicity | H9c2 | 25 |
| | | Strain | μM |
| | MIC on mycobacteria | *M. smegmatis* | 6 |
| | | Strain | μM |
| MD-129 | MIC | *E. coli*<br>*B. subtilis* | >50<br>>50 |
| | | Strain | Sensitization fold |
| | Sensitization | *E. coli*<br>*B. subtilis* | No effect up to 25 μM<br>4-fold at 12 μM |
| | | Cell line | $CC_{50}$ (μM) |
| | Cytotoxicity | H9c2<br>HEK293<br>3T3 | 25<br>50<br>25 |
| | | Strain | μM |
| | MIC on mycobacteria | *M. smegmatis* | 25 |
| | | Strain | μM |
| DB2538 | MIC | *E. coli*<br>*B. subtilis* | >50<br>>50 |
| | | Strain | Sensitization fold |
| | Sensitization | *E. coli*<br>*B. subtilis* | No effect up to 25 μM<br>4-fold at 12 μM |
| | | Cell line | $CC_{50}$ (μM) |
| | Cytotoxicity | H9c2 | <12.5 |
| | | Strain | μM |
| | MIC on mycobacteria | *M. smegmatis* | 12 |
| | | Strain | μM |
| DB2510 | MIC | *E. coli* | >50 |
| | | Strain | Sensitization fold |
| | Sensitization | *E. coli* | No effect up to 25 μM |

TABLE 5B-continued

| Compound ID | Results | | |
|---|---|---|---|
| | | Cell line | $CC_{50}$ (μM) |
| | Cytotoxicity | H9c2 | 25 |
| | | Strain | μM |
| | MIC on mycobacteria | *M. smegmatis* | 25 |
| | | Strain | μM |
| DB2554 | MIC | *E. coli* | >50 |
| | | Strain | Sensitization fold |
| | Sensitization | *E. coli* | No effect up to 25 μM |
| | | Cell line | $CC_{50}$ (μM) |
| | Cytotoxicity | H9c2 | 50 |
| | | Strain | μM |
| DB2555 | MIC | *E. coli* | >50 |
| | | Strain | Sensitization fold |
| | Sensitization | *E. coli* | No effect up to 25 μM |
| | | Cell line | $CC_{50}$ (μM) |
| | Cytotoxicity | H9c2 | 50 |
| | | Strain | μM |
| | MIC on mycobacteria | *M. smegmatis* | 25 |
| | | Strain | μM |
| MD-100 | MIC | *E. coli*<br>*B. subtilis*<br>MRSA | 100<br>50<br>25 |
| | | Strain | Sensitization fold |
| | Sensitization | *E. coli*<br><br>*B. subtilis*<br><br>MRSA | 32-fold at 25 μM<br>8-fold at 10 μM<br>32-fold at 12 μM;<br>8 fold at 6 μM.<br>32-fold at 6 μM |
| | | Cell line | $CC_{50}$ (μM) |
| | Cytotoxicity | H9c2<br>HEK293<br>3T3<br>Animal | 50<br>100<br>100<br>$LD_{50}$ |
| | | Strain | μM |
| | MIC on mycobacteria | *M. smegmatis* | 12 |
| | | Strain | μM |
| MD-101 | MIC | *E. coli*<br>*B. subtilis* | 100<br>25 |
| | | Strain | Sensitization fold |
| | Sensitization | *E. coli*<br>*B. subtilis* | No effect up to 25 μM<br>4-fold at 6 μM,<br>2-fold at 3 μM. |
| | | Cell line | $CC_{50}$ (μM) |
| | Cytotoxicity | H9c2<br>HEK293<br>3T3 | 50<br>>100<br>>100 |
| | | Strain | μM |
| | MIC on mycobacteria | *M. smegmatis* | 3-6 |
| | | Strain | μM |
| MD-102 | MIC | *E. coli*<br>*B. subtilis*<br>MRSA | 50<br>6<br>25 |
| | | Strain | Sensitization fold |
| | Sensitization | *E. coli*<br>*B. subtilis*<br>MRSA | No effect up to 25 μM.<br>4-fold at 2 μM<br>32-fold at 4 μM |
| | | Cell line | $CC_{50}$ (μM) |
| | Cytotoxicity | H9c2<br>HEK293<br>3T3 | >100<br>>100<br>>100 |
| | | Strain | μM |
| | MIC on mycobacteria | *M. smegmatis* | 3 |
| | | Strain | μM |
| MD-103 | MIC | *E. coli*<br>*B. subtilis*<br>MRSA | 50<br>6<br>25 |
| | | Strain | Sensitization fold |
| | Sensitization | *E. coli*<br><br>MRSA | 4-fold at 25 μM<br>2-fold at 10 μM<br>8 to 16-fold at 12 μM,<br>2 to 4-fold at 6 μM |
| | | Cell line | $CC_{50}$ (μM) |
| | Cytotoxicity | H9c2<br>HEK293<br>3T3 | >100<br>100<br>100 |
| | | Strain | μM |
| | MIC on mycobacteria | *M. smegmatis* | 12.5 |
| | | Strain | μM |
| MD-104 | MIC | *E. coli*<br>*B. subtilis* | 50<br>25 |
| | | Strain | Sensitization fold |
| | Sensitization | *E. coli*<br>*B. subtilis* | No effect up to 25 μM.<br>8-fold at 12 μM<br>2-fold at 6. |
| | | Strain | μM |
| | MIC on mycobacteria | *M. smegmatis* | 6-12 |

TABLE 5B-continued

| Compound ID | Results | | |
|---|---|---|---|
| | | Strain | μM |
| MD-105 | MIC | *E. coli* | 25 |
| | | *B. subtilis* | 6 |
| | | Strain | Sensitization fold |
| | Sensitization | *E. coli* | 16-fold at 10 μM. |
| | | Cell line | $CC_{50}$ (μM) |
| | Cytotoxicity | H9c2 | 25 |
| | | Strain | μM |
| | MIC on mycobacteria | *M. smegmatis* | 6 |
| | | Strain | μM |
| MD-106 | MIC | *E. coli* | 100 |
| | | *B. subtilis* | >50 |
| | | MRSA | >50 |
| | | Strain | Sensitization fold |
| | Sensitization | *E. coli* | 4-fold at 25 μM |
| | | *B. subtilis* | 16-fold at 12 μM |
| | | | 4-fold at 4 μM |
| | | Cell line | $CC_{50}$ (μM) |
| | Cytotoxicity | H9c2 | 12.5 |
| | | HEK293 | 25 |
| | | 3T3 | 25 |
| | | Strain | μM |
| MD-107 | MIC | *E. coli* | 50 |
| | | *B. subtilis* | 12.5 |
| | | Strain | Sensitization fold |
| | Sensitization | *E. coli* | 8-fold at 25 μM |
| | | | 4-fold at 12.5 μM |
| | | *B. subtilis* | 8-fold at 6 μM |
| | | Cell line | $CC_{50}$ (μM) |
| | Cytotoxicity | H9c2 | >100 |
| | | HEK293 | >100 |
| | | 3T3 | >100 |
| | | Strain | μM |
| | MIC on mycobacteria | *M. smegmatis* | 3-6 |
| | | Strain | μM |
| MD-108 | MIC | *E. coli* | 100 |
| | | *B. subtilis* | 25 |
| | | MRSA | 12 |
| | | Strain | Sensitization fold |
| | Sensitization | *E. coli* | 32-fold at 25 μM; |
| | | | 16-fold at 10 μM. |
| | | *B. subtilis* | 32-fold at 6 μM. |
| | | MRSA | 16-fold at 3 μM |

TABLE 5B-continued

| Compound ID | Results | | |
|---|---|---|---|
| | | Cell line | $CC_{50}$ (μM) |
| | Cytotoxicity | H9c2 | 12.5 |
| | | HEK293 | 50 |
| | | 3T3 | 50 |
| | | Strain | μM |
| | MIC on mycobacteria | *M. smegmatis* | 6-12 |
| | | Strain | μM |
| MD-109 | MIC | *E. coli* | 100 |
| | | *B. subtilis* | 50 |
| | | Strain | Sensitization fold |
| | Sensitization | *E. coli* | 32-fold at 25 μM |
| | | | 8-fold at 10 μM |
| | | *B. subtilis* | 32-fold at 12 μM |
| | | Cell line | $CC_{50}$ (μM) |
| | Cytotoxicity | HEK293 | 100 |
| | | 3T3 | 100 |
| | | Strain | μM |
| MD-110 | MIC | *E. coli* | 25 |
| | | *B. subtilis* | 25 |
| | | MRSA | 12.5 |
| | | Strain | Sensitization fold |
| | Sensitization | *E. coli* | No effect up to 25 μM. |
| | | *B. subtilis* | No effect at 6 μM. |
| | | MRSA | 16-fold at 4 μM. |
| | | Cell line | $CC_{50}$ (μM) |
| | Cytotoxicity | HEK293 | >100 |
| | | 3T3 | >100 |
| | | Strain | μM |
| | MIC on mycobacteria | *M. smegmatis* | 3 |
| | | Strain | μM |
| MD-111 | MIC | *E. coli* | 50 |
| | | *B. subtilis* | 25 |
| | | MRSA | 50 |
| | | Strain | Sensitization fold |
| | Sensitization | *E. coli* | No effect up to 25 μM. |
| | | *B. subtilis* | No effect up to 12 μM. |
| | | MRSA | 16-fold at 12 μM, |
| | | | 8 -fold at 6 μM. |
| | | Cell line | $CC_{50}$ (μM) |
| | Cytotoxicity | HEK293 | >100 |
| | | 3T3 | >100 |
| | | Strain | μM |
| | MIC on mycobacteria | *M. smegmatis* | 12 |

TABLE 5B-continued

| Compound ID | Results | | |
|---|---|---|---|
| | | Strain | μM |
| MD-112 | MIC | *E. coli* | >100 |
| | | *B. subtilis* | 50 |
| | | MRSA | 50 |
| | | Strain | Sensitization fold |
| | Sensitization | *E. coli* | No effect up to 25 μM. |
| | | *B. subtilis* | No effect up to 50 μM. |
| | | MRSA | 16-fold at 25 μM, 8-fold at 12 μM. |
| | | Cell line | $CC_{50}$ (μM) |
| | Cytotoxicity | HEK293 | >100 |
| | | 3T3 | >100 |
| | | Strain | μM |
| MD-113 | MIC | *E. coli* | >100 |
| | | *B. subtilis* | 50 |
| | | MRSA | >50 |
| | | Strain | Sensitization fold |
| | Sensitization | *E. coli* | No effect up to 25 μM. |
| | | *B. subtilis* | No effect up to 12 μM. |
| | | MRSA | 8-fold at 25 μM, 4-fold at 12 μM. |
| | | Cell line | $CC_{50}$ (μM) |
| | Cytotoxicity | HEK293 | >100 |
| | | 3T3 | >100 |
| | | Strain | μM |
| MD-114 | MIC | *E. coli* | 100 |
| | | *B. subtilis* | 25 |
| | | MRSA | 12 |
| | | Strain | Sensitization fold |
| | Sensitization | *E. coli* | 8-fold at 12.5 μM |
| | | *B. subtilis* | 8-fold at 12 μM |
| | | Cell line | $CC_{50}$ (μM) |
| | Cytotoxicity | HEK293 | 100 |
| | | 3T3 | 50 |
| | | Strain | μM |
| MD-115 | MIC | *E. coli* | 50 |
| | | *B. subtilis* | 50 |
| | | MRSA | 25 |
| | | Strain | Sensitization fold |
| | Sensitization | *E. coli* | 256-fold at 10 μM |
| | | *B. subtilis* | 8-fold at 6 μM |
| | | Cell line | $CC_{50}$ (μM) |
| | Cytotoxicity | H9c2 | 25 |
| | | HEK293 | 25-50 |
| | | 3T3 | 25-50 |
| | | Strain | μM |
| MD-116 | MIC | *E. coli* | 100 |
| | | *B. subtilis* | 50 |
| | | MRSA | 25 |

TABLE 5B-continued

| Compound ID | Results | | |
|---|---|---|---|
| | | Strain | Sensitization fold |
| | Sensitization | *E. coli* | 8-fold at 25 μM |
| | | *B. subtilis* | 32-fold at 12 μM |
| | | MRSA | 4-fold at 12.5 μM. |
| | | Cell line | $CC_{50}$ (μM) |
| | Cytotoxicity | HEK293 | >100 |
| | | 3T3 | >100 |
| | | Strain | μM |
| MD-117 | MIC | *E. coli* | 50 |
| | | *B. subtilis* | 25 |
| | | MRSA | 12.5 |
| | | Strain | Sensitization fold |
| | Sensitization | *E. coli* | 32-fold at 12.5 μM 8-fold at 6 μM. |
| | | *B. subtilis* | 32-fold at 6 μM 8-fold at 3 μM. |
| | | Cell line | $CC_{50}$ (μM) |
| | Cytotoxicity | HEK293 | 25-50 |
| | | 3T3 | 25-50 |
| | | Strain | μM |
| MD-118 | MIC | *E. coli* | >50 |
| | | *B. subtilis* | >25 |
| | | Strain | Sensitization fold |
| | Sensitization | *E. coli* | No effect up to 25 μM. |
| | | *B. subtilis* | 16-fold at 6 μM, 4-fold at 3 μM |
| | | Cell line | $CC_{50}$ (μM) |
| | Cytotoxicity | HEK293 | 25 |
| | | 3T3 | 12.5 |
| | | Strain | μM |
| MD-119 | MIC | *E. coli* | 100 |
| | | *B. subtilis* | 25 |
| | | Strain | Sensitization fold |
| | Sensitization | *E. coli* | 32-fold at 25 μM, 4-fold at 12.5 μM. |
| | | *B. subtilis* | 32-fold at 12 μM, 16-fold at 6 μM |
| | | Cell line | $CC_{50}$ (μM) |
| | Cytotoxicity | H9c2 | |
| | | HEK293 | |
| | | 3T3 | |
| | | Strain | μM |
| MD-120 | MIC | *E. coli* | 100 |
| | | MRSA | 12 |
| | | Strain | Sensitization fold |
| | Sensitization | *E. coli* | 64-fold at 25 μM 32-fold at 10 μM |
| | | MRSA | 4-fold at 6 μM |

TABLE 5B-continued

| Compound ID | Results | | |
|---|---|---|---|
| | | Cell line | $CC_{50}$ (μM) |
| | Cytotoxicity | HEK293<br>3T3 | 100<br>100 |
| | | Strain | μM |
| MD-123 | MIC | *E. coli* | 25 |
| | | Strain | Sensitization fold |
| | Sensitization | *E. coli* | 256-fold at 10 μM |
| | | Cell line | $CC_{50}$ (μM) |
| | Cytotoxicity | H9c2<br>HEK293<br>3T3 | 25<br>25<br>25 |
| | | Strain | μM |
| MD-124 | MIC | *E. coli*<br>MRSA | 100<br>10 |
| | | Strain | Sensitization fold |
| | Sensitization | *E. coli*<br>*B. subtilis*<br>MRSA | 512-fold at 10 μM<br><br>32-fold at 5 μM |
| | | Cell line | $CC_{50}$ (μM) |
| | Cytotoxicity | H9c2<br>HEK293<br>3T3 | 50<br>100<br>100 |
| | | Strain | μM |
| | MIC on mycobacteria | *M. smegmatis* | 12 |
| | | Strain | μM |
| MD-125 | MIC | *E. coli* | 100 |
| | | Strain | Sensitization fold |
| | Sensitization | *E. coli* | 32-fold at 25 μM<br>8-fold at 10 μM |
| | | Cell line | $CC_{50}$ (μM) |
| | Cytotoxicity | H9c2<br>HEK293<br>3T3 | 100<br>100<br>100 |
| | | Strain | μM |
| MD-126 | MIC | *E. coli* | >50 |
| | | Strain | Sensitization fold |
| | Sensitization | *E. coli* | 2-fold at 10 μM |
| | | Cell line | $CC_{50}$ (μM) |
| | Cytotoxicity | HEK293<br>3T3 | 100<br>100 |

TABLE 5B-continued

| Compound ID | Results | | |
|---|---|---|---|
| | | Strain | μM |
| MD-127 | MIC | *E. coli* | 100 |
| | | Strain | Sensitization fold |
| | Sensitization | *E. coli* | 516-fold at 10 μM |
| | | Strain | μM |
| MD-128 | MIC | *E. coli* | 100 |
| | | Strain | Sensitization fold |
| | Sensitization | *E. coli* | 516-fold at 10 μM |

Select data from Table 5B are described below (Table 6).

Sensitization fold of 10 μM compounds was tested on bacteria using rifampicin as the antibiotic; $IC_{50}$ was tested on HEK293 cells. MD-129, 113, 102, 106 and 112 showed no sensitization activity at up to 10 μM.

Scheme 1. Structures of bacterial sensitizers synthesized and evaluated.

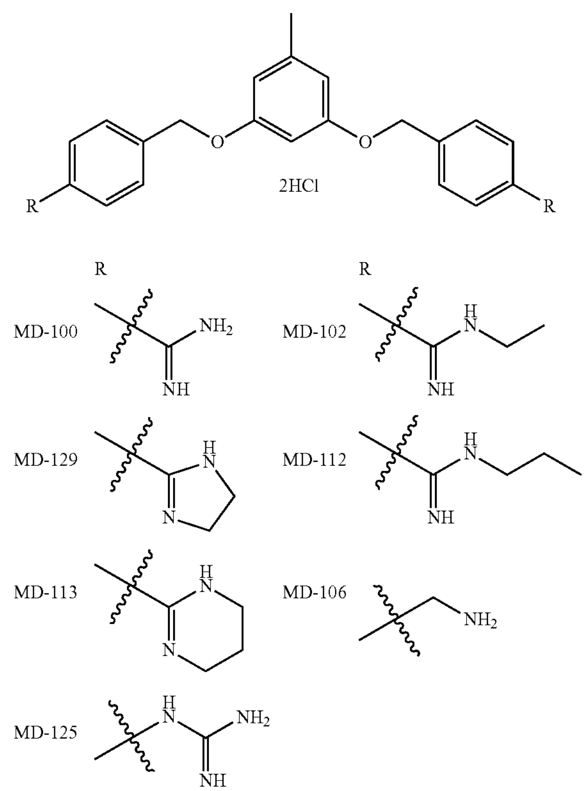

2HCl

MD-100 MD-102 MD-129 MD-112 MD-113 MD-106 MD-125

-continued

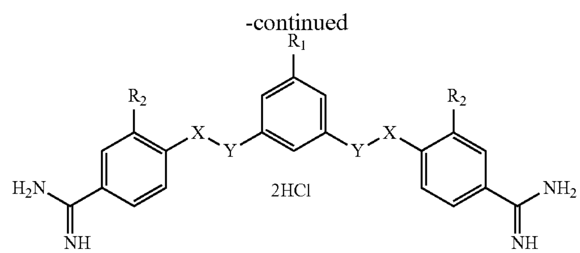

MD-100: X = O; Y = $CH_2$; $R_1$ = $CH_3$; $R_2$ = H
MD-109: X = $CH_2$; Y = O; $R_1$ = $CH_3$; $R_2$ = H
MD-103: X = O; Y = $CH_2$; $R_1$ = $CH_3$; $R_2$ = $OCH_3$
MD-126: X = $CH_2$; Y = O; $R_1$ = $OCH_3$; $R_2$ = H
MD-124: X = $CH_2$; Y = O; $R_1$ = $CF_3$; $R_2$ = H
MD-120: X = O; Y = $CH_2$; $R_1$ = $CH_3$; $R_2$ = F
MD-108: X = $CH_2$; Y = $CH_2$; $R_1$ = $CH_3$; $R_2$ = H
MD-117: X = S; Y = $CH_2$; $R_1$ = $CH_3$; $R_2$ = H
MD-105: X = O; Y = $CH_2$; $R_1$ = t-butyl; $R_2$ = H
MD-123: X = $CH_2$; Y = O; $R_1$ = n-butyl; $R_2$ = H
MD-115: X = O; Y = $CH_2$; $R_1$ = t-butyl; $R_2$ = F

MD-107

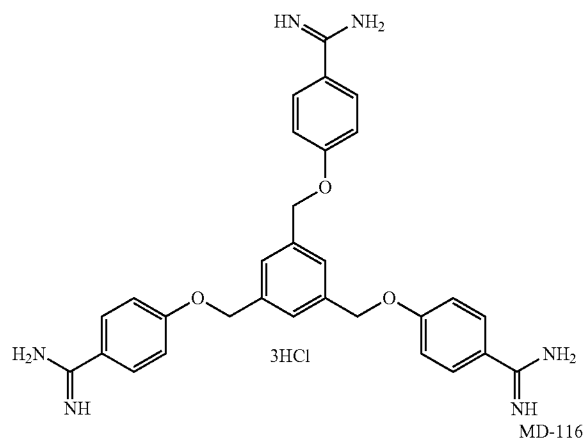

MD-116

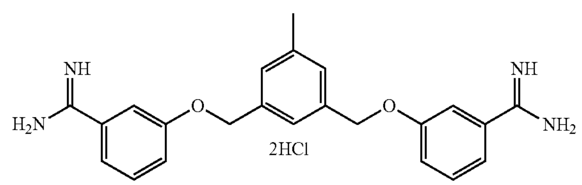

*E. coli* was cultured with rifampicin at various concentrations in the presence or absence of 5 μg/ml MD-124 for 20 h at 37° C. Then bacterial growth density was determined by measuring $OD_{600}$. Several compounds were capable of sensitizing *E. coli* towards narrow-spectrum antibiotics, with some by 32-fold at 10 μg/ml or less (Table 7).

TABLE 6

| | Sensitization fold | $IC_{50}$ (μM) |
|---|---|---|
| MD-100 | 8 | 100 |
| MD-125 | 8 | 100 |
| MD-109 | 8 | 100 |
| MD-103 | 2 | 100 |
| MD-126 | 2 | 100 |
| MD-124 | 512 | 100 |
| MD-120 | 32 | 100 |
| MD-108 | 16 | 50 |
| MD-117 | 32 | 25-50 |
| MD-105 | 16 | 25-50 |
| MD-123 | 256 | 25 |
| MD-115 | 256 | 25-50 |

Figure 1A:
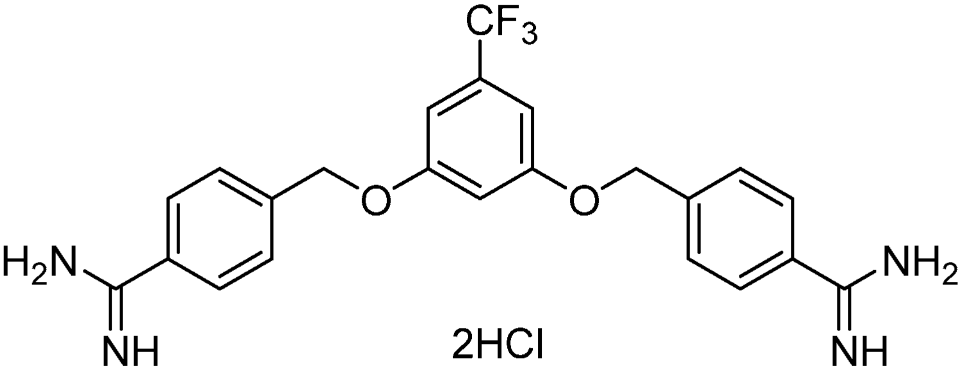
FIG. 1 demonstrates that MD-124 sensitizes Gram-negative bacteria towards various existing antibiotics. Panel (A) is the structure of MD-124. Panel (B) shows that 5 μg/ml MD-124 sensitizes *E. coli* towards rifampicin (Rif). Values are means±SD. n=3. Panel (C) demonstrates that 5 μg/ml MD-124 itself showed no bacterial the growth inhibition effect. Values are means±SD. n=3. Panel (D) shows the results of a checkerboard assay of MD-124 (0 to 100 μg/ml) and rifampicin on *E. coli*. Panel (E) shows the results of a checkerboard assay of MD-124 (0 to 10 μg/ml) and rifampicin on *E. coli*. Panel (F) is a graph showing that MD-124 sensitizes various Gram-negative bacterial strains towards rifampicin (Rif). Sensitization fold=MIC of rifampicin only/MIC of rifampicin with MD-124. Panel (G) is a graph showing the bacterial sensitizations of *E. coli* towards rifampicin activity comparison between MD-124, pentamidine and PMBN. Panel (H) shows that 5 μg/ml MD-124 sensitizes *E. coli* toward a broad range of existing antibiotics. All results represent 3 replications.
Figure 1B:
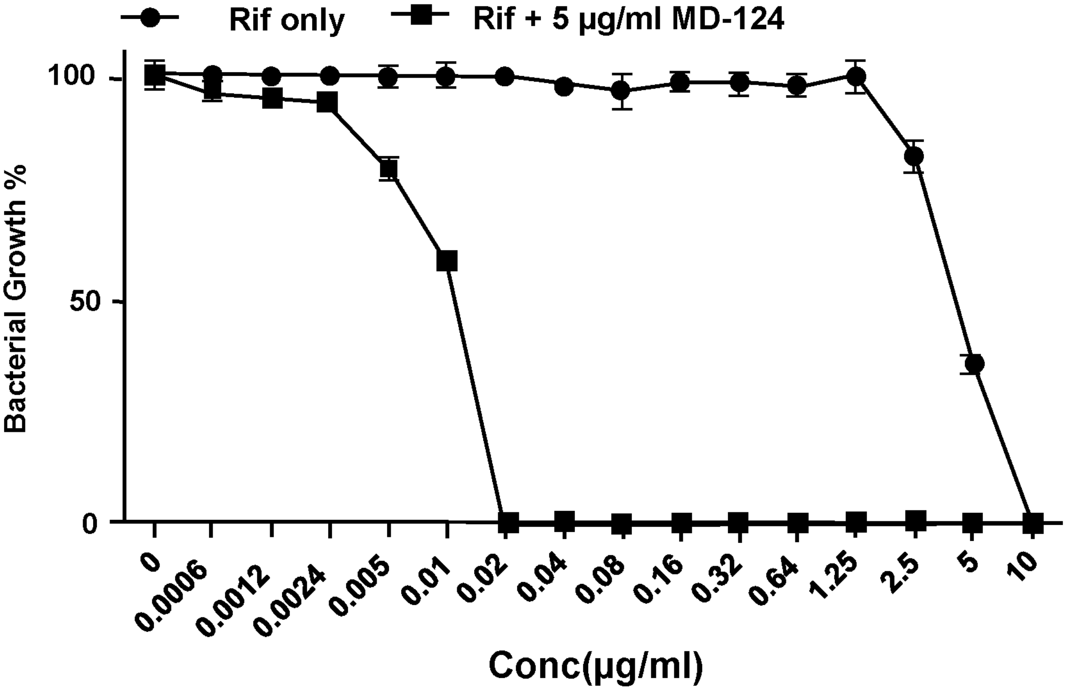
Figure 1C:
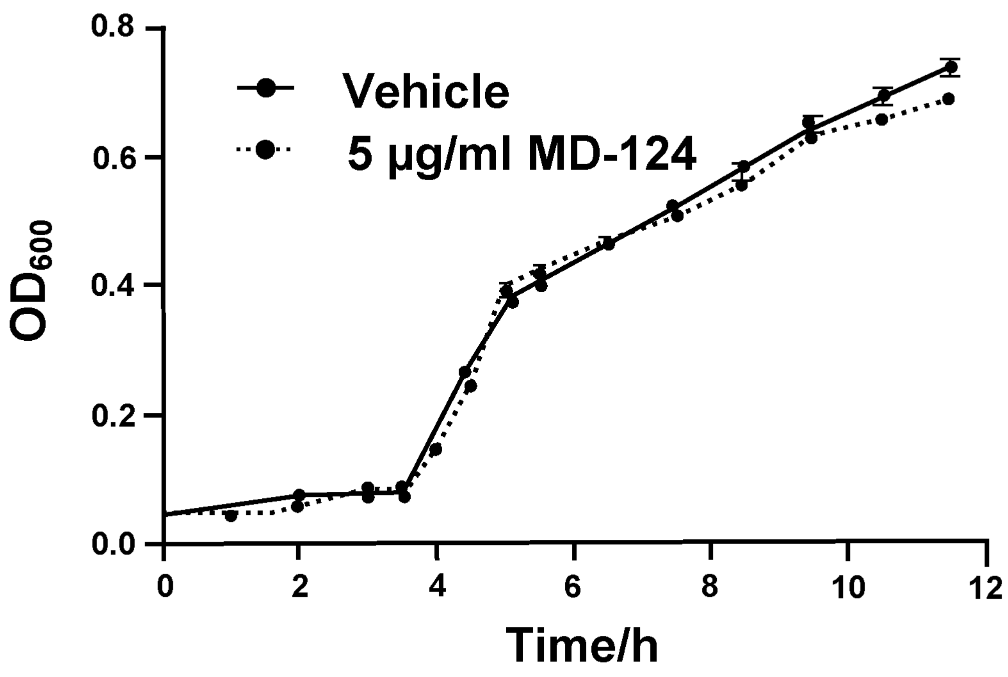

BW-MD-124 (MD-124) showed superior bacterial sensitization activities and was chosen for further biological evaluation (FIG. 1A). MD-124 at a concentration of 5 μg/ml was able to sensitize *E. coli* toward rifampicin by 512-fold, lowering the MIC of rifampicin from 10 to 0.02 μg/ml (FIG. 113). *E. coli* ($5\times10^5$ CFUs/ml) was then cultured in the absence and presence of 5 μg/ml MD-124 and $OD_{600}$ at different time points were recorded. MD-124 itself at the same concentration showed no effect on bacterial growth (FIG. 1C). These results demonstrate that MD-124 has no direct bacteriostatic effect and works as adjuvant to other antibiotics.

TABLE 7

| Compound Name | Structure | Sensitization fold | $IC_{50}$ |
|---|---|---|---|
| DB2560 (MD-100) | 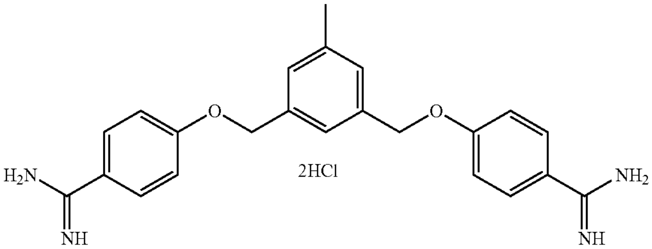 [SMILES: Cc1cc(COc2ccc(C(=N)N)cc2)cc(COc2ccc(C(=N)N)cc2)c1] | 32[a] | 100 μM |

TABLE 7-continued

| Compound Name | Structure | Sensitization fold | $IC_{50}$ |
|---|---|---|---|
| DB1213 | 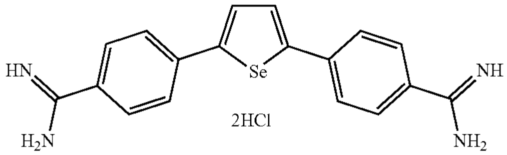 [SMILES: N=C(N)c1ccc(-c2ccc(-c3ccc(C(=N)N)cc3)[se]2)cc1] | 32[a] | 50 μM |
| DB1079 | 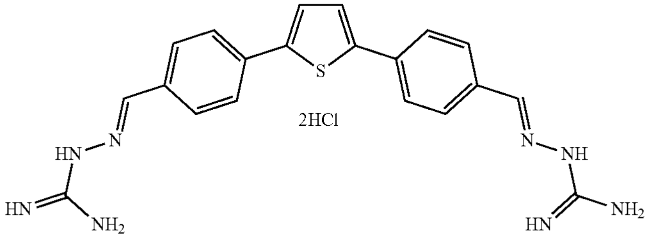 [SMILES: N=C(N)N/N=C/c1ccc(-c2ccc(-c3ccc(/C=N/NC(=N)N)cc3)s2)cc1] | 64[b] | 12 μM |
| DB704 | 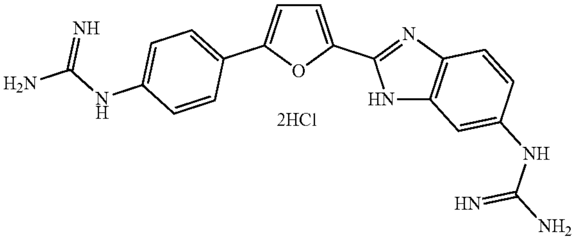 [SMILES: N=C(N)Nc1ccc(-c2ccc(-c3nc4ccc(NC(=N)N)cc4[nH]3)o2)cc1] | 16[a] | 100 μM |

Figure 1D:
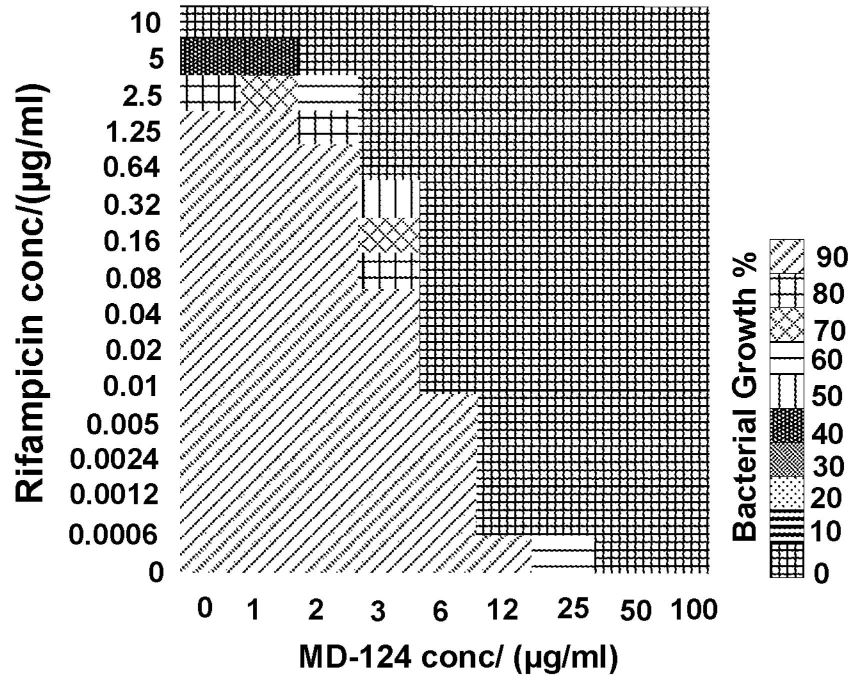
Figure 1E:
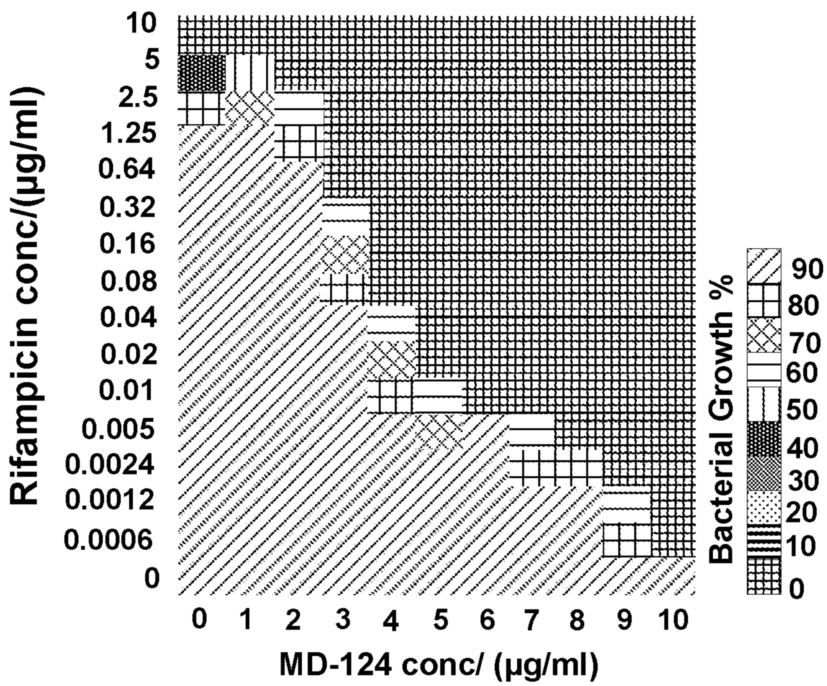
Figure 1F:
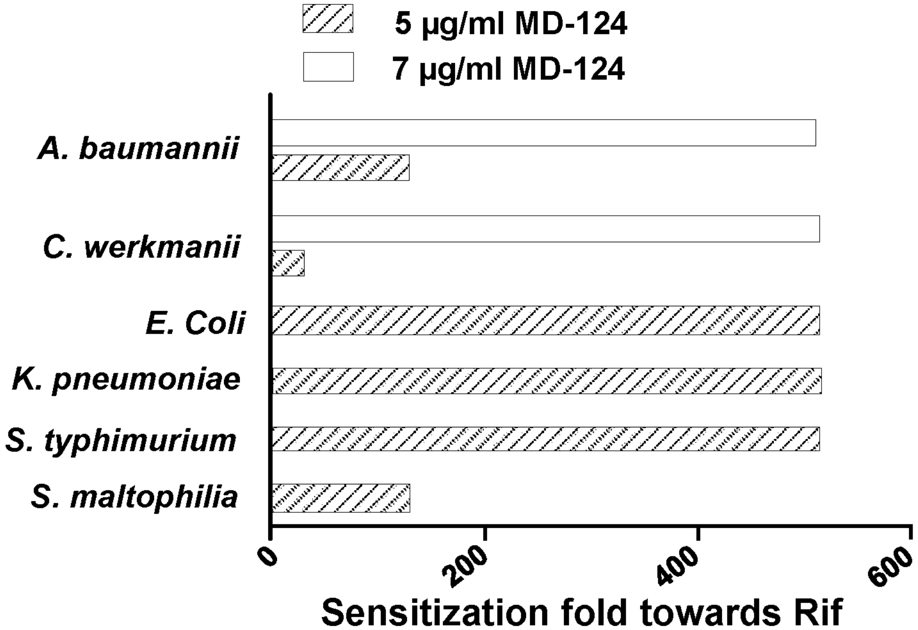
Figure 1G:
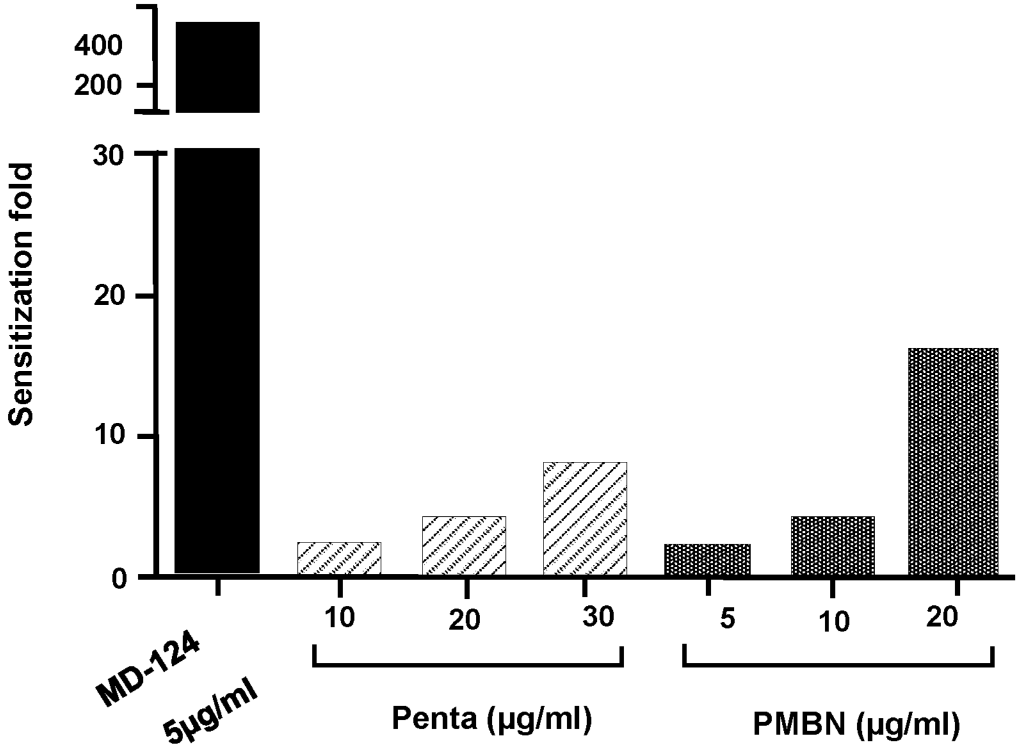
Figure 1H:
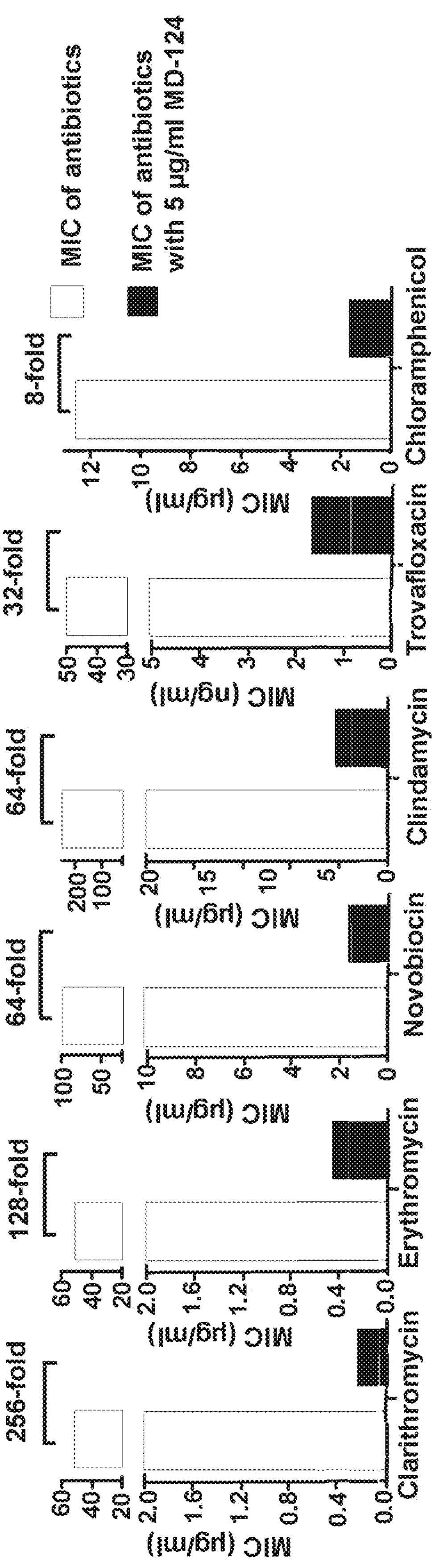

Sensitization fold was tested on *E. coli* using rifampicin as antibiotic.
a: 10 μg/ml bacterial sensitizer was used;
b: 5 μg/ml bacterial sensitizer was used A checkerboard assay shows that MD-124 sensitizes *E. coli* toward rifampicin in a concentration-dependent manner, reaching over 16,000-fold when ~10 μg/ml MD-124 was used with a MIC of rifampicin being 0.6 ng/ml (FIG. 1D). The fractional inhibitory concentration (FIC) index was calculated to be 0.09 based on the checkerboard assay (The MIC of MD-124 itself on *E. coli* is 50 μg/ml), indicating the strong synergistic effect between MD-124 and rifampicin. The sensitization ability of MD-124 changed drastically in the range of 3 to 12 μg/ml, and as a result, a checkerboard assay of MD-124 varying from 0 to 10 μg/ml was performed (FIG. 1E). 5 μg/ml MD-124 sensitizes *E. coli* toward a broad range of existing antibiotics including narrow spectrum antibiotics such as clarithromycin (256-fold), erythromycin (128-fold), novobiocin (64-fold) and broad-spectrum antibiotics like trovafloxacin (32-fold), polymyxin B (32-fold) and chloramphenicol (8-fold) (FIG. 1H and Table 8). A greater sensitization fold was achieved when MD-124 was used with narrow-spectrum antibiotics than broad-spectrums. When combined with MD-124, the MIC of various narrow-spectrum antibiotics tested was lowered to around 1 μg/ml or below, which is similar to the MIC with broad-spectrum antibiotics on *E. coli* (FIG. 1H and Table 8). Compared with previously discovered bacterial sensitizers such as pentamidine and polymyxin B nonapeptide (PMBN), MD-124 showed much more potent sensitization activity (FIG. 1G). For example, 20 μg/ml pentamidine and PMBN were shown to sensitize *E. coli* towards rifampicin by 4 and 16-fold respectively, while 5 μg/ml MD-124 was able to sensitize by 512-fold. Besides *E. coli*, MD-124 also showed sensitization effect in various other Gram-negative bacterial strains such as *A. baumannii, K. pneumoniae* and *S. typhimurium*, the resistant strains of which are listed as WHO priority 1 pathogens in urgent need of new antibiotics (FIG. 1F).

TABLE 8

| Antibiotics (AB) | MIC of AB only | MIC of AB with MD-124 | Sensitization fold |
|---|---|---|---|
| Rifampicin | 10 | 0.019 | 516 |
| Rifapentine | 25 | 0.8 | 32 |
| Rifaximin | 12.5 | 0.2 | 64 |
| Clarithromycin | 50 | 0.2 | 256 |
| Erythromycin | 50 | 0.4 | 128 |
| Azithromycin | 6.2 | 0.4 | 16 |
| Novobiocin | 100 | 1.6 | 64 |
| Clindamycin | 200 | 3.2 | 64 |
| Fusidic acid | >200 | 6.25 | 32 |
| Polymyxin B | 1.2 | 0.04 | 32 |
| Chloramphenicol | 12.5 | 1.6 | 8 |
| Trovafloxacin | 0.05 | 0.0015 | 32 |
| Besifloxacin | 0.1 | 0.0125 | 8 |
| Moxifloxacin | 0.05 | 0.0062 | 8 |
| Levofloxacin | 0.05 | 0.0062 | 8 |
| Ciprofloxacin | 0.05 | 0.0125 | 4 |
| Nafcillin | >300 | 75 | >4 |
| Cloxacillin | >300 | 75 | >4 |
| Meropenem | 0.063 | 0.063 | 1 |
| Tetracycline | 1.2 | 0.6 | 2 |
| Trimethoprim | 2.5 | 1.25 | 2 |

Unit for AB: μg/ml; MD-124 concentration: 5 μg/ml.

Resistance Frequency of MD-124

Figure 2A:
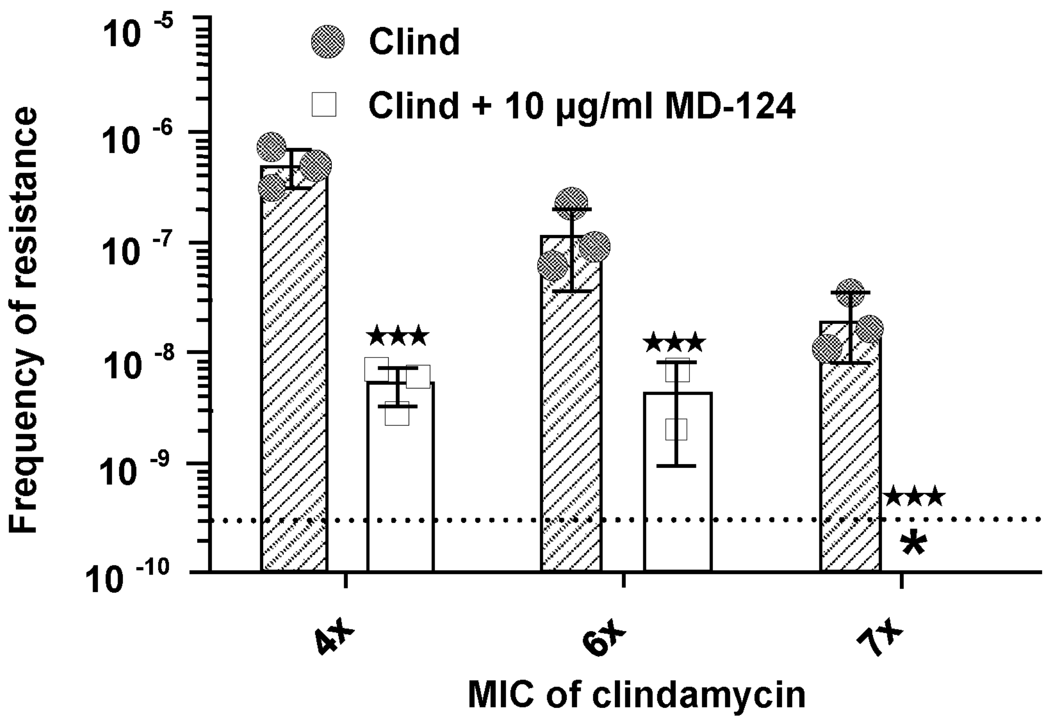
FIG. 2 shows the results of a resistance frequency study of MD-124. Panel (A) shows the resistance frequency of *E. coli* towards clindamycin (4, 6 and 7 times of the MIC) and clindamycin/MD-124 combination. Panel (B) shows the resistance frequency of *E. coli* towards trovafloxacin (2, 3 and 4 times of the MIC) and trovafloxacin/MD-124 combination. Panel (C) shows the resistance frequency of *E. coli* towards novobiocin (4, 5 and 6 times of the MIC) and novobiocin/MD-124 combination. The blue stars in Panels (A), (B), and (C) means no resistant colony was observed from $3\times10^9$ CFUs. Values are means±SD. n=3. ***: P<0.001.
Figure 2B:
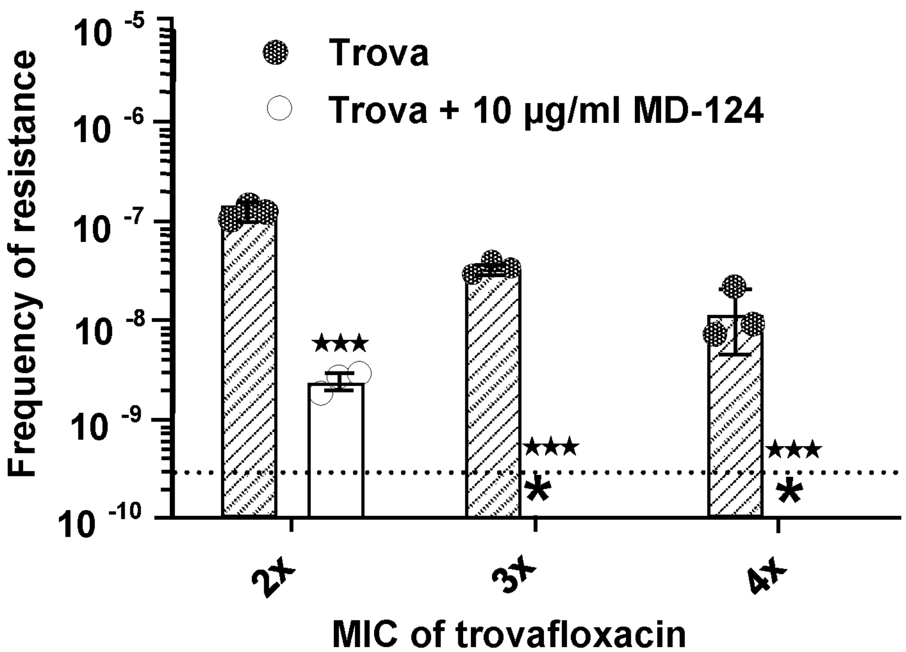
Figure 2C:
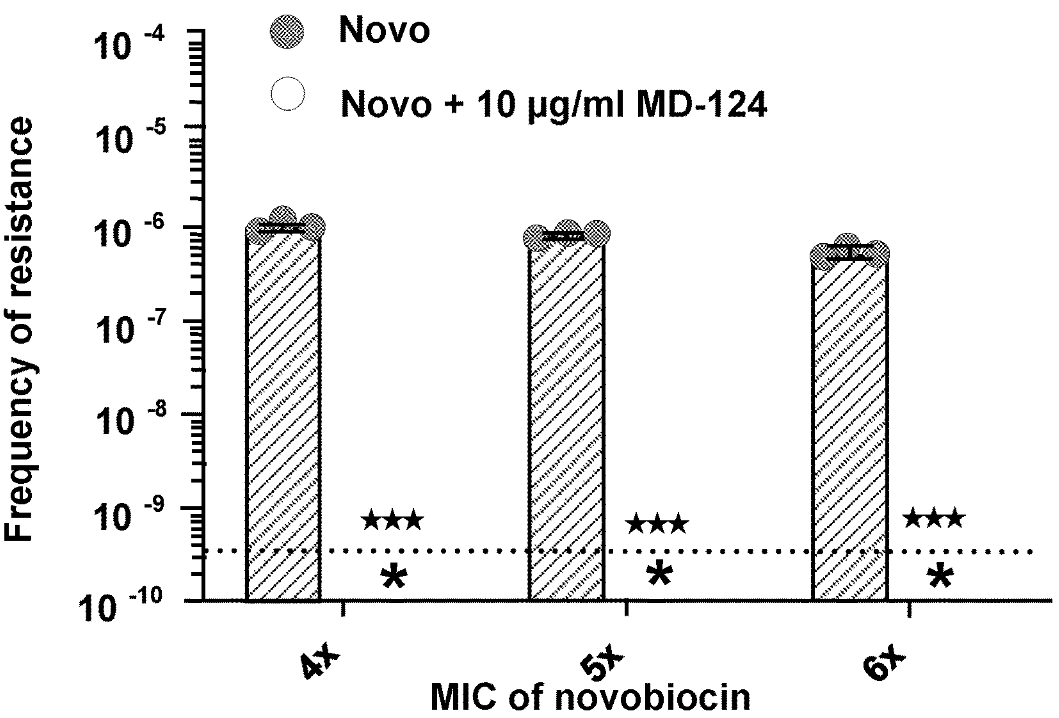
Figure 2D:
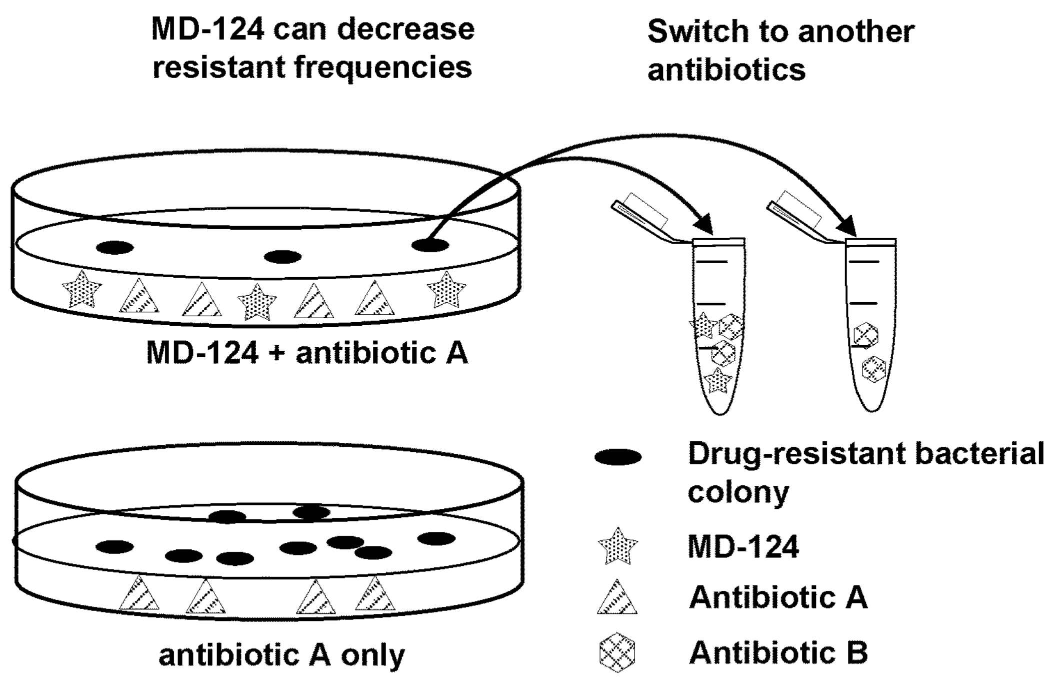

Because bacteria can quickly develop resistance to new antimicrobial agents, the frequency of resistance development for *E. coli* towards MD-124 was evaluated. Briefly, *E. coli* was cultured with various concentrations of antibiotic (2 to 7-old of MIC) in the presence and absence of 10 μg/ml MD-124. Then, the bacterial resistance frequency towards MD-124/antibiotic combination and antibiotic itself was calculated (FIG. 2D). *E. coli* showed 2 to 3 orders of magnitude lower resistance frequency towards MD-124/antibiotic combination than the antibiotic itself (FIG. 2). For colonies that were resistant MD-124 and antibiotic combination, there is a need to determine whether the resistant strains were resistant to MD-124 or antibiotics used in the combination. As a result, the combination therapy resistant colonies were then subjected to another antibiotic combination: MD-124 and rifampicin (FIG. 2B). MD-124 was still effective in sensitizing those strains towards rifampicin with the same potency as on wild-type *E. coli*. Such results demonstrate that these resistant strains are not resistant to MD-124. No strain was found to be resistant to 10 μg/ml MD-124 out of $2.7\times10^{10}$ CFUs, giving a resistant frequency of $<1/2.7\times10^{10}$ ($<3.7\times10^{-11}$). The resistance frequency here is not defined based on direct inhibition/bactericidal effect like the case of traditional antibiotics but based on the sensitization effect of MD-124. These studies show: 1) MD-124 is able to lower the resistant frequency of bacteria towards antibiotics when used in combination; 2) bacteria show lower resistant frequency towards MD-124 than toward the antibiotic; and 3) even bacteria showing resistance towards one type of antibiotic/MD-124 combination, a simple switch to another antibiotic/MD-124 combination would re-gain the sensitization effectiveness towards the resistant strains.

Mechanism of Bacterial Sensitization Activity

Figure 3A:
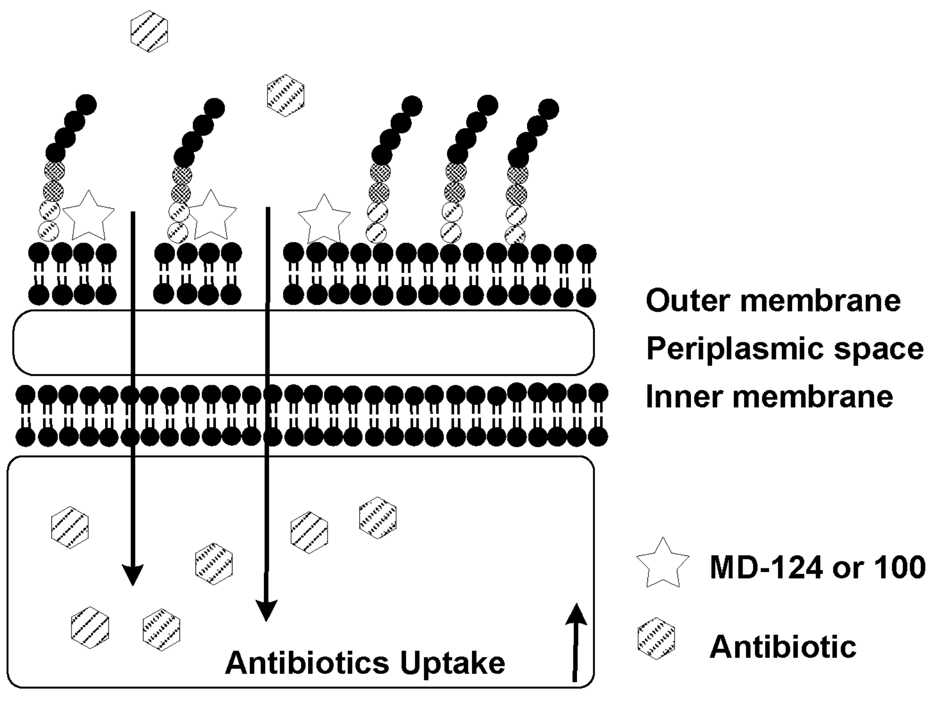
FIG. 3 depicts results from a mechanistic study that revealed that MD-100 and MD-124 sensitize *E. coli* by disrupting the outer membrane and increasing antibiotics uptake. Panel (A) shows the proposed sensitization mechanism of MD-124 and MD-100. Panel (B) is a graph depicting that MD-124 showed compromised ability to sensitize a mutated, outer membrane "leaky" *E. coli* strain NR698 towards clarithromycin. Values are means±SD. n=3. Panel (C) shows that bacterial sensitizers can facilitate the *E. coli* lysis process by lysozyme. *E. coli* stock was incubated with 50 μg/ml lysozyme in the presence and absence of various bacterial sensitizers for 10 minutes at r.t and then the $OD_{600}$ was recorded. Poly B and penta are short for polymyxin B and pentamidine, respectively. *E. coli* stock was also incubated with the same concentration of various bacterial sensitizers in the absence of lysozyme as control. Values are means±SD. n=3. ***: P<0.001 compared with vehicle group. Panel (D) shows the correlation between outer membrane disruption ability and bacterial sensitization activity of the various bacterial sensitizer. Panel (E) shows the HPLC results of the O-methyl novobiocin concentration inside *E. coli* in the presence (a) and absence (b) of 25 μg/ml MD-100.
Figure 3B:
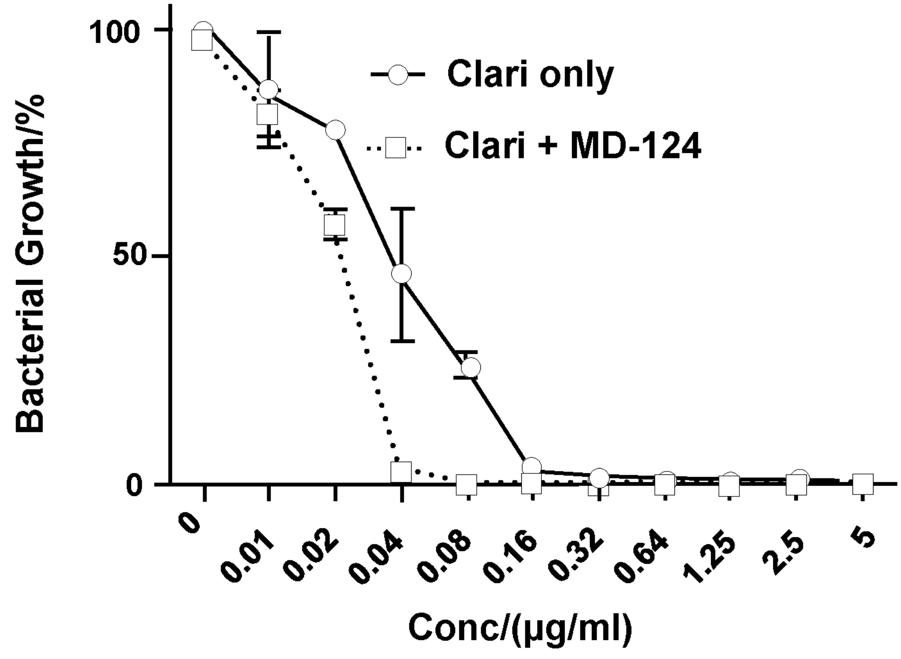
Figure 3C:
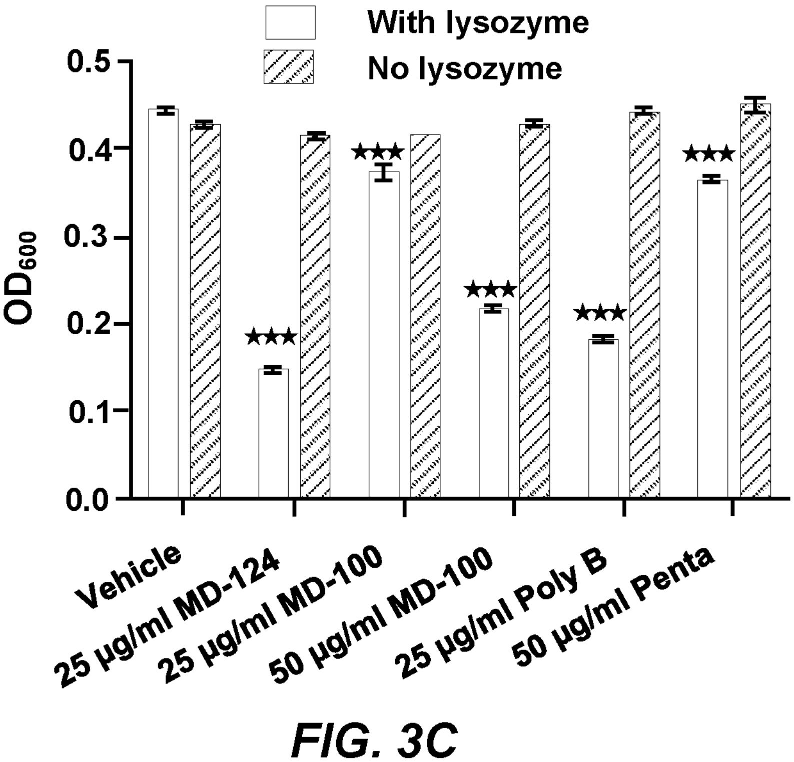
Figure 3D:
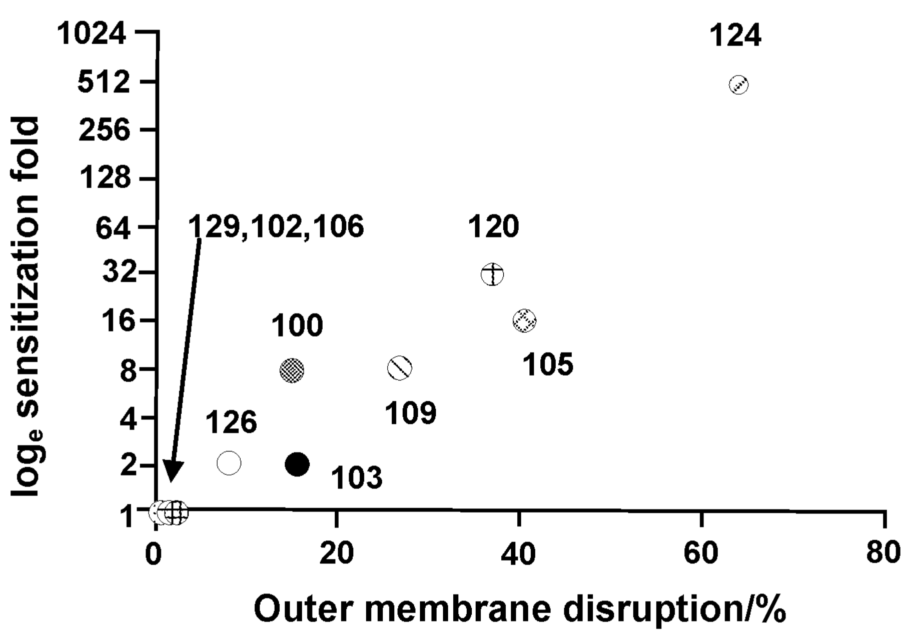
Figure 7A:
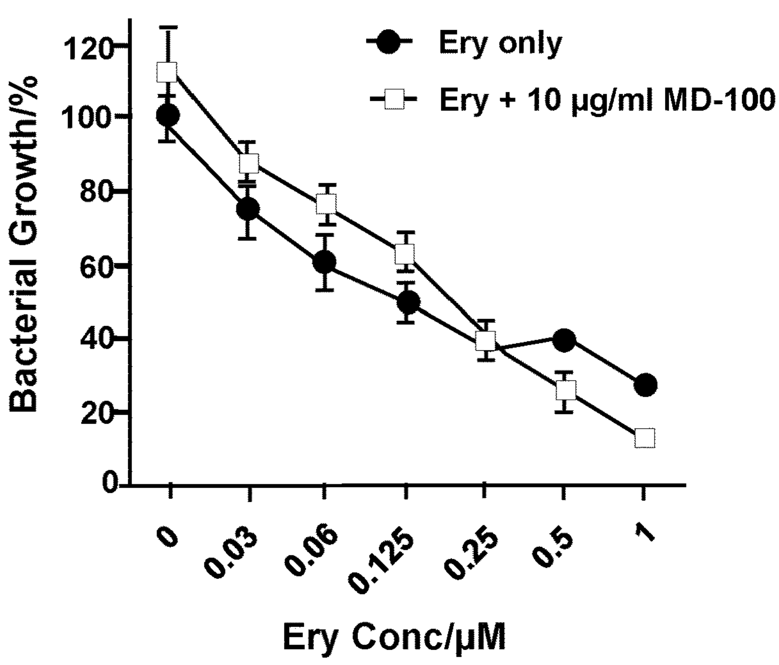
FIG. 7 shows the results of a molecular mechanism study of bacterial sensitizers. Panel (A) shows that MD-100 failed to sensitize a mutated, outer membrane "leaky" *E. coli* strain NR698. Ery is short for erythromycin. 10 μg/ml MD-100 sensitized wild-type *E. coli* towards erythromycin for 32-fold (the comparison between the "Ery+10 μg/ml MD-100 line" and the "Ery only" line in Figure B, MIC of erythromycin is 50 μg/ml, and the MIC of erythromycin in the presence of 10 μg/ml MD-100 is 1.6 μg/ml). *E. coli*

The mechanism of the bacterial sensitization activity was then investigated. Because MD-124 can sensitize Gram-negative bacterial towards a broad range of antibiotics and the outer membrane is the major barrier of antibiotic uptake, MD-124's ability to disrupt bacterial outer membrane was determined (FIG. 3A). MD-124 and MD-100 were used to study the sensitization mechanisms. MD-124 showed compromised ability to sensitize an outer membrane "leaky" mutant of *E. coli* strain NR698 (FIG. 3B), which is already susceptible to narrow-spectrum antibiotics such as clarithromycin and erythromycin. MD-124 at a concentration of 5 μg/ml was shown to sensitize wild-type *E. coli* towards clarithromycin by 256-fold, and NR698 by 4-fold. The same phenomenon was observed when MD-100 was used on wild-type and NR698 *E. coli* (FIG. 7). Such results demonstrate if a bacterial strain already has increased permeability because of compromised outer membrane integrity, the sensitization ability of MD-124 and MD-100 would be diminished. This is consistent with the sensitization mechanism of MD-124 being on the bacterial outer membrane. The disruption of bacterial outer membrane by MD-124 through the lysozyme assay was then determined. Briefly, lysozyme (14 KDa) can break down peptidoglycan and lead to bacterial lysis. However, lysozyme cannot penetrate intact Gram-negative bacterial outer membrane. With impaired Gram-negative bacterial membrane, lysozyme would be able to diffuse across the disrupted membrane and enzymatically cleave peptidoglycan, leading to bacterial lysis. In the presence of 25 μg/ml MD-124 or 50 μg/ml MD-100, lysozyme resulted in quick bacterial lysis while in the absence of the sensitizer, no cell lysis was observed (FIG. 3C, left histogram in each pair). MD-124 and MD-100 themselves did not lead to bacterial lysis (FIG. 3C, right histogram in each pair). These results indicate that MD-124 was able to disrupt membrane integrity. 25 μg/ml polymyxin B and 50 μg/ml pentamidine, which were used here as positive controls, also led to bacterial lysis when incubated together with lysozyme. 25 μg/ml MD-124 showed a similar potency as 25 μg/ml polymyxin B and was much more potent than 50 μg/ml pentamidine in disrupting bacterial outer membrane. The results also showed a positive correlation between the ability of the various bacterial sensitizers to disrupt outer membrane in the lysozyme assay and their ability to sensitize *E. coli* towards rifampicin (FIG. 3D, the structure and sensitization fold of those bacterial sensitizers can be found in Scheme 1 and Table 6). Outer membrane disruption ability was based on lysozyme assay as described above and all bacterial sensitizer were used same concentration. 25 μg/ml bacterial sensitizers were used in the lysozyme assay. The bacterial sensitization activity was measured based on the sensitization fold on *E. coli* towards rifampicin, which was listed in detail in Table 1. MD-102, 106 and 129 fails to sensitize *E. coli*, thus the sensitization fold was determined as 1.

Figure 3E:
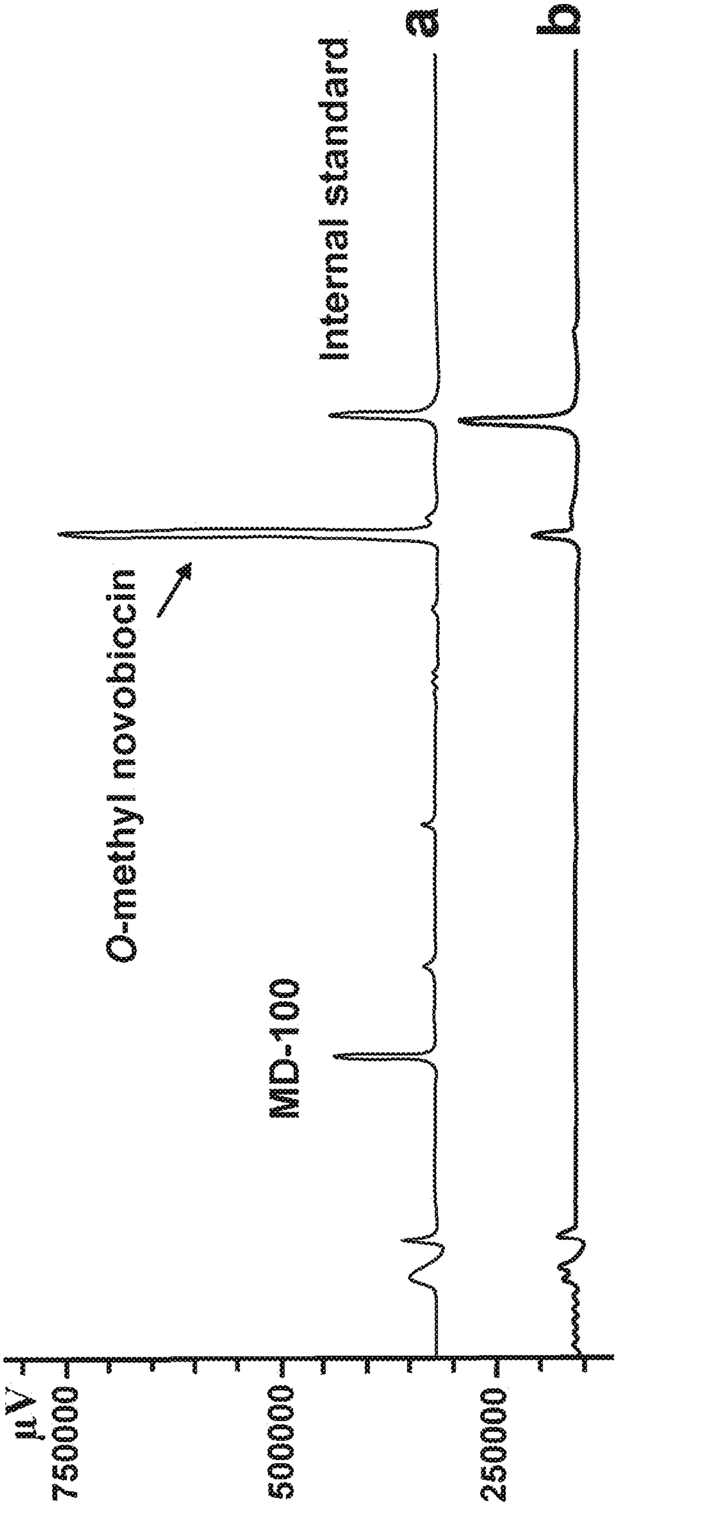

Next, the intracellular concentration of an antibiotic in the presence and absence of MD-100 were compared to assess membrane permeabilization by MD-100. The concentration of antibiotic inside the bacteria was directly measured by analyzing bacterial lysates using HPLC after treatment with and without MD-100. As shown in FIG. 3E, the relative intracellular concentration of an inactive novobiocin analog (O-methyl novobiocin, Scheme 2) was greatly increased in the presence MD-100. O-Methyl novobiocin, which is inactive, was used in order to avoid bacterial killing after intracellular enrichment. Collectively, these results show that MD-124 sensitizes bacteria by permeabilizing membrane and allowing for increased antibiotic entry.

Scheme 2

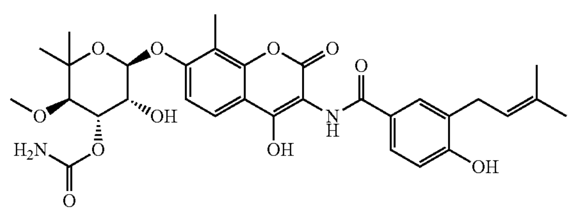

Novobiocin

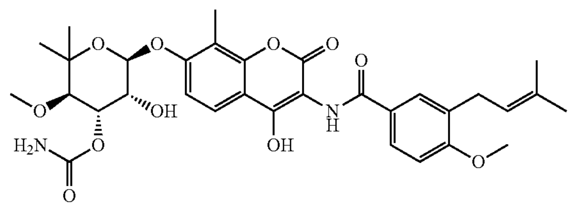

O-methyl novobiocin

Molecular Mechanistic Studies of Bacterial Sensitizers

Figure 4A:
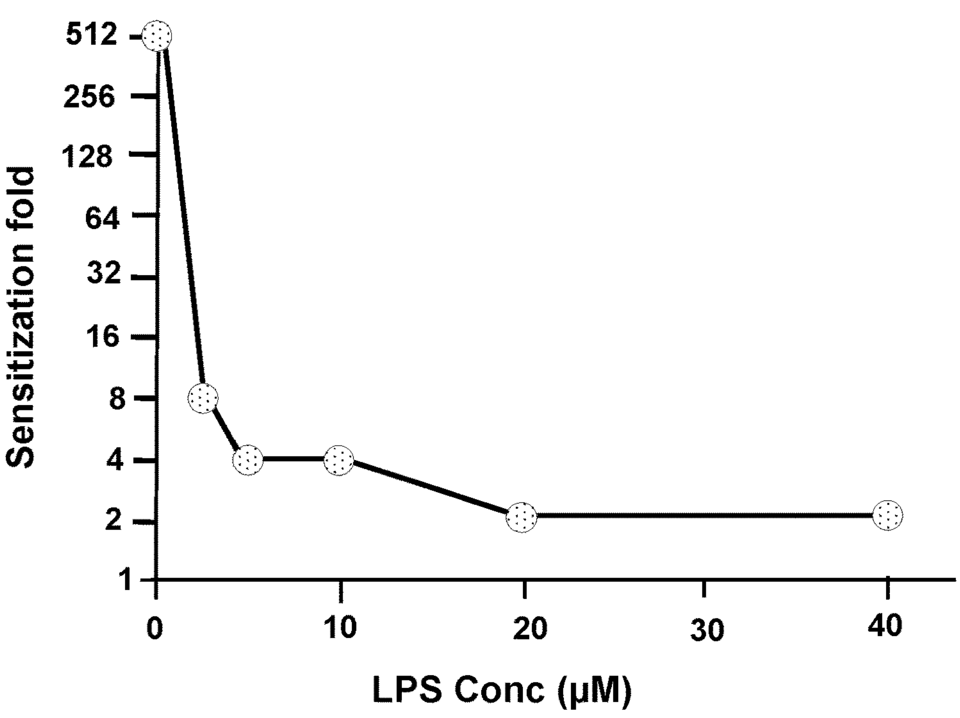
FIG. 4 shows molecular mechanistic studies of bacterial sensitizers. Panel (A) shows that LPS can decrease the sensitization ability of MD-124 in a concentration dependent manner. *E. coli* was treated with 10 μM MD-124 (about 5 μg/ml) and rifampicin combination with varying concentration of LPS (from 0 to 40 μM) for 20 h at 37° C., then the $OD_{600}$ was measured and the sensitization fold were calculated as mentioned above. Panel (B) shows that $Mg^{2+}$ can decrease the sensitization ability of MD-124 in a concentration dependent manner. *E. coli* was treated with 10 μM MD-124 (about 5 μg/ml) with vary concentration of $Mg^{2+}$ (from 0 to 15 mM) for 20 hours at 37° C., then the $OD_{600}$ was measured and the sensitization fold under different conditions were calculated. Panel (C) depicts a Dansyl-PMBN displacement assay. To *E. coli* stock ($OD_{600}$=0.3) in HEPES buffer (pH=7.4) was added 10 μM Dansyl-PMBN and the fluorescent intensity was recorded as F1 (Ex=340 nm; Em=520 nm), then different concentration of bacterial sensitizers was added, and the fluorescent intensity was recorded as Fx. The fluorescent intensity of 10 μM Dansyl-PMBN in HEPES buffer was recorded as baseline F0. Fluorescent intensity/%=(F1−Fx)/(F1−F0). Values are means SD. n=3; D) MD-124 sensitize mcr-1 over-expressing *E. coli* strains towards rifampicin. All results are triplicates.
Figure 4B:
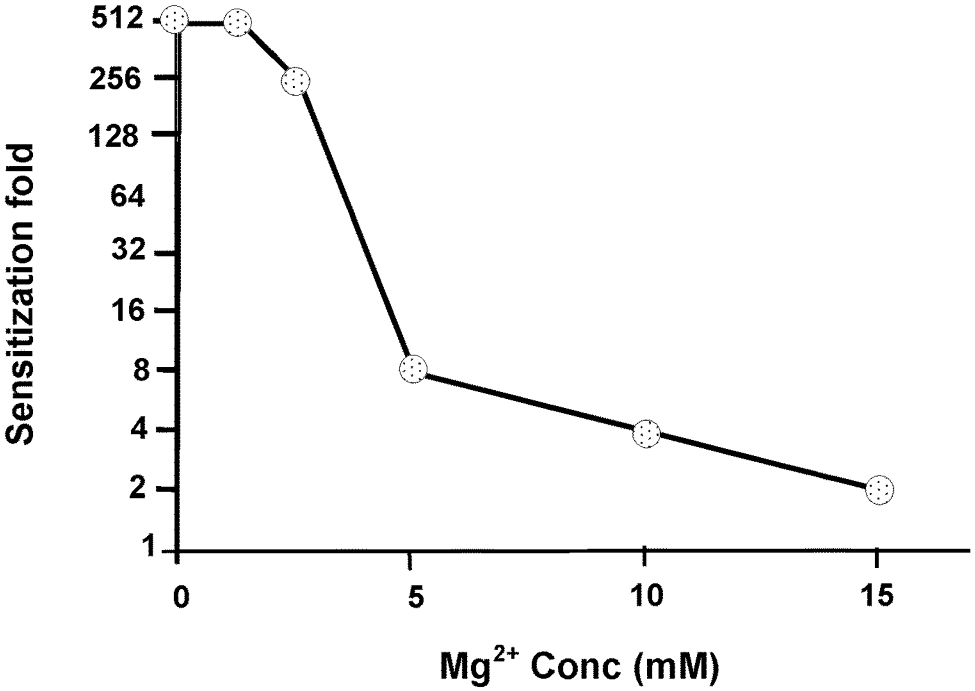
Figure 7B:
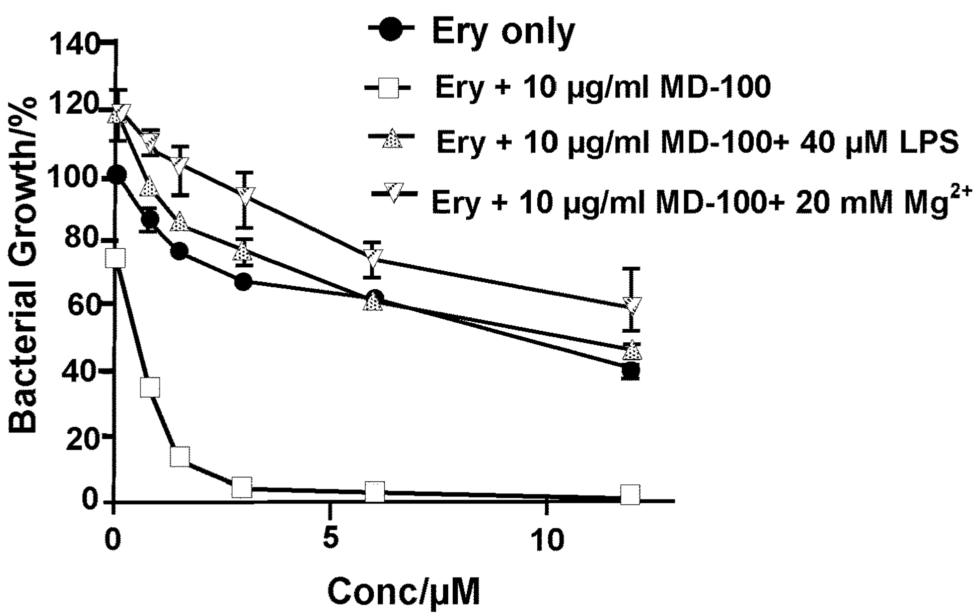

Various experiments were then conducted to examine the molecular target(s). Adding extra LPS to the culture media abolished the sensitization effect of MD-124 and MD-100 (FIG. 4A, Table 9 and FIG. 7B). Briefly, *E. coli* was treated with 5 μg/ml MD-124 (about 10 μM) with varying concentrations of LPS (from 0 to 40 μM) for 20 h. Then $OD_{600}$ was measured. The MIC of rifampicin only is 10 μg/ml.

TABLE 9

| LPS Conc. (μM) | MIC of rifampicin with 5 μg/ml MD-124 | Sensitization fold |
|---|---|---|
| 0 | 0.02 | 512 |
| 2.5 | 1.25 | 8 |
| 5 | 2.5 | 4 |
| 10 | 2.5 | 4 |
| 20 | 5 | 2 |
| 40 | 5 | 2 |

Sensitization fold = MIC of rifampicin only/MIC of rifampicin with 10 μM MD-124 in the presence or absence of LPS.

$Mg^{2+}$ dampened the bacterial sensitization activity of MD-124 on *E. coli* in a concentration dependent manner (FIG. 43, Table 10). Briefly, *E. coli* was treated with 5 pg/ml MD-124 (about 10 μM) with varying concentrations of $Mg^{2+}$ (from 0 to 15 mM) for 20 h. Then $OD_{600}$ was measured. The MIC of rifampicin only is 10 μg/ml.

$Mg^{2+}$ can bridge between adjacent lipid A and enhance the membrane integrity. Thus, high concentrations of this divalent cation may displace the diamidine and thus exert antagonistic effects against MD-124. This phenomenon was also observed on MD-100. The culture medium for *E. coli* is Muller Hinton Broth (Cation adjusted), which already has at least 0.5 mM $Mg^{2+}$, so the "zero concentration point of $Mg^{2+}$" in FIG. 4 represents the amount of exogenous $Mg^{2+}$, not the total $Mg^{2+}$ in the culture medium. The free magnesium concentration in human blood is between 0.55-0.75 mM, indicating that physiological concentrations of $Mg^{2+}$ would not affect the sensitization ability of MD-124. A fluorescent conjugate of a polymyxin-B derivative (Dansyl-PMBN, Scheme 3), which would show increased fluorescent intensity after binding to the lipid A part of LPS, was used to further probe this issue. In the presence of another component that can also binding to lipid A, Dansyl-PMBN would be replaced, leading to decreased fluorescent intensity.

TABLE 10

| $Mg^{2+}$ (mM) | MIC of rifampicin with 5 μg/ml MD-124 | Sensitization fold |
|---|---|---|
| 0 | 0.02 | 512 |
| 1.25 | 0.02 | 512 |
| 2.5 | 0.04 | 256 |
| 5 | 1.25 | 8 |
| 10 | 2.5 | 4 |
| 15 | 5 | 2 |

Sensitization fold = MIC of rifampicin only/MIC of rifampicin with 10 μM MD-124 in the presence or absence of $Mg^{2+}$.

Scheme 3

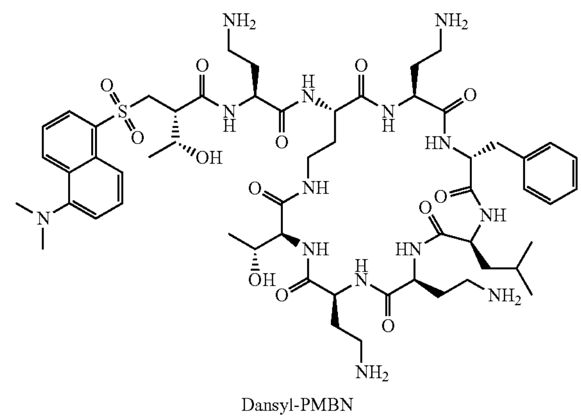

Dansyl-PMBN

Figure 4C:
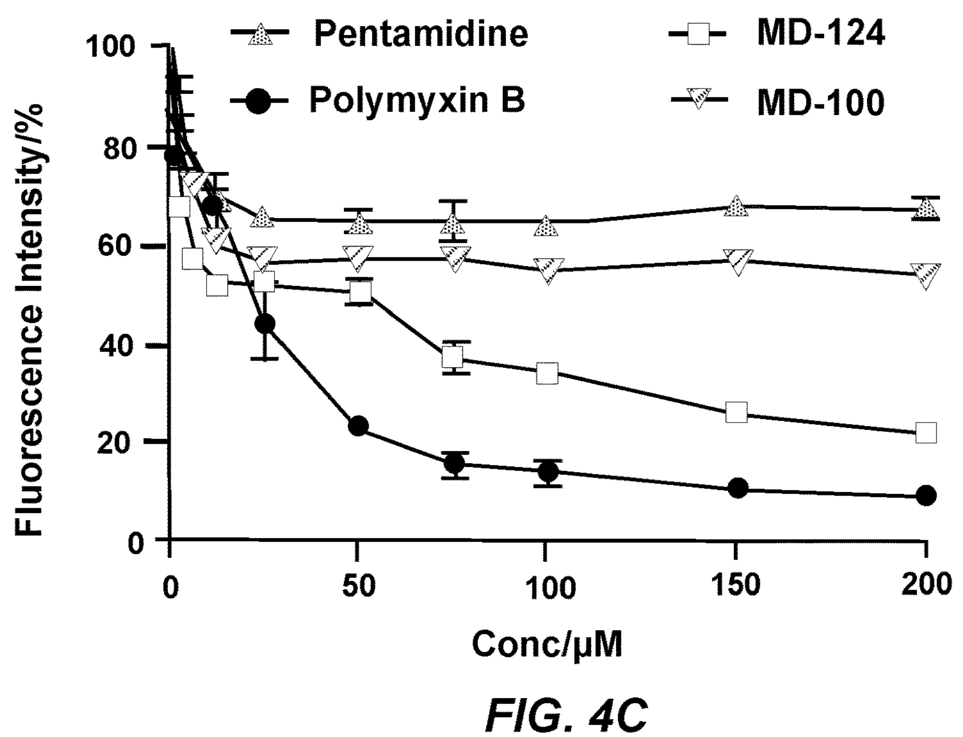
Figure 4D:
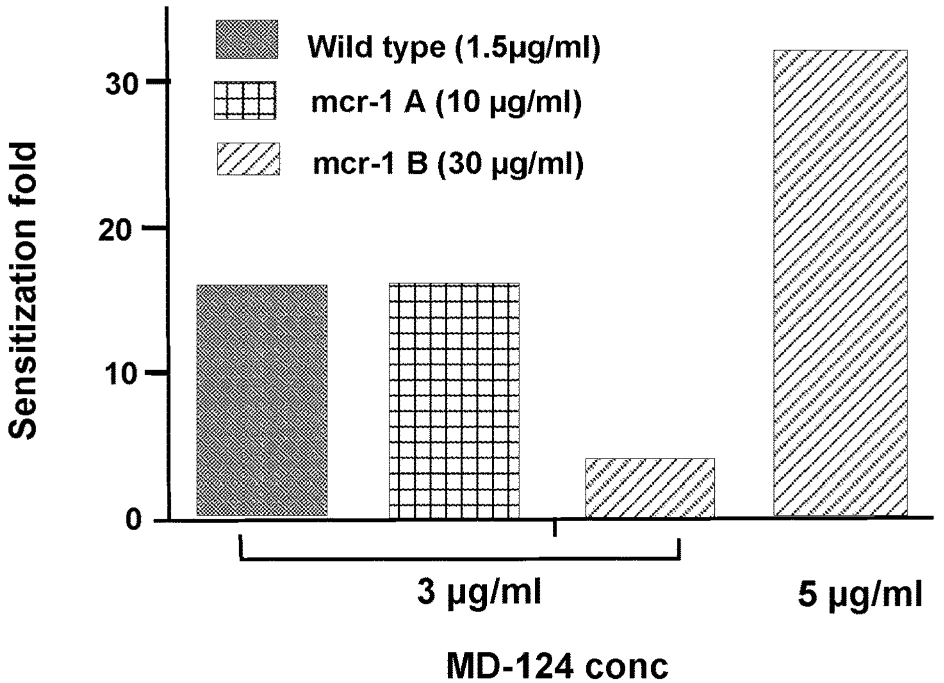

With the incremental addition of MD-124 to a mixture of *E. coli* and 10 μM Dansyl-PMBN, the fluorescent intensity of Dansyl-PMBN steadily decreased in a concentration dependent fashion, indicating binding of MD-124 to lipid A (FIG. 4C). Pentamidine and MD-100 were also able to displace Dansyl-PMBN although not as much as MD-124. A mutant of the lipid A strain was constructed with an over-expression mobilized colistin resistance-1 (mcr-1) gene, which would modify the phosphate group on lipid A, induce decreased negative charge density on Gram-negative bacteria outer membrane and lead to the resistance to colistin.[26,27] Two mcr-1 over-expressing strains, mcr-1 A and mcr-1 B were used to test the response of MD-124 towards the modified lipid A. The MIC of polymyxin B on these two strains were 10 and 30 μg/ml respectively, while the MIC on the wild type was 1.2 μg/ml (Table 11).

TABLE 11

| Strains | MIC of Rif polymyxin B (μg/ml) | MIC of Rif only (μg/ml) | MIC of Rif with 3 μg/ml MD-124 | Sensitization fold with 3 μg/ml MD-124 | MIC of Rif with 5 μg/ml MD-124 | Sensitization fold with 5 μg/ml MD-124 |
|---|---|---|---|---|---|---|
| mcr-1 A | 10 | 5 | 0.32 | 16 | NA | NA |
| mcr-1 B | 30 | 5 | 1.25 | 4 | 0.16 | 32 |

While 3 μg/ml MD-124 sensitized wild type *E. coli* towards rifampin by 16-fold, it was only able to sensitize mcr-1 B strain by 4-fold, and 5 μg/ml MD-124 were required to re-gain 32-fold sensitization on mcr-1 B strain (FIG. 4E). This showed decreased activity for MD-124 when lipid A was modified, supporting lipid A being the molecular target of MD-124. It is worth mentioning that 3 μg/ml MD-124 was still able to sensitize mcr-1 A (MIC 10 μg/ml) strains towards rifampin by 32-fold, which means mcr-1 stains with this level of resistance of polymyxin B did not achieve resistance towards MD-124 (FIG. 4E). The clinical isolated mcr-1 over-expressing strains usually have a MIC of 10 μg/ml or below for polymyxin B, indicating MD-124's effectiveness on clinical those strains. Even those mcr-1 strains that showed greater resistance towards polymyxin B (MIC 30 μg/ml) only induced mild resistance towards MD-124, raising the concentration required for 32-fold sensitization from 3 to 5 μg/ml. Collectively, these results not simply demonstrate that lipid A is the molecular target of MD-124, but also suggest a therapeutic potential of MD-124 in the fight colistin resistant bacteria induced by mcr-1. MD-124 was also found to sensitize mcr-1 over-expressing stains towards many other antibiotics besides rifampicin (Table 16).

Figure 5A:
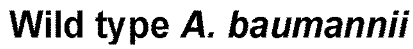
FIG. 5 shows that MD-124 sensitizes wild type *A. baumannii, K. pneumoniae* and drug-resistant Gram-negative strains towards existing antibiotics. Panels (A) and (B) are the results from checkerboard assays that showed MD-124 sensitized *A. baumannii* towards rifampicin and novobiocin. Panels (C) and (D) are the results from checkerboard assays that showed MD-124 sensitized *K. pneumoniae* towards rifampicin and clarithromycin. Panel (E) shows that MD-124 sensitized NDM-1 overexpression *E. coli* towards rifampicin. Panel (F) shows that MD-124 sensitized MCR-1 overexpression *E. coli* towards rifampicin. All experiments are at least duplicate results.
Figure 5A:
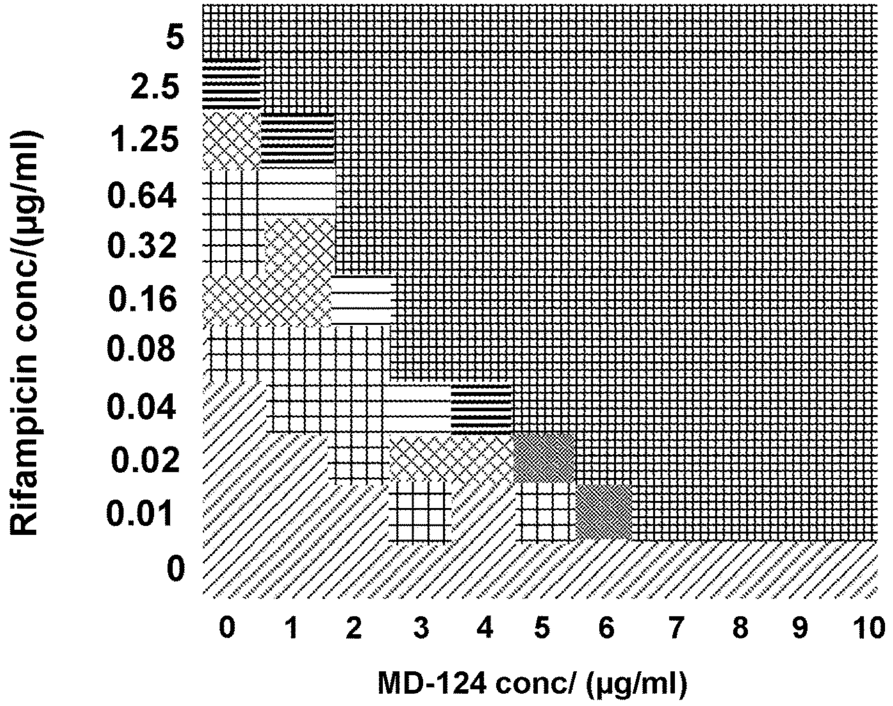
Figure 5B:
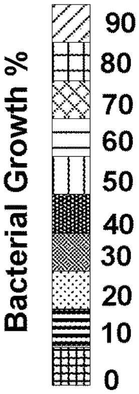
Figure 5B:
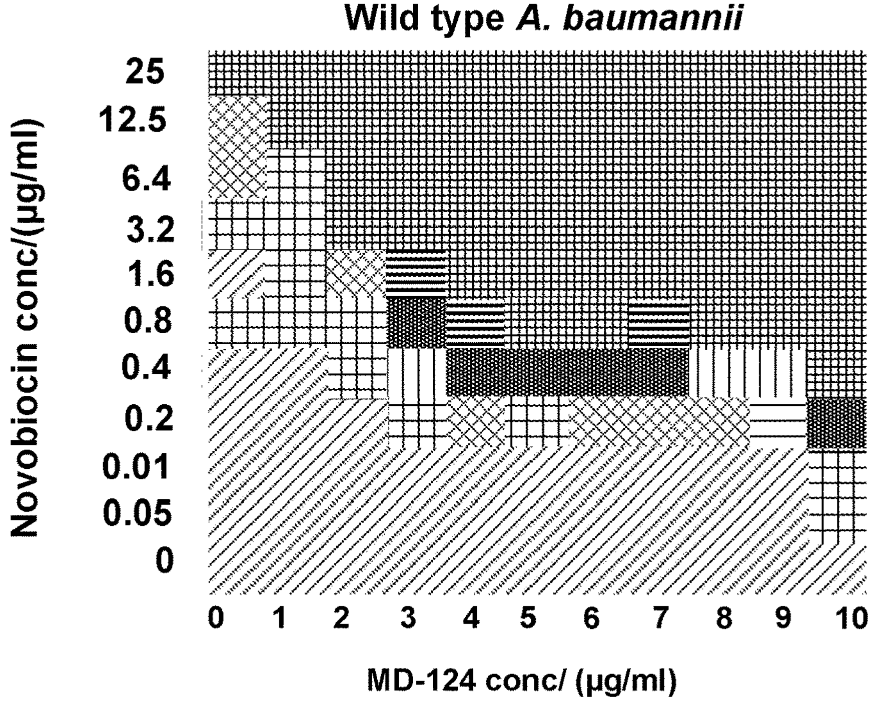
Figures 5C, 5D:
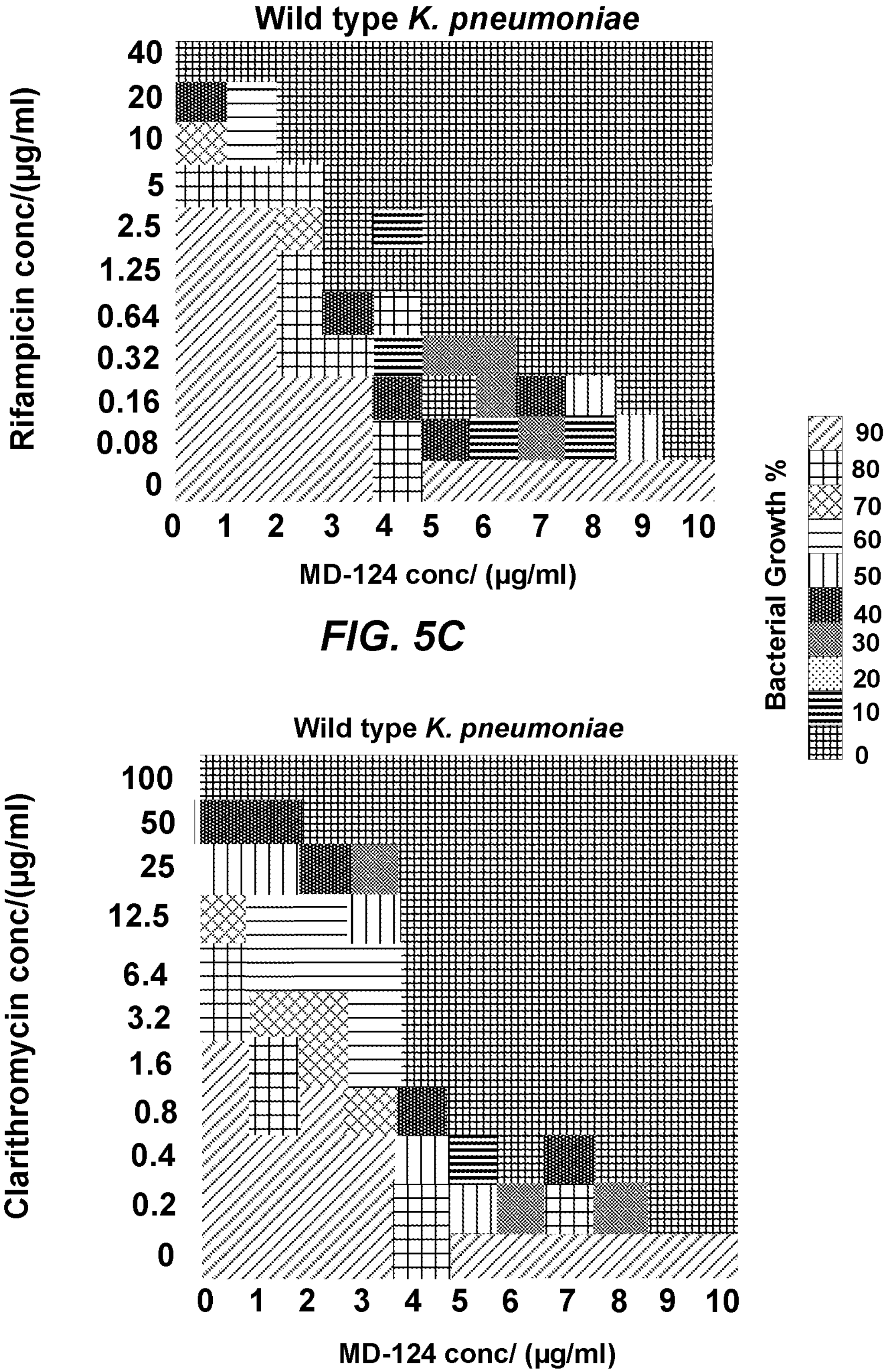

The sensitization effect of MD-124 on various clinically relevant strains and drug-resistant strains, especially the Gram-negative bacteria in ESKAPE category of pathogens, was then examined. Checkerboard assays revealed MD-124 was able to sensitize *A. baumannii* towards rifampicin, decreasing the MIC from 5 μg/ml to 0.04 and 0.01 μg/ml when 5 and 7 pg/ml of the sensitizer were used respectively (FIG. 5A). The FIC index between MD-124 and rifampicin was calculated to be 0.14. Similar sensitization effect on *A. baumannii* was also observed with novobiocin through a checkerboard assay and the FIC index between MD-124 and novobiocin was determined to be 0.20 (FIG. 5B). 5 μg/ml MD-124 also sensitized *A. baumannii* towards a variety of other antibiotics such as clarithromycin, fusidic acid and clindamycin, achieving 64, 128 and 8-fold sensitizations, respectively (Table 12).

TABLE 12

| Antibiotics (AB) | MIC of AB only | MIC of AB with 5 μg/ml MD-124 | Sensitization fold with 5 μg/ml MD-124 |
|---|---|---|---|
| Rifampicin | 5 | 0.04 | 128 |
| Clarithromycin | 25 | 0.4 | 64 |
| Novobiocin | 25 | 0.8 | 32 |
| Fusidic acid | 50 | 0.4 | 128 |
| Clindamycin | 100 | 12.5 | 8 |
| Polymyxin B | 1.6 | 0.04 | 4 |
| Chloramphenicol | 100 | 25 | 4 |
| Ciprofloxacin | 0.05 | 0.0125 | 4 |
| Trimethoprim | 25 | 12.5 | 2 |
| Tetracycline | 1.2 | 0.6 | 2 |
| Trovafloxacin | 0.032 | 0.016 | 2 |
| Kanamycin | 12.5 | 0.62 | 2 |
| Nafcillin | 200 | 100 | 2 |

Unit for AB: μg/ml; MIC of MD-124 on *A. baumannii* is 25 μg/ml.

Another ESKAPE pathogens—*K. pneumoniae*, was also susceptible to MD-124. As shown in FIGS. 5 C and D, MD-124 was able to sensitize *K. pneumoniae* towards rifampicin and clarithromycin by 512-fold or more; 10 μg/ml of MD-124 brought the MIC of rifampicin and clarithromycin from more than 20 μg/ml to 0.2 μg/ml or less. FIC index between MD-124 and rifampicin or clarithromycin was determined to be 0.15 and 0.16, respectively. Many other antibiotics can also be combined with 5 μg/ml MD-124 such as clindaycin, chloraphenicol, fusidic acid and novobiocin to inhibit *K. pneumoniae* growth (Table 13).

TABLE 13

| Antibiotics (AB) | MIC of AB only | MIC of AB with 5 μg/ml MD-124 | Sensitization fold with 5 μg/ml MD-124 |
|---|---|---|---|
| Rifampicin | 40 | 0.016 | 252 |
| Clarithromycin | 200 | 0.8 | 252 |
| Novobiocin | 200 | 6.4 | 32 |
| Chloramphenicol | >100 | 1.6 | >64 |
| Clindamycin | >200 | 25 | >8 |
| Fusidic acid | 100 | 25 | 4 |

Unit for AB: μg/ml; MIC of MD-124 on *K. pneumoniae* is 25 μg/ml.

Carbapenem-resistant Enterobacteriaceae is causing rising concerns and is listed as WHO priority 1 pathogens for R&D of new antibiotics. To test the effect of MD-124 on carbapenem-resistant bacteria, NDM-1 expressing *E. coli* strain was constructed to induce carbapenem-resistance. Compared with wild-type, NDM-1 expressing *E. coli* strain showed a 30 to 100-fold increase of MIC towards β-lactam antibiotics such as ampicillin, ceftazidime and carbapenem antibiotics meropenem (Table 14 and Table 12).

TABLE 14

| Antibiotics | MIC on wild-type *E. coli* (μg/ml) | MIC on NDM-1 over-expression *E. coli* (μg/ml) |
|---|---|---|
| Ampicillin | 6 | >300 |
| Ceftazidime | <0.2 | >6.25 |
| Meropenem | 0.03 | 12.5 |

Figure 5E:
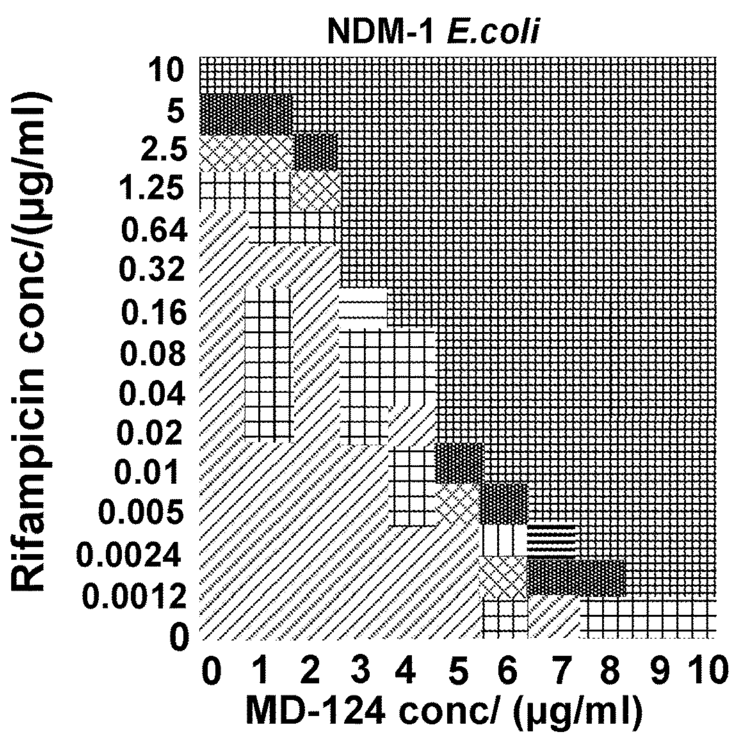

NDM-1 expressing *E. coli* strain did not show significant changes in MIC towards other family of antibiotics compared with the wild type (Table 15 vs Table 8). MD-124 was able to sensitize NDM-1 expressing *E. coli* strain with the same potency as for the wild-type *E. coli*. MD-124 sensitized NDM-1 expressing *E. coli* towards rifampicin in a concentration-dependent manner, decrease the MIC from 10 to 0.02 and 0.012 μg/ml when 5 and 10 μg/ml were used (FIG. 5E). MD-124 also showed synergistic effect with rifampicin as the FIC index calculated to be 0.09. MD-124 sensitized carbapenem-resistant *E. coli* towards other narrow-spectrum antibiotics such as clarithromycin, novobiocin and broad-spectrum such as trovafloxacin, chloramphenicol (Table 15).

TABLE 15

| Antibiotics (AB) | MIC of AB only | MIC of AB with 5 μg/ml MD-124 | Sensitization fold with 5 μg/ml MD-124 |
|---|---|---|---|
| Rifampicin | 10 | 0.02 | 516 |
| Clarithromycin | 25 | 0.4 | 64 |
| Novobiocin | 50 | 1.6 | 32 |
| Clindamycin | 200 | 3.2 | 64 |
| Trovafloxacin | 0.025 | 0.0008 | 32 |
| Chloramphenicol | 12.5 | 1.6 | 8 |
| Polymyxin B | 2.5 | 0.32 | 8 |
| Tetracycline | 12.5 | 3.2 | 4 |
| Meropenem | 12.5 | 6.2 | 2 |
| Ampicillin | >300 | 300 | >1 |

Unit for AB: μg/ml; MIC of MD-124 on NDM-1 expressing *E. coli* is 50 μg/ml.

Figure 5F:
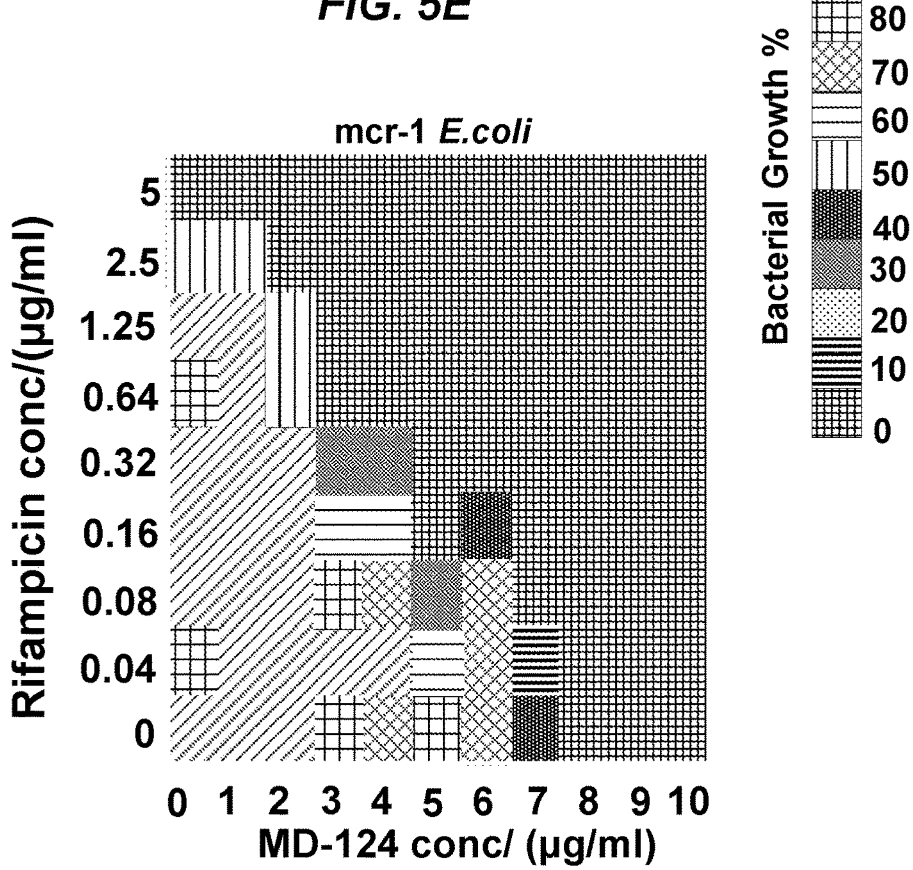

Polymyxin and colistin-resistant strains induced by mcr-1 gene are threatening the last line of defense of antimicrobial treatment. It was observed that MD-124 sensitized mcr-1 expressing *E. coli* (MIC of polymyxin B is 30 μg/ml) towards rifampicin and several other antibiotics (FIG. 5F, Table 16).

TABLE 16

| Antibiotics (AB) | MIC of AB only | MIC of AB with 5 μg/ml MD-124 | Sensitization fold with 5 μg/ml MD-124 |
|---|---|---|---|
| Rifampicin | 5 | 0.16 | 32 |
| Clarithromycin | 25 | 0.2 | 128 |
| Polymyxin B | 30 | 1 | 30 |

Unit for AB: μg/ml; The MIC of polymyxin B on this mcr-1 over-expression *E. coli* strain is 30 μg/ml. MIC of MD-124 on this mcr-1 over-expression *E. coli* is 12.5 μg/ml.

MD-124 showed synergistic effect with rifampicin on mcr-1 expressing *E. coli* as the FIC index calculated to be 0.37. It is worth noting that compared with wild-type *E. coli*, MD-124 showed slightly deceased sensitization ability on this mcr-1 expressing strain (FIG. 1D vs FIG. 5F). However, 5 μg/ml MD-124 still brought the MIC of rifampicin and clarithromycin to 0.2 μg/ml or below on this mcr-1 induced polymyxin B resistant strain. Surprisingly, MD-124 sensitized this strain towards polymyxin B, bringing the MIC from 30 to 1 μg/ml. Such results mean that MD-124 was able to convert this polymyxin B resistant strain to a polymyxin B sensitive strain (FIG. 8).

Figure 6A:
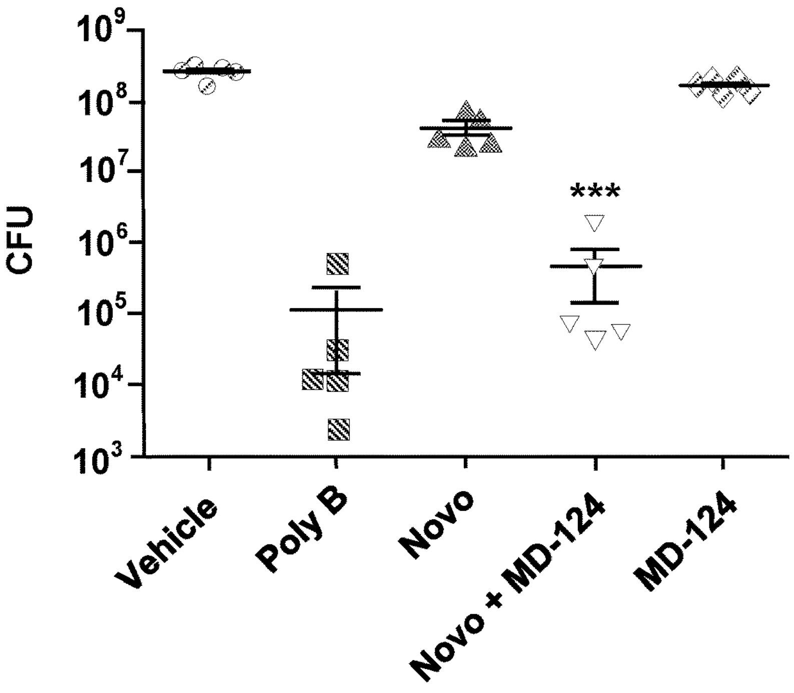
FIG. 6 shows that MD-124 and antibiotic combinations achieved *E. coli* (wild-type and drug-resistant strain) growth inhibition in an ex vivo skin burn infection model. Panel (A) shows that MD-124 and novobiocin combination inhibited wild-type *E. coli* growth. Concentration (w/w) for polymyxin B (poly B), novobiocin (Novo) and MD-124 were 1‰, 4‰ and 1.5‰. The same novobiocin and MD-124 concentration was used in the combination group (Novo+MD-124). Panel (B) shows that MD-124 and clindamycin combination inhibited NDM-1 expressing *E. coli* growth. The concentrations (w/w) for polymyxin B (poly B), clindamycin (Clind) and MD-124 were 1‰, 3‰ and 1.5‰, respectively. The same clindamycin and MD-124 concentration was used in the combination group (Clind+MD-124). Values are means±SEM. n=5, ***P<0.001 vs vehicle or antibiotic alone group. Panel (C) shows that the combination of MD-124 with various polymyxin B led to growth inhibition of mcr-1 positive *E. coli* in an ex vivo skin burn infection model. Concentration (w/w) for polymyxin B (poly B) and MD-124 were 3‰ and 1.5‰. The same concentration was used for polymyxin B and MD-124 in the combination groups (Poly B+MD-124). Values are means f SEM. n=5, ***P<0.001 vs antibiotics or the MD-124 alone group.
Figure 6B:
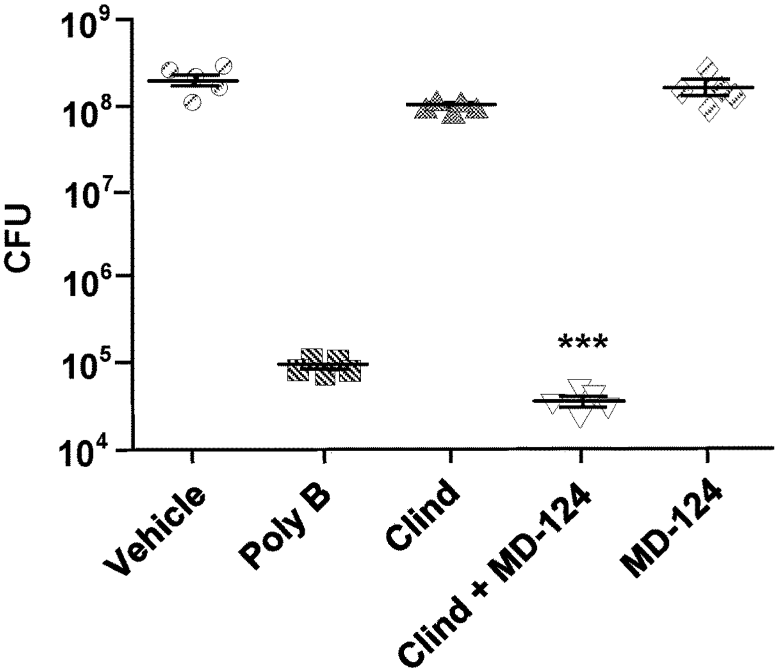

The effect of MD-124 in an ex vivo skin burn infection model was determined. To achieve topical application, compounds were formulated as hypromellose gel. Briefly, human skin (about 1 cm×1 cm) was burnt with a soldering iron (95° C.) for 10 s; then 105 CFU *E. coli* was inoculated to the burnt skin and was cultured at 37° C. for 1 hour. After that, skin was loaded with hypromellose gel with different antibiotics and cultured at 37° C. for 24 hours. After 24 hours incubation, the skin sample was homogenized and the supernatants were serially diluted and plated on agar plates, from which bacterial counts on the skin was calculated. While neither 4‰ (w/w) novobiocin nor 1.5‰ MD-124 themselves achieved significant *E. coli* growth inhibition, novobiocin and MD-124 combination effectively decreased the bacterial load when compared with vehicle group (FIG. 6A). 1‰ polymyxin B hypromellose gel was used as positive control. To further investigate the scope and effectiveness of MD-124, a MD-124 and clindamycin combination was tested on drug-resistant Gram-negative bacteria. MD-124 and clindamycin can also effectively treat skin infection caused by NDM-1 expressing *E. coli*, which reduce the bacteria load for more than 1,000-fold than clindamycin alone (FIG. 6B). The dosages used are comparable to or lower than the commonly used 0.5-2% antibiotics in ointment preparations.

Figure 6C:
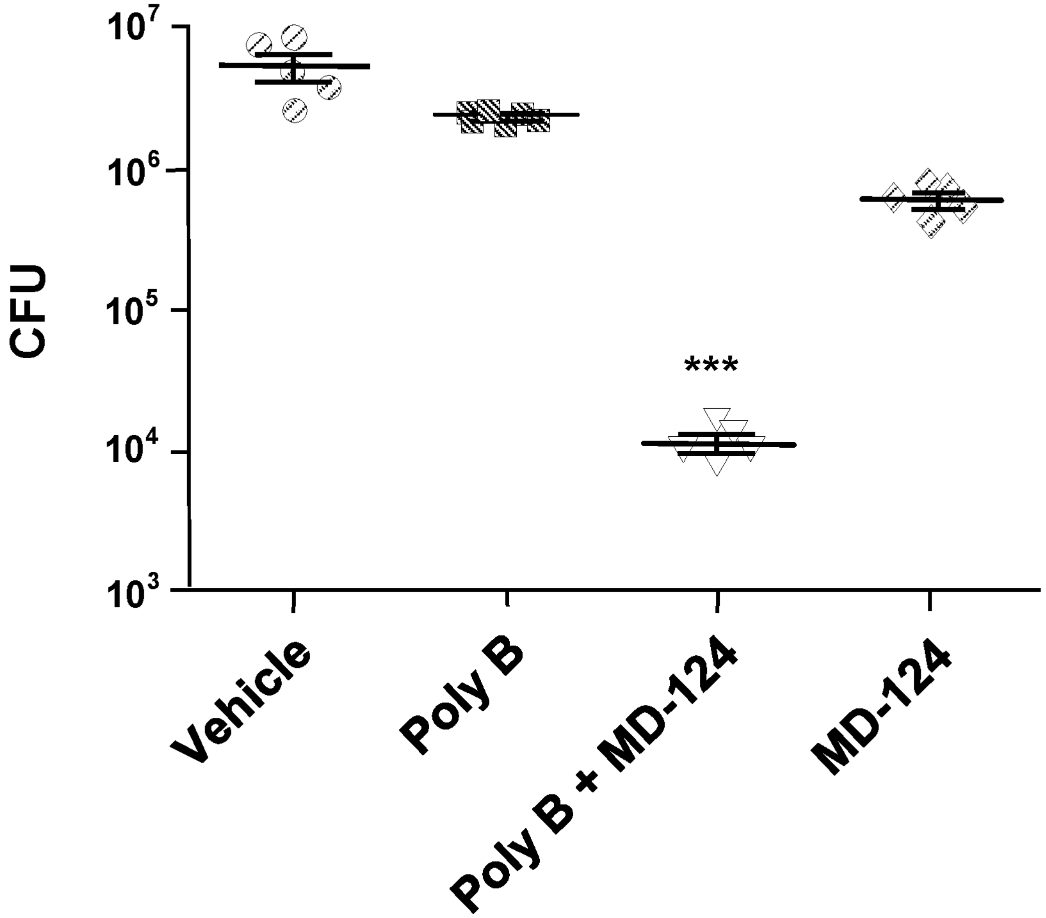

MD-124 was shown to restore the effectiveness of polymyxin B towards *E. coli* expressing mcr-1. Specifically, it was investigated whether a MD-124-polymyxin B combination would be effective in treating MCR-1 bacterial infection in this skin-burn model (FIG. 6C). Polymyxin B alone (3‰, w/w) only had minor effects as compared with vehicle group (FIG. 6C). In contrast, the MD-124-polymyxin B combination (3‰ (w/w) polymyxin B and 1.5‰ (w/w)) reduced the bacterial load by ~200-fold (FIG. 6C). Taken together, these results showed that the sensitization effect of MD-124 allows the use of narrow-spectrum antibiotics in treating Gram-negative bacterial infection and restores the sensitivity of drug-resistant strains towards tested certain antibiotics.

The effect of phosphatidylcholine on MD-124 sensitization activity was also determined. *E. coli* was treated with 10 μM MD-124 (about 5 μg/ml) and rifampicin combination with varying concentrations of phosphatidylcholine (from 0 to 320 μM) for 20 h at 37° C., then the $OD_{600}$ was measured and the sensitization folds were calculated as mentioned above. The results are shown in FIG. 9.

Example 7. Antibacterial Activity Against MRSA

The sensitization fold of select compounds described herein on Gram-positive bacteria was determined.

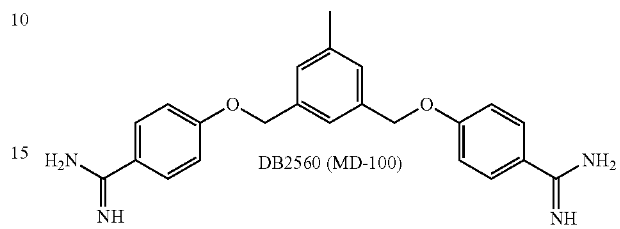

DB2560 (MD-100)

Figure 10A:
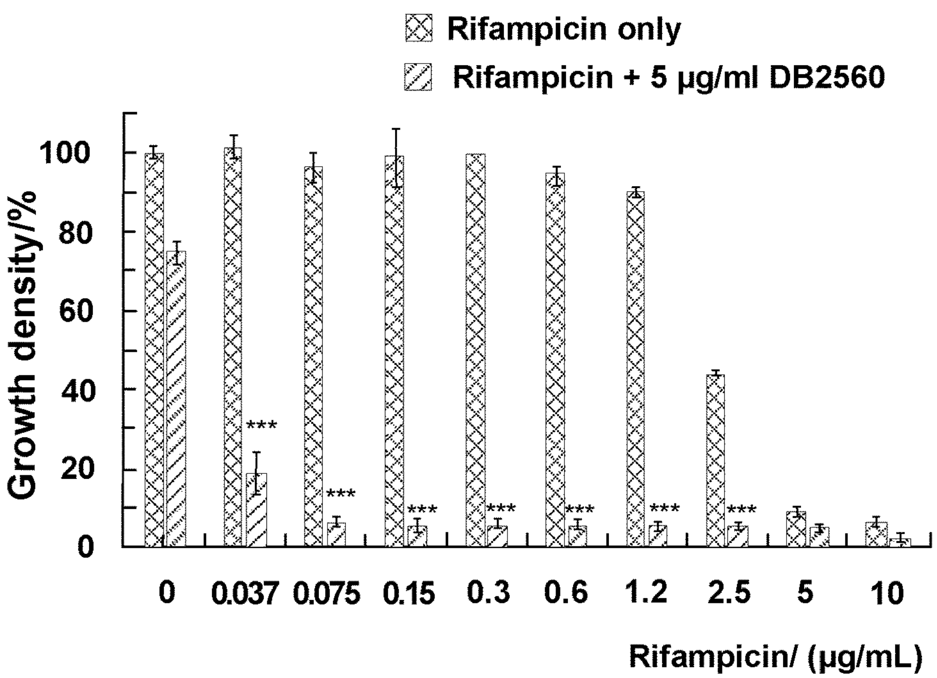
Figure 10B:
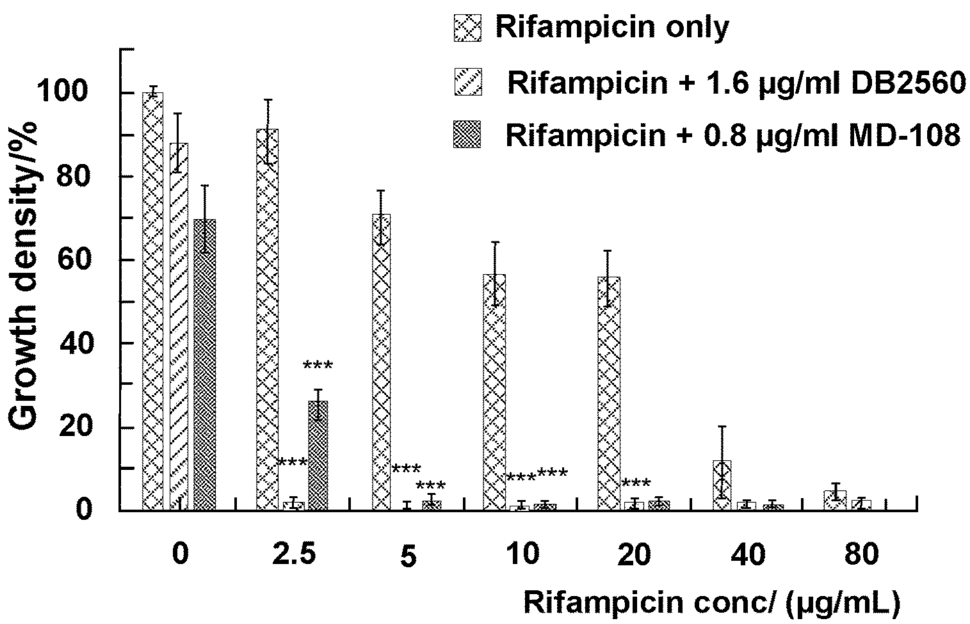

DB2560 (also referred as MD-100 herein and shown above) sensitizes Gram-positive bacteria such as *B. subtilis* towards traditional antibiotics. The MIC of DB2560 on wild type *B. subtilis* is 50 μg/ml. As shown in FIG. 10A, 5.5 μg/ml of DB2560 alone (i.e., without any additional antibiotic) failed to significantly impact bacterial growth (80% growth density compared with the control (no treatment) group). The MIC of rifampicin on *B. subtilis* in the presence of 5.5 μg/ml of DB2560 was 0.037 μg/ml, a concentration at which rifampicin has little inhibition effect. The sensitization fold and FIC index was calculated to be 256-fold and 0.11. The MIC of erythromycin in the presence of and absence of DB2560 was determined to be 1.5 and 50 pg/mL, which gave DB2560 a 32-fold sensitization and a FIC index of 0.14. A concentration of 5.5 μg/ml DB2560 sensitizes *B. subtilis* towards a wide range of antibiotics with distinct anti-microbial mechanisms, such as clindamycin (16-fold), clarithromycin (32-fold), novobiocin (4-fold), methicillin (4-fold), entrapenem (4-fold), trovafloxacin (8-fold).

The fact that DB2560 significantly sensitizes *B. subtilis* towards rifampicin, erythromycin and clindamycin indicates Gram-positive bacteria membrane are a very effective barrier for those antibiotics. DB2560, at a concentration of 2.7 μg/ml, sensitized MRSA towards existing antibiotics such as rifampicin (32-fold) (FIG. 10B) and trovafloxacin (16-fold). Rifampicin is the first line of defense against MRSA and many MRSA strains become resistant to rifampicin through overexpression of efflux pumps and other mechanisms. The combination of the bacterial sensitizers as described herein, such as DB2560, and rifampicin can be used more as a more effective therapeutic against MRSA.

The MIC of many antibiotics such as erythromycin, rifampicin, and trovafloxacin on MRSA is significantly higher than wild type *E. coli*, which means even narrow-spectrum antibiotics such as rifampicin, a first-line of defense of MRSA, can cause severe collateral damage to benign Gram-negative bacteria like *E. coli* before it can kill MRSA. As a proof of concept, the relative ratio of *E. coli* and MRSA or *B. subtilis* and MRSA was measured with and without MD-108 (FIGS. 11A and B). Trovafloxacin (16 ng/ml) would prefer the inhibition of *E. coli*, leaving MRSA the dominant species (78% of the bacteria population). When supplied with 1.5 μg/ml MD-108 and 8 ng/ml trovafloxacin, the MRSA inhibition was achieved, leaving *E. coli* as the dominant species (89% of the bacteria population). Under 16 ng/ml trovafloxacin, the relative survival ratio between *B. subtilis* and MRSA is 1:1, while under 8 ng/ml trovafloxacin and 1.5 μg/ml MD-108, *B. subtilis* would dominate the composition (99.5%).

Although the foregoing invention has been described in some detail by way of illustration and example for the purposes of clarity of understanding, it will be readily apparent to one of ordinary skill in the art in light of the teaching of this invention that certain changes and modifications may be made thereto without departing from the spirit and scope of the invention as defined in the appended.

What is claimed is:

1. A pharmaceutical composition comprising a compound of Formula VI:

(VI)

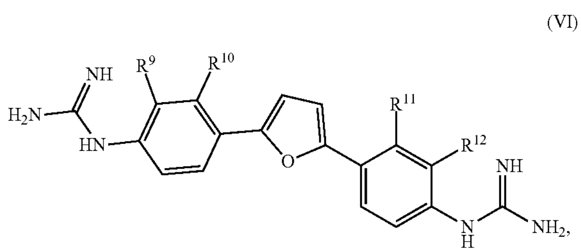

or a pharmaceutically acceptable salt thereof, optionally in a pharmaceutically acceptable carrier, in combination with an effective amount of an antibacterial antibiotic for treating a bacterial infection in a host in need thereof wherein:

$R^3$ is independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, carbocyclic, $C_2$-$C_6$alkenyl, $C_2$-$C_6$alkynyl, heteroaryl, aryl, heterocyclyl, —COOR, —C(O)R, fluorine, chlorine, bromine, and iodine $R^9$ and $R^{12}$ are independently at each occurrence selected from the group consisting of hydrogen, hydroxyl, $C_1$-$C_6$alkyl, $C_1$-$C_6$alkoxy, $C_1$-$C_6$haloalkoxy, $C_1$-$C_6$alkanoyl, aliphatic, carbocyclic, $C_1$-$C_6$hydroxyalkyl, $C_1$-$C_6$haloalkyl, $N(R^3)_2$, —$NHSO_2$alkyl, —N(alkyl) $SO_2$alkyl, —$NHSO_2$aryl, —N(alkyl)$SO_2$aryl, —$NHSO_2$alkenyl, —N(alkyl) $SO_2$alkenyl, —$NHSO_2$alkynyl, —N(alkyl)$SO_2$alkynyl, $NO_2$, —COOH, —$CONH_2$, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, chlorine, bromine, iodine, thiol, and cyano; and $R^{10}$ and $R^{11}$ are independently at each occurrence selected from the group consisting of hydroxyl, $C_1$-$C_6$alkanoyl, carbocyclic, $C_1$-$C_6$hydroxyalkyl, $C_1$-$C_6$haloalkyl, $N(R^3)_2$, —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl) $SO_2$alkynyl, $NO_2$, —COOH, —$CONH_2$, —C(O)R, —$P(O)(OH)_2$, —$S(O)R^3$, —$SO_2R^3$, —$SO_3R^3$, —$SO_2N(R^3)_2$, —$OSO_2R^3$, —$N(R^3)SO_2R^3$, azide, aryl, heteroaryl, heterocyclyl, fluorine, bromine, iodine, thiol, and cyano;

wherein at least one of $R^{10}$ or $R^{11}$ is not fluorine.

2. A pharmaceutical composition comprising Compound D

Compound D

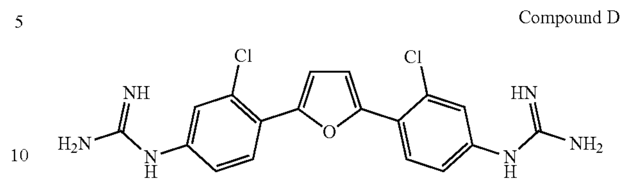

or a pharmaceutically acceptable salt thereof, optionally in a pharmaceutically acceptable carrier, in combination with an effective amount of an antibacterial antibiotic for treating a bacterial infection in a host in need thereof.

3. The pharmaceutical composition of claim 1, wherein the antibacterial antibiotic is a macrolide.

4. The pharmaceutical composition of claim 1, wherein the antibacterial antibiotic is a macrolide selected from the group consisting of azithromycin, clarithromycin, erythromycin, fidaxomicin, telithromycin, carbomycin A, josamycin, kitasanmycin, midecamycin, oleandomycin, solithromycin, spiramycin, troleandomycin, tylosin, and roxithromycin.

5. The pharmaceutical composition of claim 1, wherein the antibacterial antibiotic is clarithromycin.

6. A method for treating a bacterial infection comprising administering a pharmaceutical composition of claim 1 to a host in need thereof.

7. A method for treating a bacterial infection comprising administering a pharmaceutical composition of claim 2 to a host in need thereof.

8. A method for treating a bacterial infection comprising administering a pharmaceutical composition of claim 3 to a host in need thereof.

9. A method for treating a bacterial infection comprising administering a pharmaceutical composition of claim 4 to a host in need thereof.

10. A method for treating a bacterial infection comprising administering a pharmaceutical composition of claim 5 to a host in need thereof.

11. The method of claim 6, wherein the bacterial infection is caused by a gram-positive or a gram-negative bacterial infection.

12. The method of claim 6, wherein the bacterial infection is caused by a gram-positive or a *Mycobacterium*.

13. The method of claim 7, wherein the bacterial infection is caused by a gram-positive or a gram-negative bacterial infection.

14. The method of claim 7, wherein the bacterial infection is caused by a gram-positive or a *Mycobacterium*.

15. The method of claim 8, wherein the bacterial infection is caused by a gram-positive or a gram-negative bacterial infection.

16. The method of claim 8, wherein the bacterial infection is caused by a gram-positive or a *Mycobacterium*.

17. The method of claim 9, wherein the bacterial infection is caused by a gram-positive or a gram-negative bacterial infection.

18. The method of claim 9, wherein the bacterial infection is caused by a gram-positive or a *Mycobacterium*.

19. The method of claim 10, wherein the bacterial infection is caused by a gram-positive or a gram-negative bacterial infection.

20. The method of claim 10, wherein the bacterial infection is caused by a gram-positive or a *Mycobacterium*.

* * * * *